(12) United States Patent
Coulthard

(10) Patent No.: US 7,193,512 B1
(45) Date of Patent: Mar. 20, 2007

(54) LOAD SAFEGUARD SYSTEMS

(75) Inventor: John J. Coulthard, Scottsdale, AZ (US)

(73) Assignee: Radio Data Corporation, Scottsdale, AZ (US)

(*) Notice: Subject to any disclaimer, the term of this patent is extended or adjusted under 35 U.S.C. 154(b) by 65 days.

(21) Appl. No.: 11/128,530

(22) Filed: May 13, 2005

Related U.S. Application Data

(63) Continuation-in-part of application No. 10/650,545, filed on Aug. 27, 2003, now Pat. No. 6,972,677.

(60) Provisional application No. 60/452,261, filed on Mar. 6, 2003, provisional application No. 60/406,110, filed on Aug. 27, 2002.

(51) Int. Cl.
*G08B 1/00* (2006.01)

(52) U.S. Cl. ............. 340/531; 340/539.13; 340/539.15

(58) Field of Classification Search ............... 340/531, 340/505, 506, 539.13–539.17, 539.31, 539.32, 340/572.1, 10.1, 5.92
See application file for complete search history.

(56) References Cited

U.S. PATENT DOCUMENTS

| | | | |
|---|---|---|---|
| 5,658,607 A * | 8/1997 | Herdeman | 426/263 |
| 5,686,888 A * | 11/1997 | Welles et al. | 340/539.13 |
| 5,793,290 A | 8/1998 | Eagleson et al. | |
| 5,867,801 A * | 2/1999 | Denny | 701/35 |
| 5,886,634 A | 3/1999 | Muhme | |
| 6,058,374 A | 5/2000 | Guthrie et al. | |
| 6,084,513 A | 7/2000 | Stoffer | |
| 6,211,790 B1 | 4/2001 | Radomsky et al. | |
| 6,289,684 B1 * | 9/2001 | Guidry et al. | 62/229 |
| 6,512,455 B2 | 1/2003 | Finn et al. | |
| 6,685,012 B2 * | 2/2004 | Bowden et al. | 206/213.1 |
| 6,697,103 B1 | 2/2004 | Fernandez et al. | |
| 6,826,514 B1 * | 11/2004 | Antico et al. | 702/188 |

\* cited by examiner

*Primary Examiner*—Toan N. Pham
(74) *Attorney, Agent, or Firm*—Stoneman Law Offices, Ltd; Marty Stoneman

(57) ABSTRACT

A system for improved monitoring of changes in the location and conditions surrounding vehicles and shippable property, utilizing fixed and moveable logic processors, which communicate with each other as well as receivers. Non-continuous signaling may be used to provide for reduced power consumption, and network coupling may be used to provided for exporting information to anywhere in the world by means of, for example GSM/GPS infrastructures.

20 Claims, 129 Drawing Sheets

RADIODATA APPLICATION DESCRIPTIONS TRANSPONDER FIRMWARE PROPOSAL

1. GENERIC TRANSPONDER FIRMWARE
   A. ALL TRANSPONDERS REQUIRE A GROUP CODE. THIS CAN BE ONE OF TWO OPTIONS BUILDING TO 64 LATER IN 2003
   B. ALL TRANSPONDERS REQUIRE A UNIQUE CODE. THIS CAN CONSIST *OF 64* OPTIONS, BUILDING TO 1000 IN THE SECOND QUARTER AND 1 MILLION IN THE THIRD QUARTER.
   C. ALL TRARNSPONDERS SHOULD BEACON REGULARLY AT A BEACON RATE THAT IS PROGRAMMABLE FROM THREE TIMES A SECOND TO ONCE AN HOUR.
   D. ALL TRANSPONDERS SHOULD BE ABLE TO TRANSMIT IMMEDIATELY WHEN A SELECTED PIN ON THE MICROPROCESSOR GOES HIGH.
   E. ALL TRANSPONDERS SHOULD TRANSMIT THEIR DATA THREE TIMES WITH A 40MS SPACE BETWEEN EACH.
   F. ALL TRANSPONDERS SHOULD TRANSMIT EACH BIT IN A 200uS TIME SLOT. AN "0" IS REPRESENTED BY A 40 MICROSECOND PULSE (THE FIRST *25%* OF THE TIME SLOT) AND A "1", BY THREE CONSECUTIVE 40 MICROSECOND PULSES (THE FIRST *75%* OF THE TIME SLOT). START BITS CAN BE MORE THAN 3 CONSECUTIVE 40 MICROSECOND PULSES AND STOP BITS CAN BE ONE OR TWO TIME SLOTS WITHOUT A TRANSMISSION.
   G. ALL TRANSPONDERS NEED BY Q3'2003 TO BE ABLE TO TRANSMIT DATA REPRESENTING TEMPERATURE AND BATTERY CONDITION (FUNCTIONS PROVIDED BY THE MICROPROCESSOR).

FIG. 2-06A

RADIODATA APPLICATION DESCRIPTIONS TRANSPONDER FIRMWARE PROPOSAL (continued)

2. SPECIFIC APPLICATION FIRMWARE
   A. THE FIRST TRANSPONDER IS A BEACON TAG WITH STANDARD GENERIC FIRMWARE, THAT WILL BE USED FOR SIMPLE DEMONSTRATIONS AND FOR LOCATION ONLY APPLICATIONS.
   B. THE SECOND TRANSPONDER WILL INCLUDE THE ABILITY TO APPEND STATUS BITS TO THE CODE. THESE STATUS BITS WILL REPORT THE HIGH OR LOW STATUS OF THREE TO FIVE MICROPROCESSOR I/Os.
   C. THE THIRD TRANSPONDER NEEDS TO BE ABLE TO APPEND TO THE TRANSPONDER'S CODE A SIMPLE THREE BIT CODED INPUT TO A PIN ON THE MICROPROCESSOR (A POLLING SIGNAL).
   D. THE FOURTH TRANSPONDER NEEDS TO BE ABLE TO SWITCH ON POWER TO EXTERNAL SENSORS AND TAKE ANALOG DATA INPUT TO THREE I/O PINS. IT NEEDS TO TAKE THREE CONSECUTIVE SAMPLES, AVERAGE THE CLOSEST TWO AND STORE THAT DATA. IT NEEDS TO DO THIS EVERY 2 TO 5 SECONDS, STORING THE AVERAGE OF THE THREE LAST READINGS. THEN IT NEEDS TO COMPUTE THE DIFFERENCE BETWEEN THE LAST TWO AVERAGES AND COMPARE THE RATE OF CHANGE WITH THREE POSITIVE/NEGATIVE RATE OF CHANGE LIMITS AND MODIFY ITS BEACON RATE DEPENDING ON ANY VIOLATION OF THESE LIMITS. FURTHER IT NEEDS TO COMPARE THIS AVERAGE OF AVERAGES WITH THREE HIGH/LOW PAIRS OF LIMITS AND MODIFY ITS BEACON RATE DEPENDING ON ANY VIOLATION OF THESE LIMITS. THE LATEST AVERAGE OF AVERAGES DATA IS ALWAYS TRANSMITTED AT THE BEACON RATE OR THE SELECTED VIOLATION OVERRIDE RATE. THE TRANSPONDER HAS THREE MODES OF OPERATION 1. SLEEP MODE; 2. WAKE-UP MODE, POWER SENSORS, TAKE READINGS, PROCESS THEM AND COMPARE WITH LIMITS, RETURNING TO SLEEP MODE IF NO ANOMALY IS FOUND; 3. TRANSMIT MODE.

FIG. 2-06B

RADIODATA APPLICATION DESCRIPTIONS TRANSPONDER FIRMWARE PROPOSAL (continued)

E. A FIFTH TRANSPONDER NEEDS TO CONTROL AND TAKE DIGITAL DATA INPUT AND TRANSMIT IT AT A PRESCRIBED BEACON RATE OR IMMEDIATELY WHEN POLLED, APPENDING ONE BIT TO INDICATE WHETHER IT IS TRANSMITTING ON A NORMAL BEACON SCHEDULE OR BECAUSE IT WAS POLLED.

SCHEDULE

A.  1.a TWO GROUP CODES
    1.b SIXTY-FOUR UNIQUE CODES
    1.c BEACON RATE TWO SECONDS
    1.d POLLING OPTION (UNCODED)
    1.e TRANSMIT THREE TIMES SPACED 40mS
    1.f STANDARD 40uS PULSE WIDTH & 200uS TIME SLOT -10000 "0", 11110 "1"
    1.g OMIT
    2. OMIT ALL

B.  1.a TWO GROUP CODES
    1.b SIXTY-FOUR UNIQUE CODES
    1.c BEACON RATE TWO SECONDS
    1.d POLLING OPTION (UNCODED)
    1.e TRANSMIT THREE TIMES SPACED 40mS
    1.f STANDARD 40U5 PULSE WIDTH & 200U5 TIME SLOT -10000 "0", 11110 "1"
    1.G OMIT
    2.a
    2.b

FIG. 2-06C

TRANSPONDER TRANSMISSION PERIODICITY DECISION TABLE

Example of a Sensor Sampling Plan (Truck Wheel Monitoring)

| | |
|---|---|
| Step 1 | Wake up every 2 seconds, take 3 samples, average closest two readings, store in A |
| Step 2 | Wake up every 2 seconds, move store A to store B, take 3 samples, average closest two readings, store in A |
| Step 3 | Wake up every 2 seconds, move store B to store C, move store A to store B, take 3 samples, average closest two readings, store in A |
| Step 4 | Compare value of data stored in A with limit table and react accordingly |
| Step 5 | Average the averages stored in A, B and C and store in D |
| Step 6 | Compare value of data stored in A with data stored in B, check change with Rate of Change Table and react accordingly |
| Step 7 | plus Continue to repeat steps 3 through 6 indefinitely |

Example of a Limit Table (Truck Wheel Monitoring)

| Normal plus/minus | Convert every | Transmit every | Repeat eaTx | |
|---|---|---|---|---|
| 0 to 12.5% | 300 secs | 300 secs | 3 times | |
| 12.5 to 25% | 90 secs | 90 secs | 6 times | Warn |
| 25 to 50% | 30 secs 3 | 0 secs | 25 times | Alert |
| over 50% | 10 secs | 10 secs | 50 times | Alarm |

Example of Rate of Change Table (Truck Wheel Monitoring)

| Change | Convert | Transmit | Repeat | Action |
|---|---|---|---|---|
| greater than | everyev | ery | ea Tx | |
| 0% | 450 secs | 900 secs | 3 times | |
| 6.25% | 150 secs | 300 secs | 6 times | Warn |
| 12.50% | 90 secs | 90 secs | 12 times | Alert 1 |
| 25% | 30 secs | 30 secs | 25 times | Alert 2 |

FIG. 2-07A

TRANSPONDER TRANSMISSION PERIODICITY TABLE II

Example of a Sensor Sampling Plan (Home/Big. Monitoring)

Step 1   Wake up every 2 seconds, take 3 samples of all sensed parameters, average closest two readings, store in A Step 2   Wake up every 2 seconds, take 3 samples of all sensed parameters, move store A to store B, take 3 samples of all sensed parameters, average closest two readings, store Step 3   Wake up every 2 seconds, move store A to store B, move store B to store C, move store A to store B, take 3 samples, average closest two readings, store Step 4   Compare value of data stored in A with limit tables for each sensed parameter and react accordingly Step 5   Average the averages stored in A, B and C and store in D for each sensed parameter Step 6   Compare value of data stored in A with data stored in B, check change with Rate of Change Tables for each and react according Step 7   Compare changes in several selected parameters to stored relationships to determine any relationship anomalies and react accordingly Step 8 plus Continue to repeat steps 3 through 6 indefinitely Example of a Limit Table (Home/Big. Monitoring)

| | Convert every | Transmit every | Repeat eaTx | |
|---|---|---|---|---|
| Normal plus/minus | | | | |
| 0 to 125% | 30 mins | 60 mins | 3 times | |
| 12.5 to 25% | 90 secs | 90 secs | 6 times | Warn |
| 25 to 50% | 30 secs | 30 secs | 25 times | Alert |
| over 50% | 10 secs | 10 secs | 50 times | Alarm |

FIG. 2-07B

TRANSPONDER TRANSMISSION PERIODICITY TABLE II (CONT.)

Example of Rate of Change Table (Home/Bld. Monitoring)

| Change greater than | Convert every | Transmit every | Repeat ea Tx | Action |
|---|---|---|---|---|
| 0% | 30 mins | 60 mins | 3 times | |
| 6.25% | 150 secs | 300 secs | 6 times | Warn |
| 12.50% | 90 secs | 90 secs | 12 times | Alert 1 |
| 25% | 30 secs | 30 secs | 25 times | Alert 2 |
| 50% | 10 secs | 10 secs | 50 times | Alarm |

Example of Parameter Relationship Table (Home/Bld. Monitoring)

| Change relationship | Convert/Transmit/Repeat/Action every/every/ea Tx |
|---|---|
| A less than 5% greater or less than B or C, or B greater or less than C | 30 mins /60 mins/3 times |
| A greater than 5% greater or less than B or C, or B greater or less than C | 150 secs/300 secs/6 times/Warn |
| A greater than 15% greater or less than B or C, or B greater or less than C | 90 secs/90 secs/12 times/Alert 1 |
| A greater than 15% greater or less than B or C, or B greater or less than C* | 30 secs/30 secs/25 times/Alert 2 |
| A greater than 25% greater or less than B or C, or B greater or less than C | 10 secs/10 secs/50 times/Alarm |

* When either of A, B or C has a limit failure of over 10% and a Rate of Change of over 5%

Note: Each sensed parameter and appropriate parameter relationship is analyzed, and the response is determined for each parameter or parameter relationship. However the data transmission periodicity and repetition is determined by the most critical parameter or parameter relationship (the transmission format is always the same).

FIG. 2-08

TRANSPONDER FREQUENCY, POLLING, AND
FIRMWARE OPTIONS

| Part Number | Frequency | Modulation | Polling | Firmware |
|---|---|---|---|---|
| 03-000139-01-01 | 433.92MHz | Optional | None | Basic Demo |
| 03-000139-01-02 | 433.92MHz | Optional | None | SSI WAMS |
| 03-000139-01-03 | 433.92MHz | Optional | None | S&G Code |
| 03-000139-01-04 | 433.92MHz | Optional | None | Medical 1 |
| 03-000139-02-05 | 433.92MHz | Optional | None | Home Sec. 1 |
| 03-000139-02-01 | 433.92MHz | OOK | None | Basic Demo |
| 03-000139-02-02 | 433.92MHz | OOK | None | SSI WAMS |
| 03-000139-02-03 | 433.92MHz | OOK | None | S&G Code |
| 03-000139-02-04 | 433.92MHz | OOK | None | Medical 1 |
| 03-000139-02-05 | 433.92MHz | OOK | None | Home Sec. 1 |
| 03-000139-03-01 | 433.92MHz | ASK | None | Basic Demo |
| 03-000139-03-02 | 433.92MHz | ASK | None | SSI WAMS |
| 03-000139-03-03 | 433.92MHz | ASK | None | S&G Code |
| 03-000139-03-04 | 433.92MHz | ASK | None | Medical 1 |
| 03-000139-03-05 | 433.92MHz | ASK | None | Home Sec. 1 |
| 03-000139-11-01 | 303.825MHz | Optional | None | Basic Demo |
| 03-000139-11-02 | 303.825MHz | Optional | None | SSI WAMS |
| 03-000139-11-03 | 303.825MHz | Optional | None | S&G Code |
| 03-000139-11-04 | 303.825MHz | Optional | None | Medical 1 |
| 03-000139-11-05 | 303.825MHz | Optional | None | Home Sec. 1 |
| 03-000139-12-01 | 303.825MHz | OOK | None | Basic Demo |
| 03-000139-12-02 | 303.825MHz | OOK | None | SSI WAMS |
| 03-000139-12-03 | 303.825MHz | OOK | None | S&G Code |
| 03-000139-12-04 | 303.825MHz | OOK | None | Medical 1 |
| 03-000139-12-05 | 303.825MHz | OOK | None | Home Sec. 1 |
| 03-000139-13-01 | 303.825MHz | ASK | None | Basic Demo |
| 03-000139-13-02 | 303.825MHz | ASK | None | SSI WAMS |
| 03-000139-13-03 | 303.825MHz | ASK | None | S&G Code |
| 03-000139-13-04 | 303.825MHz | ASK | None | Medical 1 |
| 03-000139-13-05 | 303.825MHz | ASK | None | Home Sec. 1 |

FIG. 2-10A

TRANSPONDER FREQUENCY, POLLING, AND
FIRMWARE OPTIONS

| Part Number | Frequency | Modulation | Polling | Firmware |
|---|---|---|---|---|
| 03-000139-21-01 | 418MHz | Optional | None | Basic Demo |
| 03-000139-21-02 | 418MHz | Optional | None | SSI WAMS |
| 03-000139-21-03 | 418MHz | Optional | None | S&G Code |
| 03-000139-21-04 | 418MHz | Optional | None | Medical 1 |
| 03-000139-22-05 | 418MHz | Optional | None | Home Sec. 1 |
| 03-000139-22-01 | 418MHz | OOK | None | Basic Demo |
| 03-000139-22-02 | 418MHz | OOK | None | SSI WAMS |
| 03-000139-22-03 | 418MHz | OOK | None | S&G Code |
| 03-000139-22-04 | 418MHz | OOK | None | Medical 1 |
| 03-000139-22-05 | 418MHz | OOK | None | Home Sec. 1 |
| 03-000139-23-01 | 418MHz | ASK | None | Basic Demo |
| 03-000139-23-02 | 418MHz | ASK | None | SSI WAMS |
| 03-000139-23-03 | 418MHz | ASK | None | S&G Code |
| 03-000139-23-04 | 418MHz | ASK | None | Medical 1 |
| 03-000139-23-05 | 418MHz | ASK | None | Home Sec. 1 |
| 03-000139-31-01 | 916.5MHz | Optional | None | Basic Demo |
| 03-000139-31-02 | 916.5MHz | Optional | None | SSI WAMS |
| 03-000139-31-03 | 916.5MHz | Optional | None | S&G Code |
| 03-000139-31-04 | 916.5MHz | Optional | None | Medical 1 |
| 03-000139-31-05 | 916.5MHz | Optional | None | Home Sec. 1 |
| 03-000139-32-01 | 916.5MHz | OOK | None | Basic Demo |
| 03-000139-32-02 | 916.5MHz | OOK | None | SSI WAMS |
| 03-000139-32-03 | 916.5MHz | OOK | None | S&G Code |
| 03-000139-32-04 | 916.5MHz | OOK | None | Medical 1 |
| 03-000139-32-05 | 916.5MHz | OOK | None | Home Sec. 1 |
| 03-000139-33-01 | 916.5MHz | ASK | None | Basic Demo |
| 03-000139-33-02 | 916.5MHz | ASK | None | SSI WAMS |
| 03-000139-33-03 | 916.5MHz | ASK | None | S&G Code |
| 03-000139-33-04 | 916.5MHz | ASK | None | Medical 1 |
| 03-000139-33-05 | 916.5MHz | ASK | None | Home Sec. 1 |

FIG. 2-10B

TRANSPONDER FREQUENCY, POLLING, AND
FIRMWARE OPTIONS

| Part Number | Frequency | Modulation | Polling | Firmware |
|---|---|---|---|---|
| 03-000139-06-01 | 433.92MHz | Optional | 13.56MHz Unc | Basic Demo |
| 03-000139-06-02 | 433.92MHz | Optional | 13.56MHz Unc | SSI WAMS |
| 03-000139-06-03 | 433.92MHz | Optional | 13.56MHz Unc | S&G Code |
| 03-000139-06-04 | 433.92MHz | Optional | 13.56MHz Unc | Medical 1 |
| 03-000139-06-05 | 433.92MHz | Optional | 13.56MHz Unc | Home Sec. 1 |
| 03-000139-07-01 | 433.92MHz | OOK | 13.56MHz Unc | Basic Demo |
| 03-000139-07-02 | 433.92MHz | OOK | 13.56MHz Unc | SSI WAMS |
| 03-000139-07-03 | 433.92MHz | OOK | 13.56MHz Unc | S&G Code |
| 03-000139-07-04 | 433.92MHz | OOK | 13.56MHz Unc | Medical 1 |
| 03-000139-07-05 | 433.92MHz | OOK | 13.56MHz Unc | Home Sec. 1 |
| 03-000139-08-01 | 433.92MHz | ASK | 13.56MHz Unc | Basic Demo |
| 03-000139-08-02 | 433.92MHz | ASK | 13.56MHz Unc | SSI WAMS |
| 03-000139-08-03 | 433.92MHz | ASK | 13.56MHz Unc | S&G Code |
| 03-000139-08-04 | 433.92MHz | ASK | 13.56MHz Unc | Medical 1 |
| 03-000139-08-05 | 433.92MHz | ASK | 13.56MHz Unc | Home Sec. 1 |
| 03-000139-16-01 | 303.825MHz | Optional | 13.56MHz Unc | Basic Demo |
| 03-000139-16-02 | 303.825MHz | Optional | 13.56MHz Unc | SSI WAMS |
| 03-000139-16-03 | 303.825MHz | Optional | 13.56MHz Unc | S&G Code |
| 03-000139-16-04 | 303.825MHz | Optional | 13.56MHz Unc | Medical 1 |
| 03-000139-16-05 | 303.825MHz | Optional | 13.56MHz Unc | Home Sec. 1 |
| 03-000139-17-01 | 303.825MHz | OOK | 13.56MHz Unc | Basic Demo |
| 03-000139-17-02 | 303.825MHz | OOK | 13.56MHz Unc | SSI WAMS |
| 03-000139-17-03 | 303.825MHz | OOK | 13.56MHz Unc | S&G Code |
| 03-000139-17-04 | 303.825MHz | OOK | 13.56MHz Unc | Medical 1 |
| 03-000139-17-05 | 303.825MHz | OOK | 13.56MHz Unc | Home Sec. 1 |
| 03-000139-18-01 | 303.825MHz | ASK | 13.56MHz Unc | Basic Demo |
| 03-000139-18-02 | 303.825MHz | ASK | 13.56MHz Unc | SSI WAMS |
| 03-000139-18-03 | 303.825MHz | ASK | 13.56MHz Unc | S&G Code |
| 03-000139-18-04 | 303.825MHz | ASK | 13.56MHz Unc | Medical 1 |
| 03-000139-18-05 | 303.825MHz | ASK | 13.56MHz Unc | Home Sec. 1 |

FIG. 2-10C

TRANSPONDER FREQUENCY, POLLING, AND
FIRMWARE OPTIONS

| Part Number | Frequency | Modulation | Polling | Firmware |
|---|---|---|---|---|
| 03-000139-26-01 | 418MHz | Optional | 13.56MHz Unc | Basic Demo |
| 03-000139-26-02 | 418MHz | Optional | 13.56MHz Unc | SSI WAMS |
| 03-000139-26-03 | 418MHz | Optional | 13.56MHz Unc | S&G Code |
| 03-000139-26-04 | 418MHz | Optional | 13.56MHz Unc | Medical 1 |
| 03-000139-26-05 | 418MHz | Optional | 13.56MHz Unc | Home Sec. 1 |
| 03-000139-27-01 | 418MHz | OOK | 13.56MHz Unc | Basic Demo |
| 03-000139-27-02 | 418MHz | OOK | 13.56MHz Unc | SSI WAMS |
| 03-000139-27-03 | 418MHz | OOK | 13.56MHz Unc | S&G Code |
| 03-000139-27-04 | 418MHz | OOK | 13.56MHz Unc | Medical 1 |
| 03-000139-27-05 | 418MHz | OOK | 13.56MHz Unc | Home Sec. 1 |
| 03-000139-28-01 | 418MHz | ASK | 13.56MHz Unc | Basic Demo |
| 03-000139-28-02 | 418MHz | ASK | 13.56MHz Unc | SSI WAMS |
| 03-000139-28-03 | 418MHz | ASK | 13.56MHz Unc | S&G Code |
| 03-000139-28-04 | 418MHz | ASK | 13.56MHz Unc | Medical 1 |
| 03-000139-28-05 | 418MHz | ASK | 13.56MHz Unc | Home Sec. 1 |
| 03-000139-36-01 | 916.5MHz | Optional | 13.56MHz Unc | Basic Demo |
| 03-000139-36-02 | 916.5MHz | Optional | 13.56MHz Unc | SSI WAMS |
| 03-000139-36-03 | 916.5MHz | Optional | 13.56MHz Unc | S&G Code |
| 03-000139-36-04 | 916.5MHz | Optional | 13.56MHz Unc | Medical 1 |
| 03-000139-36-05 | 916.5MHz | Optional | 13.56MHz Unc | Home Sec. 1 |
| 03-000139-37-06 | 916.5MHz | OOK | 13.56MHz Unc | Basic Demo |
| 03-000139-37-07 | 916.5MHz | OOK | 13.56MHz Unc | SSI WAMS |
| 03-000139-37-08 | 916.5MHz | OOK | 13.56MHz Unc | S&G Code |
| 03-000139-37-09 | 916.5MHz | OOK | 13.56MHz Unc | Medical 1 |
| 03-000139-37-10 | 916.5MHz | OOK | 13.56MHz Unc | Home Sec. 1 |
| 03-000139-38-01 | 916.5MHz | ASK | 13.56MHz Unc | Basic Demo |
| 03-000139-38-02 | 916.5MHz | ASK | 13.56MHz Unc | SSI WAMS |
| 03-000139-38-03 | 916.5MHz | ASK | 13.56MHz Unc | S&G Code |
| 03-000139-38-04 | 916.5MHz | ASK | 13.56MHz Unc | Medical 1 |
| 03-000139-38-05 | 916.5MHz | ASK | 13.56MHz Unc | Home Sec. 1 |

FIG. 2-10D

PLUG-IN ASK

GROUND MOISTURE

FLOATING POOL SENSOR

MOTION/ACOUSTIC SENSOR

ITEM/PERSONNEL TRACKER

GATE/DOOR OPEN SENSOR

TEMP/SMOKE/FIRE SENSOR

RADIOACTIVE SENSOR

WIND VELOCITY SENSOR

RAIN GAUGE

BLOOD PRESSURE MONITOR

DASCORE INCORPORATED

"DASCORE Inc...Technology for Water Quality Monitoring"

Six-CENSE
*6-in-I Water Quality Sensor*

The Six-CENSE tm is a 6-in-1 multiparameter in-line sensor that can measure Chlorine (free chlorine), Chloramines (combined chlorine) or Dissolved Oxygen, pH, Conductivity, Oxidation-Reduction Potential, and Temperature. This electrochemical technology sits on a robust ceramic chip. Six-CENSE is the only multi-parameter sensor designed for direct insertion into pressurized water mains from 2 inches to 36 inches in diameter. This capability makes the Six-CENSE tm ideally suited to fulfill the requirements of water utilities to monitor the water quality throughout their distribution system. The unit is easy to install, simple to calibrate, and is designed for durability and minimum operator maintenance.

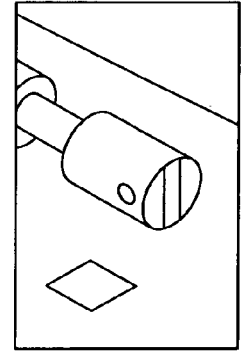
PROBE HEAD & CHIP

Six-CENSE tm simultaneously measures: Chlorine - No reagents required, Monochloramine or Dissolved Oxygen, pH , Temperature , Conductivity, and ORP/REDOX

*FEATURES:*
- All data time-date stamped for analysis and liability protection.
- Data available in 4-20 mA output or LONWORKS® network variable format.
- Direct and reagent-free measurement of Chlorine.
- Capability for measuring Combined Chlorine for plants using chloramination.
- Membrane-free measurement of Dissolved Oxygen.
- Sensor chip field replaceable with typical six-month service
- life.
- Units available in NEMA 4X/1P66 enclosures.
- Installs in 1.5" or 2" saddle valve, gate valve, or ball valve.

71 Tallwood Road 866-321-3804 - Toll free
Jacksonvile FL 32250 904- 249-9283 - Facsimile
www.dascore.com

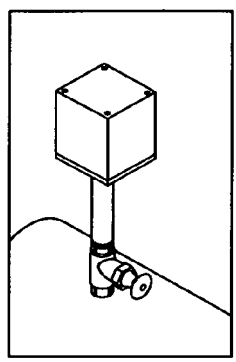
Six-CENSE tm INSERTION INTO PIPE

FIG. 2-15a

DASCORE INCORPORATED

"DASCORE Inc...Technology for Water Quality Monitoring"

Applications:

Chlorine
Range 0 - 5 mg/L
Sensitivity <0.01 mg/L
Accuracy ±0.04 mg/L or 5% of reading, whichever is greater

Chloramines
Range 0-20 mg/L
Sensitivity <0.05 mg/L or 5% of reading, whichever is greater
Repeatability +/- 0.1 mg/L or 5% of reading, whichever is greater
Accuracy +/- 0.1 mg/L or 5% of reading, whichever is greater

*(Customer specifies either chloramines or dissolved oxygen.)*

Dissolved Oxygen
Range 0- 20 mg/L or 0 - 200% saturation
Sensitivity <0.1 mg/L
Accuracy ±0.1 mg/L or 5% of reading, whichever is greater

Temperature
Range 0 - +50 DEGREES C
Sensitivity <0.1%
Repeatability ±0.1%
Accuracy ±0.25 DEGREES C or ±0.1% of reading, whichever is greater

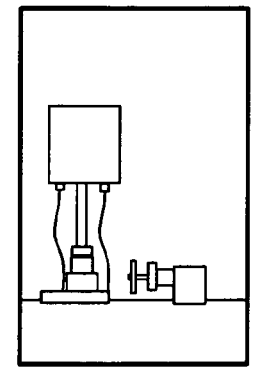

FINISHED WATER

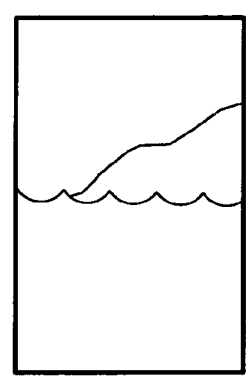

SOURCE WATER

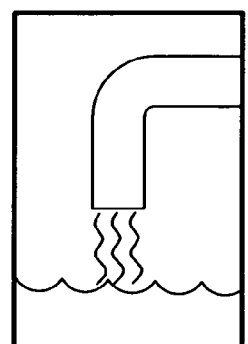

WASTEWATER FINAL EFFLUENT

FIG. 2-15b

Applications (cont.):
Conductivity
Range 0.1 - 10.0 mS/cm
Sensitivity <10uS/cm
Repeatability ±10uS/cm or ±1% of reading, whichever is greater pH
Range 2 - 12
Sensitivity <0.1 pH
Repeatability ±0.1 pH
Accuracy ±0.5 pH

Redox/ORP Range -1.4 to 1.4 V
Sensitivity <1% of range
Repeatability ±1% of range
Accuracy ±1% of range

Reference Electrode
Silver/Silver Chloride type
Drift <5mV in six months
Operational life: Typical six-month continuous operation

Probe Head
Diameter 37 mm (1.48")
Quick release bayonet fitting of sensor chip
Pressure tested to 350 psi, 230 psi continuous rating
Direct insertion into pipe, through gate valve or metering box

Electronics
Available with 4-20 mA or LONWORKS® output. Please contact your Dascore Inc. sales representative.

Specifications subject to change without notice.

Our goal is to provide the most cost-effective water quality monitoring technology worldwide.

71 Tallwood Road 866-321-3804 - Toll free
Jacksonvile FL 32250 904- 249-9283 - Facsimile
www.dascore.com

DASCORE INCORPORATED

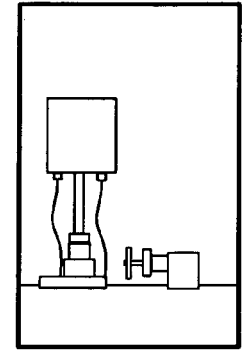
FINISHED WATER

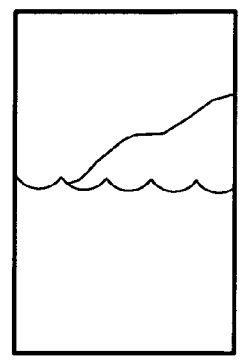
SOURCE WATER

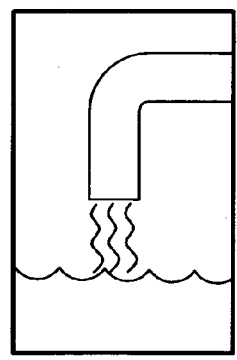
WASTEWATER FINAL EFFLUENT

FIG. 2-15c

Signal Processing Group Inc. 561 E. Elliot Road, Chandler, Arizona, 85225, Tel: (480) 892 1399

Specifications for the LFAFE, the low frequency analog front end. SPGO402

General Description: The LFAFE is a mixed signal CMOS monolithic device that acts as an analog front end or interface to a set of sensors. The device provides a programmable current to energize these sensors and measures the response from the sensors. A clock oscillator is provided on chip for timing purposes. A voltage reference is implemented on chip for use in A/D conversion of the sensed outputs. A communication interface using a three-wire channel is used to communicate with the device. Communications consist of programming a channel identification, sensor drive current and settling time delay for the AID conversion. Control logic for the various operations resides on chip. External components consist of sensors and miscellaneous resistors and capacitors for timing. The device is packaged in a 16 pin plastic package or can be delivered as a die for direct chip on board mounting.

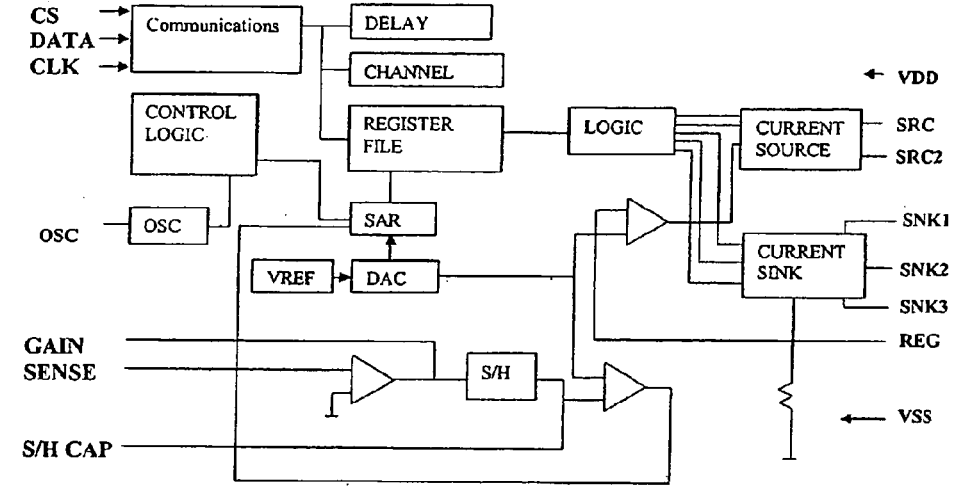

FIG. 2-18a

| LFAFE PACKAGE PINS | | |
|---|---|---|
| Pin | Name | Description |
| 1 | SDA | Bi-directional pin. Serial data. |
| 2 | SCL | Input Pin. Serial Clock |
| 3 | ECS | Output pin. EEPROM Select. |
| 4 | SRC1 | Output pin. SENSOR Drive (Current Drive). |
| 5 | SRC2 | Output pin. SENSOR Drive (Current Drive) |
| 6 | REG | Output pin. Establish level of current drive for SRC1, SRC2. |
| 7 | SNK3 | Output pin. Current sink 3. |
| 8 | VSS | Ground or common. |
| 9 | SNK2 | Output pin. Current sink 2. |
| 10 | SNK1 | Output pin. Current sink 1. |
| 11 | GAIN | Output pin. Gain set for internal amplifier for sensing the response current. |
| 12 | SHCAP | Input pin. External capacitor for sample and hold function |
| 13 | SENSE | Input pin. Sense the output currents from photo- |

LFAFE OPERATION

The LFAFE typically needs an EEPROM and a host micro-controller for its operation. The host controls the LFAFE operation and communicates with the EEPROM via read/write commands transmitted over the serial interface. Only two signals are required to operate the serial interface, SDA and SCL. In a custom system on a chip, application the customer may choose to implement all these macro blocks on the same chip, thereby evolving a new machine. *Since the LFAFE is a fully tested functional block as well as the EEPROMs and uC this is a perfectly viable choice and a low risk implementation.*

FIG. 2-18b1

LFAFE OPERATION(cont.)

The LFAFE typically needs an EEPROM and a host micro-controller for its operation. The host controls the LFAFE operation and communicates with the EEPROM via read/write commands transmitted over the serial interface. Only two signals are required to operate the serial interface, SDA and SCL. In a custom system on a chip, application the customer may choose to implement all these macro blocks on the same chip, thereby evolving a new machine. *Since the LFAFE is a fully tested functional block as well as the EEPROMs and uC this is a perfectly viable choice and a low risk implementation.*

Data is clocked in to the LFAFE on the positive edge of SCL. Normally SDA only changes when SCL is low. There are two exceptions: the START and STOP conditions.

START Condition: Positive transition on SDA when SCL is high. STOP Condition: Negative transition on SDA when SCL is high.

The first data bit following the start condition determines whether the LFAFE is to be selected or the EEPROM. The complement of this bit is output on ECS which is connected to the CS pin on the EEPROM. When the EEPROM is selected the LFAFE ignores any further start conditions or data and disables itself until a stop condition is selected. A stop condition also causes the EEPROM chip select signal to be pulsed low.

FIG. 2-18b2

<u>Signal Processing Group Inc. 561 E. Elliot Road, Chandler, Arizona, 85225, Tel: (480) 892 1399</u>

The stop condition can occur at any time and terminates any operation that may be in progress.

The LFAFE is selected with the first data bit being a 1. The next bit specifies a read (0) or a write(1) operation followed by a 4 bit address. If a write operation is specified the following bits are read in to the selected register, *high bit first*. If a read operation is selected the LFAFE pulls SDA low when the data is ready to be transmitted and the data bits are then clocked out following the negative SCL transition.

There are 14 logical registers, 8 real read/write registers (LD1 LD6, DLY and OC) and 6 "sensor reading" read-only registers (CII 1 CH6). The 8 real registers are the 6 SENSOR (or current drive) registers, a delay register and an oscillator compensation register. These registers are initialized by the host with the corresponding calibration values stored in the neighboring EEPROM. The 6 sensor reading registers are not actual registers. A read operation of one of these pseudo registers causes the LFAFE to take a reading of the sensor specified by the address and return this value as the data portion of the read operation. The take-readings operation is triggered by the negative transition of SCL of the last address bit. The LFAFE pulls the SDA line low when the reading has been taken and the data is ready to be clocked out.

The following table (FIG. 2-18c2) lists the available commands. The SDA bits driven by the LFAFE are underlined.

FIG. 2-18c1

| Select | R/W | Address | Ready | Data |
|---|---|---|---|---|
| Read SENSOR Drive Registers 1-6 | | | | |
| 0 | 0 | 0000 | 0 | LLLLLLL |
| 0 | 0 | 0001 | 0 | LLLLLLL |
| 0 | 0 | 0010 | 0 | LLLLLLL |
| 0 | 0 | 0011 | 0 | LLLLLLL |
| 0 | 0 | 0100 | 0 | LLLLLLL |
| 0 | 0 | 0101 | 0 | LLLLLLL |
| Read Delay Register | | | | |
| 0 | 0 | 0110 | 0 | DDDDD |
| Read Oscillator | | | | |

FIG. 2-18c2

| Register | | | | | |
|---|---|---|---|---|---|
| | 0 | 0 | 0111 | 0 | SSSSS |
| Register Table continued. | | | | | |
| Obtain Current Readings from Channel 1-6 | | | | | |
| | 0 | 0 | 1000 | 0 | RRRRRRRR |
| | 0 | 0 | 1001 | 0 | RRRRRRRR |
| | 0 | 0 | 1010 | 0 | RRRRRRRR |
| | 0 | 0 | 1011 | 0 | RRRRRRRR |
| | 0 | 0 | 1100 | 0 | RRRRRRRR |
| | 0 | 0 | 1101 | 0 | RRRRRRRR |
| Undef. | | | | | |
| | 0 | 0 | 1110 | | |
| | 0 | 0 | 1111 | | |
| Write output current drive registers | | | | | |
| | 0 | 1 | 0000 | | LLLLLLLL |
| | 0 | 1 | 0001 | | LLLLLLLL |
| | 0 | 1 | 0010 | | LLLLLLLL |
| | 0 | 1 | 0011 | | LLLLLLLL |
| | 0 | 1 | 0100 | | LLLLLLLL |
| | 0 | 1 | 0101 | | LLLLLLLL |
| Write Delay Register | | | | | |
| | 0 | 1 | 0110 | | DDDDD |
| Write Osc. | | | | | |

FIG. 2-18d

| Register | | | | | |
|---|---|---|---|---|---|
| | 0 | 1 | 0111 | | SSSSS |

After a read operation, SDA is released to a high state following the last output bit. A write to a register occurs after the rising edge of the last data bit clocked in. Additional data bits clocked in after a write operation are either ignored or treated as a new command or used to write the next real register.

Normal Operation

The host micro-controller initializes the LFAFE by reading the calibration values from the EEPROM. This is achieved by generating a start condition, clocking in a 0 data bit at which point the LFAFE will pull the EEPROM's chip select pin high. The host can now communicate with the EEPROM since its CS pin is high and the LFAFE is ignoring SDA and SCL apart from waiting for a stop condition. Once the FEPROM has been read, the host issues a stop condition, at which point the LFAFE pulls the EEPROM's CS pin low. The host then issues another start condition followed by a 1, followed in turn by the address of the LD1 register, 0000. This is followed by the 8 data bits to be written to LD 1. Then a stop condition is issued. LD2 through OC are written in the same fashion to complete the initialization sequence.

During normal operation, the host will obtain a set of readings from the LFAFE by issuing a set of read commands in order. Detailing this sequence, the host first issues a start condition followed by a 1 to select the LFAFE. Then a 0 will be issued indicating a read followed by the first sensors pseudo register's address, 1000. The host leaves the SCL signal low and lets SDA go high and waits for the LFAFE to pull SDA low to indicate the take-reading operation is completed and the reading is available. The host then drives SCL to clock the data bits out of the LFAFE and finishes with a stop condition. This process is repeated for sensors 2 through 6.

The host can issue a stop condition to terminate the take reading operation prematurely. This major be useful for situations where the current drive may be causing a brown-out in low power situations.

See FIG. 2-18e2 for LFAFE operation timing diagram

FIG. 2-18e1

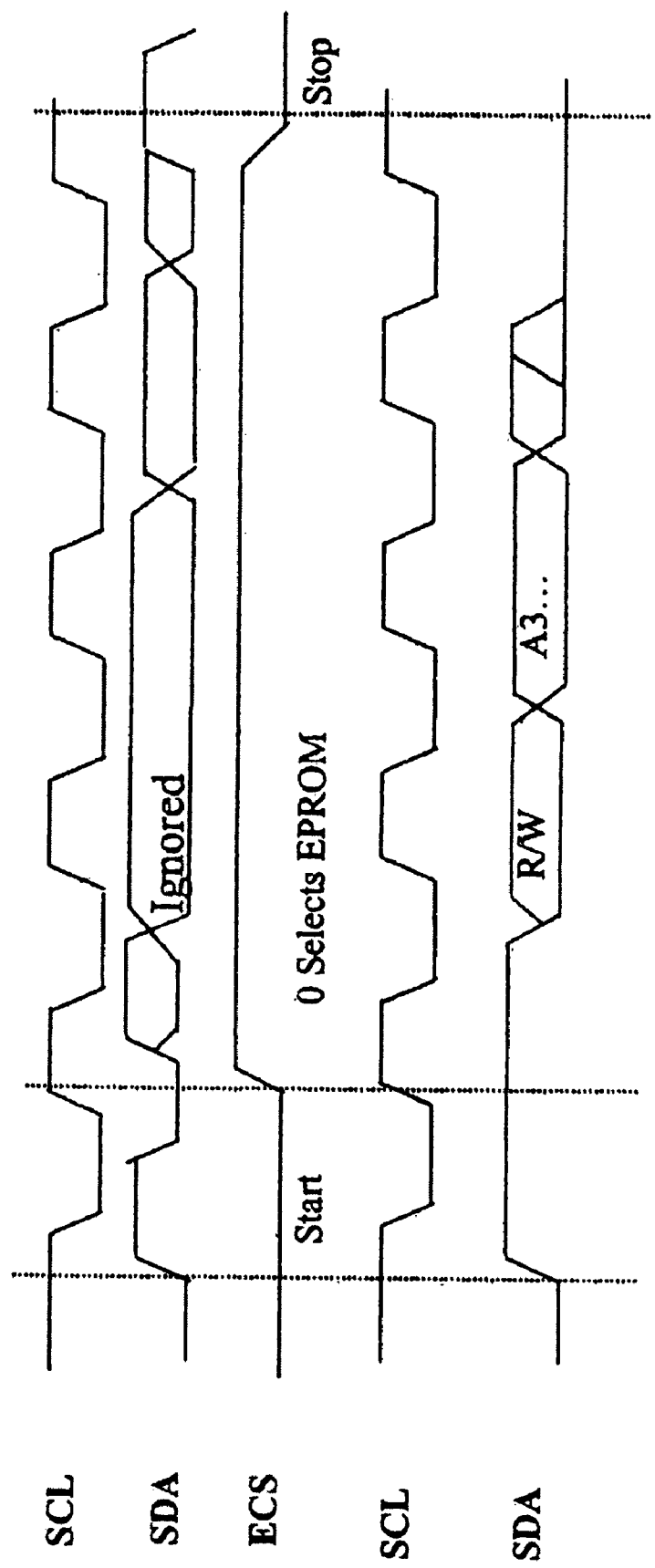
FIG. 2-18e2

ECS   Start  I Selects LFAFE   Stop

Summary of Operation

The LFAFE generates two current drives. These drives are used to power drive elements. The drive element state is sensed by a set of sensors. The sensor output, current is sensed by an amplifier which pre-conditions the outputs for A/D conversion. The LFAFE does a A/D conversion and stores the output into a register for transmission to the outside world on command. The current drives are determined by a DAC and the reference current is determined by a voltage reference and a reference resistor. Registers are provided for storage and control of the operation. An oscillator sets the timing of the operation. A few external components are needed such as the oscillator capacitance, the current setting resistor, the sample and hold capacitance and the gain setting resistor. Other components for system level operation are the FEPROM which stores calibration coefficients and the host micro-controller which is a 8 bit uC.

Electrical Specifications:

ABSOLUTE MAXIMUM RATINGS

| Parameter | Symbol | Rating | Units |
|---|---|---|---|
| Voltage at any pin | VMAX | 7.0 | Volt |
| Current at any pin | IMAX | 100 | mA |
| Operating Temperature | TMAX | 100 | Deg C |
| Storage Temperature | TST | 160 | Deg C |
| Soldering Temperature for 10 sec | TSOL | 300 | Deg C |

Note: Sustained operation at or above these ratings may cause permanent damage to the device.

STATIC ELECTRICAL PARAMETERS

| Parameter | Conditions | Min | Typ | Max | Units |
|---|---|---|---|---|---|
| VDD Supply | Operating | 4.5 | 5.0 | 5.5 | Volt |
| IDD Supply current | Except for current drive | | | 2.5 | mA |
| Temperature | Operating | 0 | | 70 | Deg C |

FIG. 2-18f

| Voltage Reference | Max at REG output, depends on DAC output. | | | 3.6 | Volt |
|---|---|---|---|---|---|
| DIGITAL SPECIFICATIONS | | | | | |
| Parameter | Conditions | Min | Typ | Max | Units |
| CMOS High Level Output VOH | Iout=10uA | VCC-0.5 | | | Volt |
| CMOS Low level Output VOL | Iout=100uA | | | 0.5 | Volt |
| CMOS High Level Input VIH | | VCC-0.5 | | | Volt |
| CMOS Low Level Input VIL | | | | 0.5 | Volt |
| Clock rate | | | | 1 | MHz |
| Data Length | | | | 20 | Bits |
| CS Hold time | | | | 500 | ns |
| CS Setup time | | | | 500 | ns |
| Register File Rows | | | | 8 | |
| Register File Columns | | | | 8 | |
| Register read/write setup time | | | | 500 | Ns |
| Register read/write hold time | | | | 500 | Ns |
| Delay Time | | 50 | | 3200 | ms |
| OSCILLATOR CHARACTERISTICS | | | | | |
| Parameter | Conditions | Min | Typ | Max | Units |
| OSC frequency range | | 100 | | 500 | KHz |
| OSC frequency tolerance | Trimmed OSC | | | 2.5 | % |
| OSC Capacitance. | | | 560 | | pF |
| Note: The oscillator requires an external capacitance which determines the frequency. The oscillator provides timing for the A/D Conversion and the delay. | | | | | |

FIG. 2-18g

| TRACK AND HOLD CHARACTERISTICS | | | | | |
|---|---|---|---|---|---|
| Parameter | Conditions | Min | Typ | Max | Units |
| Hold Capacitance | | 50 | 100 | 220 | nF |
| Settling Time | | 200 | 300 | 600 | usec |
| A/D CHARACTERISTICS | | | | | |
| Parameter | Conditions | Min | Typ | Max | Units |
| A/D resolution | | | 10 | | Bits |
| A/D conversion time | OSC Frequency dependent | | | | |
| A/D linearity | | | 1 | | LSB |
| A/D FSR | | | | 3.6 | Volt |
| CURRENT DRIVE CHARACTERISTICS | | | | | |
| Parameter | Conditions | Min | Typ | Max | Units |
| Current Rise Time | | 500 | | | ns |
| Current fall Time | | 500 | | | ns |
| Current | Operating | 2.0 | | 30.0 | mA |
| Current Turn ON time | To 90% of max | | | 25.0 | us |
| Current Turn OFF time | To 10% of max | | | 25.0 | us |
| SENSED CURRENT OR FEEDBACK CHARACTERISTICS | | | | | |
| Parameter | Conditions | Min | Typ | Max | Units |
| Input sense current | | | 25.0 | 500.0 | uA |
| Availability and options for applications: The LFAFE device is available either as packaged devices or die for COB mounting. | | | | | |

FIG. 2-18h

For a full custom application the LFAFE device can be integrated as a custom device with a 'HC05 micro-controller to generate a new device. This is a full custom development option at the customer's request only.

Typical Applications: 3-D graphics input device, 3-D game controllers, serial input devices, appliances, sensor interfaces, smart lighting, toys and games.

FIG. 2-18i

RadioData Corporation

7-ELEMENT YAGI ANTENNA SPECSIFICATIONS

1.0 Introduction & Scope

This specification applies to a High Gain Yagi Antenna that provides the ability to extend the range of the RadioData Reader to cover large areas.

2.0 Product Overview

The 7-element Yagi antenna provides high gain for large area coverage and needs to be used in orthogonally mounted pairs in order to provide the necessary diversity to minimize the read range variability that otherwise will occur with random tag orientation. Read Ranges can be in excess of 800 feet with Spider Tags in a line of sight, open field environment.

The low profile and "EverSealed" feed reduces the vulnerability of the antenna to the impact of a harsh environments and the computer-optimized design combines maximum performance with survivability, resulting in outstanding durability.

3.0 Specifications

| | |
|---|---|
| Frequency Range: | 290 to 310 MHz |
| Gain | 9 dBd minimum |
| Front to Back Ratio | 18 dB minimum |
| VSWR *(50 ohms)* | 1.2:1 typical |
| Bandwidth (1.5:1) | 20 MHz minimum |
| Beamwidth (3dB) | E Plane 49 DEGREE, H Plane 600 |
| Stacking Distance | B Plane 39.5", H Plane *32.5"* |
| Termination: | 1 foot, RG58 coax with N-type male connector |
| Material: | Aluminum |
| Boom Length: | 4.2 feet |
| Mast (mount) Diam.: | 1.25 to 2.00" |
| Wind Surface Area: | 0.4 sq. feet |
| Wind Survival: | 125 mph |
| Weight: | 2.25 lbs |

4.0 Available Accessories

The antenna comes with all necessary mounting hardware. A kit includes two antennae with two 15' RG58 coax cables having SMA and N-type connectors,

FIG. 2-21

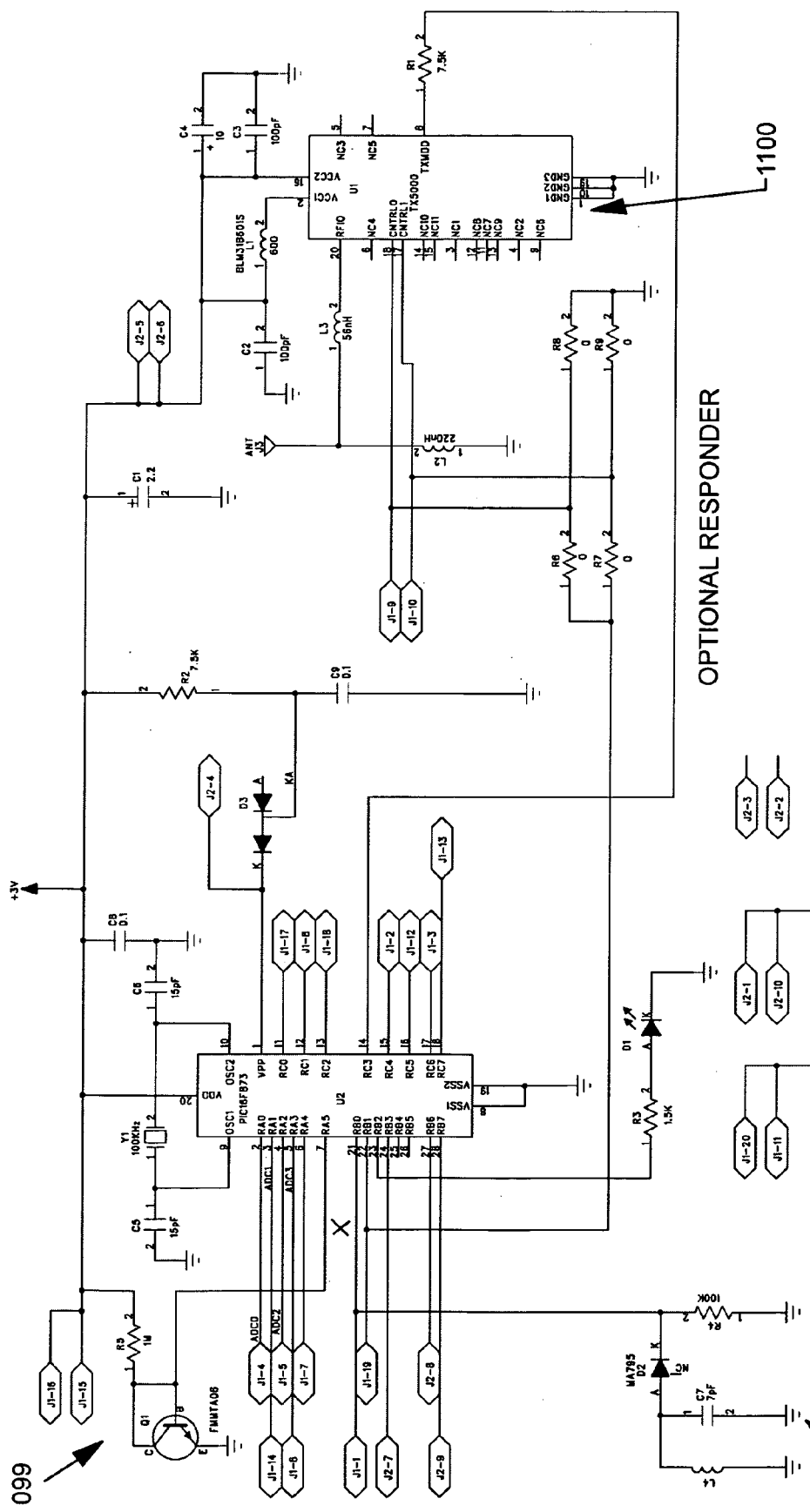
FIG. 2-25 OPTIONAL RESPONDER

| RADIODATA CORPORATION | | LITMIS SENSOR STATUS REPORT | | | MODEL DTO 10021 | | |
|---|---|---|---|---|---|---|---|
| CHANGE FROM PRIOR REPORT | | TRANSPONDER NOT REPORTING (LAST STATUS) | | | SENSING OF DOOR STATUS | | |
| TRANSPONDER CODE GROUP INDIVIDUAL | | SENSOR A | SENSOR B | SENSOR C | SENSOR D | SENSOR E | |
| 01 | ADFJ-1 | 132658 | OPEN | CLOSED | CLOSED | OPEN | OPEN |
| 02 | ADFJ-1 | 132659 | OPEN | OPEN | OPEN | OPEN | OPEN |
| 03 | ADFJ-1 | 132660 | CLOSED | CLOSED | OPEN | OPEN | OPEN |
| 04 | ADFJ-1 | 132661 | CLOSED | OPEN | CLOSED | OPEN | OPEN |
| 05 | ADFJ-1 | 132662 | OPEN | OPEN | CLOSED | CLOSED | OPEN |
| 06 | ADFJ-1 | 132663 | OPEN | OPEN | OPEN | OPEN | CLOSED |
| 07 | ADFJ-1 | 132664 | OPEN | CLOSED | OPEN | OPEN | OPEN |
| 08 | ADFJ-1 | 132665 | OPEN | CLOSED | CLOSED | OPEN | OPEN |
| 09 | ADFJ-1 | 132666 | CLOSED | CLOSED | OPEN | CLOSED | OPEN |
| 10 | ADFJ-1 | 132667 | OPEN | OPEN | OPEN | CLOSED | CLOSED |
| 11 | ADFJ-2 | 132745 | OPEN | OPEN | OPEN | CLOSED | CLOSED |
| 12 | ADFJ-2 | 132746 | OPEN | CLOSED | CLOSED | OPEN | OPEN |
| 13 | ADFJ-2 | 132747 | CLOSED | CLOSED | CLOSED | CLOSED | OPEN |
| 14 | ADFJ-2 | 132748 | CLOSED | OPEN | OPEN | OPEN | OPEN |
| 15 | ADFJ-2 | 132749 | CLOSED | OPEN | OPEN | OPEN | OPEN |
| 16 | ADFJ-2 | 132750 | CLOSED | OPEN | OPEN | OPEN | CLOSED |
| 17 | ADFJ-2 | 132751 | CLOSED | OPEN | CLOSED | CLOSED | OPEN |
| 18 | ADFJ-2 | 132752 | CLOSED | CLOSED | CLOSED | CLOSED | OPEN |
| 19 | ADFJ-2 | 132753 | OPEN | CLOSED | OPEN | CLOSED | OPEN |
| 20 | ADFJ-2 | 132754 | CLOSED | CLOSED | OPEN | OPEN | CLOSED |
| REPORT AC-10235 | | DATE JUNE 14, 2003 | | TIME 12:45 AM | | STATUS BETA TEST 2A | |

FIG. 2-26

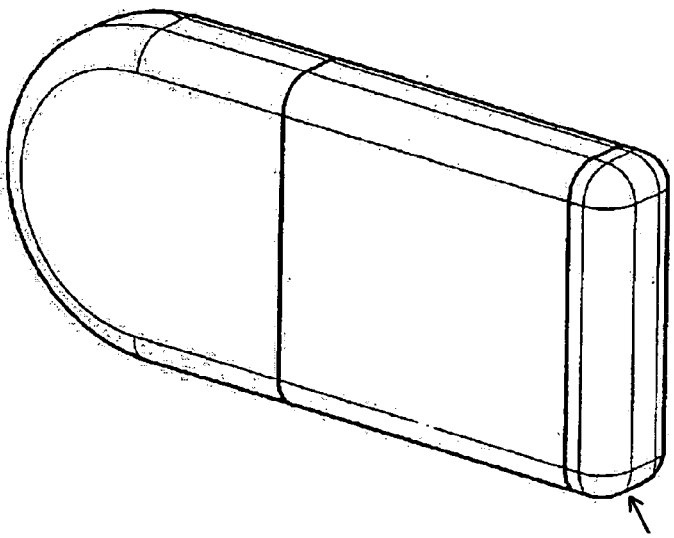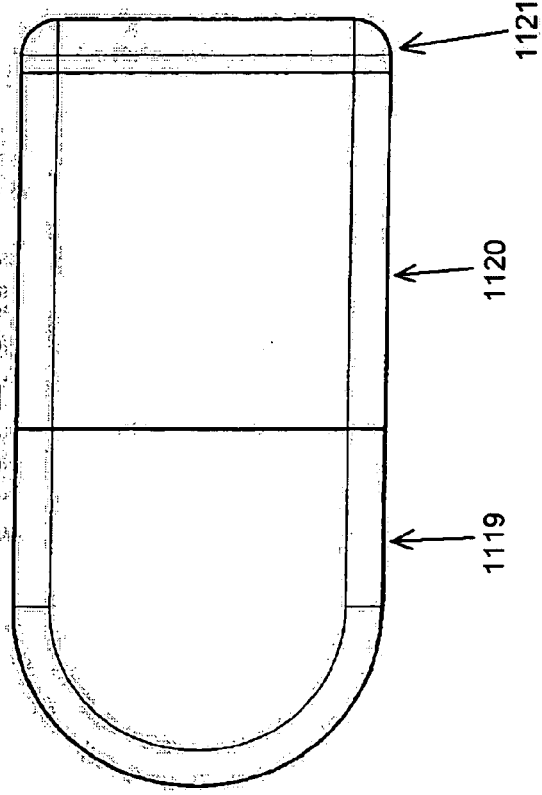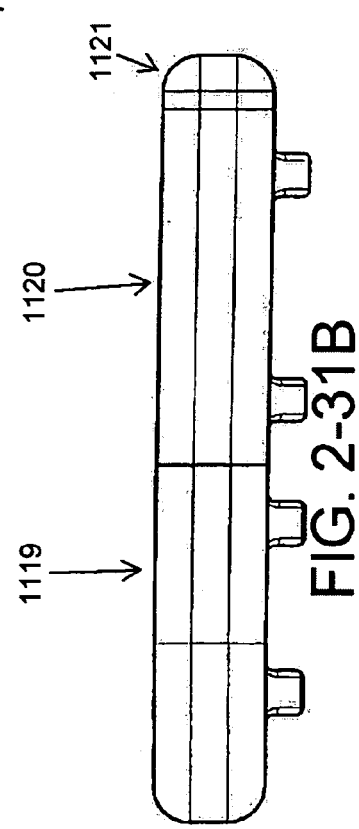

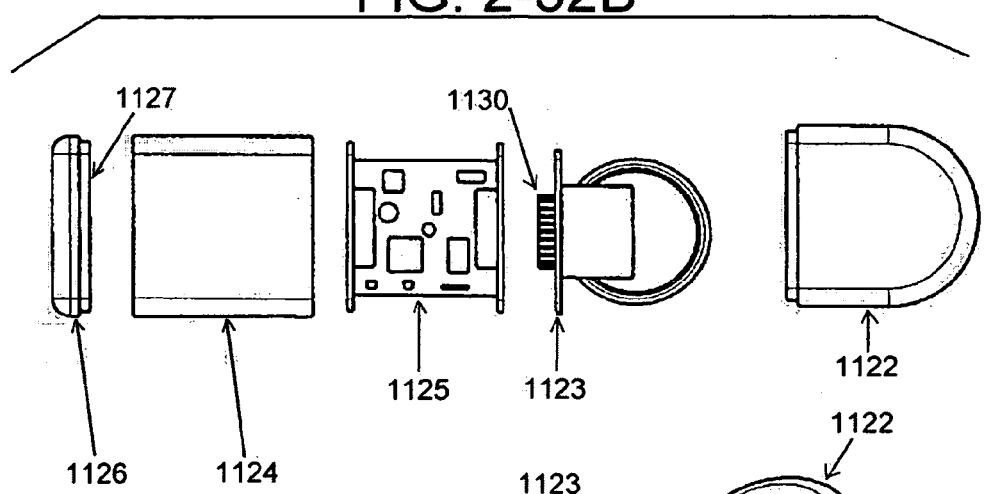
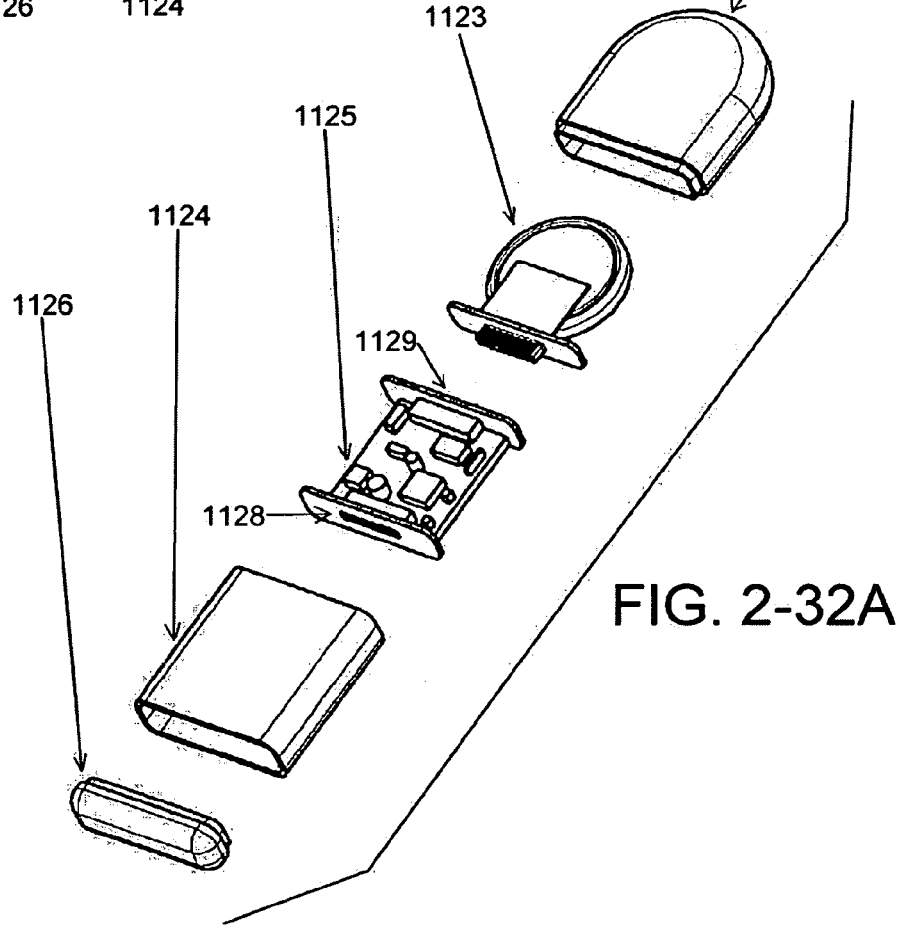
FIG. 2-32B
FIG. 2-32A

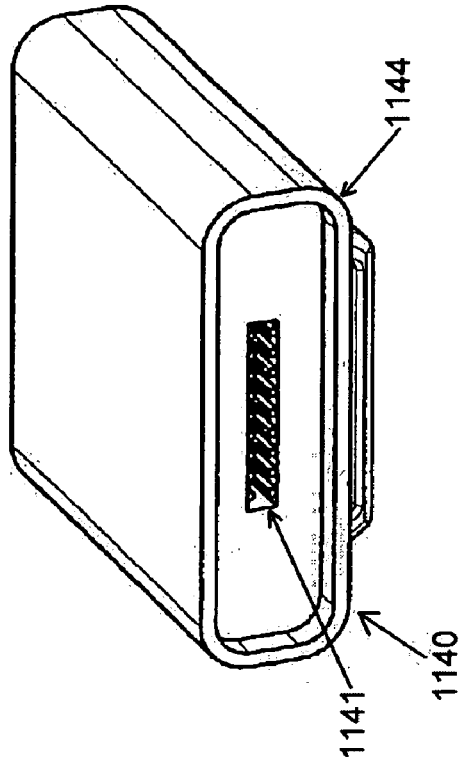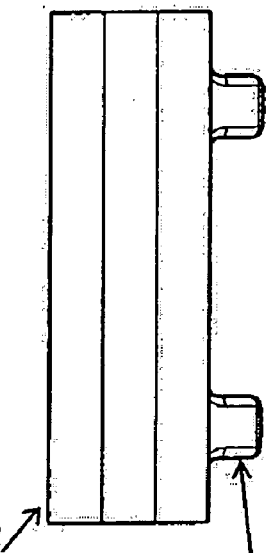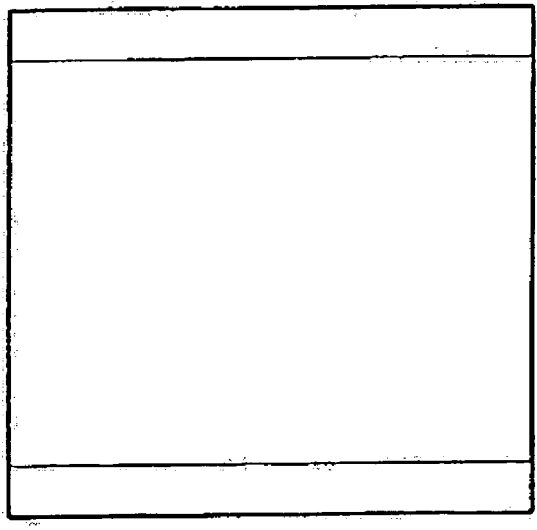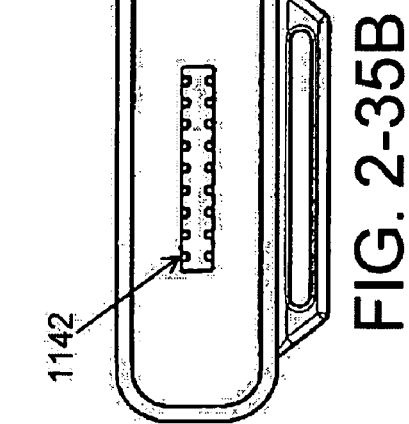

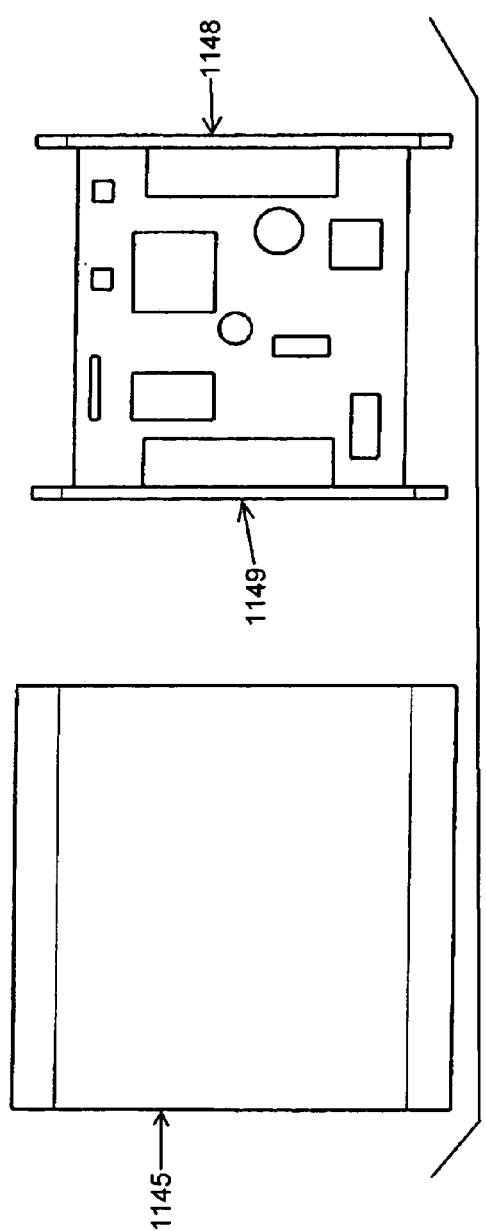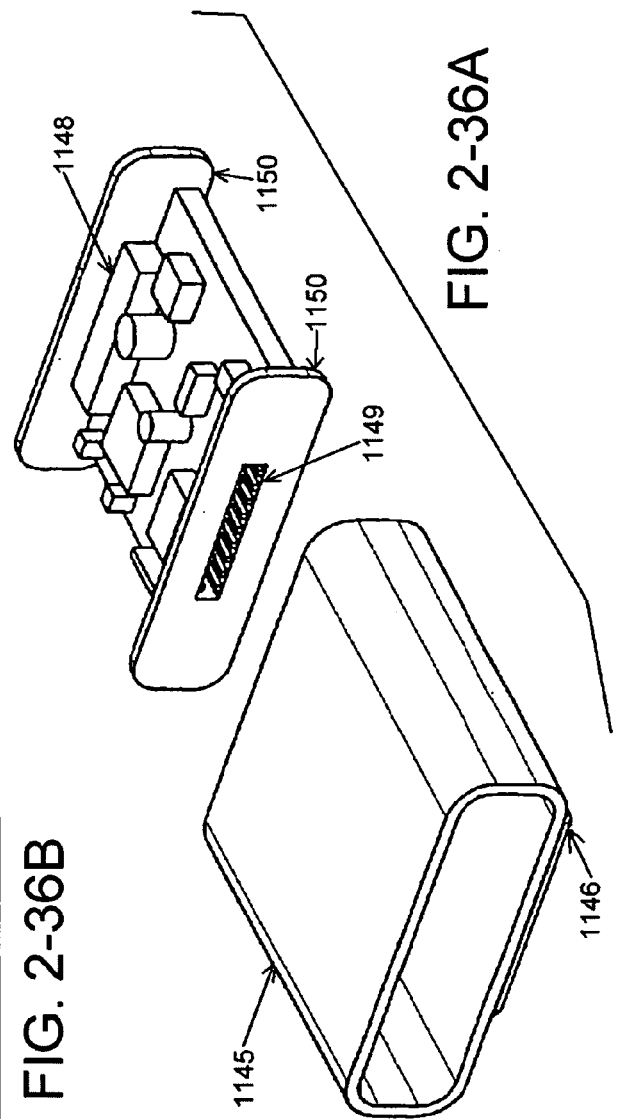
FIG. 2-36A
FIG. 2-36B

FIG. 2-38B
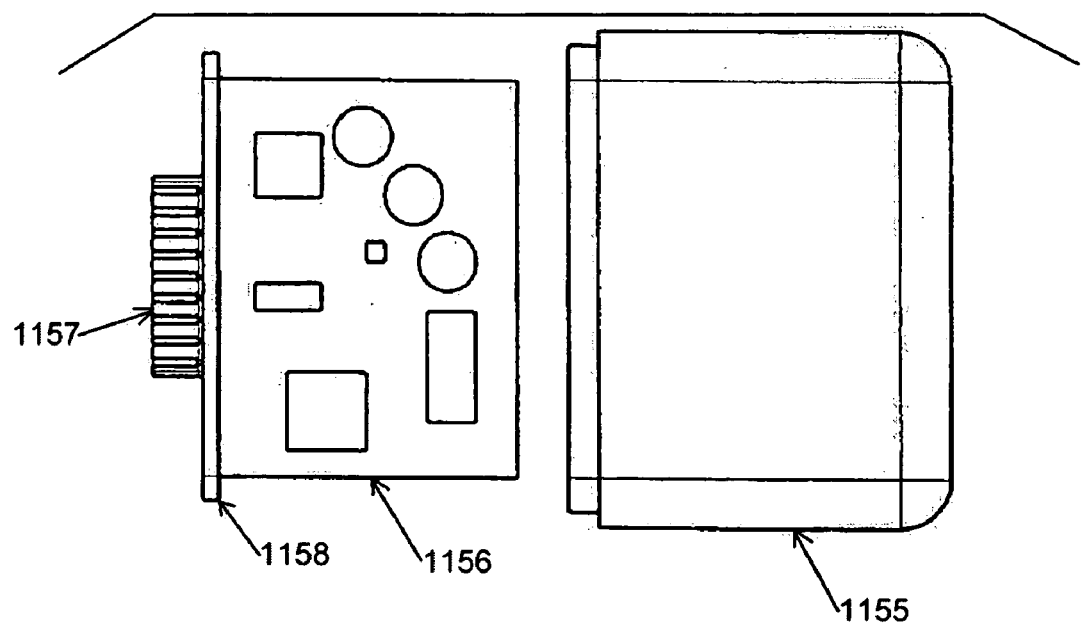
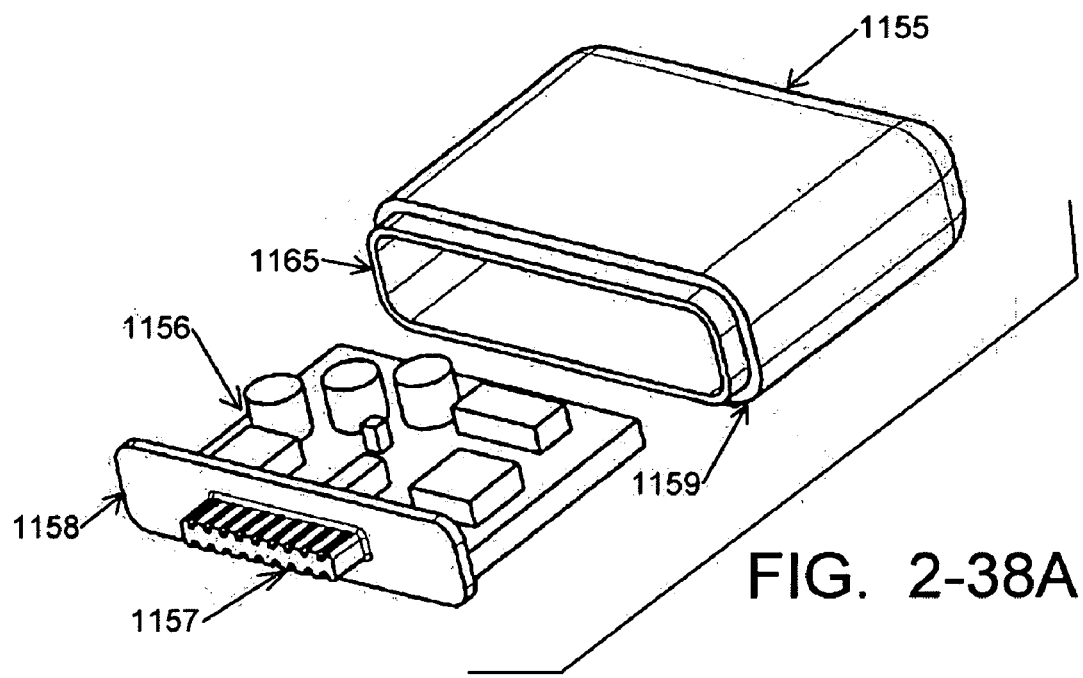
FIG. 2-38A

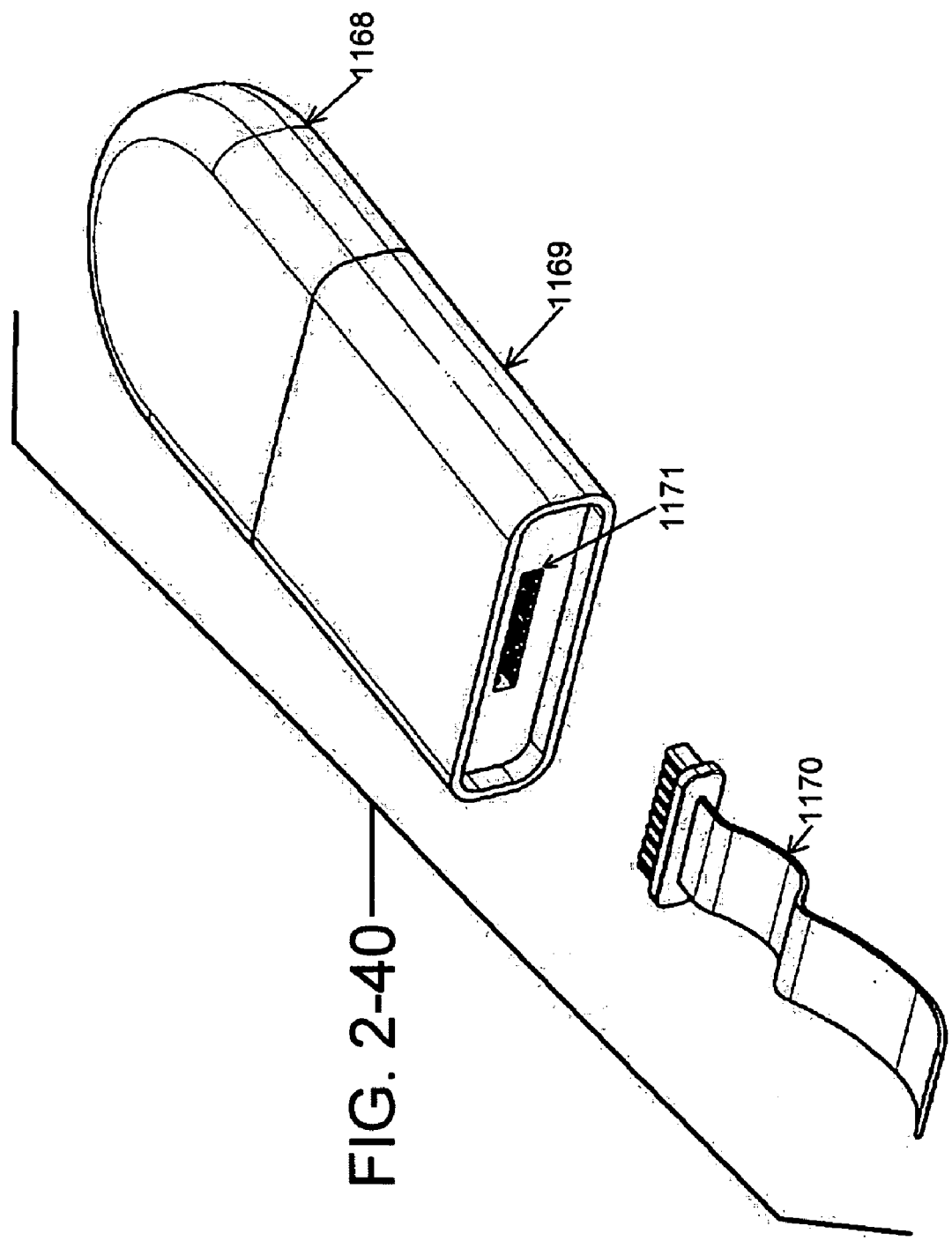

RF SECTION RF RECEIVER SECTION

THE RF RECEIVER CONSISTS OF A CONNECTOR FOR THE ANTENNA, AN ANTENNA-RECEIVER IMPEDANCE MATCHING CIRCUIT AND A 00K/ASK RECEIVER. THERE ARE TWO IDENTICAL RF SECTIONS PER CIRCUIT.

ANALOG SECTION

GAIN SECTION

THE GAIN SECTION CONSISTS OF A DIFFERENTIAL AMP AND A SUMMING AMP. THE DIFFERENTIAL AMP PROVIDES GAIN AND OFFSET ADJUSTMENT. THE SUMMING AMP ADDS THE TWO (L PER RECEIVER) SIGNALS TOGETHER.

FILTER SECTION

THE FILTER SECTION CONSISTS OF AN ACTIVE FILTER. THE ACTIVE FILTER REDUCES SIGNAL NOISE.

16 LEVEL DETECTOR

THE LEVEL DETECTOR CONSISTS OF A 16 LEVEL VOLTAGE DIVIDER, 16 COMPARATORS AND A UPPER AND LOWER LEVEL VOLTAGE ADJUSTMENT.
THE VOLTAGE DIVIDER PROVIDES 16 EQUALLY SPACED VOLTAGE REFERENCE LEVELS FOR THE 16 COMPARATORS. EACH COMPARATORS DETECTS IF THE RECEIVED SIGNAL IS HIGH OR LOWER THAN ITS VOLTAGE REFERENCE. THE UPPER AND LOWER VOLTAGE REFERENCES ARE ADJUSTED USING A POTENTIOMETER.

CPLD SECTION

16 LEVEL TO 4 BIT CONVERTERS

THE 16 LEVEL TO 4 BIT CONVERTER DEBOUNCES THE INCOMING BITS AND CONVERTS THE DATA TO A 4 BIT BINARY CODE.

DIGITAL SQUELCH

THE DIGITAL SQUELCH IS A FUNCTION USED TO SET A MINIMUM SIGNAL VALUE. ANY SIGNALS BELOW THE DIGITAL SQUELCH LEVEL ARE IGNORED.

DIGITAL FILTERING

FIG. 2-44a

HARDWARE_BLOCK_DESC

THE DIGITAL FILTER PERFORMS A WEIGHTED AVERAGE ON THE SIGNAL. EACH SAMPLE IS WEIGHTED BASED ON THE AGE OF THE SAMPLE. THE OLDER THE SAMPLE THE LESS WEIGHT A SAMPLE HAS IN THE AVERAGE.
THIS SMOOTHES THE SIGNAL AND REDUCES NOISE.

SLOPE DETECTOR
THE SLOPE DETECTOR LOOKS FOR SLOPE CHANGES IN THE SIGNAL. THERE ARE CURRENTLY 3 TYPES OF SLOPES DETECTED (UP, DOWN & LEVEL)
ANY CHANGE IN SLOPE TYPE IS DETECTED AND A PULSE IS SENT.

18 BIT COUNTER
AN 18 BIT COUNTER IS USED TO KEEP A ROLLING COUNT OF THE 4MHz CLOCK IN A BINARY FORMAT.

TIME STAMP LATCH
A TIME STAMP IS LATCHED WHENEVER A PULSE IS LATCHED FROM THE 18 BIT COUNTER WHENEVER A PULSE IS RECEIVED FROM THE SLOPE DETECTOR. ALL ROLL-OVER EVENTS ARE ALSO LATCH TO AID IN TRACKING
EVENT TIMING.

4K X 18 BIT FIFO
ALL DATA CAPTURED IN THE TIME STAMP LATCH IS ALSO LOADED IN THE FIFO (FIRST IN FIRST OUT) MEMORY DEVICE. THE FIFO IS USED TO STORE TIME STAMPS UNTIL THE MICRO-PROCESSOR IS READY TO READ IT.

EVENT RATE DETECTOR
WHEN TIME STAMPS OCCUR AT A RATE THAT IS FASTER THAN THE KNOWN SIGNAL RATE THE EVENT RATE DETECTOR MAKES AN AUTOMATIC ADJUSTMENT TO THE DIGITAL SQUELCH CIRCUIT. THIS EFFECTIVELY ELIMINATES FAST NOISE SIGNALS.

MICRO PROCESSOR
THE MICROPROCESSOR READS DATA FROM THE FIFO AND ANALYZES THE TIME STAMPS TO DECODE DATA FROM THE TRANSMITTER. THE MICROPROCESSOR ALSO CONTROLS THE POTENTIOMETERS THAT ADJUST THE UPPER AND LOWER THRESHOLD LEVELS. THE MICRO PROCESSOR SETS THE LEVEL IN THE DIGITAL SQUELCH CIRCUIT.

FIG. 2-44b

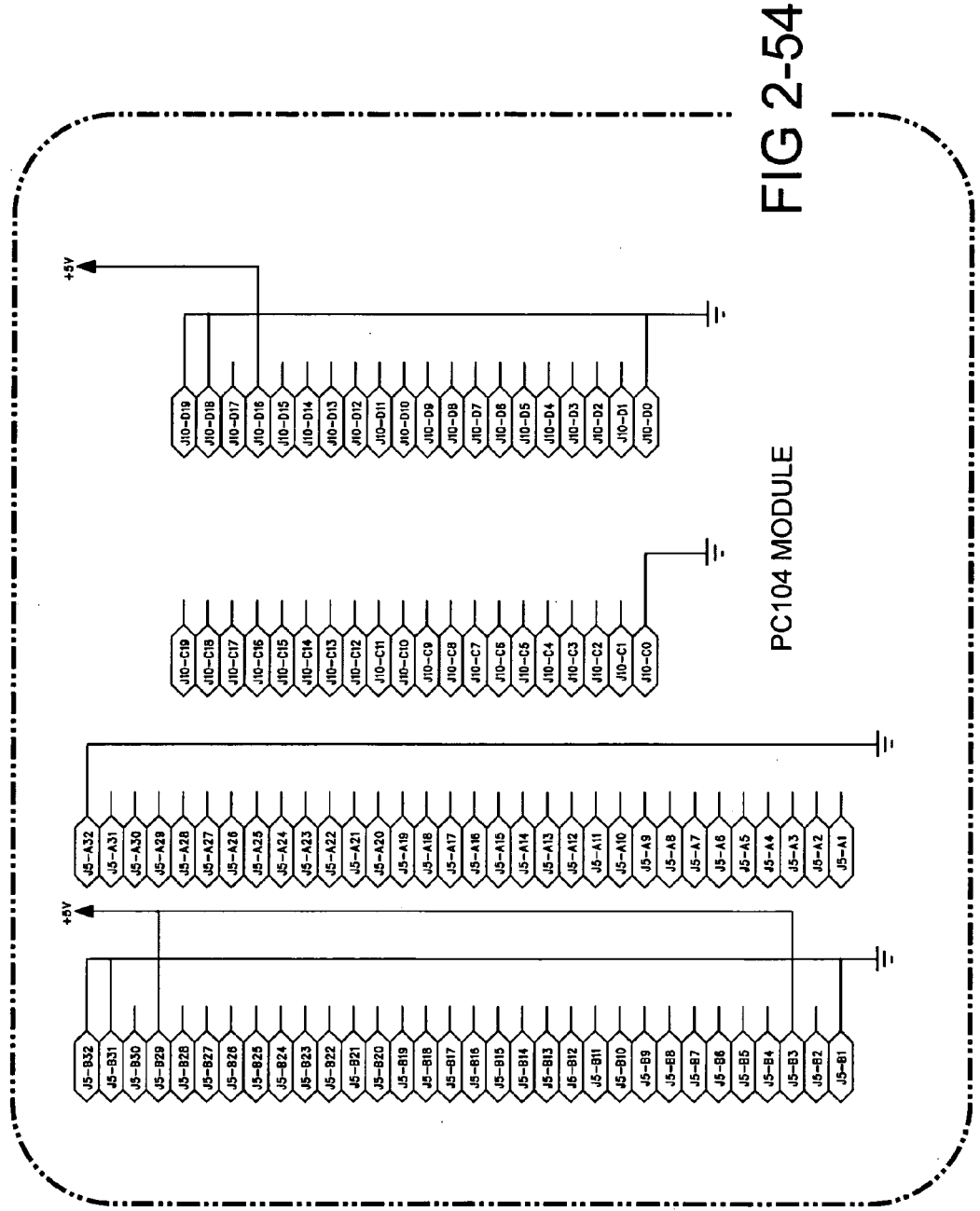

Splatch Antenna

WIRELESS PRODUCTS  
TEL 70 22 69 70  
FAX 70 22 69 80  
WWW. WIRELESS-PRODUCTS.DK

SPLATCH PLANAR ANTENNA  WP-L-ANT-XXX-SP

SP SERIES

THE SPLATCH USES A GROUNDED LINE TECHNIQUE TO ACHIEVE OUTSTANDING PERFORMANCE FROM A TINY SURFACE-MOUNT ELEMENT. THIS UNIQUE ANTENNA IS DESIGNED FOR HAND OR REFLOW MOUNTING DIRECTLY TO A PRODUCT'S CIRCUIT BOARD. ITS LOW COST MAKES IT IDEAL FOR VOLUME APPLICATION. UNLIKE MANY COMPACT ANTENNAS THE SPLATCH EXHIBITS GOOD PROXIMITY PERFORMANCE MAKING IT AN APPROPRIATE CHOICE FOR HAND-HELD APPLICATIONS SUCH AS REMOTE CONTROLS, PAGERS, AND ALERT DEVICES. TYPICAL PERFORMANCE IS BELOW THAT OF MANY EXTERNAL ANTENNAS BUT THE SPLATCH IS AN EXCELLENT CHOICE WHEN COSMETIC OR MECHANICAL ISSUES DICTATE THE USE OF AN INTERNAL ANTENNA.

TECHNICAL DRAWING

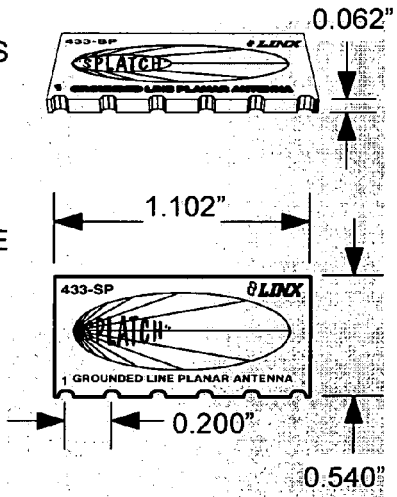

FEATURES

- IDEAL FOR CONCEALED/INTERNAL MOUNTING
- DIRECT PCB ATTACHMENT
- ULTRA-COMPACT PACKAGE
- VERY LOW COST
- SUITABLE FOR HAND OR REFLOW ASSEMBLY
- RESISTANT TO PROXIMITY EFFECT
- PERFECT FOR COMPACT PORTABLE DEVICES

ORDERING INFORMATION

| PART NO. | DESCRIPTION |
|---|---|
| WP-L-ANT-315-SP | 315 MHZ SPLATCH PLANAR ANTENNA |
| WP-L-ANT-418-SP | 418 MHZ SPLATCH PLANAR ANTENNA |
| WP-L-ANT-433-SP | 433 MHZ SPLATCH PLANAR ANTENNA |
| WP-L-ANT-868-SP | 868 MHZ SPLATCH PLANAR ANTENNA |
| WP-L-ANT-916-SP | 916 MHZ SPLATCH PLANAR ANTENNA |

Page 1 of 1  BlueTooth • GSM Engine • GPS Engine • Radio Modules • Data Radio • RF RemoteVideo TX/RX • Antenners • Security • Point to Point • Point to Multi Point Radio • Dect engineSynthesised multi-channel • Xplore PC • Embedded-WEB • Paging • RTU • IQ • SMS

FIG. 2-74 either a fixed or mobile mode. Applications include nonproliferation monitoring, spent fuel safeguards, and long-term monitoring of stored radioactive wastes.

Features
- Gamma-ray attribute measurement of each item in storage
- Discriminator lower level adjustment to correspond to an energy peak of uranium-235 (98 keV) or plutonium-239 (130 keV)
- Automatic indication of system problems
- Pulse height discrimination of unwanted noise
- Analog signal output
- Single +9 V supply requirement for power and detector bias (with optional high-voltage bias output)
- Stable low-cost preamplifier-amplifier electronics

System Operation
RADTELL™ sensors monitor the gamma-ray emission from special nuclear materials (SNMs). The sensors are affected by source (SNM) distance, collimation of the source, and the SNM container thickness and material. The

FIG. 2-79b1 count-rate is maximized by placing the sensors as close as possible to the source.

Main elements within the sensor unit are a CdZnTe gamma-ray detector, a low-noise preamplifier, and a pulse-shaping amplifier. Signal levels can be selected by a pulse height discriminator, lower-level adjustment for precise gamma-ray energy band monitoring of uranium-235. The Surface Mount Technology (SMT) circuit board is designed for use with either a silicon-PIN photodiode or a CdZnTe gamma-ray radiation detector.

Pulses resulting from the photon interactions in the RADTELL™ detector are produced at an approximate rate of 75,000 counts per second per R per hour. Filters in the pulse-shaping amplifier provide an impulse response having a pulse-width of 20 to 50 microseconds. After leaving the pulse-shaping amplifier, the output signals go to a pulse height discriminator where the discriminator lower level is adjusted to correspond to an energy peak of uranium-235 (98 keV) or plutonium-239 (130 keV). The gamma-ray energy band from either the calibrated uranium or plutonium peak to the highest energy from the Compton

FIG. 2-79b2 interaction pulses provides a sensitivity band with a precise region for monitoring either uranium enrichment or plutonium. The SMT circuit board is 1.5 cm wide by 7.2 cm long.

Hardware/Software Requirements
- ORSENS Sensor Concentrator
- ORSENS Common Sensor Interface Unit
- An Intel Pentium II based computer (or higher)
- At least 32 MB of RAM
- A minimum of 15 MB of free hard disk space For more information, contact
Mr. Chris A. Pickett
Y-12 National Security Complex
Voice: (865) 574-0891    Fax: (865) 576-2782
email: pickettca@y12.doe.gov

FIG. 2-79c

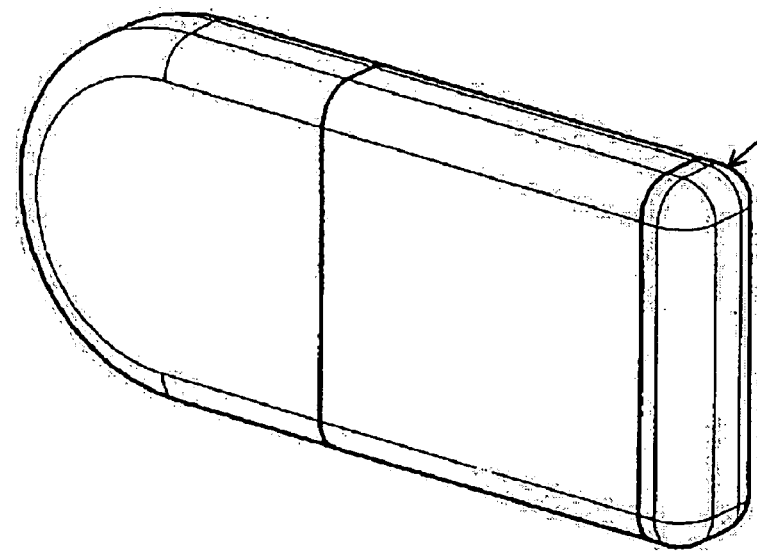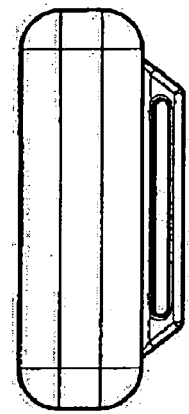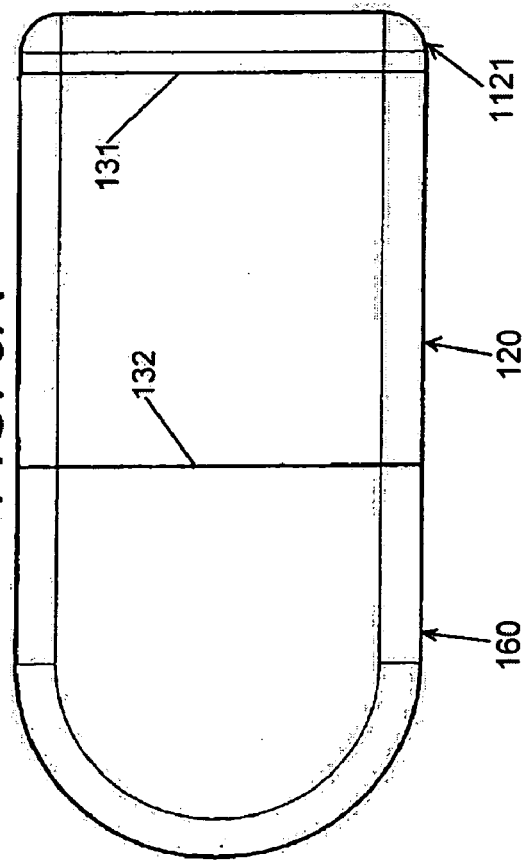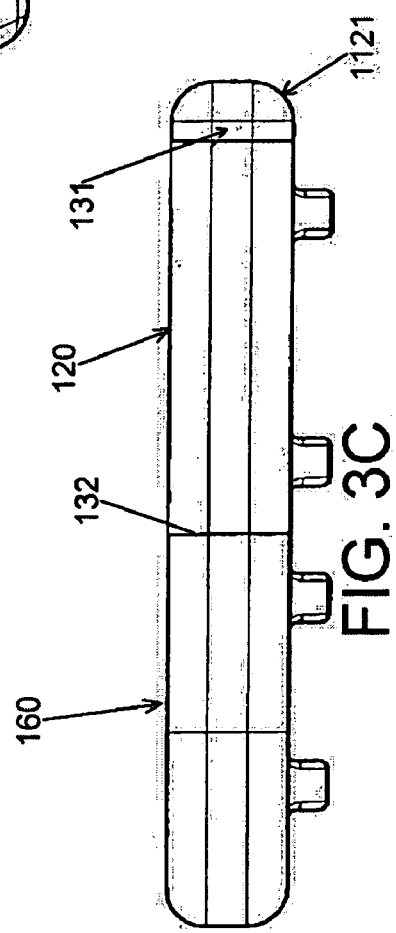

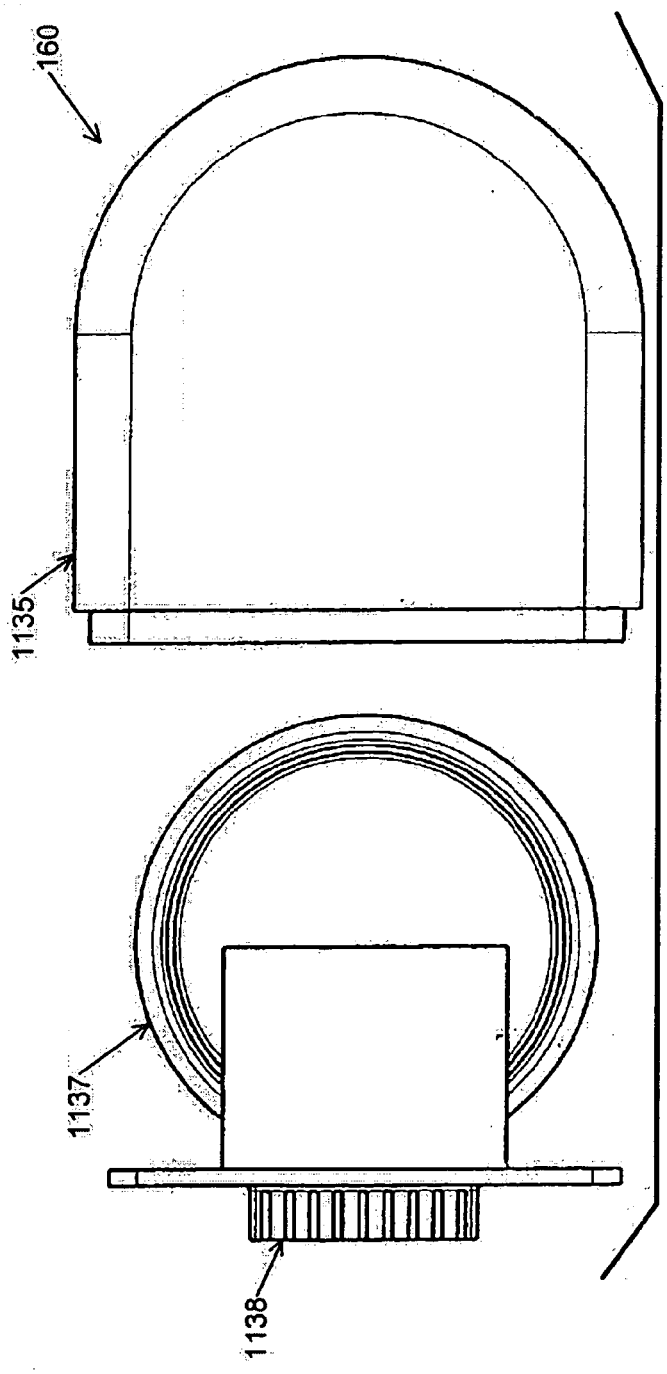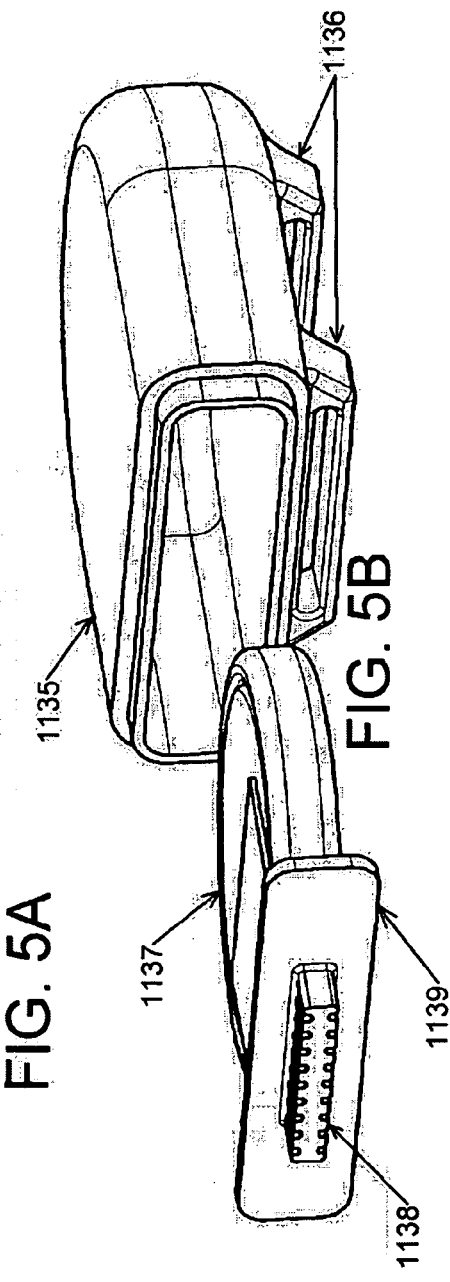
FIG. 5A
FIG. 5B

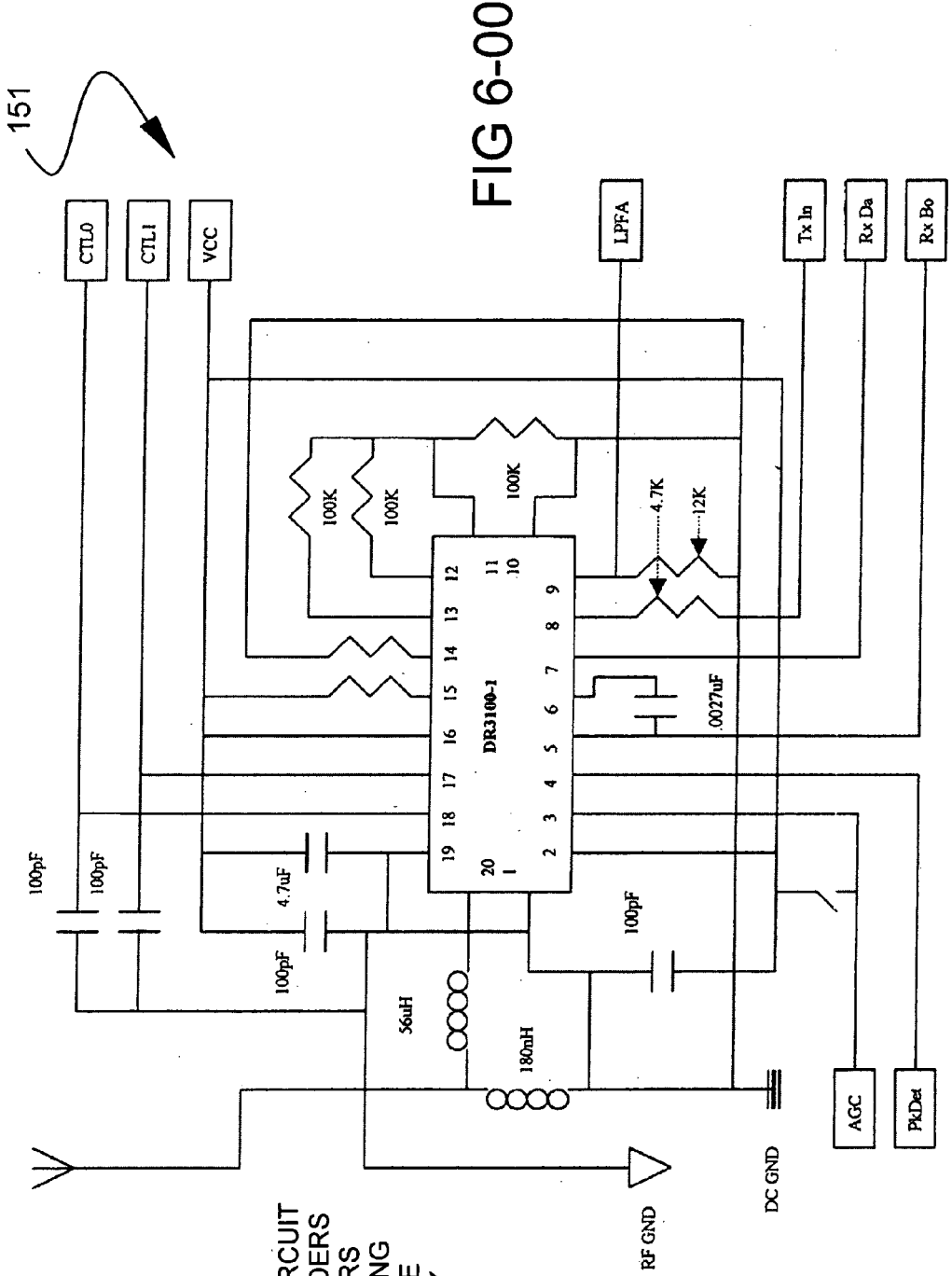

TRANSPONDER FREQUENCY, POLLING, AND
FIRMWARE OPTIONS

| Part Number | Frequency | Modulation | Polling | Firmware |
|---|---|---|---|---|
| 03-000139-01-01 | 433.92MHz | Optional | None | Basic Demo |
| 03-000139-01-02 | 433.92MHz | Optional | None | SSI WAMS |
| 03-000139-01-03 | 433.92MHz | Optional | None | S&G Code |
| 03-000139-01-04 | 433.92MHz | Optional | None | Medical 1 |
| 03-000139-02-05 | 433.92MHz | Optional | None | Home Sec. 1 |
| 03-000139-02-01 | 433.92MHz | OOK | None | Basic Demo |
| 03-000139-02-02 | 433.92MHz | OOK | None | SSI WAMS |
| 03-000139-02-03 | 433.92MHz | OOK | None | S&G Code |
| 03-000139-02-04 | 433.92MHz | OOK | None | Medical 1 |
| 03-000139-02-05 | 433.92MHz | OOK | None | Home Sec. 1 |
| 03-000139-03-01 | 433.92MHz | ASK | None | Basic Demo |
| 03-000139-03-02 | 433.92MHz | ASK | None | SSI WAMS |
| 03-000139-03-03 | 433.92MHz | ASK | None | S&G Code |
| 03-000139-03-04 | 433.92MHz | ASK | None | Medical 1 |
| 03-000139-03-05 | 433.92MHz | ASK | None | Home Sec. 1 |
| 03-000139-11-01 | 303.825MHz | Optional | None | Basic Demo |
| 03-000139-11-02 | 303.825MHz | Optional | None | SSI WAMS |
| 03-000139-11-03 | 303.825MHz | Optional | None | S&G Code |
| 03-000139-11-04 | 303.825MHz | Optional | None | Medical 1 |
| 03-000139-11-05 | 303.825MHz | Optional | None | Home Sec. 1 |
| 03-000139-12-01 | 303.825MHz | OOK | None | Basic Demo |
| 03-000139-12-02 | 303.825MHz | OOK | None | SSI WAMS |
| 03-000139-12-03 | 303.825MHz | OOK | None | S&G Code |
| 03-000139-12-04 | 303.825MHz | OOK | None | Medical 1 |
| 03-000139-12-05 | 303.825MHz | OOK | None | Home Sec. 1 |
| 03-000139-13-01 | 303.825MHz | ASK | None | Basic Demo |
| 03-000139-13-02 | 303.825MHz | ASK | None | SSI WAMS |
| 03-000139-13-03 | 303.825MHz | ASK | None | S&G Code |
| 03-000139-13-04 | 303.825MHz | ASK | None | Medical 1 |
| 03-000139-13-05 | 303.825MHz | ASK | None | Home Sec. 1 |

FIG. 7A

TRANSPONDER FREQUENCY, POLLING, AND
FIRMWARE OPTIONS

| Part Number | Frequency | Modulation | Polling | Firmware |
|---|---|---|---|---|
| 03-000139-21-01 | 418MHz | Optional | None | Basic Demo |
| 03-000139-21-02 | 418MHz | Optional | None | SSI WAMS |
| 03-000139-21-03 | 418MHz | Optional | None | S&G Code |
| 03-000139-21-04 | 418MHz | Optional | None | Medical 1 |
| 03-000139-22-05 | 418MHz | Optional | None | Home Sec. 1 |
| 03-000139-22-01 | 418MHz | OOK | None | Basic Demo |
| 03-000139-22-02 | 418MHz | OOK | None | SSI WAMS |
| 03-000139-22-03 | 418MHz | OOK | None | S&G Code |
| 03-000139-22-04 | 418MHz | OOK | None | Medical 1 |
| 03-000139-22-05 | 418MHz | OOK | None | Home Sec. 1 |
| 03-000139-23-01 | 418MHz | ASK | None | Basic Demo |
| 03-000139-23-02 | 418MHz | ASK | None | SSI WAMS |
| 03-000139-23-03 | 418MHz | ASK | None | S&G Code |
| 03-000139-23-04 | 418MHz | ASK | None | Medical 1 |
| 03-000139-23-05 | 418MHz | ASK | None | Home Sec. 1 |
| 03-000139-31-01 | 916.5MHz | Optional | None | Basic Demo |
| 03-000139-31-02 | 916.5MHz | Optional | None | SSI WAMS |
| 03-000139-31-03 | 916.5MHz | Optional | None | S&G Code |
| 03-000139-31-04 | 916.5MHz | Optional | None | Medical 1 |
| 03-000139-31-05 | 916.5MHz | Optional | None | Home Sec. 1 |
| 03-000139-32-01 | 916.5MHz | OOK | None | Basic Demo |
| 03-000139-32-02 | 916.5MHz | OOK | None | SSI WAMS |
| 03-000139-32-03 | 916.5MHz | OOK | None | S&G Code |
| 03-000139-32-04 | 916.5MHz | OOK | None | Medical 1 |
| 03-000139-32-05 | 916.5MHz | OOK | None | Home Sec. 1 |
| 03-000139-33-01 | 916.5MHz | ASK | None | Basic Demo |
| 03-000139-33-02 | 916.5MHz | ASK | None | SSI WAMS |
| 03-000139-33-03 | 916.5MHz | ASK | None | S&G Code |
| 03-000139-33-04 | 916.5MHz | ASK | None | Medical 1 |
| 03-000139-33-05 | 916.5MHz | ASK | None | Home Sec. 1 |

FIG. 7B

TRANSPONDER FREQUENCY, POLLING, AND
FIRMWARE OPTIONS

| Part Number | Frequency | Modulation | Polling | Firmware |
|---|---|---|---|---|
| 03-000139-06-01 | 433.92MHz | Optional | 13.56MHz Unc | Basic Demo |
| 03-000139-06-02 | 433.92MHz | Optional | 13.56MHz Unc | SSI WAMS |
| 03-000139-06-03 | 433.92MHz | Optional | 13.56MHz Unc | S&G Code |
| 03-000139-06-04 | 433.92MHz | Optional | 13.56MHz Unc | Medical 1 |
| 03-000139-06-05 | 433.92MHz | Optional | 13.56MHz Unc | Home Sec. 1 |
| 03-000139-07-01 | 433.92MHz | OOK | 13.56MHz Unc | Basic Demo |
| 03-000139-07-02 | 433.92MHz | OOK | 13.56MHz Unc | SSI WAMS |
| 03-000139-07-03 | 433.92MHz | OOK | 13.56MHz Unc | S&G Code |
| 03-000139-07-04 | 433.92MHz | OOK | 13.56MHz Unc | Medical 1 |
| 03-000139-07-05 | 433.92MHz | OOK | 13.56MHz Unc | Home Sec. 1 |
| 03-000139-08-01 | 433.92MHz | ASK | 13.56MHz Unc | Basic Demo |
| 03-000139-08-02 | 433.92MHz | ASK | 13.56MHz Unc | SSI WAMS |
| 03-000139-08-03 | 433.92MHz | ASK | 13.56MHz Unc | S&G Code |
| 03-000139-08-04 | 433.92MHz | ASK | 13.56MHz Unc | Medical 1 |
| 03-000139-08-05 | 433.92MHz | ASK | 13.56MHz Unc | Home Sec. 1 |
| 03-000139-16-01 | 303.825MHz | Optional | 13.56MHz Unc | Basic Demo |
| 03-000139-16-02 | 303.825MHz | Optional | 13.56MHz Unc | SSI WAMS |
| 03-000139-16-03 | 303.825MHz | Optional | 13.56MHz Unc | S&G Code |
| 03-000139-16-04 | 303.825MHz | Optional | 13.56MHz Unc | Medical 1 |
| 03-000139-16-05 | 303.825MHz | Optional | 13.56MHz Unc | Home Sec. 1 |
| 03-000139-17-01 | 303.825MHz | OOK | 13.56MHz Unc | Basic Demo |
| 03-000139-17-02 | 303.825MHz | OOK | 13.56MHz Unc | SSI WAMS |
| 03-000139-17-03 | 303.825MHz | OOK | 13.56MHz Unc | S&G Code |
| 03-000139-17-04 | 303.825MHz | OOK | 13.56MHz Unc | Medical 1 |
| 03-000139-17-05 | 303.825MHz | OOK | 13.56MHz Unc | Home Sec. 1 |
| 03-000139-18-01 | 303.825MHz | ASK | 13.56MHz Unc | Basic Demo |
| 03-000139-18-02 | 303.825MHz | ASK | 13.56MHz Unc | SSI WAMS |
| 03-000139-18-03 | 303.825MHz | ASK | 13.56MHz Unc | S&G Code |
| 03-000139-18-04 | 303.825MHz | ASK | 13.56MHz Unc | Medical 1 |
| 03-000139-18-05 | 303.825MHz | ASK | 13.56MHz Unc | Home Sec. 1 |

FIG. 7C

TRANSPONDER FREQUENCY, POLLING, AND
FIRMWARE OPTIONS

| Part Number | Frequency | Modulation | Polling | Firmware |
|---|---|---|---|---|
| 03-000139-26-01 | 418MHz | Optional | 13.56MHz Unc | Basic Demo |
| 03-000139-26-02 | 418MHz | Optional | 13.56MHz Unc | SSI WAMS |
| 03-000139-26-03 | 418MHz | Optional | 13.56MHz Unc | S&G Code |
| 03-000139-26-04 | 418MHz | Optional | 13.56MHz Unc | Medical 1 |
| 03-000139-26-05 | 418MHz | Optional | 13.56MHz Unc | Home Sec. 1 |
| 03-000139-27-01 | 418MHz | OOK | 13.56MHz Unc | Basic Demo |
| 03-000139-27-02 | 418MHz | OOK | 13.56MHz Unc | SSI WAMS |
| 03-000139-27-03 | 418MHz | OOK | 13.56MHz Unc | S&G Code |
| 03-000139-27-04 | 418MHz | OOK | 13.56MHz Unc | Medical 1 |
| 03-000139-27-05 | 418MHz | OOK | 13.56MHz Unc | Home Sec. 1 |
| 03-000139-28-01 | 418MHz | ASK | 13.56MHz Unc | Basic Demo |
| 03-000139-28-02 | 418MHz | ASK | 13.56MHz Unc | SSI WAMS |
| 03-000139-28-03 | 418MHz | ASK | 13.56MHz Unc | S&G Code |
| 03-000139-28-04 | 418MHz | ASK | 13.56MHz Unc | Medical 1 |
| 03-000139-28-05 | 418MHz | ASK | 13.56MHz Unc | Home Sec. 1 |
| 03-000139-36-01 | 916.5MHz | Optional | 13.56MHz Unc | Basic Demo |
| 03-000139-36-02 | 916.5MHz | Optional | 13.56MHz Unc | SSI WAMS |
| 03-000139-36-03 | 916.5MHz | Optional | 13.56MHz Unc | S&G Code |
| 03-000139-36-04 | 916.5MHz | Optional | 13.56MHz Unc | Medical 1 |
| 03-000139-36-05 | 916.5MHz | Optional | 13.56MHz Unc | Home Sec. 1 |
| 03-000139-37-06 | 916.5MHz | OOK | 13.56MHz Unc | Basic Demo |
| 03-000139-37-07 | 916.5MHz | OOK | 13.56MHz Unc | SSI WAMS |
| 03-000139-37-08 | 916.5MHz | OOK | 13.56MHz Unc | S&G Code |
| 03-000139-37-09 | 916.5MHz | OOK | 13.56MHz Unc | Medical 1 |
| 03-000139-37-10 | 916.5MHz | OOK | 13.56MHz Unc | Home Sec. 1 |
| 03-000139-38-01 | 916.5MHz | ASK | 13.56MHz Unc | Basic Demo |
| 03-000139-38-02 | 916.5MHz | ASK | 13.56MHz Unc | SSI WAMS |
| 03-000139-38-03 | 916.5MHz | ASK | 13.56MHz Unc | S&G Code |
| 03-000139-38-04 | 916.5MHz | ASK | 13.56MHz Unc | Medical 1 |
| 03-000139-38-05 | 916.5MHz | ASK | 13.56MHz Unc | Home Sec. 1 |

FIG. 7D

TRANSPONDER TRANSMISSION PERIODICITY DECISION TABLE

Example of a Sensor Sampling Plan (Truck Wheel Monitoring)

Step 1  Wake up every 2 seconds, take 3 samples, average closest two readings, store in A
Step 2  Wake up every 2 seconds, move store A to store B, take 3 samples, average closest two readings, store in A
Step 3  Wake up every 2 seconds, move store B to store C, move store A to store B, take 3 samples, average closest two readings, store in A
Step 4  Compare value of data stored in A with limit table and react accordingly
Step 5  Average the averages stored in A, B and C and store in D
Step 6  Compare value of data stored in A with data stored in B, check change with Rate of Change Table and react accordingly
Step 7 plus  Continue to repeat steps 3 through 6 indefinitely Example of a Limit Table (Truck Wheel Monitoring)

| Normal plus/minus | Convert every | Transmit every | Repeat ea Tx | |
|---|---|---|---|---|
| 0 to 12.5% | 300 secs | 300 secs | 3 times | |
| 12.5 to 25% | 90 secs | 90 secs | 6 times | Warn |
| 25 to 50% | 30 secs | 30 secs | 25 times | Alert |
| over 50% | 10 secs | 10 secs | 50 times | Alarm |

FIG 10A

Example of Rate of Change Table (Truck Wheel Monitoring)

| Change greater than | Convert every | Transmit every | Repeat ea Tx | Action |
|---|---|---|---|---|
| 0% | 450 secs | 900 secs | 3 times | |
| 6.25% | 150 secs | 300 secs | 6 times | Warn |
| 12.50% | 90 secs | 90 secs | 12 times | Alert 1 |
| 25% | 30 secs | 30 secs | 25 times | Alert 2 |
| 50% | 10 secs | 10 secs | 50 times | Alarm |

Note: Each sensed parameter is analysed and the response is determined for each parameter. However the data transmission periodicity and repetition is determined by the most critical parameter (the transmission format is always the same).

FIG 10B

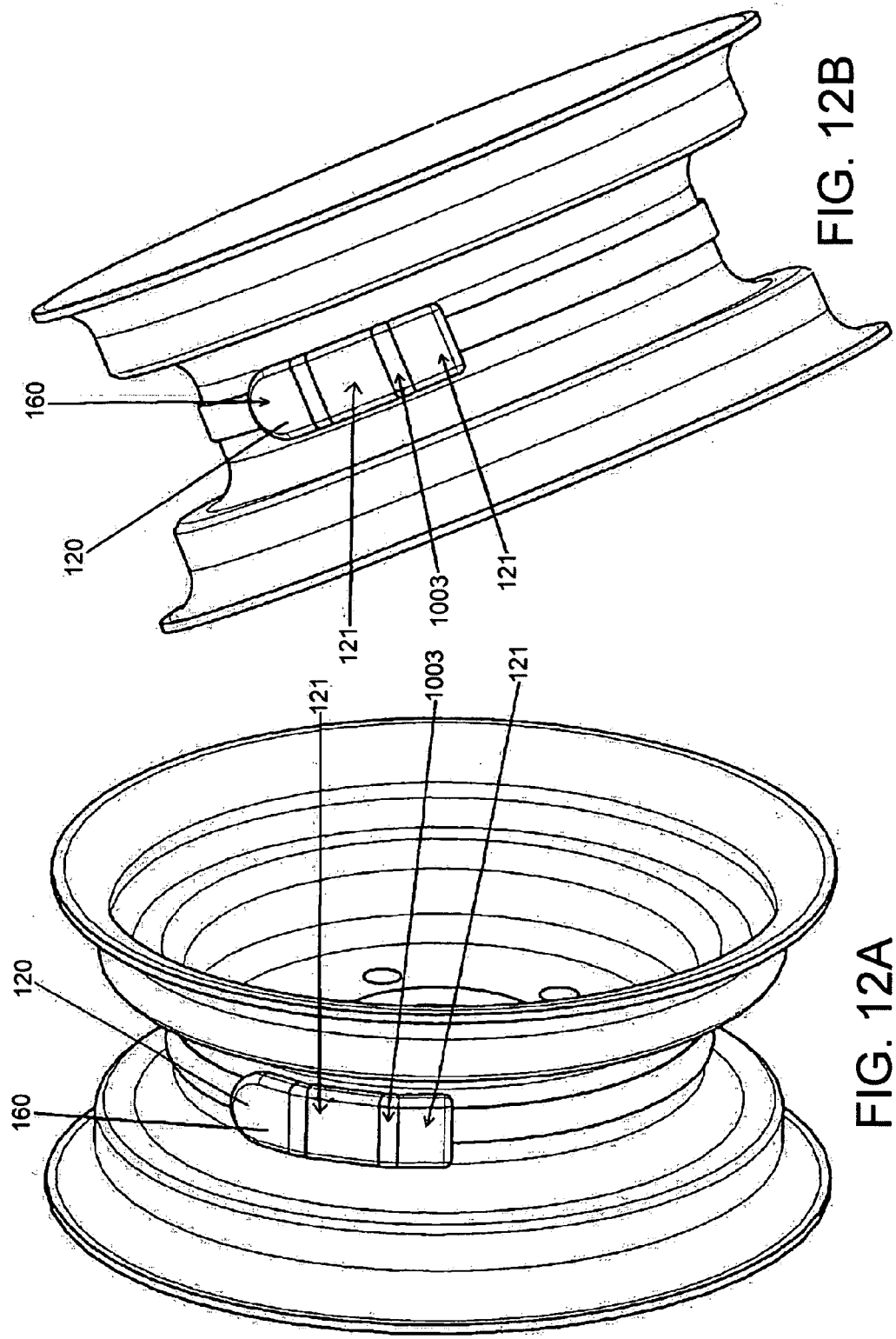

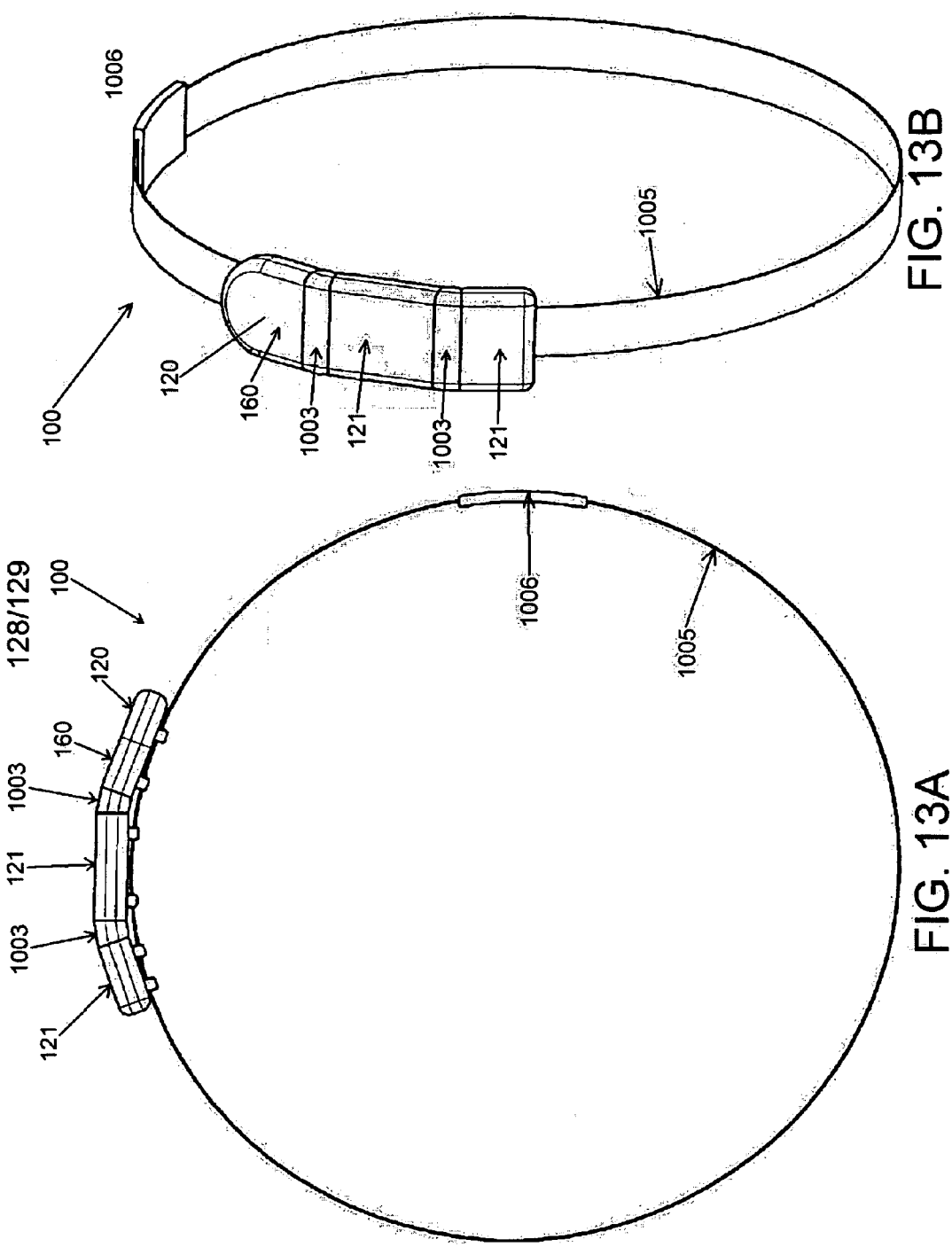

LOAD SAFEGUARD SYSTEMS

CROSS-REFERENCE TO RELATED APPLICATIONS

The present application is a continuation-in-part of, and claims priority from, related U.S. non-provisional application Ser. No. 10/650,545, filed Aug. 27, 2003 now U.S. Pat. No. 6,972,677, entitled "MONITORING SYSTEM", which is related to and claims priority from prior U.S. provisional patent application Ser. No. 60/406,110, filed Aug. 27, 2002, entitled "MODULAR, POST-PROGRAMMABLE RADIO FREQUENCY LOCATION, IDENTIFICATION, TRACKING, MONITORING, INTERROGATION AND SENSING SYSTEM, COMPONENTS AND METHODS" and also from related U.S. provisional patent application Ser. No. 60/452,261, filed Mar. 6, 2003, entitled "UNIVERSAL RADIO LOCATION, INTERPRETIVE MONITORING AND EVEN TIMING SYSTEM AND METHOD" the contents of all of which are incorporated herein by this reference and are not admitted to be prior art with respect to the present invention by the mention in this cross-reference section.

BACKGROUND

This invention relates to providing systems for improved monitoring of changes in the location and conditions within vehicles and the materials transported by vehicles. More specifically, this invention relates to real-time monitoring of changes in the location and conditions within shipping vehicles and the loads transported within such shipping vehicles.

Perishable products now arrive at distribution centers and stores from increasingly distant production sites. The increasing shipping distances now imposed on product supply chains greatly increase the risk of product deterioration during transit. A wide variety of food, pharmaceutical, and chemical products are degraded by improper exposure to temperature, humidity, light or other contaminants. For example, maintaining optimal temperatures throughout the supply chain is vital for perishable, refrigerated and frozen products. Transport storage temperatures above or below a narrow optimum range for a perishable item often reduces a product's shelf life by hours or days. In the case of perishable produce, damage often becomes apparent only after the product shipment has been delivered and accepted; thus more and more a deliveree may hesitant to accept a load unless there is sufficient evidence that the load has been maintained during shipment in this desired temperature range. For pharmaceuticals, the efficacy of a product degraded during transit may have immediate life-threatening consequences.

In addition, national security interest has recently focused on the motor trucking industry. The trucking industry is a major component of the U.S. transportation sector, but currently lacks effective systems to prevent trucks and cargo from being used as tools by terrorists or as a means for moving contraband. The ability to track and monitor, in real time, the contents and location of vehicles during transit would provide an effective means for countering illegal or terror-based activities.

Inadequate monitoring of changes in the location and conditions surrounding shipping vehicles and shipped materials has resulted in spoilage, damage, misplacement, loss, and theft of extremely valuable property. A system capable of efficiently monitoring, in real-time, changes in location and surrounding conditions of hazardous, perishable, refrigerated and frozen materials, during transit, would be extremely beneficial to many.

OBJECTS AND FEATURES OF THE INVENTION

A primary object and feature of this invention is to overcome the above-stated problems.

Another primary object and feature of the present invention is to provide a system for coupled communication between logic processors and a receiver within on or more transport vehicles. It is a further object and feature of the present invention to provide such a system for providing coupled communication between sensors and receivers. It is a further object and feature of the present invention to provide such a system capable of communicating at varied frequencies. It is a further object and feature of the present invention to provide such a system capable of communicating at periodic frequencies. It is a further object and feature of the present invention to provide such a system capable of communicating at non-continuous frequencies. It is a further object and feature of the present invention to provide such a system capable of optimized power consumption when communicating at non-continuous frequencies.

It is a further object and feature of the present invention to provide such a system utilizing wireless systems. It is a further object and feature of the present invention to provide such a system utilizing logic-processor specific power sources. It is a further object and feature of the present invention to provide such a system utilizing electric circuits. It is a further object and feature of the present invention to provide such a system utilizing electric circuit firmware. It is a further object and feature of the present invention to provide such a system utilizing signal-modified firmware.

It is a further object and feature of the present invention to provide such a system utilizing wireless receptors. It is a further object and feature of the present invention to provide such a system utilizing wireless receptors capable or targeting particular signals by modifying their read-range. It is a further object and feature of the present invention to provide such a system where a receiver is communicatively coupled to external networks.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a load safeguard system, co-operable with at least one database, for monitoring, within at least one determinable environment, at least one item requiring monitoring of at least one sensible condition, comprising, in combination: a set of first logic-processor means, for logical transacting with receivable information, respectively associated with a respective set of locations within at least one determinable environment; and a plurality of second logic-processor means, for logical transacting with receivable information, respectively associated with a plurality of such at least one items; wherein essentially each of said set of first logic-processor means comprises first communicator means for communicative coupling with essentially each of said plurality of second logic-processor means; wherein essentially each of said plurality of second logic-processor means comprises second communicator means for communicative coupling with essentially each of said set of first logic-processor means; wherein essentially each of said plurality of second logic-processor means comprises sensor means for sensing at least one environmental condition; and wherein essentially each of said set of first logic-processor means comprises third communicator means for communicative coupling with such at least one database. Moreover, it provides such a system, wherein: such at least one item comprises at least one shippable package; and such at least one determinable environment comprises at least one shipping environment. Additionally, it provides such a system, wherein: such at least one item comprises perishable produce; and such at least one determinable environment comprises at least one temperature-controllable shipping truck.

In accordance with another preferred embodiment hereof, this invention provides a system, co-operable with at least one centrally-readable database, for monitoring items within a local area, comprising, in combination: a plurality of first logic-processor means, for logical transacting with receivable information, respectively associated with a plurality of locations within the local area; and a plurality of second logic-processor means, for logical transacting with receivable information, respectively associated with a plurality of the items; wherein essentially each of such plurality of first logic-processor means comprises first communicator means for communicative coupling with essentially each of such plurality of second logic-processor means; and wherein essentially each of such plurality of second logic-processor means comprises second communicator means for communicative coupling with essentially each of such plurality of first logic-processor means.

Moreover, it provides such a system further comprising receiver means for receiving communicated information from at least one of the group consisting essentially of each of such plurality of first logic-processor means and each of such plurality of second logic-processor means. Additionally, it provides such a system further comprising database means for manipulating such receivable information. Also, it provides such a system wherein such first communicator means and such second communicator means each comprise wireless system means for wirelessly assisting communicative coupling. In addition, it provides such a system wherein such receiver means comprises wireless receptor means for receiving communicated information. And, it provides such a system wherein essentially each of such plurality of first logic-processor means and essentially each of such plurality of second logic-processor means comprise identifier means for uniquely identifying essentially each one of such plurality of first logic-processor means and essentially each one of such plurality of second logic-processor means.

Further, it provides such a system further comprising sensor means, for sensing local information, attachable to at least one subset of at least one of the group consisting essentially of each of such plurality of first logic-processor means and each of such plurality of second logic-processor means. Even further, it provides such a system wherein essentially each of such plurality of first logic-processor means and essentially each of such plurality of second logic-processor means comprise power source means for providing electrical power. Moreover, it provides such a system wherein essentially each of such plurality of first logic-processor means and essentially each of such plurality of second logic-processor means comprise power-life-extender means for extending at least one life of such power source means by assisting intermittent operation. Additionally, it provides such a system wherein such first communicator means and such second communicator means comprise at least one frequency within the range consisting of: radio frequency; ultrasonic frequency; and UV frequency.

Also, it provides such a system wherein such first communicator means and such second communicator means comprise non-continuous signaler means for providing non-continuous communications. In addition, it provides such a system wherein such non-continuous signaling means comprises optimized signaler means for providing optimized power consumption when generating non-continuous communications. And, it provides such a system wherein essentially each of such plurality of first logic-processor means and essentially each of such plurality of second logic-processor means comprises electric circuit means for processing data. Further, it provides such a system wherein such electric circuit means comprises firmware means for providing modification of such plurality of first logic-processor means and modification of such plurality of second logic processor means.

It also provides such a system wherein such first communicator means from at least one of such plurality of first logic-processor means is communicatively coupleable with at least one of such plurality of second logic-processor means so that such firmware means of such at least one of such plurality of second logic-processor means may be modified by such first communicator means. Even further, it provides such a system wherein such second communicator means from at least one of such plurality of second logic-processor means is communicatively coupleable with at least one of such plurality of first logic-processor means so that such firmware means of such at least one of such plurality of first logic-processor means may be modified by such second communicator means. Moreover, it provides such a system wherein such receiver means comprises network coupler means for communicative coupling with at least one of the group consisting of: Internet; personal computers; personal digital assistants; local area networks; radios; cellular phones; wireless networks; and personal computer memory card international associations (PCMCIA's) for wireless applications.

In accordance with another preferred embodiment hereof, this invention provides a system, co-operable with at least one centrally-readable database, for monitoring items within a local area, comprising, in combination: a plurality of first logic-processors structured and arranged to provide logical transaction with receivable information, respectively associated with a plurality of locations within the local area; and a plurality of second logic-processors structured and arranged to provide logical transaction with receivable information, respectively associated with a plurality of the items; wherein essentially each of such plurality of first logic-processors comprises at least one first communicator structured and arranged to communicatively couple with essentially each of such plurality of second logic-processors; and wherein essentially each of such plurality of second logic-processors comprises at least one second communicator structured and arranged to communicatively couple with essentially each of such plurality of first logic-processors.

Additionally, it provides such a system further comprising at least one receiver structured and arranged to receive communicated information from at least one of the group consisting essentially of each of such plurality of first logic-processors and each of such plurality of second logic-processors. Also, it provides such a system further comprising at least one database structured and arranged to manipulate such receivable information. In addition, it provides such a system wherein such at least one first communicator and such at least one second communicator each comprise at least one wireless system structured and arranged to wirelessly assist communicative coupling. And, it provides such a system wherein such at least one receiver comprises at least one wireless receptor structured and arranged to receive such receivable information.

Further, it provides such a system wherein essentially each of such plurality of first logic-processors and essentially each of such plurality of second logic-processors comprise at least one identifier structured and arranged to uniquely identify essentially each one of such plurality of first logic-processors and essentially each one of such plurality of second logic-processors. Even further, it provides such a system further comprising at least one sensor structured and arranged to sense local information, attachable to at least one subset of at least one of the group consisting essentially of each of such plurality of first logic-processors and each of such plurality of second logic-processors. Moreover, it provides such a system wherein essentially each of such plurality of first logic-processors and essentially each of such plurality of second logic-processors comprise at least one power source structured and arranged to provide electrical power.

Additionally, it provides such a system wherein essentially each of such plurality of first logic-processors and essentially each of such plurality of second logic-processors comprise at least one power-life-extender structured and arranged to extend at least one life of such at least one power source by assisting intermittent operation. Also, it provides such a system wherein such at least one first communicator and such at least one second communicator comprise at least one frequency within the range consisting of: radio frequency; ultrasonic frequency; and UV frequency.

In addition, it provides such a system wherein such at least one first communicator and such at least one second communicator comprise at least one non-continuous signaler structured and arranged to provide non-continuous communications. And, it provides such a system wherein such at least one non-continuous signaler comprises at least one optimized signaler structured and arranged to provide optimized power consumption when generating non-continuous communications. Further, it provides such a system wherein essentially each of such plurality of first logic-processors and essentially each of such plurality of second logic-processors comprise at least one electric circuit structured and arranged to process data. Even further, it provides such a system wherein such at least one electric circuit comprises at least one firmware structured and arranged to provide modification of such plurality of first logic-processors and modification of such plurality of second logic-processors.

The system wherein such at least one first communicator from at least one of such plurality of first logic-processors is communicatively coupleable with at least one of such plurality of second logic-processors so that such at least one firmware of such at least one of such plurality of second logic-processors may be modified by such at least one first communicator. Moreover, it provides such a system wherein such at least one second communicator from at least one of such plurality of second logic-processors is communicatively coupleable with at least one of such plurality of first logic-processors so that such at least one firmware of such at least one of such plurality of first logic-processors may be modified by such at least one second communicator.

Additionally, it provides such a system wherein such at least one receiver comprises at least one network coupler structured and arranged to communicatively couple such at least one receiver with at least one of the group consisting of: internet; personal computers; personal digital assistants; local area networks; radios; cellular phones; wireless networks; and personal computer memory card international associations (PCMCIA's) for wireless applications.

In accordance with another preferred embodiment hereof, this invention provides a method and system for monitoring at least one state of at least one item associated with at least one healthcare facility by storing in at least one database such at least one state of such at least one item, received from a plurality of fixed status broadcasters and a plurality of mobile status broadcasters comprising the steps of: receiving at least one state change of such at least one item from at least one state sensor by at least one of such plurality of fixed status broadcasters; receiving at least one state change of such at least one item from at least one state sensor by at least one of such plurality of mobile status broadcasters; determining requirement to broadcast such at least one state change by such at least one such plurality of fixed status broadcasters; determining requirement to broadcast such at least one state change by such at least one of such plurality of mobile status broadcasters; broadcasting required such at least one state change by such at least one of such plurality of fixed status broadcasters; broadcasting required such at least one state change by such at least one of such plurality of mobile status broadcasters; receiving such required such at least one state change from such at least one of such plurality of fixed status broadcasters; receiving such required such at least one state change from such at least one of such plurality of mobile status broadcasters; storing such required such at least one state change in such at least one database; and reporting such required such at least one state change.

Also, it provides such a method and system wherein such at least one state change comprises: occurrence of at least one event affecting such at least one item; change of location change of such at least one item; and change of at least one monitored value affecting such at least one item. In addition, it provides such a method and system wherein the step of determining requirement to broadcast such at least one state change by such at least one of such plurality of fixed status broadcasters comprises: receiving at least one broadcast requirement rule; and comparing such at least one state change to such at least one broadcast requirement rule. And, it provides such a method and system wherein the step of determining requirement to broadcast such at least one state change by such at least one of such plurality of mobile status broadcasters comprises: receiving at least one broadcast requirement rule; and comparing such at least one state change to such at least one broadcast requirement rule.

Further, it provides such a method and system wherein the step of reporting such required such at least one state change comprises: transmission of such required such at least one state change to at least one local area network; transmission of such required such at least one state change to at least one personal computer; transmission of such required such at least one state change to at least one cellular telephone; transmission of such required such at least one state change to at least one personal digital assistant; and transmission of such required such at least one state change to at least one radio frequency receiver. Even further, it provides such a method and system wherein such at least one item comprises: infant patients; adult patients; fixed equipment; and mobile equipment. Even further, it provides such a method and system wherein such step of broadcasting required such at least one state change by such at least one of such plurality of fixed status broadcasters comprises: activating at least one broadcasting transmitter; broadcasting such required such at least one state change using such at least one broadcasting transmitter; and de-activating such at least one broadcasting transmitter.

Even further, it provides such a method and system wherein such step of broadcasting required such at least one state change by such at least one of such plurality of mobile status broadcasters comprises: activating at least one broadcasting transmitter; broadcasting such required such at least one state change using such at least one broadcasting transmitter; and de-activating such at least one broadcasting transmitter. Even further, it provides such a method and system wherein such at least one healthcare facility comprises: hospitals; nursing homes; assisted living facilities; offices of medical practitioners; and personal residences. Even further, it provides such a method and system further comprising the step of determining a plurality of steady-state values for the conditions surrounding such at least one state sensor and using such plurality of steady-state values as a reference for determining, in the future, when a state change has occurred.

And this invention provides a useful new format for communicative bits/bytes.

This invention also provides that both First logic-processors and Second logic-processors may have the programmed capability to establish their own sampling rates and statistical analysis methods to determine the normal or typical sensed conditions of the environment, preferably the steady-state environment, in terms of absolute values, rate of change of these values and the relationships of the various sensed parameters being monitored by the First logic-processor or Second logic-processor; and the result of this analysis may result in the onboard microprocessor changing the sampling rates for one or more sensors, increasing the size of a sample for one or more sensors, switching to a different analysis algorithm and determining an appropriate transmission schedule, power level and even modulation scheme.

Yet further, this invention provides each and every novel detail, feature, article, process, system and/or method disclosed in or mentioned by or shown in this specification, including the drawings, the claims, the abstract, and any appendices.

BRIEF DESCRIPTION OF THE DRAWINGS

FIG. 1-01 is a diagram of the monitoring system according to a preferred embodiment of FIG. 1-00.

FIG. 1-02 is a diagram of the monitoring system according to a preferred embodiment of FIG. 1-00.

FIG. 1-03 is a diagram of the monitoring system according to another preferred embodiment of the present invention.

FIG. 2-00 is another perspective view of the monitoring system according to a preferred embodiment of the present invention.

FIG. 2-01 through FIG. 2-81 provide detailed descriptions of a preferred embodiment of the present invention.

FIG. 3, comprising FIG. 3A, FIG. 3B, FIG. 3C, and FIG. 3D, is a perspective view of a Second logic-processor according to a preferred embodiment of the present invention.

FIG. 6-00 is a perspective view of an electric circuit according to a preferred embodiment of the present invention.

FIG. 6-01 is another perspective view of an electric circuit according to a preferred embodiment of the present invention.

FIG. 7, comprising FIG. 7A, FIG. 7B, FIG. 7C, and FIG. 7D, is a wireless system configurations table according to a preferred embodiment of the present invention.

FIG. 10, comprising FIG. 10A and FIG. 10B, is a sensor sampling-plan according to a preferred embodiment of the present invention.

FIG. 12, comprising FIG. 12A and FIG. 12B, is an alternative perspective view of a Second logic-processor according to a preferred embodiment of the present invention.

FIG. 13, comprising FIG. 13A and FIG. 13B, is a side view of the sections of a Second logic-processor according to a preferred embodiment of the present invention.

Figures 0, 2:
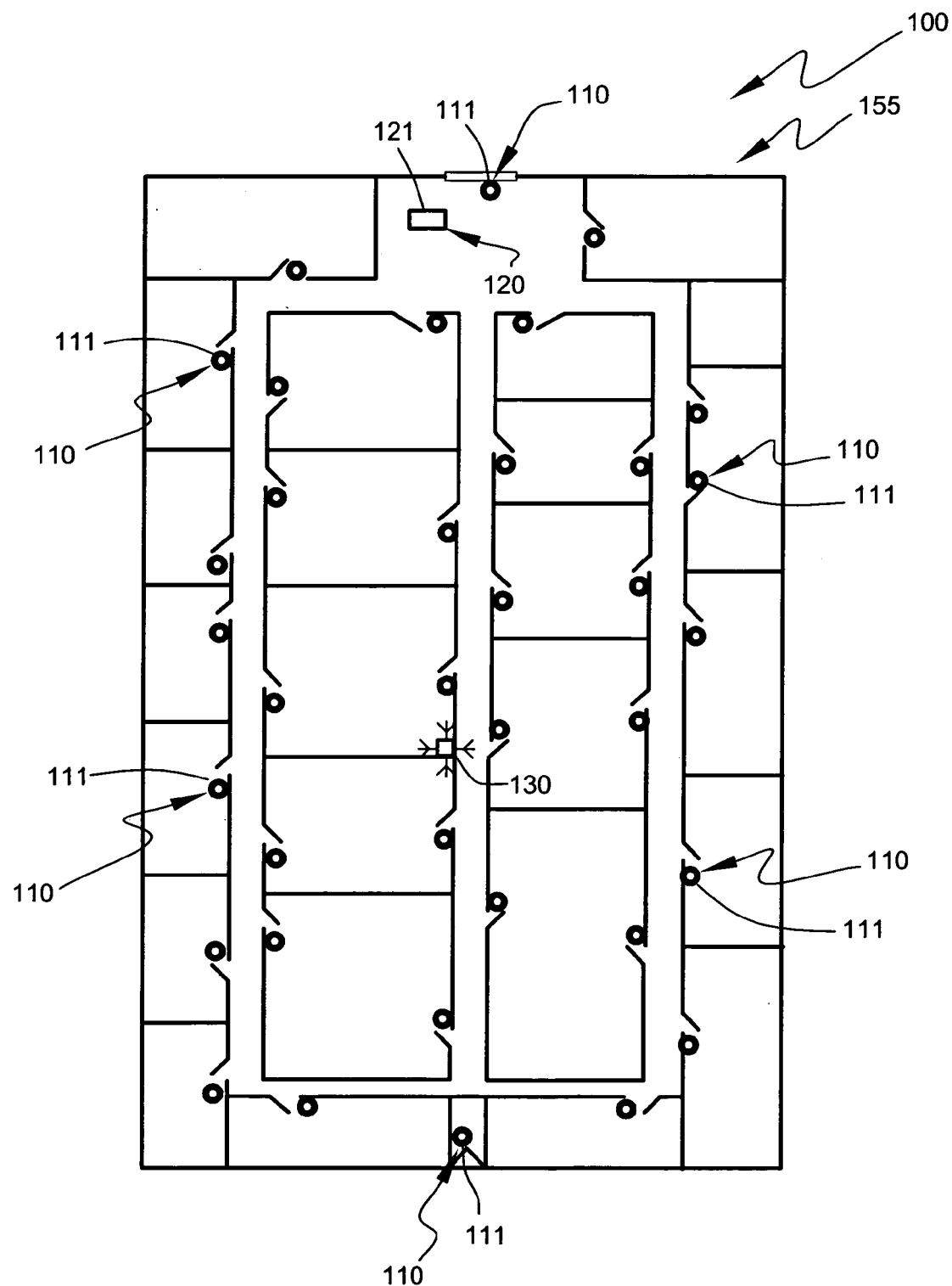
Figures 1, 2:
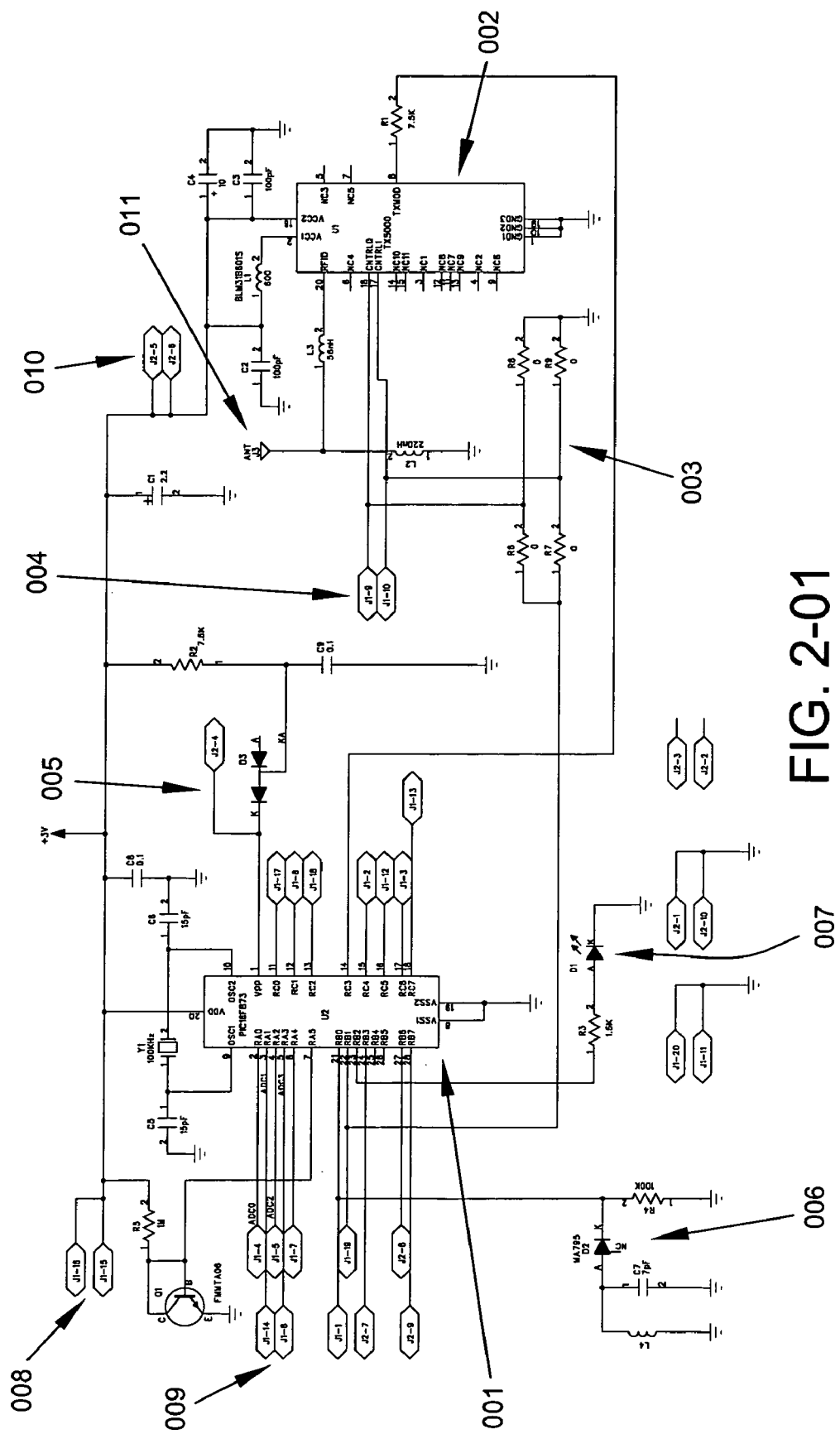
Figures 2, 3:
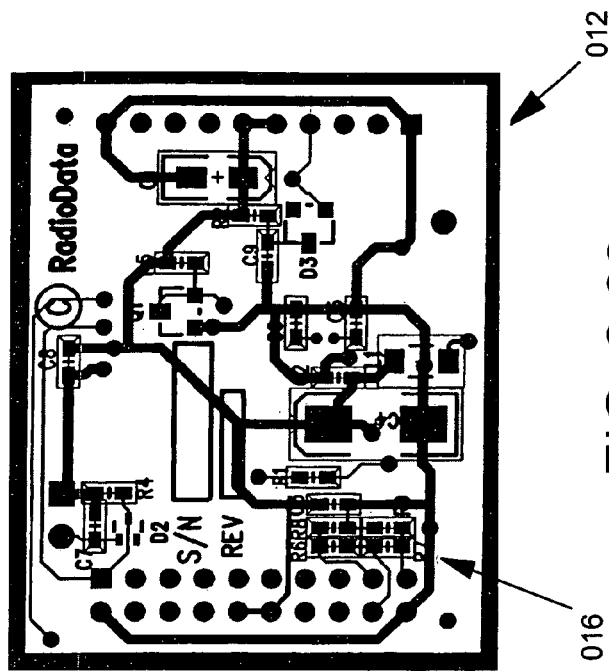
Figure 2:
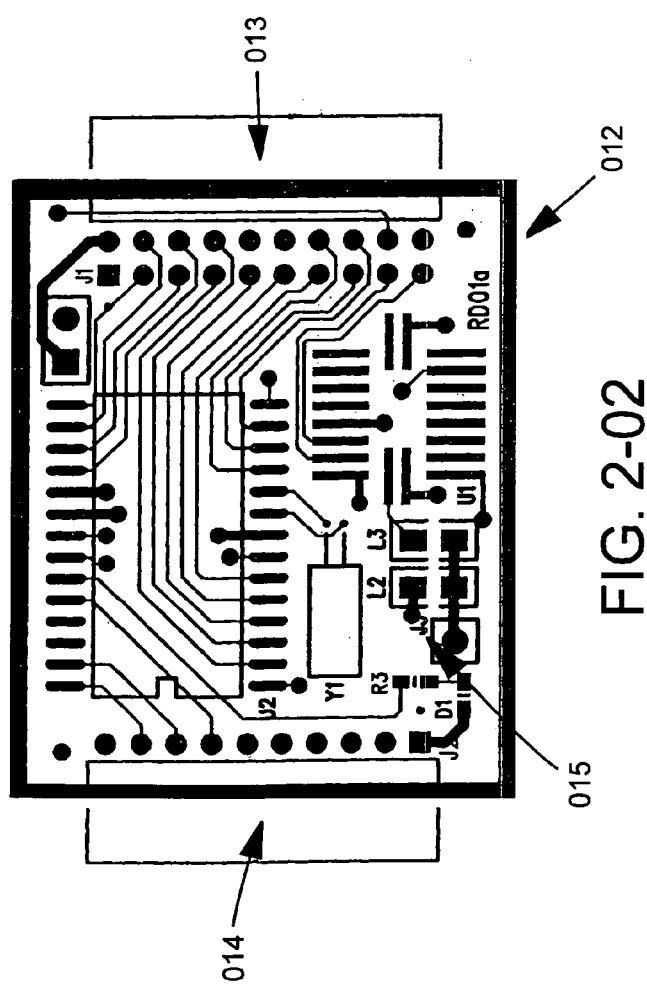
Figures 2, 3, 4:
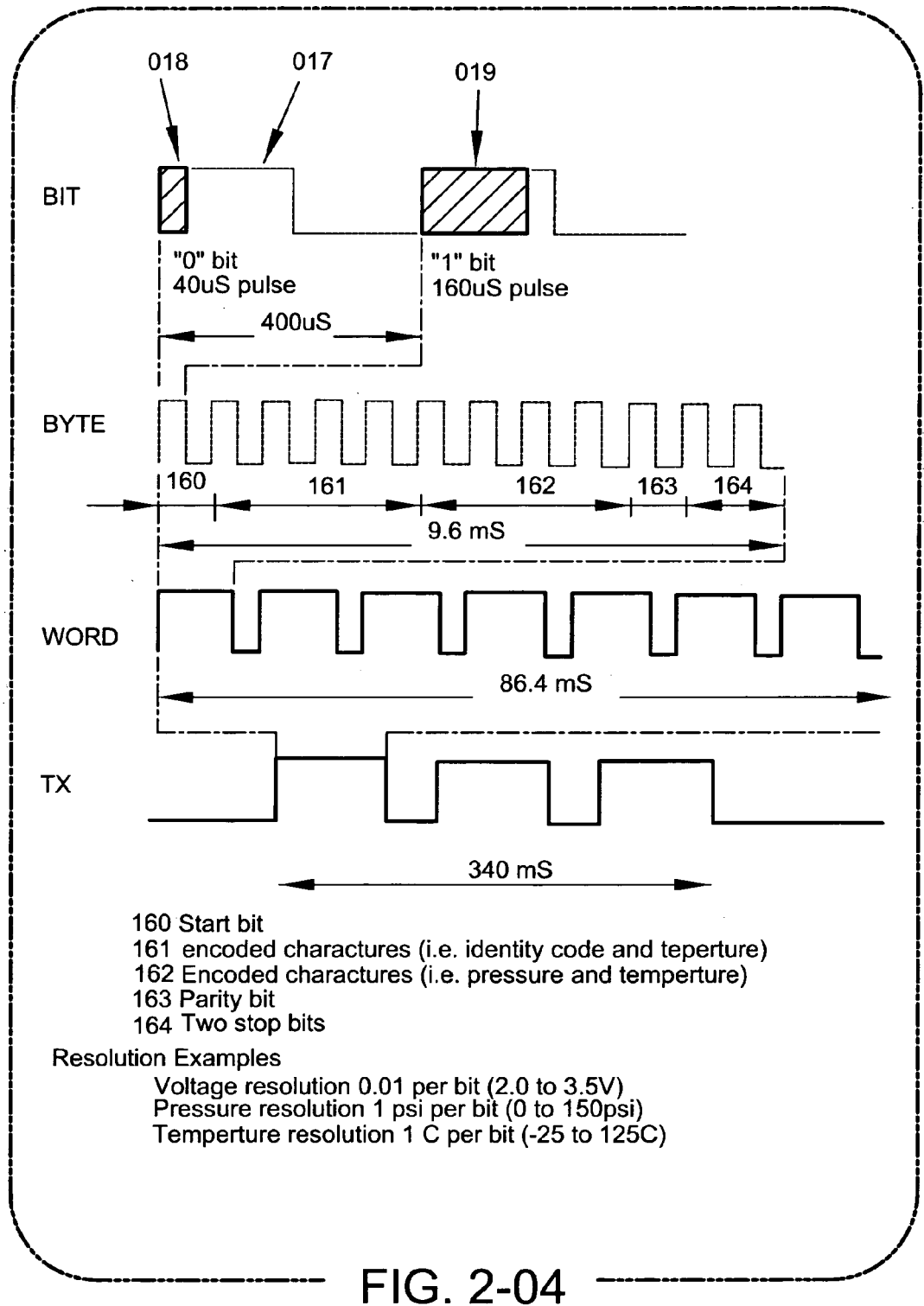
Figures 2, 3, 4, 5, 5A:
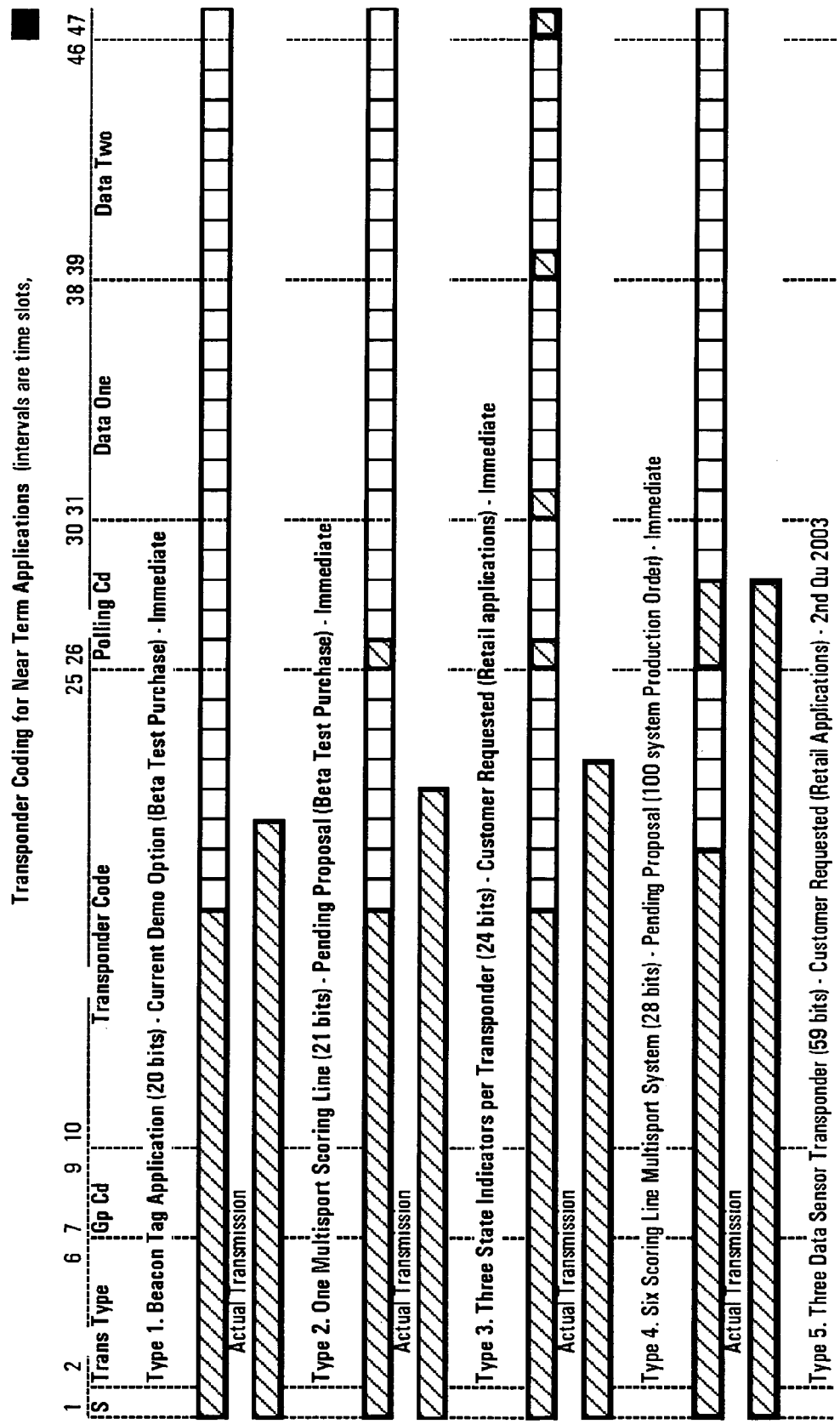
Figures 2, 3, 4, 5, 5B:
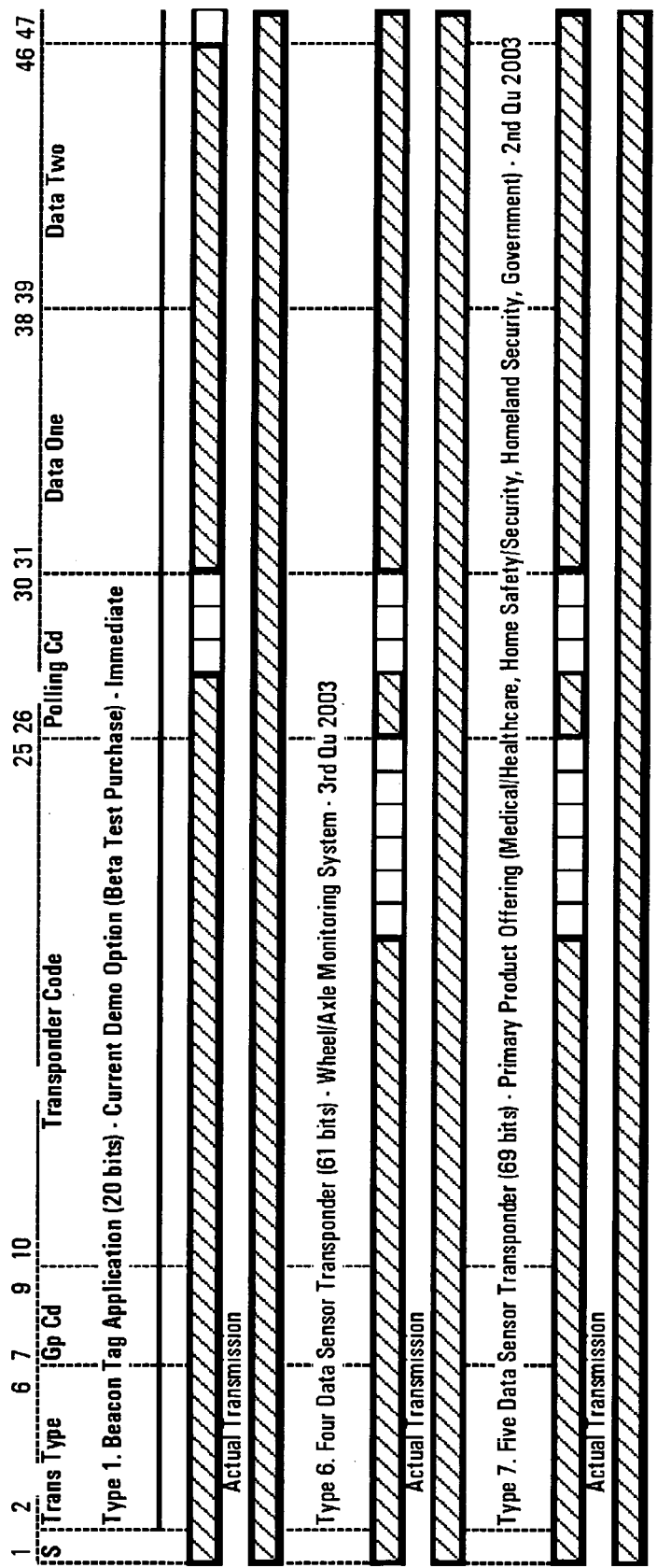
Figure 2:
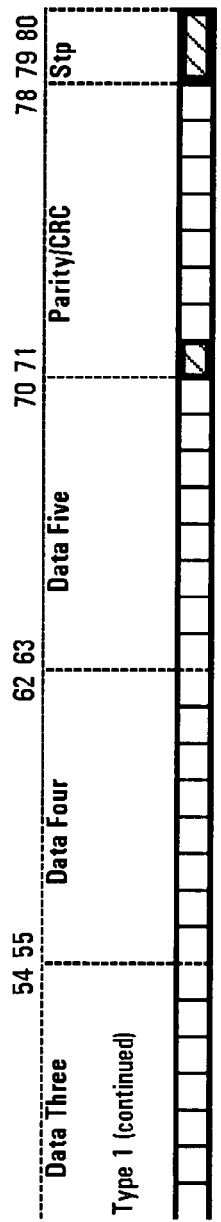
Figure 3:
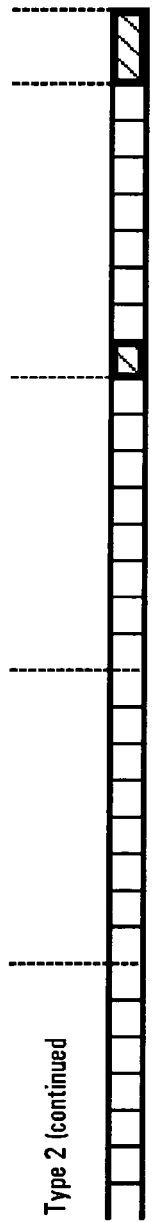
Figure 4:
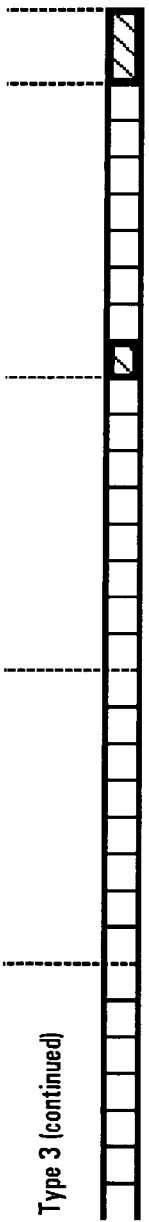
FIG. 4 is a Receiver flowchart according to a preferred embodiment of the present invention.
Figure 5:
FIG. 5, comprising
Figure 5C:
FIG. 5A and FIG. 5B, is a perspective view of a power source according to a preferred embodiment of the present invention.
Figures 2, 3, 4, 5, 5D:
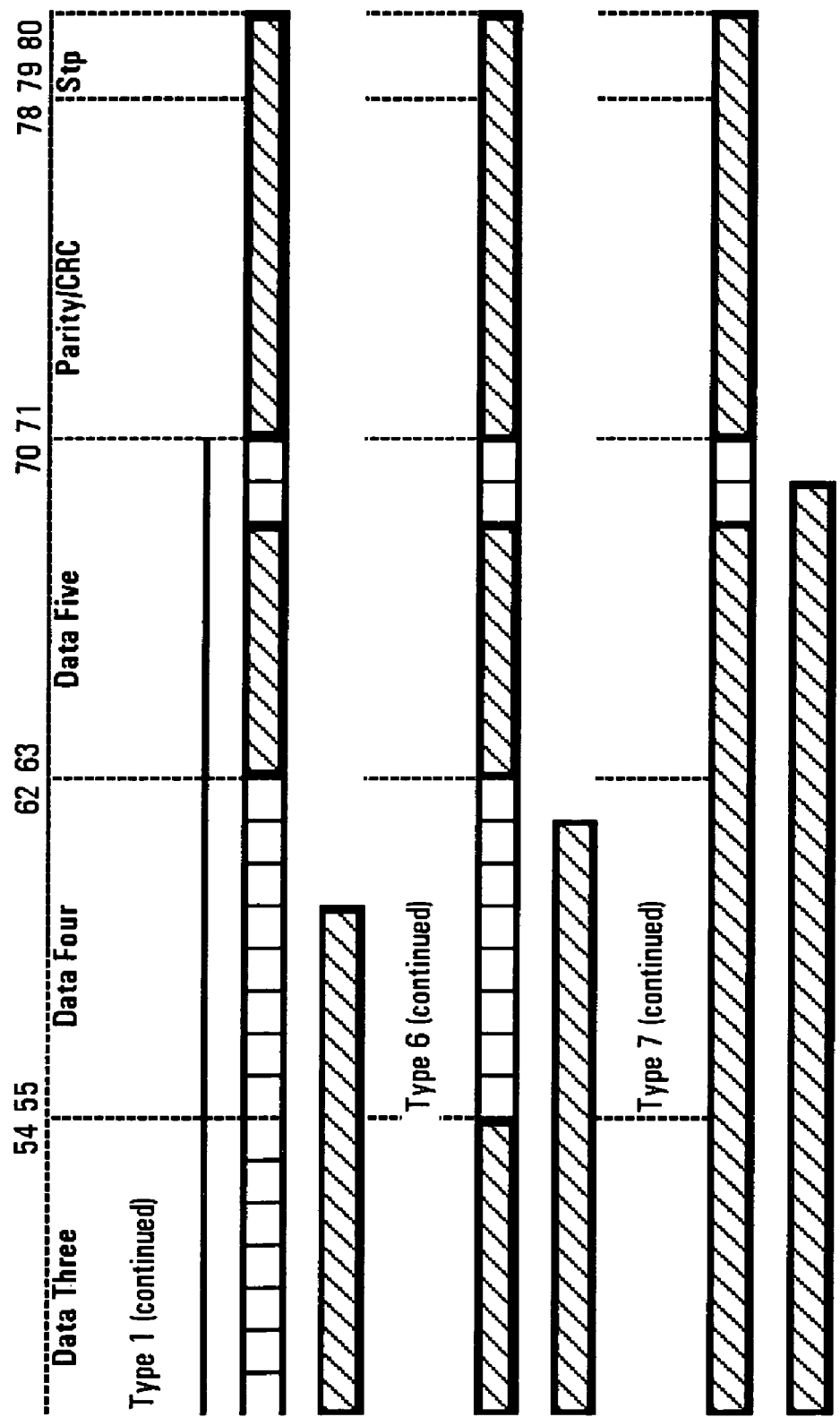
Figures 2, 3, 4, 5, 6, 7, 8, 9:
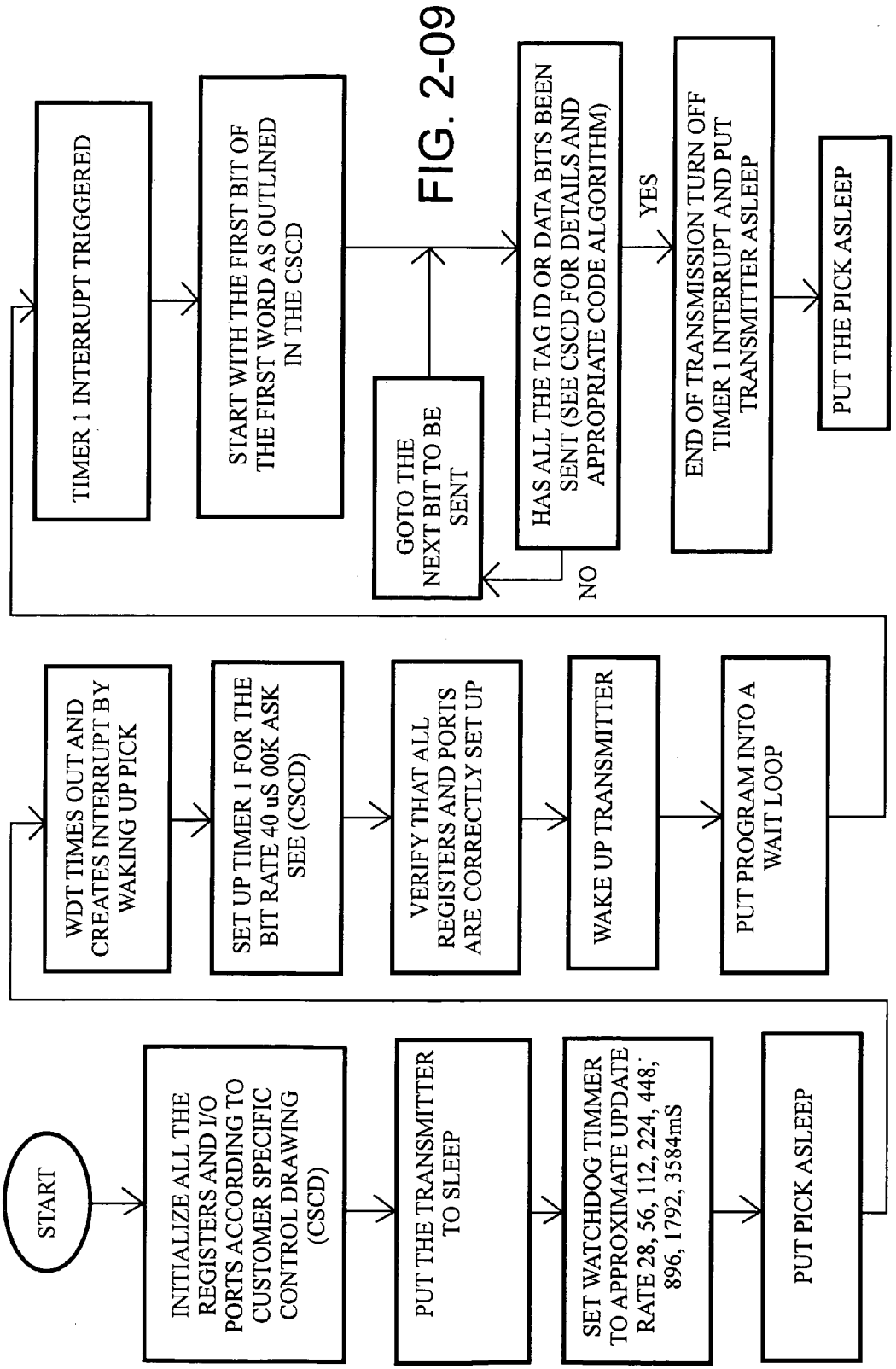

Within the specification, reference to a figure number indicates reference to the set of all lettered figures for that number (for example, reference to "FIG. 7" indicates reference to FIG. 7A, FIG. 7B, FIG. 7C, and FIG. 7D).

DETAILED DESCRIPTION OF THE BEST MODE AND PREFERRED EMBODIMENTS OF THE INVENTION

Figures 0, 1:
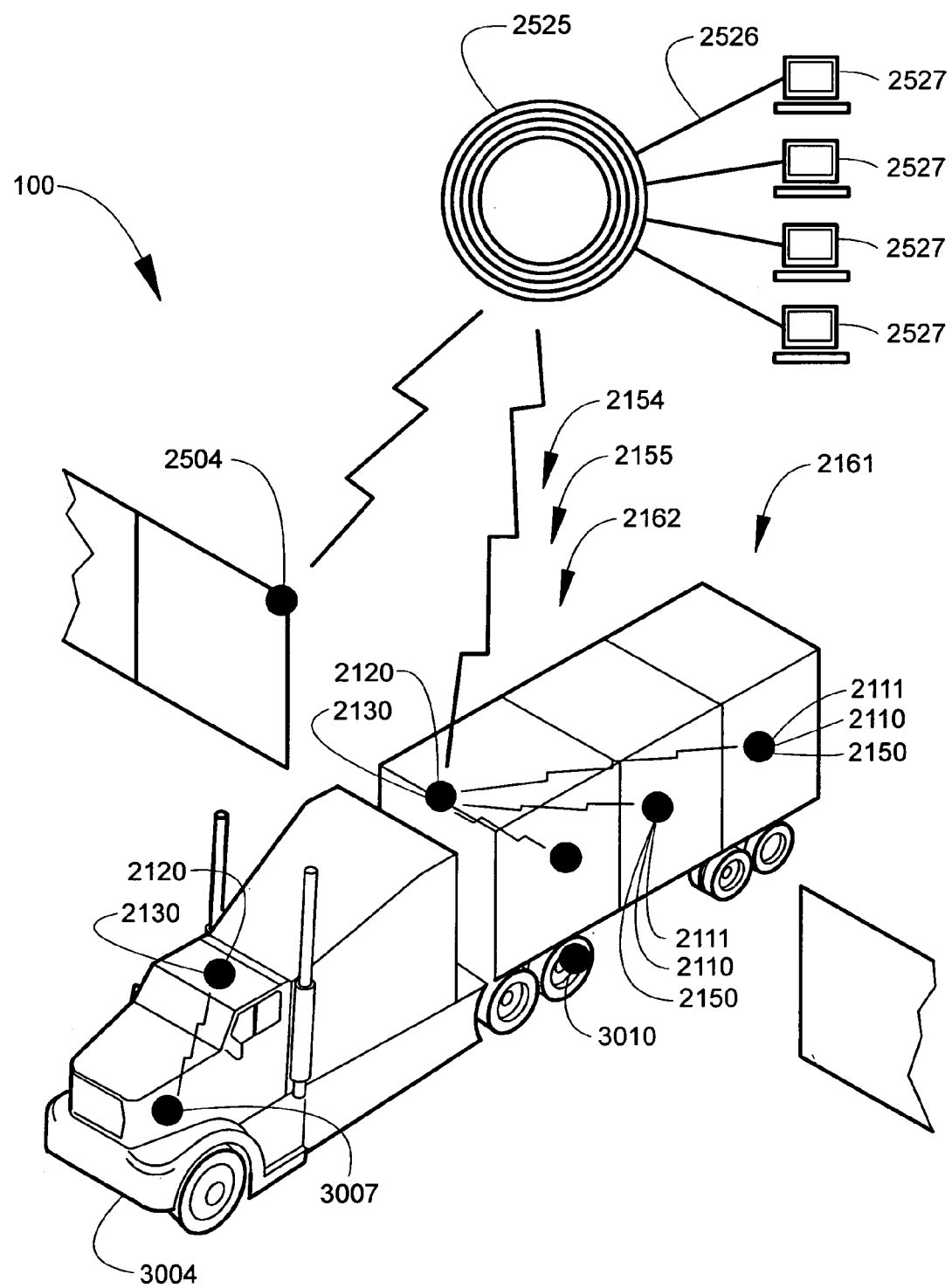
FIG. 1-00 is a perspective view of the monitoring system according to a preferred embodiment of the present invention.
Figure 1:
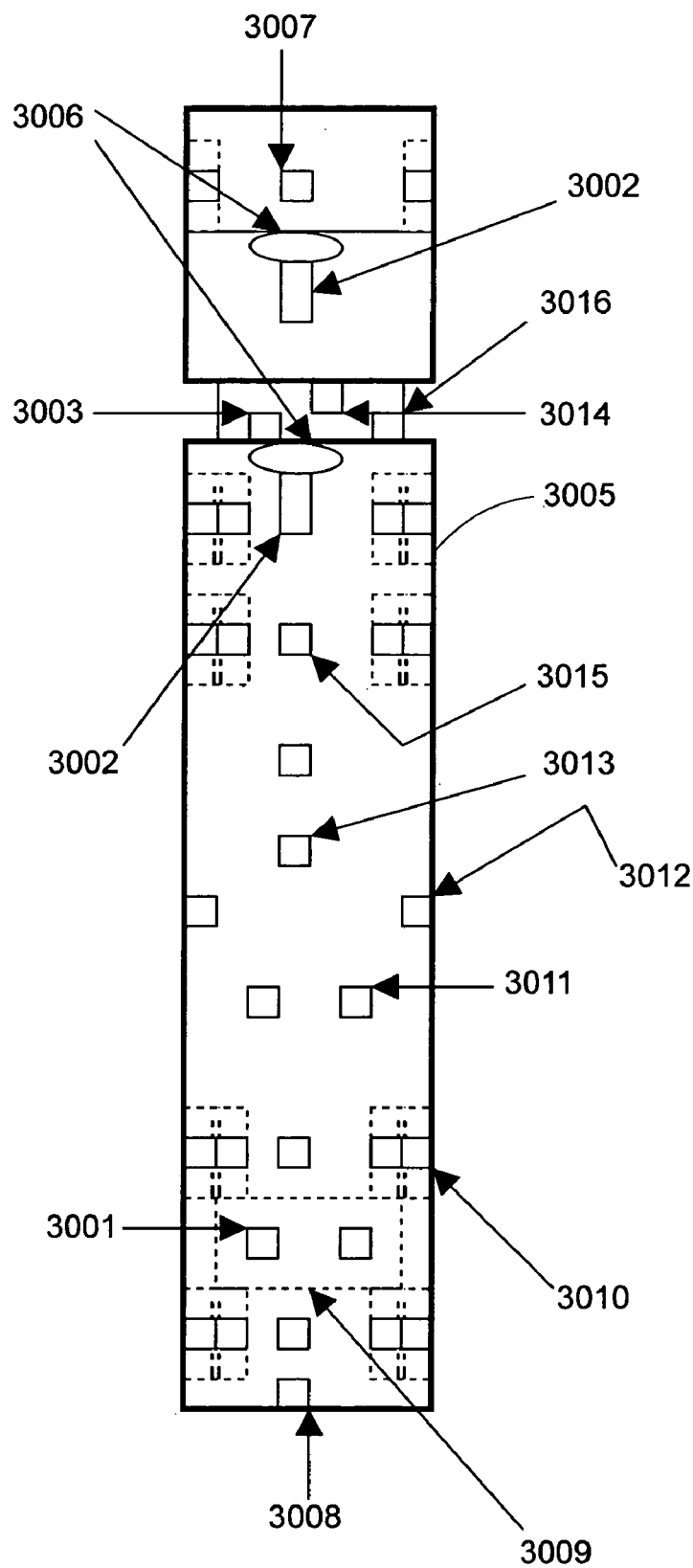

FIG. 1-00 is a perspective view of the monitoring system according to a preferred embodiment of the present invention. FIG. 1-01 is a diagram of the monitoring system according to a preferred embodiment of FIG. 1-00. Preferably, system 100 comprises systems for improved monitoring of changes in the location and conditions within vehicle 2500 and the materials transported vehicle 2500 within trailer 2502, as shown.

Preferably, system 100 comprises First logic-processors 2110, Second logic-processors 2120, first communicators 2111, and second communicators 2121. Preferably, First logic-processors 2110 provide logical transaction with receivable information, respectively associated with a plurality of locations within a local area (vehicle 2500 and trailer 2502). Preferably, Second logic-processors 2120 provide logical transaction with receivable information, respectively associated with a plurality of the items. Preferably, First logic-processors 2110 comprise first communicators 2111, communicatively coupled with Second logic-processors 2120. Preferably, Second logic-processors 2120 comprise second communicators 2121, communicatively coupled with First logic-processors 2110. Preferably, First logic-processors 2110 "poll", or transmit signals, to Second logic-processors 2120. Preferably, First logic-processors 110 may also "poll" for other First logic-processors 2120 (and may sometimes be referred to as "pollers"). However, Second logic-processors 2120 may also "poll" for First logic-processors 2110, as well as other Second logic-processors 2120 (and may sometimes be referred to as "transponders") (embodying herein a plurality of first logic-processor means, for logical transacting with receivable information, respectively associated with a plurality of locations within the local area; and embodying herein a plurality of second logic-processor means, for logical transacting with receivable information, respectively associated with a plurality of the items).

Preferably, system 100 further comprises Receiver 2130. Preferably, Receiver 2130 receives communicated information from First logic-processors 110. Preferably, Receiver 2130 receives communicated information from Second logic-processors 2120. Preferably, Receiver 2130 receives information resulting from "polling", or signals transmitted between logic-processors 2110 and 2120 (embodying herein receiver means for receiving communicated information from at least one of the group consisting essentially of each of said plurality of first logic-processor means and each of said plurality of second logic-processor means). Preferably, both First logic-processors 2110 and Second logic-processors 2120 may comprise Receivers 2130.

Preferably, Receiver 2130 comprises wireless receptor 2162. Preferably, wireless receptor 2162 receives wireless communications. Preferably, Receivers 2130 comprise 16-bit digital attenuators that can be controlled by the on-board microprocessor either as a result of wireless or wired instructions from the control center in the case of Receivers 2130, or instructions from a logic-processor 2110 or 2120, or a PDA in the case of a Second logic-processor. Furthermore, the microprocessor in each case can automatically increase the level of attenuation and reduce the read range if the signal density reaches a point that collisions can occur causing an excessive level of data errors. A further alternative in the case of First logic-processors 2110 and Second logic-processors 2120 is to reprogram the First logic-processors 2110 or Second logic-processors 2120 set attenuation level, on site, using the ribbon cable programming option. Preferably, wireless receptor 2162 is structured to enhance sensitivity to signals intended for reception by wireless receptor 2162 (embodying herein wireless receptor means for receiving communicated information). Preferably, system 100 further comprises database 2140. Preferably, database 2140 manipulates the information communicated between Receiver 2130, First logic-processor 2110, and Second logic-processor 2120 (embodying herein database means for manipulating such receivable information).

Preferably, first communicators 2111 and second communicators 2121 each comprise wireless systems 2155. Preferably, wireless systems 2155 provide for wireless communication of information (embodying herein wireless system means for wirelessly assisting communicative coupling). Upon reading the teachings of this specification, persons of ordinary skill in the art will now understand that, considering issues such as technology, cost, and efficiency, other wireless systems such as infrared, ultraviolet, acoustic, magnetic, non-radio, etc., may suffice. Preferably, First logic-processors 2110 and Second logic-processors 2120 each comprise identifiers 2154. Preferably, identifier 2154 uniquely identifies each of the First logic processors 2110. Preferably, identifier 2154 uniquely identifies each of the Second logic processors 2120 (embodying herein identifier means for uniquely identifying essentially each one of said plurality of first logic-processor means and essentially each one of said plurality of second logic-processor means).

Preferably, the above-described devices are preferably adaptable to comprise on-vehicle components or off-vehicle components as illustrated by gate detector 2504.

Preferably, system 100 further comprises sensor 2150. Preferably, sensor 2150 senses local environmental vehicle information. As examples of sensor 2150 types the following table is provided:

TABLE A

Speed, position and orientation:

1) Magnetic position sensors
2) Proximity sensors
3) Hall effect sensors
4) Motion sensors
5) Accelerometers (1D/2D/3D)
6) Fiber optic sensors
7) Infra-red sensors
8) Linear and rotary sensors
9) Liquid level indicators
10) Optical switches
11) Potentiometers
12) Resolvers
13) Turbidity sensors
14) Ultrasonic sensors
15) Speed Sensors
16) Vibration sensors
17) Angular sensors
18) Displacement sensors
19) Inclination sensors Pressure, force and flow:

20) Force Sensers
21) Load Sensors
22) Mass airflow sensors
23) Pressure sensers
24) Barometric sensors
25) Vacuum sensors
26) Torque Sensors
27) Differential pressure
28) Contact sensors
29) Bearing wear detectors Thermal and humidity 30) Heat Sensors
31) Humidity Sensors
32) Temperature Sensors
33) Thermal Fuses
34) Thermistors
35) Thermostats
36) Dew point detectors Electronic and electrical:

37) Voltage DC/AC
38) Current DC/AC
39) RF signal strength
40) Magnetic field
41) Electric field
42) Electrostatic field
43) Electromagnetic field Biological (TBD):

Radiation (Ionizing):

44) Alpha
45) Beta
46) Gamma
47) Neutron
X-ray

Optical and photoelectric:

48) Color sensors
49) Glossometers
50) Contrast sensors
51) Laser detectors
52) Flame detectors
53) Object detectors
54) Light Intensity sensors TABLE A-continued Chemical (liquid/gas):

55) Oxygen concentration
56) Nitrogen concentration
57) Carbon dioxide conc.
58) Ozone concentration
59) Air quality
60) Water purity
61) Propane sensors
62) Natural gas sensors
63) Gasoline sensors
64) pH level
65) Chlorine Sensors
66) Soil Moisture Preferably, sensor 2150 senses local information attachable to at least one subset First logic-processors 2110. Preferably, sensor 2150 senses local information attachable to at least one subset of Second logic-processors 2120 (embodying herein sensor means, for sensing local information, attachable to at least one subset of at least one of the group consisting essentially of each of said plurality of first logic-processor means and each of said plurality of second logic-processor means). Upon reading the teachings of this specification, persons of ordinary skill in the art will now understand that, considering issues such as efficiency, technology, and cost, other wireless systems may suffice.

Preferably, communicators 2111 and 2121 comprise communication frequencies of light or sound, which may travel unobstructed between First logic-processors 2110, Second logic-processors 2120, receivers 2130, and other transmitting and receiving sources. Preferably, communicators 2111 and 2121 comprise communication frequencies within the range of radio frequency. Preferably, communicators 2111 and 2121 comprise communication frequencies within the range of ultrasonic frequency. Preferably, communicators 2111 and 2121 comprise communication frequencies within the range of ultraviolet frequency (embodying herein first communicator means for communicative coupling with essentially each of said plurality of second logic-processor means, and embodying herein second communicator means for communicative coupling with essentially each of said plurality of first logic-processor means). Upon reading the teachings of this specification, persons of ordinary skill in the art will now understand that, considering issues such as location mediums, technology, and cost, other frequencies such as infrared, x-ray, etc., may suffice.

Preferably, First logic-processors 2110 and Second logic-processors 2120 each comprises power source 2160. Preferably, power source 2160 provides electrical power. Preferably, power source 2160 comprises power life extender 2161. Preferably, power life extender 2161 extends the life of power source 2160 by assisting intermittent operation (embodying herein power source means for providing electrical power; and embodying herein power-life-extender means for extending at least one life of said power source means by assisting intermittent operation).

Preferably, first communicator 2111 and second communicator 2121 each operate at a frequency within the range consisting of radio frequency. Preferably, first communicator 2111 and second communicator 2121 each operate at a frequency within the range consisting of ultrasonic frequency. Preferably, first communicator 2111 and second communicator 2121 each operate at a frequency within the range consisting of UV frequency. Preferably, first communicator 2111 and second communicator 2121 each comprise non-continuous signaler 2156. Preferably, non-continuous signaler 2156 (substantially equivalent to 156 of the following Figures) provides for non-continuous communication between First logic-processors 2110, Second logic processors 2120, and receivers 2130. Preferably, first communicator 2111 and second communicator 2121 each comprise optimized signaler 2157 (substantially equivalent to 157 of the following Figures). Preferably, optimized signaler 2157 provides optimized power consumption when generating non-continuous communications (embodying herein non-continuous signaler means for providing non-continuous communications, and embodying herein optimized signaler means for providing optimized power consumption when generating non-continuous communications).

Preferably, First logic-processor 2110 and Second logic processor 2120 each comprise electric circuit 2151. Preferably, electric circuit 2151 processes information. Preferably, electric circuit 2151 comprises firmware 2152. Preferably, firmware 2152 provides for hardware, which can be modified as if it were software. Firmware 2152 is also referred to in the arts as "middleware". Preferably, firmware 2152 can be modified by wireless system 2155 (embodying herein electric circuit means for processing data, embodying herein firmware means for providing modifiable hardware, embodying herein communicatively coupleable with at least one of said plurality of second logic-processor means so that said firmware means of said at least one of said plurality of second logic-processor means may be modified by said first communicator means, and embodying herein communicatively coupleable with at least one of said plurality of first logic-processor means so that said firmware means of said at least one of said plurality of first logic-processor means may be modified by said second communicator means).

Preferably, Receiver 2130 comprises network couplers 2158. Preferably, network couplers 2158 communicatively couples Receiver 2130 to outside networks 2525, as shown. Preferably, outside networks 2525 is accessible to remote data points 2527 over at least public network such as Internet 2526, as shown. Preferably, network couplers 2158 comprise the Internet, Personal Digital Assistants (PDA's), Local Area Networks (LAN's), and Personal Computer Memory Card International Associations (PCMCIA's). Upon reading the teachings of this specification, persons of ordinary skill in the art will now understand that, considering issues such as technology, cost, and efficiency, other network couplers such as radios, cellular phones, personal computers (PC's), etc., may suffice.

Preferably, system 100 can be used in a wide variety of applications such as remotely locating, identifying and tracking people, items, vehicles or other objects particular to the time they pass a certain location, and they can be configured to monitor and adapt to a variety of sensed conditions. This enables system 100 to be configured for use in locating and determining the status of people, equipment, and other items. Such people, equipment, and items may be located in both multistory and underground buildings. Preferably, First logic-processors 2110 and Second logic-processors 2120 provide for data transmission, as well as interpretation of data and instructions from remote sources. Preferably, logic-processors 2110 and 2120 provide for coded transmission between Receiver 2130 and any other sources. Preferably, Receiver 2130 receives, decodes, and presents the information for review, analysis, and determination of appropriate action. Preferably, such information is stored in database 2140. Furthermore with the ability of the Receiver 2130 to send information immediately utilizing wireless system 2155, any information can be delivered in real time to anywhere in the world, all with a single Receiver 2130 or with an arrayed set of identical receivers 2130.

An important aspect of the invention is the modularized nature of the Second logic-processor 2120 and its mechanical and functional versatility. Preferably, it consists of three primary elements, two of which are common to all applications and environments described previously. They are the power source 2160 and the communicator 2121. Preferably, these two connectors are sealed and plug together to achieve an electrical link. Preferably, signal modifiable firmware 2153 can be modified by plugging into connector portions 2131 or 2132, as shown in FIG. 3. Preferably, Second logic-processor 2120 comprises at least two connection portions, whereby first connector portion 2131 is used for programming, and the second connector portion 2132 is used for testing and selecting certain functional options. Preferably, first connector portion 2131 utilizes a ribbon-type connector. Preferably, first connector portion 2131 is located on the portion of Second logic-processor 2120 on which power source 2160 is attached. Preferably, second connector portion 2132 is located on an opposite portion from first connector portion 2131 (as described for first connector portion 131 and second connector portion 132).

Preferably, second connector portion 2132 is used for testing and selecting certain functional options such as transmitter modulation mode, pulse widths, and frequencies. Preferably, additional connector may also be connected utilizing second connector 2132. Preferably, connector portions 2131 and 2132 can have a variety of uses from simply a sealed cap that selects the transmission characteristics and protects the connector when used only for beacon applications, to use as a connector for power source 2160, to a choice of active status sensor 2150 connections that provide information regarding its host, such as power off or power on, door open or door closed, switch up or switch down, temperature hot or temperature cold, light or no light, item moving or nonmoving, etc.

Another key feature of the system is the method by which Second logic-processor 2120, although configured for real time inventory tracking, can be customized for a wide variety of sensing and conditions applications that can all be read together using the same Receiver 2130. Preferably, the method described herein also requires that the content of communication from Second logic-processor 2120 to the Receiver 2130 contain a variable word length and a variable number of words in each transmission, depending on its circumstances and instructions from First logic-processor 2110. This is possible because, preferably, the Second logic-processor 2120, for all these applications, is the same except for its transmission data content and the choice of desired connectors for connector portions 2131 and 2132. Preferably, the data-encoding format is the same for all Second logic-processors 2120 except for the word length, number of words in a transmission and the nature of the encoded information, although these variables are limited to a pre-determined set of options, the option being identified at the beginning of the transmission. Preferably, the Universal Coding Format used in the Second logic-processor 2120's transmissions contain information needed by the decoder to recognize the data as coming from a particular Second logic-processor 2120 configuration. Preferably, the Universal Coding Format provides information regarding the type of the transmission encoding scheme (Transmission Type Code), an application specific group code, a unique Second logic-processor 2120 code, a First logic-processor 2110 code, and a variety of event status or sensor 2150 data bytes, which can each have a different number of bits, or even none at all. Preferably, the nature of the encoded information is programmed into the Receiver 2130 software as a look-up table and identified through the Second logic-processor 2120's individual code. Preferably, database 2140 comprises the encoded information.

The polling scheme can have a variety of features depending on the nature of the application. If the Second logic-processor 2120 is stationary, the polling signal may either be received from a hand held PDA (serving both as a First logic-processor 2110 and a Receiver 2130) in order to have it send its current status and location information immediately instead of at its normal periodic rate, or the polling signal will have been received from a First logic-processor 2110 located in the vicinity. Typically, the latter signal will be ignored when the Second logic-processor 2120 is stationary. It is important that First logic-processor 2110 (whether part of a PDA or a site-located First logic-processor 2110) should have only a limited range so as to address only those Second logic-processors 2120 within a desired range or radius of First logic-processor 2110. Preferably, the transmission scheme is set up to have a maximum bit count for each byte, which may be different for each byte, and a maximum byte count for each word, which may be different for each byte. Preferably, there may be a different number of words in each Second logic-processor 2120 transmission. Preferably, there are only a specific number of different transmission schemes that are defined by the Transmission Type Code, which is programmed into Receiver 2130 memory as a look up table.

FIG. 1-01 provides an overview of the basic system components of system 100. Preferably, Secure Container Monitoring (SCM) 3001 is adapted to provide monitoring of temperature, humidity, motion, gas concentration, radiation levels, and the presence of certain chemicals, biochemicals and other environmental conditions. Preferably, Transponder/Reader 3002 is adapted to read all on-vehicle sensors and either passes selected data to at least one GPS/GSM/GPRS unit 3006 (or stores it for data download), as shown. Preferably, GPS/GSM/GPRS unit 3006 is located within tractor 3004 or trailer 3005; most preferably, at least one GPS/GSM/GPRS unit 3006 is located within both tractor 3004 and trailer 3005. Preferably, Electrical Hook-up Detector (EHD) 3003 detects the electrical hook up and the timing of hook up between tractor 3004 and trailer 3005. Preferably, Engine Sensors (ES) 3007 is be incorporated into preferred embodiments of the system, preferably at tractor 3004, as shown. Preferably, Rear Door Status (RDS) 3008 identifies the condition of the doors and when they are opened and closed. Commonly, trailer 3005 is subdivided into multiple compartments, as shown. The dashed lines of FIG. 1-101 generally indicate the position of such subdivided section, identified herein as Security Container (SC) 3009. Typically, Security Container (SC) 3009 is hung between the rear wheels of trailer 3005 (but may also be located inside the trailer). Preferably, system 100 is adapted to monitor Wheel/Axle components 3010 for pressure, wheel temperature, balance, alignment, vibration, brake condition, bearing lubrication, tire condition. Preferably, Trailer Interior Monitor (TIM) 3011 monitors interior temperature, humidity, motion, atmosphere. Preferably, Deflection and Vibration Sensors (DVS) 3012, combined with load sensors, can predict potential bed failures. Preferably, Trailer Contents Monitoring (TCM) 3013 monitors temperature, humidity, motion, gas concentration, radiation levels, presence of certain chemical and biochemicals atmosphere within trailer 3005. Preferably, Mechanical Hook up Sensor (MHS) 3014 comprises a motion/vibration sensor to identify the hook up to a trailer and the timing of hook up. Preferably, Load Sensor (LS) 3015 measures trailer weight before and after loading or mid-trip load or unload. Preferably, Trailer Refrigeration Sensors (TRS) 3016 are preferably incorporated into preferred embodiments of system 100, as shown.

Figures 1, 2:
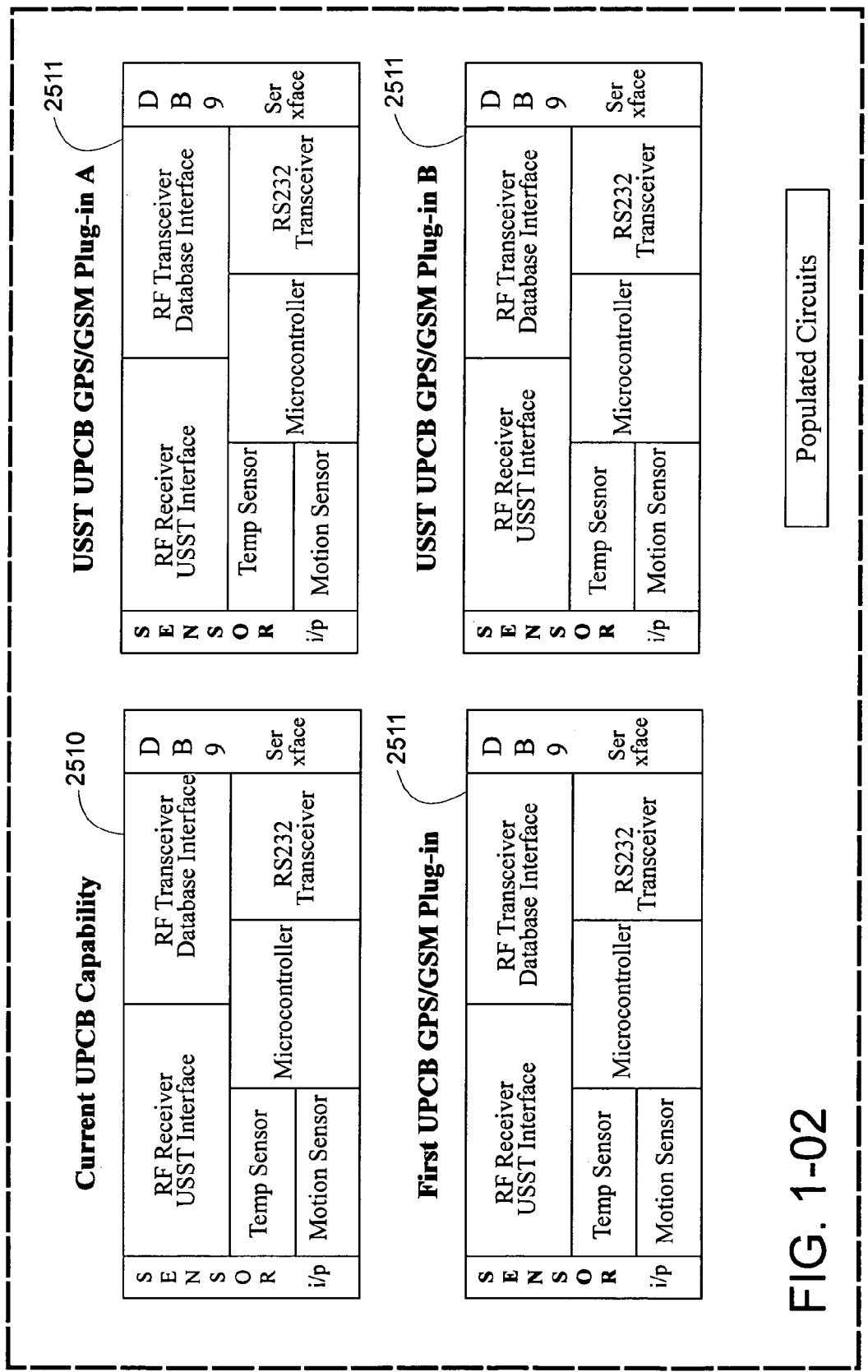
Figures 1, 2, 3:
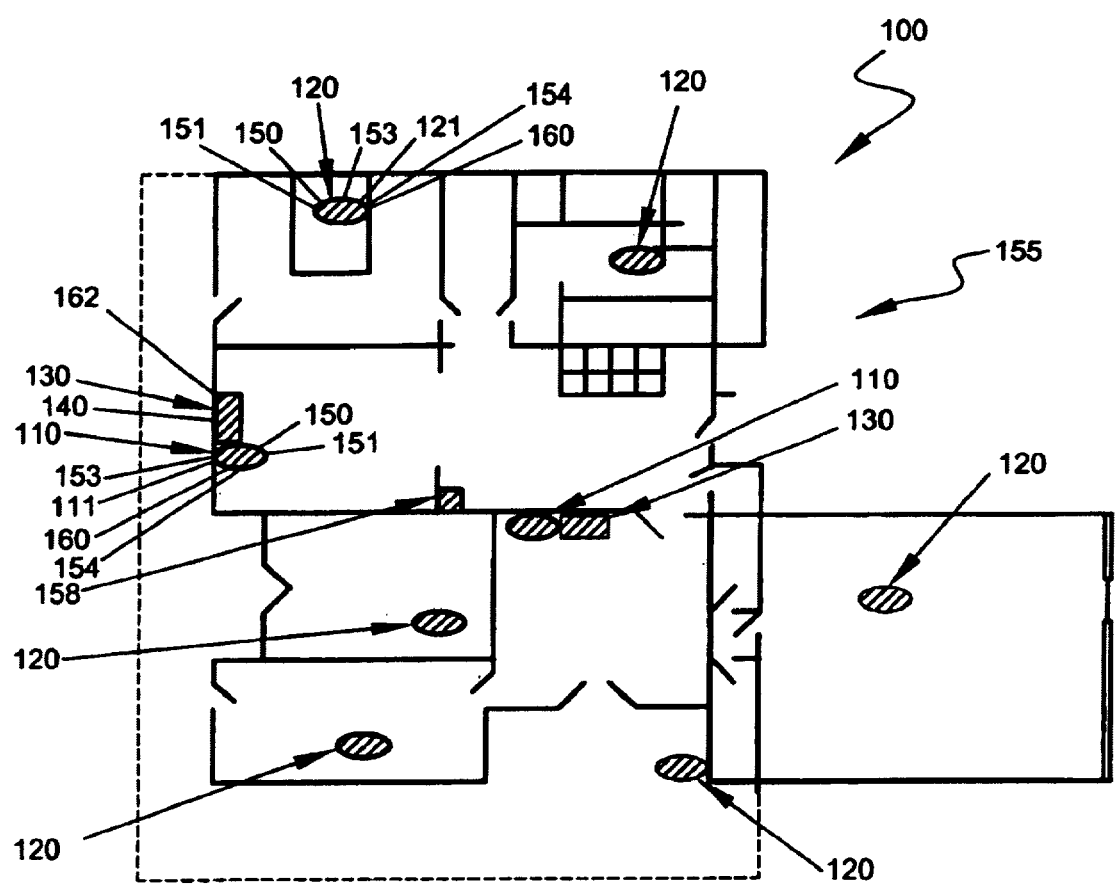

FIG. 1-02 is a diagram of the monitoring system according to a preferred embodiment of FIG. 1-00. Preferably, system 100 comprises a basic UPCB component gouping 2510 comprising at least RF Receiver USST Interface, RF Transceiver Database Interface, Temp Sensor, Motion Sensor, Microcontroller, and RS232. Furthermore, system 100 preferably comprises a set of modular "add-on" USST UPCB GPS/GSM plug-in components 2511, as shown.

FIG. 1-03 is a diagram of the monitoring system according to another preferred embodiment of the present invention. Preferably, system 100 comprises First logic-processors 110, Second logic-processors 120, first communicators 111, and second communicators 121. Preferably, First logic-processors 110 provide logical transaction with receivable information, respectively associated with a plurality of locations within a local area. Preferably, Second logic-processors 120 provide logical transaction with receivable information, respectively associated with a plurality of the items. Preferably, First logic-processors 110 comprise first communicators 111, communicatively coupled with Second logic-processors 120. Preferably, Second logic-processors 120 comprise second communicators 121, communicatively coupled with First logic-processors 110. Preferably, First logic-processors 110 "poll", or transmit signals, to Second logic-processors 120. Preferably, First logic-processors 110 may also "poll" for other First logic-processors 120 (and may sometimes be referred to as "pollers"). However, Second logic-processors 120 may also "poll" for First logic-processors 110, as well as other Second logic-processors 120 (and may sometimes be referred to as "transponders") (embodying herein a plurality of first logic-processor means, for logical transacting with receivable information, respectively associated with a plurality of locations within the local area; and embodying herein a plurality of second logic-processor means, for logical transacting with receivable information, respectively associated with a plurality of the items).

Preferably, system 100 further comprises Receiver 130. Preferably, Receiver 130 receives communicated information from First logic-processors 110. Preferably, Receiver 130 receives communicated information from Second logic-processors 120. Preferably, Receiver 130 receives information resulting from "polling", or signals transmitted between logic-processors 110 and 120 (embodying herein receiver means for receiving communicated information from at least one of the group consisting essentially of each of said plurality of first logic-processor means and each of said plurality of second logic-processor means). Preferably, both First logic-processors 110 and Second logic-processors 120 may comprise Receivers 130.

Preferably, Receiver 130 comprises wireless receptor 162. Preferably, wireless receptor 162 receives wireless communications. Preferably, Receivers 130 comprise 16-bit digital attenuators that can be controlled by the on-board microprocessor either as a result of wireless or wired instructions from the control center in the case of Receivers 130, or instructions from a logic-processor 110 or 120, or a PDA in the case of a Second logic-processor. Furthermore, the microprocessor in each case can automatically increase the level of attenuation and reduce the read range if the signal density reaches a point that collisions can occur causing an excessive level of data errors. A further alternative in the case of First logic-processors 110 and Second logic-processors 120 is to reprogram the First logic-processors 110 or Second logic-processors 120 set attenuation level, on site, using the ribbon cable programming option. Preferably, wireless receptor 162 is structured to enhance sensitivity to signals intended for reception by wireless receptor 162 (embodying herein wireless receptor means for receiving communicated information). Preferably, system 100 further comprises database 140. Preferably, database 140 manipulates the information communicated between Receiver 130, First logic-processor 110, and Second logic-processor 120 (embodying herein database means for manipulating such receivable information).

Preferably, first communicators 111 and second communicators 121 each comprise wireless systems 155. Preferably, wireless systems 155 provide for wireless communication of information (embodying herein wireless system means for wirelessly assisting communicative coupling). Upon reading the teachings of this specification, persons of ordinary skill in the art will now understand that, considering issues such as technology, cost, and efficiency, other wireless systems such as infrared, ultraviolet, acoustic, magnetic, non-radio, etc., may suffice. Preferably, First logic-processors 110 and Second logic-processors 120 each comprise identifiers 154. Preferably, identifier 154 uniquely identifies each of the First logic processors 110. Preferably, identifier 154 uniquely identifies each of the Second logic processors 120 (embodying herein identifier means for uniquely identifying essentially each one of said plurality of first logic-processor means and essentially each one of said plurality of second logic-processor means).

Preferably, system 100 further comprises sensor 150. Preferably, sensor 150 senses local information. Preferably, sensor 150 senses local information attachable to at least one subset First logic-processors 110. Preferably, sensor 150 senses local information attachable to at least one subset of Second logic-processors 120 (embodying herein sensor means, for sensing local information, attachable to at least one subset of at least one of the group consisting essentially of each of said plurality of first logic-processor means and each of said plurality of second logic-processor means). Upon reading the teachings of this specification, persons of ordinary skill in the art will now understand that, considering issues such as efficiency, technology, and cost, other wireless systems may suffice.

Preferably, communicators 111 and 121 comprise communication frequencies of light or sound, which may travel unobstructed between First logic-processors 110, Second logic-processors 120, receivers 130, and other transmitting and receiving sources. Preferably, communicators 111 and 121 comprise communication frequencies within the range of radio frequency. Preferably, communicators 111 and 121 comprise communication frequencies within the range of ultrasonic frequency. Preferably, communicators 111 and 121 comprise communication frequencies within the range of ultraviolet frequency (embodying herein first communicator means for communicative coupling with essentially each of said plurality of second logic-processor means, and embodying herein second communicator means for communicative coupling with essentially each of said plurality of first logic-processor means). Upon reading the teachings of this specification, persons of ordinary skill in the art will now understand that, considering issues such as location mediums, technology, and cost, other frequencies such as infrared, x-ray, etc., may suffice.

Preferably, First logic-processors 110 and Second logic-processors 120 each comprises power source 160. Preferably, power source 160 provides electrical power. Preferably, power source 160 comprises power life extender 161. Preferably, power life extender 161 extends the life of power source 160 by assisting intermittent operation (embodying herein power source means for providing electrical power; and embodying herein power-life-extender means for extending at least one life of said power source means by assisting intermittent operation).

Preferably, first communicator 111 and second communicator 121 each operate at a frequency within the range consisting of radio frequency. Preferably, first communicator 111 and second communicator 121 each operate at a frequency within the range consisting of ultrasonic frequency. Preferably, first communicator 111 and second communicator 121 each operate at a frequency within the range consisting of UV frequency. Preferably, first communicator 111 and second communicator 121 each comprise non-continuous signaler 156. Preferably, non-continuous signaler 156 provides for non-continuous communication between First logic-processors 110, Second logic processors 120, and receivers 130. Preferably, first communicator 111 and second communicator 121 each comprise optimized signaler 157. Preferably, optimized signaler 157 provides optimized power consumption when generating non-continuous communications (embodying herein non-continuous signaler means for providing non-continuous communications, and embodying herein optimized signaler means for providing optimized power consumption when generating non-continuous communications).

Preferably, First logic-processor 110 and Second logic processor 120 each comprise electric circuit 151. Preferably, electric circuit 151 processes information. Preferably, electric circuit 151 comprises firmware 152. Preferably, firmware 152 provides for hardware, which can be modified as if it were software. Firmware 152 is also referred to in the arts as "middleware". Preferably, firmware 152 can be modified by wireless system 155 (embodying herein electric circuit means for processing data, embodying herein firmware means for providing modifiable hardware, embodying herein communicatively coupleable with at least one of said plurality of second logic-processor means so that said firmware means of said at least one of said plurality of second logic-processor means may be modified by said first communicator means, and embodying herein communicatively coupleable with at least one of said plurality of first logic-processor means so that said firmware means of said at least one of said plurality of first logic-processor means may be modified by said second communicator means).

Preferably, Receiver 130 comprises network couplers 158. Preferably, network couplers 158 communicatively couples Receiver 130 to outside networks. Preferably, network couplers 158 comprise the Internet, Personal Digital Assistants (PDA's), Local Area Networks (LAN's), and Personal Computer Memory Card International Associations (PCMCIA's). Upon reading the teachings of this specification, persons of ordinary skill in the art will now understand that, considering issues such as technology, cost, and efficiency, other network couplers such as radios, cellular phones, personal computers (PC's), etc., may suffice.

Preferably, system 100 can be used in a wide variety of applications such as remotely locating, identifying and tracking people, items, vehicles or other objects particular to the time they pass a certain location, and they can be configured to monitor and adapt to a variety of sensed conditions. This enables system 100 to be configured for use in locating and determining the status of people, equipment, and other items. Such people, equipment, and items may be located in both multistory and underground buildings. Preferably, First logic-processors 110 and Second logic-processors 120 provide for data transmission, as well as interpretation of data and instructions from remote sources. Preferably, logic-processors 110 and 120 provide for coded transmission between Receiver 130 and any other sources. Preferably, Receiver 130 receives, decodes, and presents the information for review, analysis, and determination of appropriate action. Preferably, such information is stored in database 140. Furthermore with the ability of the Receiver 130 to send information immediately utilizing wireless system 155, any information can be delivered in real time to anywhere in the world, all with a single Receiver 130 or with an arrayed set of identical receivers 130.

An important aspect of the invention is the modularized nature of the Second logic-processor 120 and its mechanical and functional versatility. Preferably, it consists of three primary elements, two of which are common to all applications and environments described previously. They are the power source 160 and the communicator 121. Preferably, these two connectors are sealed and plug together to achieve an electrical link. Preferably, signal modifiable firmware 153 can be modified by plugging into connector portions 131 or 132, as shown in FIG. 3. Preferably, Second logic-processor 120 comprises at least two connection portions, whereby first connector portion 131 is used for programming, and the second connector portion 132 is used for testing and selecting certain functional options. Preferably, first connector portion 131 utilizes a ribbon-type connector. Preferably, first connector portion 131 is located on the portion of Second logic-processor 120 on which power source 160 is attached. Preferably, second connector portion 132 is located on an opposite portion from first connector portion 131.

Preferably, second connector portion 132 is used for testing and selecting certain functional options such as transmitter modulation mode, pulse widths, and frequencies. Preferably, additional connector may also be connected utilizing second connector 132. Preferably, connector portions 131 and 132 can have a variety of uses from simply a sealed cap that selects the transmission characteristics and protects the connector when used only for beacon applications, to use as a connector for power source 160, to a choice of active status sensor 150 connections that provide information regarding its host, such as power off or power on, door open or door closed, switch up or switch down, temperature hot or temperature cold, light or no light, item moving or nonmoving, etc.

Another key feature of the system is the method by which Second logic-processor 120, although configured for real time inventory tracking, can be customized for a wide variety of sensing and conditions applications that can all be read together using the same Receiver 130. Preferably, the method described herein also requires that the content of communication from Second logic-processor 120 to the Receiver 130 contain a variable word length and a variable number of words in each transmission, depending on its circumstances and instructions from First logic-processor 110. This is possible because, preferably, the Second logic-processor 120, for all these applications, is the same except for its transmission data content and the choice of desired connectors for connector portions 131 and 132. Preferably, the data encoding format is the same for all Second logic-processors 120 except for the word length, number of words in a transmission and the nature of the encoded information, although these variables are limited to a predetermined set of options, the option being identified at the beginning of the transmission. Preferably, the Universal Coding Format used in the Second logic-processor 120's transmissions contain information needed by the decoder to recognize the data as coming from a particular Second logic-processor 120 configuration. Preferably, the Universal Coding Format provides information regarding the type of the transmission encoding scheme (Transmission Type Code), an application specific group code, a unique Second logic-processor 120 code, a First logic-processor 110 code, and a variety of event status or sensor 150 data bytes, which can each have a different number of bits, or even none at all. Preferably, the nature of the encoded information is programmed into the Receiver 130 software as a look-up table and identified through the Second logic-processor 120's individual code. Preferably, database 140 comprises the encoded information.

The polling scheme can have a variety of features depending on the nature of the application. If the Second logic-processor 120 is stationary, the polling signal may either be received from a hand held PDA (serving both as a First logic-processor 110 and a Receiver 130) in order to have it send its current status and location information immediately instead of at its normal periodic rate, or the polling signal will have been received from a First logic-processor 110 located in the vicinity. Typically, the latter signal will be ignored when the Second logic-processor 120 is stationary. It is important that First logic-processor 110 (whether part of a PDA or a site-located First logic-processor 110) should have only a limited range so as to address only those Second logic-processors 120 within a desired range or radius of First logic-processor 110. Preferably, the transmission scheme is set up to have a maximum bit count for each byte, which may be different for each byte, and a maximum byte count for each word, which may be different for each byte. Preferably, there may be a different number of words in each Second logic-processor 120 transmission. Preferably, there are only a specific number of different transmission schemes that are defined by the Transmission Type Code, which is programmed into Receiver 130 memory as a look up table.

FIG. 2-00 is a perspective view of a First logic-processor 110 according to a preferred embodiment of the present invention. Preferably, system 100 comprises First logic-processors 110. Preferably, First logic-processors 110 comprise first communicators 111, communicatively coupled with second logic-processors 120.

Preferably, each First logic-processor 110 can be programmed to send out a transmission that includes the ID of a specific Second logic-processor 120 (and/or First logic-processor 110) and each Second logic-processor 120 can be programmed to respond only if their ID is contained in a received transmission or only respond to certain preprogrammed instructions or only to respond to certain of the instructions transmitted to it by the First logic-processor 110. Preferably, First logic-processor 110 provides a security benefit by alerting authorities to the presence of a certain item in a limited access location or unauthorized removal from a location or from the building, for example, removal from a hospital of life support equipment from an area in which it is required to remain. Another example would be the operation of equipment in an unauthorized location or location intended only for storage of the equipment when not in use. Multiple pieces of the same equipment in the same location may also be an undesirable situation that can be prevented with this system, as can equipment limited to adult use, which should not be present in a children's ward. In addition, this precvention may apply to equipment that should not be used near pregnant women and hence should not be present in a maternity ward, or similar requirements in quarantined areas. Another example of use is to alert of danger that may develop if an item is moved into an area or next to another piece of equipment or person, such as oxygen or other flammable gas near an open flame or potential static sparks.

FIG. 2-01 shows the Second logic-processor 120 Second logic-processor circuit schematic with the micro-controller part 001 and the transmit hybrid TX5000 part 002. A polling Receiver 006 consisting of the tuned circuit L4 and C7, rectifier D2 and load R4. Preferably, all logic-processors 110 and 120, and Receivers 130, have the capability of transmitting and receiving in different modulation schemes for example OOK (on/off keying) or ASK (amplitude sequenced keying). The mode can be selected during the assembly process, on site, for the logic-processors 110 or 120, by attaching a cap 1121 or a sensor 150 that mechanically sets the mode. However, this can also be controlled by the microprocessor via the remote instruction method as used for setting the attenuation level. Alternatively, either system component can have two transmitters or in the case of the Reader, two receivers, one set continually for OOK modulation and the other ASK, thus providing simultaneous transmission and reception of both modes.

A resistor network 003 provides the means for onboard selection of either OOK or ASK modulation by inserting zero ohm resistors R6 and R9, or R7 and R8, respectively. Alternatively, all four of these resistors can be omitted and off board modulation decision can be made with connectors J1-9 and J1-10, shown by 004. Circuit 005 and other J2 pins provide the ability for on-board programming or subsequent reprogramming. A simple First logic-processor 006 consists of the tuned circuit L4 and C7, rectifier D2 and load R4 and a polling reception indicator 007 comprising an LED D1 that is also a means of determining battery condition by reading the voltage at the node between R3 and D1 at the micro-controller pin 2 via R6 when the LED is turned on by the polling reception signal. Also, an on-board temperature sensor 008 consists of Q1 and R5.

Preferably, the connector J1, 009, provides the connections to the power connector or power ribbon cable and also provides the connections for on-board programming and testing. Connector J2, 010 provides connections for Second logic-processor 120 testing, modulation selection and, where the application calls for it, connections to the sensor connector, sensor ribbon cable or Receiver 130 connector for coded signals. Connector 011 provides a connection for an internal flexible whip antenna that wraps around the inside of the Second logic-processor case or, in some applications, can protrude through a water tight slit in the case to provide improved range. The micro-controller (PIC16LF876A or equivalent) also has built-in temperature sensing and battery condition monitors; but when other micro-controllers are used to optimize performance that do not have these features, these alternate options are available or they can be used to provide an alternate input on these parameters.

FIG. 2-02 shows the layout of the topside of the Second logic-processor PCB 012, the Modulation Selector/Sensor connector 013, and the Power Connector/Reprogramming connector 014. A via, 015 (J3), is the flexible whip antenna connector.

FIG. 2-03 shows the layout of the bottom side of the Second logic-processor PCB 012 showing the on-board OOK/ASK selection network 016.

FIG. 2-04 shows the transmission pulse timing when OOK modulation is used. The time slot 017 is 200 uS wide and a "0" bit 018 is 40 uS wide pulse, significantly less than 50% of the time slot, while a "1" bit 019 is represented by four consecutive 40 uS wide pulses (one 160 uS pulse) that is significantly more than 50% of the time slot. One example of the use of this transmission scheme is a byte than consist of a start bit 160, a couple of sets of data bits 161 and 162, a parity bit 163 and two stop bits 164, all of this making up a word. The word may be transmitted several consecutive times (three in the example) in cases where the Receiver 130 is required to identify a word two or three times before accepting the data.

FIG. 2-05a and FIG. 2-05b show a diagram of the transmission encoding method. It shows a maximum of 80 time slots or bits, 030. Bit 1, 019, is the start bit and always a "one" followed by a five-bit byte, 020, that defines the Transmission Type, how many bytes make up the transmitted word and how many bits are in each byte. This is followed by a three-bit group code 021. These three "bytes" always make up the first nine bits transmitted. This is followed by the unique Second logic-processor code 022 that can be a byte with as many as 16 bits and a Polling code 023 with as many as 5 bits. Following this are five status or data bytes 024, 025, 026, 027, 028, each of which can have as many as eight bits. Following that there is a parity or CRC byte 029 that can have as many as 8 bits followed by two stop bits 031, both "zeros". FIG. 2-05a and FIG. 2-05b show the full eighty time-slots and the black fill shows the slots where there are transmissions. The white slots show no bits being transmitted and in the actual implementation these slots are eliminated, as shown by 032, 033, 034, 045, 036 and 037; that is why a preceding byte is needed to identify which bytes are included in the transmission and how many bits each has. This word will be transmitted several times with an interval in between that is determined by the word length and the specific nature of the application.

The polling 038 and data 039, 040, 041 bytes can consist of only one bit. In the polling case a "one" bit indicates that the Second logic-processor 120 is transmitting because of a polling instruction, a "zero" indicates that the Second logic-processor 120 transmitted according to its programmed periodicity (not polled). In the case of data bytes a single byte indicates status of a sensed input, zero or one (low or high), indicating that its monitored location is on or off, open or closed, above or below a limit, within a pair of limits or outside, or any other condition that can be represented by a single bit.

A polling byte 042 of more than one bit indicates the Second logic-processor 120 is transmitting because of a coded polling instruction and the byte represents that code. The Second logic-processor 120 can also be programmed without a polling bit at all and this indicates that the Second logic-processor 120 does not have a polling function. For other data bytes that have more than one bit, the byte represents actual data such as temperature, pressure, acceleration and humidity, or characteristics of a magnetic field, radioactivity, water quality, air contaminants or life signs, and information from thermostats, fire, smoke or security alarms. If less than five inputs are being monitored the "empty" bytes are eliminated. The Transmission Type Code includes information on the exact nature of each data byte, specifically what it represents and the bit to parameter magnitude relationship, i.e., degrees per bit, psi per bit, gauss per bit, etc., and the range of that parameter. The byte can also be used to represent a variation from a "par" value or a rate of change.

FIG. 2-06 describes a Second logic-processor 120 firmware 152 proposal for a specific application.

FIG. 2-07 describes a set of Second logic-processor 120 Transmission Periodicity Decision Tables that show a Sensor Sampling Plan and Transmission Periodicity options that might apply to a Truck Wheel Monitoring application.

FIG. 2-08 describes a set of Second logic-processor 120 Transmission Periodicity Decision Tables that show a Sensor Sampling Plan and Transmission Periodicity options that might apply to Home and Building applications. Preferably, both First logic-processors 110 and Second logic-processors 120 have the programmed capability to establish their own sampling rates and statistical analysis methods to determine the normal or typical sensed conditions of the environment, preferably the steady-state environment, in terms of absolute values, rate of change of these values and the relationships of the various sensed parameters being monitored by the First logic-processor or Second logic-processor. The result of this analysis may result in the onboard microprocessor changing the sampling rates for one or more sensors, increasing the size of a sample for one or more sensors, switching to a different analysis algorithm and determining an appropriate transmission schedule, power level and even modulation scheme.

FIG. 2-09 shows a typical Second logic-processor 120 firmware 152 flow chart for a nominal application.

FIG. 2-10a and FIG. 2-10b illustrate the various Second logic-processor 120 configuration options such as frequency, modulation mode, polling and firmware 152 options.

FIG. 2-11 and FIG. 2-12 show the means by which the test, programming and external sensor cables, and any plug in sensor or special purpose connector, include connections that select whether the Second logic-processor 120 transmits an OOK modulated signal or an ASK modulated signal, further adding to the versatility of the LITMIS product that allows field programming and field configuration, in order to optimize the system's performance for each application. In FIG. 2-27 the transmitter hybrid TX5000 01 can be connected either to operate in an OOK modulation mode or an ASK modulation mode depending on whether the transmit enable connection from the micro-controller is connected to the TX5000 pin 17 or pin 18 (the unconnected pin is grounded). To achieve this for OOK modulation, the connection (cable or connector) to the Second logic-processor 06 has four of its pins connected so that the Second logic-processor connections 02 and 03 are connected (grounding TX5000 pin 17) and connections 04 and 05 are connected (connecting TX5000 pin 18 to the micro-controller Transmit enable pin). FIG. 2-28 shows the ASK modulation where the connection (cable or connector) to the Second logic-processor 06 has four of its pins connected so that the Second logic-processor connections 02 and 04 are connected (grounding TX5000 pin 18) and connections 03 and 05 are connected (connecting TX5000 pin 17 to the micro-controller Transmit enable pin).

FIG. 2-13 shows one form of a Sensor connector where 043 is a temperature sensor, which could be a thermistor; 044 illustrates a bridge form of sensor that could be a pressure or a wide variety of bridge type sensors. The sensors are supplied by power from a voltage regulator 045 and the sensed voltages are amplified by operational amplifiers 046 and fed to comparators 047, whose outputs are delivered to the Second logic-processor 120 microprocessor.

FIG. 2-14 shows diagrams of possible designs for Second logic-processor 120 plug-in sensors; 048 shows a moisture testing probe that can be pushed into the soil and the tip of the probe has "pores" which allow a moisture sensor inside the probe to obtain a reading of relative moisture level. The Second logic-processor 120 with its power connector is simply plugged into the probe connector which includes the standard OOK or ASK selection function and other standard interconnections between sensor connectors and the Second logic-processor such as power and data lines, as well as the standard latching and sealing mechanisms. The floating pool sensor consists of a float 049 and a sensing unit 050 on the end of a "snorkel", where the sensing unit can contain a variety of elements to monitor pH, Chorine content, hardness and sensors that evaluate the water for possible dangerous contaminants. It is noted that the multi-parameter sensing unit could be built into the water filtration system in which case the Second logic-processor 120 would simply snap on to it in a similar manner to the moisture probe. An alternative form of the floating sensor would include a motion or vibration sensor (accelerometer) inside the submerged housing 051 that would provide information on momentary or sustained turbulence that might indicate something had fallen into the pool such as a small child or an elderly person.

Item 052 is a typical security sensor that detects movement of people or objects in its vicinity but designed as a plug-in Second logic-processor 120 connector; 053 is a connector that picks up polling signals; 054 monitors the status (open, open by how much or closed) or changing status (opening or closing) of doors, windows, containers, mail boxes, safes, vaults, etc; 055 represent safety monitors such as heat, fire, smoke, allergens and the presence of other harmful conditions designed as a plug-in Second logic-processor 120 connector; 056 a radioactive sensor, 057 a wind velocity sensor, 058 a rain gauge and 059 a blood pressure or pulse rate monitor. This latter application can be expanded to include anything monitoring life signs of chronically ill patients, particularly ambulatory patients who may not be under the constant care of another individual.

FIG. 2-15 shows a water Quality sensor that could be used in a pool monitoring application checking pH, chlorine concentration, hardness, etc. This Sensing Second logic-processor 120 could also include a vibration sensor that could be used to monitor water turbulence. Preferably, the Second logic-processor 120 would be programmed to sample and analyze to identify sudden changes in turbulence, typical of a person or animal falling into the pool and struggling to get out. The Receiver 130 would be programmed to distinguish between normal pool usage and unintended entry into the pool. Furthermore, the system is designed to receive information from multiple sources and analyze relationships. Children or elderly people using a pool or likely to be in the vicinity of a pool or pond could have a wrist or ankle Second logic-processor 120 with a submersion sensor that would provide further input, and a polling Receiver 130 that would provide location input when passing through a pool gate or leaving the house. Depending on how the Water Monitoring Second logic-processor 120 was situated in the pool it could also include a physical or magnetic pool level indicator.

FIG. 2-16 and FIG. 2-17 show heart beat characteristics that would be monitored by a Second logic-processor 120 attached to young babies, the elderly or chronically ill patients, along with other important life signs. Each EKG heartbeat has four positive-going voltage changes to peaks 060, 063, 069, and 068, two transition from below and cross zero volts 063 and 069; the phase of these two different wave sections can also be recorded. The fourth 068 is the start of a second heartbeat waveform P. Each heartbeat has three positive amplitudes 060, 063, and 069. These three analog parameters would be monitored and analyzed. In addition timing criteria 061, 064, 065 and the timing of the peaks 060, 063, and 069 would also be monitored. Sampling would establish norms for absolute values and the relative rate change of these characteristics which, when compared to absolute values, rate of change of values and comparison between characteristics as described in FIG. 2-08, permits anomalies requiring urgent attention to be identified.

In order to provide an effective interface between sensors of this sort and the Second logic-processor 120 microprocessor when measuring heart beat amplitudes such as R, the times are measurable from the moment the positive-going edge of R crosses zero (a little after Q) to the time the positive waveform T returns to zero, and the time from the moment one positive-going edge of R crosses zero to the same place on the "next" waveform R. This EKG Second logic-processor 120 interface connector may also include a clock, counter and timer, zero-crossing detectors, phase-angle detectors, comparators, amplitude measurements, memory and analog to digital coding. Further since "spike" R has the highest (steepest) phase angle and amplitude of the three positive wave sections in a heartbeat, this zero-crossing arid steep phase-angle (representing part of a "high" frequency waveform vs. the "low" frequency of the P and T waves) combination can be used as a start time. The negative-going wave sections from this time can be monitored and counted (Q to S, continuing through T). From start time to when the second wave section T returns to zero is the second parameter. The amplitude of all positive waveforms can be sampled, stored and counted; if the second positive waveform also has the highest phase-angle and amplitude this is R and can be can be coded.

FIG. 2-18 shows such an interface with an oscillator, timing, A/D converters, voltage reference, comparators, logic, and some memory that can also provide voltage or current to sensors. Each such interface can handle or control either one analog input/detector at a time; or with multiplexing up to six such sensors.

FIG. 2-19 shows a means for detecting the removal of a wrist or ankle Second logic-processor 120 used in instances described above. The Second logic-processor 120 Connector 070 is connected to the Power Connector 071 by a conductor 072 which passes through a clasp 073 returns to and passes under 070 around the other side of the wrist or ankle 074, to and passes under 071 back to other section of the clasp and then returns to the Power connector 071. This design makes it impossible to remove the Second logic-processor 120 from the wrist without interrupting the power supply, either by unlatching the clasp or by cutting the conductive band 074. The Second logic-processor 120 has a power storage capacitor adequate to send a final transmission when power is disconnected. A final transmission of this nature has an added bit indicating the removal of power. This data bit will remain attached to transmissions until reset, to identify removal and perhaps reconnection to another person, or simply tossed aside to sabotage tracking and monitoring functions. The key to the continuity concept is demonstrated in the Clasp Detail 075. A 4-pin plug connects to a matching 4-pin socket enabling the power wiring to cross from one to the other and return, a process that occurs both for the connection between 070 and 073, as well between 071 and 073.

FIG. 2-20 shows a system installed in a home, monitoring it for a broad range of characteristics. A single Receiver 076 placed in a central location and can receive and decode transmissions from any Second logic-processor 120 attached to any combination of sensors located on the property inside or outside the home. A fireplace 077 in the living room is monitored by Second logic-processor 078, which has temperature and smoke sensors. This may also monitor the concentration of combustion products and toxicity vapors. Similar Second logic-processor 079 and 081 are shown placed by fireplaces 080 and 082. In the event these fireplaces are gas operated, the Second logic-processor would also monitor for natural gas or propane leaks. The master bedroom Second logic-processor 120 083 would monitor in a similar manner, but in this case perhaps sensing for smoldering caused by an improperly discarded cigarette or a poorly placed candle. There could be a Second logic-processor attached to a set of life signs sensors on an elderly or chronically ill patient. Second logic-processor 084 would similarly monitor bathroom conditions but could also monitor for bath or toilet overflows or electrical problems such as shorts or ground fault over loads. Second logic-processor 085 is located in the dining room and may have an added sensor to monitor a food warmer or might monitor a normally locked china or silver cabinet for security purposes. The kitchen Second logic-processor 086 would likely have a variety of sensors with a separate Second logic-processor 120 by each appliance. With a gas range it would include a sensor for gas leaks while an electrical range would have an overload detector. Other bedroom Second logic-processor 087, 088, and 089 would be customized for the occupant, perhaps detecting for allergens, molds, bacteria or other airborne threats. Second logic-processor 090 is located outside the house perhaps by a barbeque sensing for propane leaks in addition to the temperature and other sensors. Second logic-processor 091 in the garage would sense for the same parameters as other sensors, but might also include a gasoline sensor, workbench electrical shorts and ground fault overloads. A vehicle-mounted Second logic-processor could monitor tire pressures and battery condition, alerting the owner ahead of time to a potential flat tire or dead battery in the morning. Other Second logic-processors can be monitoring movement in each room, opening and closing doors and windows, be connected to thermostats and conventional security and safety devices like fire and smoke alarms, even monitoring such obscure criteria like termite or carpenter ant infestations. Other Second logic-processors may be employed with sensors that can monitor, pool and garden gates, pools and ponds, mailboxes, even the moisture level in the soil for irrigation optimization. Solar heating systems, wind force, and earth tremors can be similarly monitored. City water can be monitored for purity and freedom from biological contaminants and for sudden surges that might indicate a leak or burst pipe when compared with motion sensors that show no one is in the house. Similarly, surges in electricity or gas usage could detect shorts or gas leaks; aand there is again the benefit of comparison with temperature rise, detection of combustion products or the detection of a high natural gas or propane concentration in the air.

FIG. 2-21 shows a high Yagi Antenna specification for achieving a desired read range.

FIG. 2-22 shows a building application with a centrally located Receiver 092 that locates Second logic-processors 093 and 094 that move, or may move, around the building, by locating fixed, coded, location First logic-processor 110 by each doorway 096, periodically along corridors 097 and at stairwells. As the moving Second logic-processor passes within the very limited range of this directional First logic-processor, it receives and decodes the polling signal, adding that code to its own. The same Receiver 130 can receive signals from other Second logic-processors monitoring various building conditions such as doors open or closed, lights on and off or the status of other items 095.

FIG. 2-23 shows a building outfitted with First logic-processor 102 that can be used to locate people, Laptop computers and other tagged assets as the move, are relocated or removed from rooms or the building, or even from one floor of the building to another. Pollable Second logic-processor 101 will pickup, extract the First logic-processor's location identification code and add it to its own identification code which it then transmits to the Receiver 103. The First logic-processor might also include an additional bit to notify the control center of the transmission, status of each door (open or closed) or even whether the light is on in the room. The key here is the very short range and directionality of the First logic-processor, that are simply another version of a Second logic-processor, with a lower power transmitter and a directional antenna where required. The Second logic-processors have been designed to be able to switch frequencies by simply a change of Transmitter hybrid component or by replacing it by a frequency programmable transmitter.

FIG. 2-24 shows a similar application to FIG. 2-23 except in this case the doorway connectors are sensing Second logic-processors, identifying open and closed doors, lights on or off, and other conditions, and transmitting the data to the Receiver 105 periodically or immediately when a change in status occurs. Preferably, the Second logic-processors, which can also be read by the Receiver, would likely be a used just for identification purposes and perhaps to provide its own sensor information. It should be noted throughout these applications that the read range of the Receiver can be programmed to limit the field being monitored. There is 16-bit remotely programmable attenuator in the Receiver before the radio frequency Receiver circuit that is used to define the read range.

FIG. 2-25 shows a Responder version of the Second logic-processor. In this application the components are only included in circuit 098 if the First logic-processor is intended to operate only when it recognizes that a Second logic-processor with a short pulse beacon is within range, it which case it will transmit its information, and where applicable its instructions, before shutting down. For First logic-processor without this circuit populated, they are programmed to transmit intermittently. As a First logic-processor 110 the temperature monitoring circuit 099 is normally not populated but in some applications temperature, or temperature history, may be part of the information to be relayed by the Second logic-processor back to the Receiver, since the Responder has only a very short range, or may be operating on a different frequency that the Receiver. An example of this application might be a Responder that is monitoring an environment but there is no requirement to send this information directly to the Receiver, or it's not practical to do so, or the information is only important when a short pulse beacon Second logic-processor is in the vicinity. The Responder transmitter hybrid 1100 can in some circumstances have the same frequency as the Second logic-processor, but in the majority of applications it would operate at a different frequency (list in FIG. 2-10) or it may preferably operate at about 13.56 MHz, or a lower frequency.

FIG. 2-26 shows an example of a control center display such as might be used in the application show in FIG. 2-24. In this case, each sensing Second logic-processor is designed to sense five conditions (this is an example of a one bit sensor response). A total of twenty Second logic-processors are each monitoring five conditions such as doors, drawers, switches and other conditions open or closed, off or on, etc. The display identifies the Group Code, as there may be more than one company using the building in which case the display might be password protected to show only a particular Group Code. The next column identifies the unique Second logic-processor code, followed by the status of each of the five conditions being monitored. A red entry indicates a change from the previous reported status and a bold line indicates that the Second logic-processor 120 is not reporting and shows the last received status. The display also provides other pertinent information. Instead of this template, a building plan could be used similar to FIG. 2-24 and the door, drawer, lights, etc., could be shown actually open or closed, on or off, and a change highlighted in red and an un-read situation in another color. This could also be used where other Second logic-processors are being monitored (such as location tags), in which case the monitoring could include location and movement around the building. Other conditions, such as temperature, natural gas concentrations and the like, can also be monitored if the appropriate Second logic-processor 120 is installed.

FIG. 2-27 shows a system block diagram of a pollable Second logic-processor 1107, a Receiver 1108 and the polling First logic-processor 1110. The First logic-processor can either instruct the Second logic-processor to send its data immediately or provide other instructions. As in other system configurations, the Receiver 1102 decodes and further analyzes the data before periodically sending the information on to a control center 1103 PC or PDA. If an anomaly is confirmed, it will send data immediately to whichever prescribed phone number or LAN address is indicated for that particular event.

FIG. 2-28 shows a system block diagram of a Second logic-processor 1101 and Receiver 1102 with two-way communication. In this case the Receiver can provide the Second logic-processor with polling or other instructions instead of a separate polling transmitter. The benefit of this type of system is that it provides the Receiver with the ability to interrogate the Second logic-processor when it detects a problem but needs to modify the collection of further data. It also leads to the ability of introducing sensor connectors 1106 that also provide control functions when called for. As in other system configurations, the Receiver 1102 decodes and further analyzes the data before periodically sending the information on to a control center 1103 PC or PDA. If an anomaly is confirmed, it will send data immediately to whichever prescribed phone number or LAN address is indicated for that particular event. The transceiver feature also provides the ability for the control center, that always has two-way communication with the Receiver, to send instructions to the Second logic-processor via the Receiver 130 that then serves as a two-way relay or repeater between the person receiving the data and the monitoring (and control) Second logic-processor. The Second logic-processor's radio frequency section in this case has the normal radio frequency hybrid transmitter replaced by a Transceiver hybrid 1105 and similarly for the Receiver 130's radio frequency receiver section 1104.

FIG. 2-29 is a view of a sensing Second logic-processor. In this application, the power connector 1105 and sensor connector 1106 each plug directly into the Second logic-processor 1107. The attachment cleats 1108 can still be used for connection to the host.

FIG. 2-30 is an exploded view of the flat sensing Second logic-processor again showing power connector housing 1109, power connector battery insert 1110, housing for the Second logic-processor 1111, Second logic-processor electronics 1112, sensor electronics 1113 and the sensor connector housing 1114. Other features shown are the sensor connector multi-pin plug 1115, matching Second logic-processor multi-pin socket 1116 and socket 1117 (for power connector attachment) and power connector plug 1118.

FIG. 2-31 is view of the basic Second logic-processor consisting of the power connector 1119 plugged into Second logic-processor 1120. In this case, a snap cap 1121 is used to seal the unused sensor connector socket. There are several versions of this cap: one being a snap-on cap used only for sealing purposes, and the others are used for setting certain Second logic-processor operating conditions. For example, the Second logic-processor's hybrid transmitter can be operated in either an OOK modulation mode or ASK modulation mode. The appropriate cap is attached to achieve the selected modulation mode. It can be removed and replaced with the alternate cap version if the modulation method needs to be changed. All of the sensor connectors and other special custom attachments have the same modulation setting option.

FIG. 2-32 is another exploded view of the basic Second logic-processor again showing power connector housing 1122, power connector battery insert 1123, housing for the Second logic-processor 1124, Second logic-processor electronics 1125 and the selected end cap 1126. Other features shown are the end cap multi-pin plug 1127, matching Second logic-processor multi-pin socket 1128 and socket 1129 (for power connector attachment) and power connector plug 1130.

FIG. 2-33 shows the use of a Transceiver Hybrid Circuit in place of the Second logic-processor transmitter and Receiver. FIG. 2-33 shows how the 16-bit programmable attenuator 200 can be inserted between the antenna and the Saw Filter (and before the inductors RFIO and ESD choke) to provide a field limiting function that prevents a Second logic-processor out of the desired range from being received and shows how the 16-bit Signal Strength Comparator circuit 201 can be used by tapping off the signal prior to the Peak Detector circuit.

FIG. 2-34 is an exploded view of power source 1160. Preferably, power source 1160 comprises housing 1135, attachment cleats 1136, and battery insert 1137 and plug 1138, and, preferably, a sealing bullhead 1139 that is present on all connector inserts.

FIG. 2-35 shows a close up view of the Second logic-processor 1140 containing the micro-controller, radio frequency transmitter, polling circuit, temperature sensor, battery condition monitor, transmit inhibit switch and poll response LED. It shows the sensor interface sockets 1141 and 1142, cleats 1143, and the sealing tongue 1144.

FIG. 2-36 is an exploded close up view of the Second logic-processor showing its case 1145, attachment cleats 1146, electronics PCB 1147, socket 1148 and 1149, and the sealing bulkheads 1150.

FIG. 2-37 shows a close up view of the sensor connector 1151 showing the plug 152 that interfaces with the Second logic-processor, cleats 1153, and the sealing tongue 1154.

FIG. 2-38 shows an exploded close up view of the sensor connector showing the case 1155, electronics PCB 1156, plug 1157 (that interfaces with the Second logic-processor and the sealing bulkhead 1158), cleats 1159, and the sealing tongue 1165.

FIG. 2-39 shows the basic Second logic-processor (power connector and Second logic-processor) and a ribbon cable 1166 plugged into the sensor interface socket 1167. This cable serves a variety of purposes that include programming the micro-controller, testing the Second logic-processor functionality (including setting the modulation method to either OOK or ASK), or to interface sensors. In an actual installation where the Second logic-processor is connected to external sensors, the plug would be built into an end cap to provide a sealed assembly.

FIG. 2-40 shows the power connector 1168 connected to the Second logic-processor 1169, showing the cable and plug assembly 1170 before insertion into the sensor connection socket 1171.

FIG. 2-41 shows the Second logic-processor 1172 in a further test configuration where the power is also supplied through a plug in cable 1173 allowing a complete in-process test of the main at various voltage levels and to measure current drain in various modes and conditions of operation and with various sensor loads. The Second logic-processor alone, or with any form of sensor connection, can also be powered from an external source using this power cable connector, but the plug would then be built into an end cap to provide a sealed assembly.

FIG. 2-42 shows the Second logic-processor 120 with the two unplugged cable connectors 1174 and 1175.

FIG. 2-43 is an exploded view of a sensing Second logic-processor 1120.

FIG. 2-44 is a block diagram of the basic LITMIS Receiver 130. The radio frequency Section consists of a radio frequency Receiver 1177 with connectors for one or two (for diversity) antennae 1176, an antenna-Receiver impedance matching circuit and an OOK/ASK Receiver (within 1177). There are two identical radio frequency sections per circuit as shown in this drawing. At least one optional 16-bit programmable attenuator stage(s) 1181 may be included between the antenna(s) and the Receiver. The attenuator stage is controlled by the Microprocessor 1186 directly or on instructions to the Receiver from the control center. This provides the ability to limit the receiving range of the Receiver to the area of interest and reduce noise or collisions from other Second logic-processor or Tags that are outside the area of interest.

The Analog Section has a gain circuit 1178 that consists of a differential amplifier and a summing amplifier. The differential amplifier provides gain and offset adjustment while the summing amplifier adds the two (I per Receiver) signals together. The Analog Section also has a filter circuit 1179 consisting of an active filter reduce signal noise. The Digital Section has a level detector 1180 consisting of a 16-level voltage divider, 16 comparators and an upper and lower level voltage adjustment. The voltage divider provides 16 equally spaced voltage reference levels for the 16 comparators. Each comparator detects if the received signal is higher or lower than its voltage reference. The upper and lower voltage references are adjusted using a potentiometer. This Level Detector serves to provide a calibrated 16 bit Signal Strength functions with the range sensitivity being controlled by the 32-bit processor 1186. Where a 16-bit Attenuator Read-range adjustment feature is used, the output of the 16-bit Signal Strength function must be linked to the attenuator setting. This could be used to provide a 256-bit Signal Strength function although this precision would rarely be used because of the many potential attenuating factors associated with radio signals. One application it can be used for, where the attenuating factors are specific to the nature of the environment and location, is to provide a very accurate analysis of these attenuating factors, which could be determined prior to an installation and then programmed into the Receiver or the central control computer and used to refine the Signal Strength readings when using the system for locating purposes.

The CPLD functions consist of a 16-level to 4-bit converter 1182 that de-bounces the incoming bits and converts the data to a 4-bit binary code. A Digital Squelch function 1182 is used to set a minimum signal value. Any signals below the digital squelch level are ignored. The Digital Filter 1184 performs a weighted average on the signal. Each sample is weighted based on the age of the sample; and the older the sample, the less weight a sample has in the average. This provides a smoother signal and reduces noise. A Slope Detector 1185 looks for slope changes in the signal. There are currently 3 types of slopes detected (up, down & level). Any change in slope type is detected in the Event Rate Detector 1187 and a pulse is generated. An 18-bit counter is used to keep a rolling count of the 4 MHz clock 1188 in a binary format. A Time Stamp Latch 1190 latches whenever a pulse is latched from the 18-bit counter 1189 whenever a pulse is received from the slope detector. All rollover events are also latched to aid in tracking event timing. All data captured in the time stamp latch 1190 is also loaded into a 4K×18 bit FIFO (First In First Out) 1191 Memory device. The FIFO is used to store time stamps until the microprocessor is ready to read them. Event Rate Detector is used when time stamps occur at a rate that is faster than the known signal rate; it makes an automatic adjustment to the digital squelch circuit, which effectively eliminates fast noise signals. The microprocessor reads data from the FIFO and analyzes the time stamps to decode data from the transmitter. The microprocessor also controls the potentiometers that adjust the upper and lower threshold levels. The microprocessor also sets the level in the digital squelch circuit, and acts as the interface to the system computer.

Figures 2, 3, 4, 5, 6, 7, 8, 9, 10, 11:
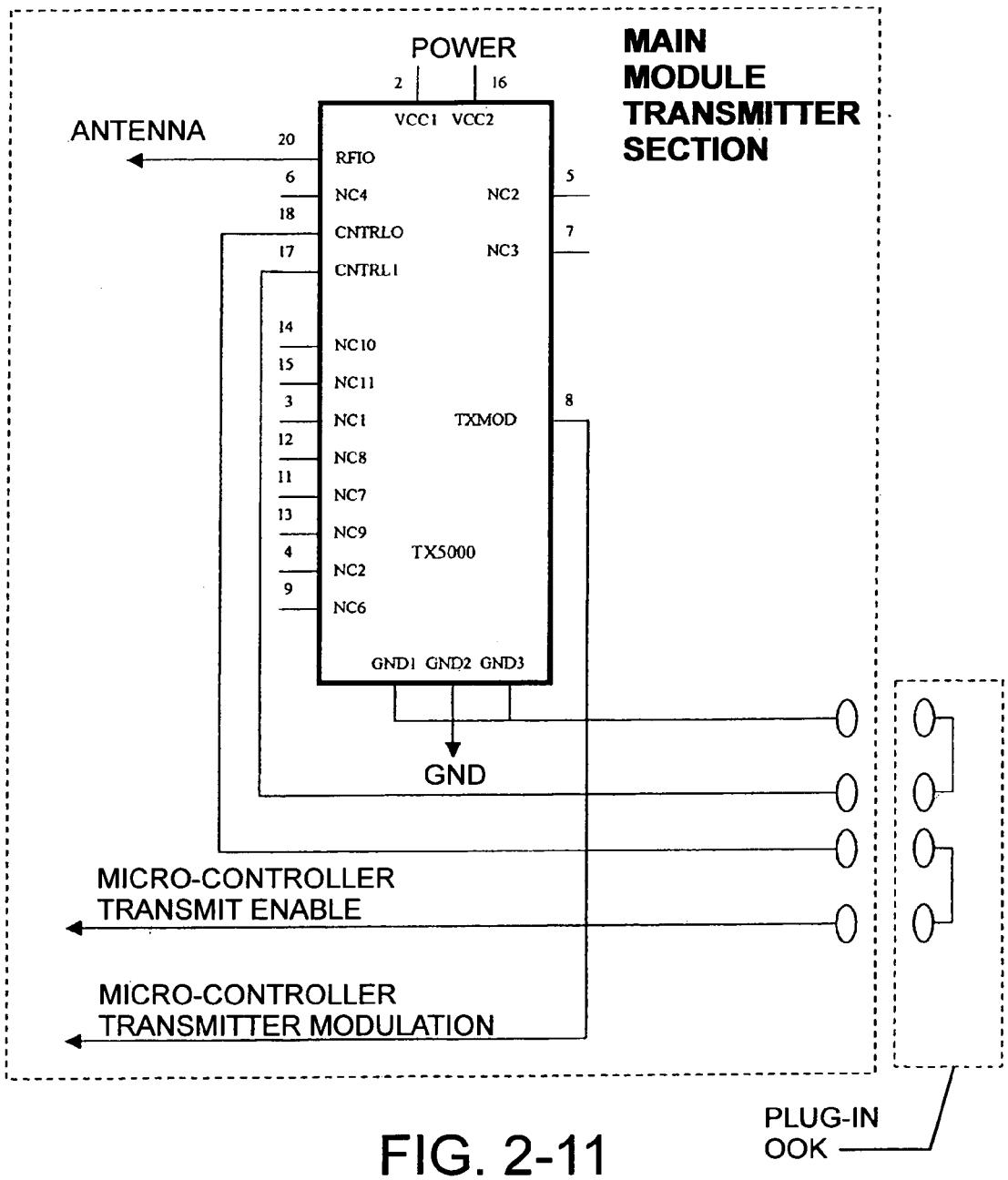
Figures 2, 3, 4, 5, 6, 7, 8, 9, 10, 11, 12:
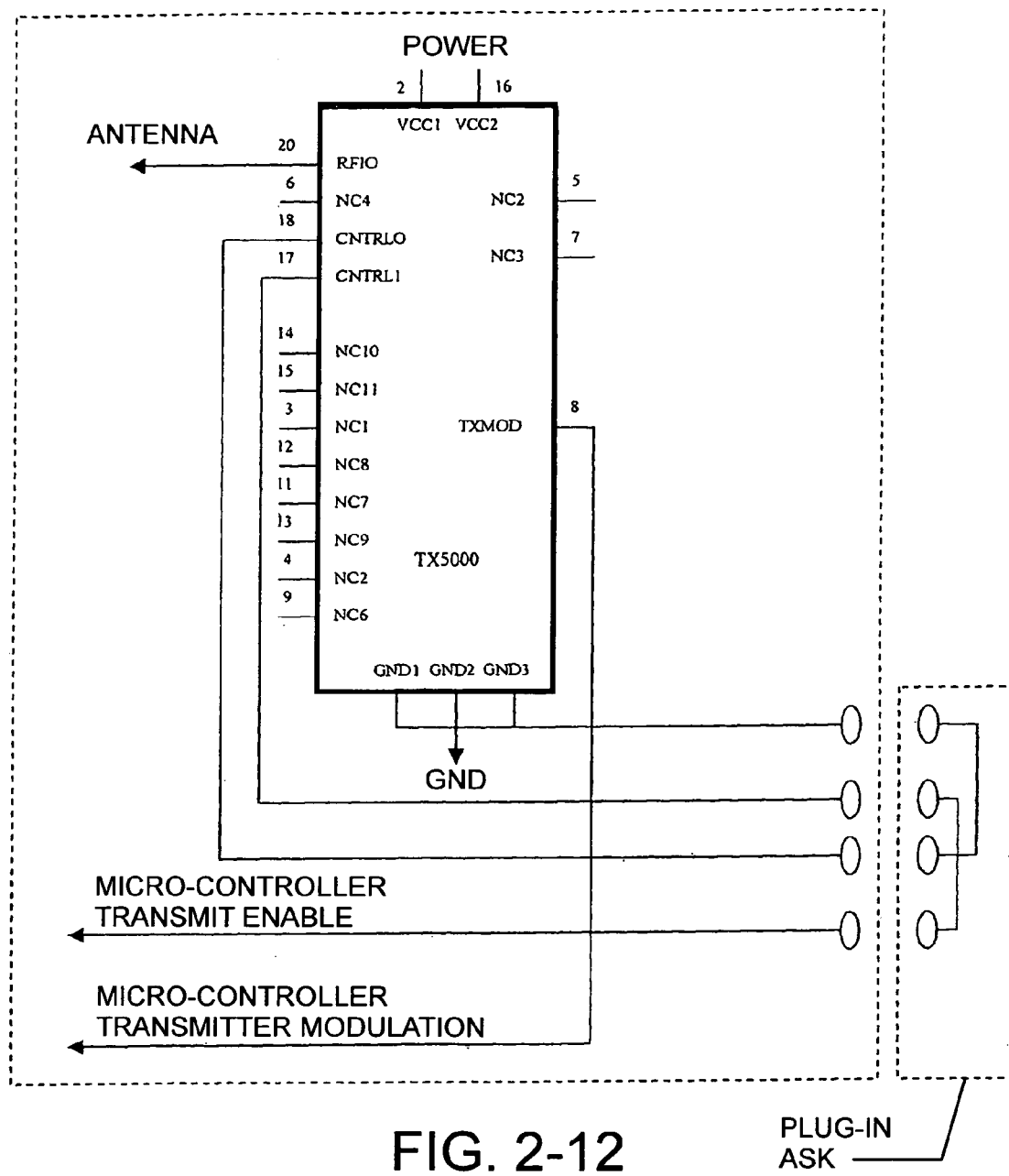
Figures 2, 3, 4, 5, 6, 7, 8, 9, 10, 11, 12, 13:
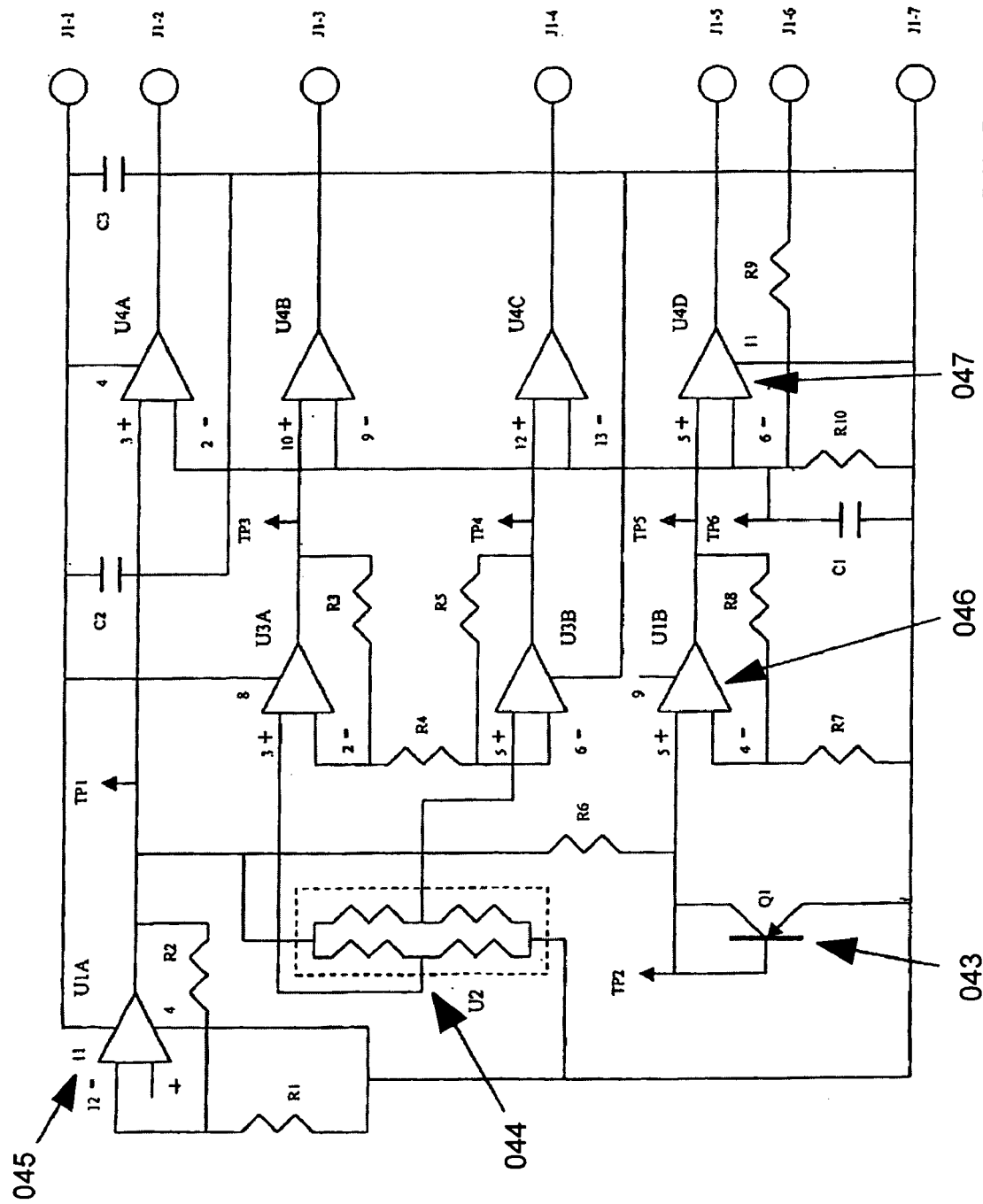
Figure 14A:
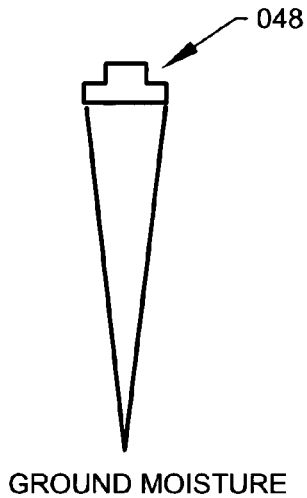
FIG. 14A and FIG. 14B, is a posterior view of the sections of a Second logic-processor for according to a preferred embodiment of the present invention.
Figure 14B:
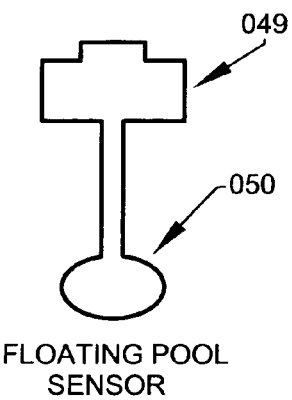
Figure 14C:
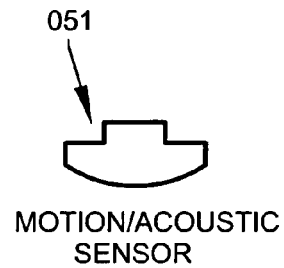
FIG. 14, comprising
Figure 14D:
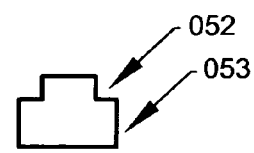
Figure 14E:
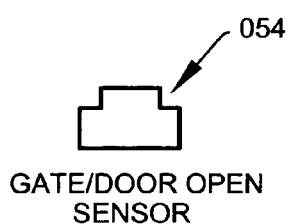
Figure 14F:
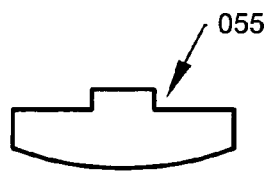
Figure 14G:
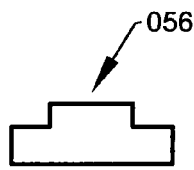
Figure 14H:
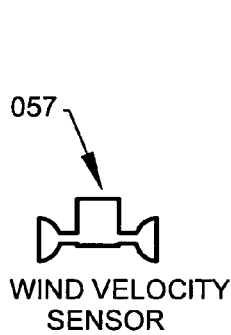
Figure 14I:
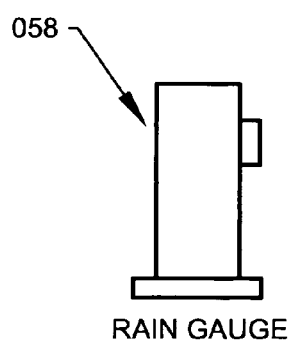
Figure 14J:
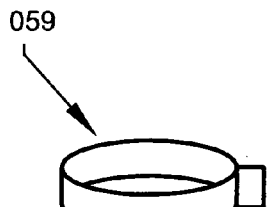
Figures 2, 3, 4, 5, 6, 7, 8, 9, 10, 11, 12, 13, 14, 15, 16:
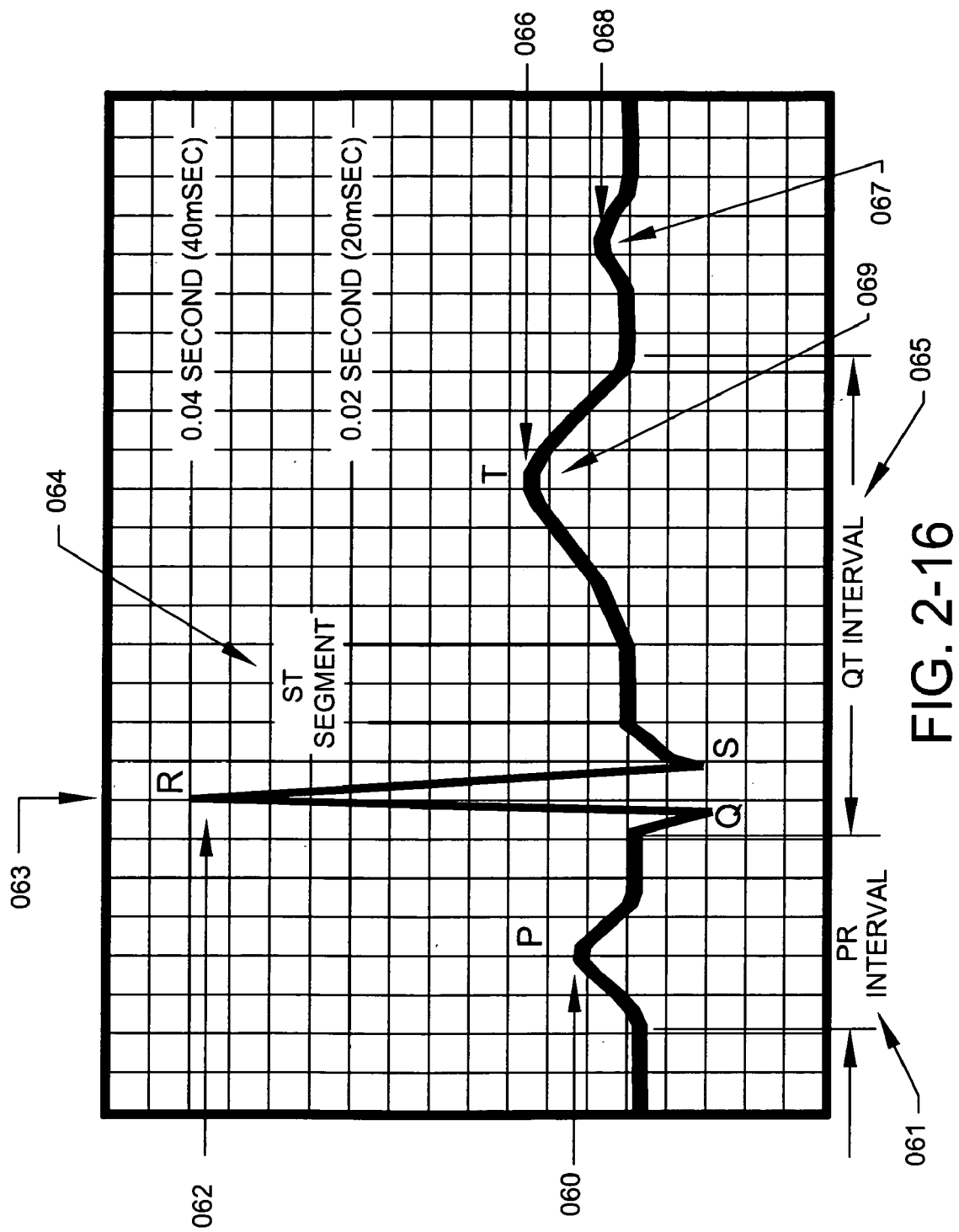
Figures 2, 3, 4, 5, 6, 7, 8, 9, 10, 11, 12, 13, 14, 15, 16, 17, 17A:
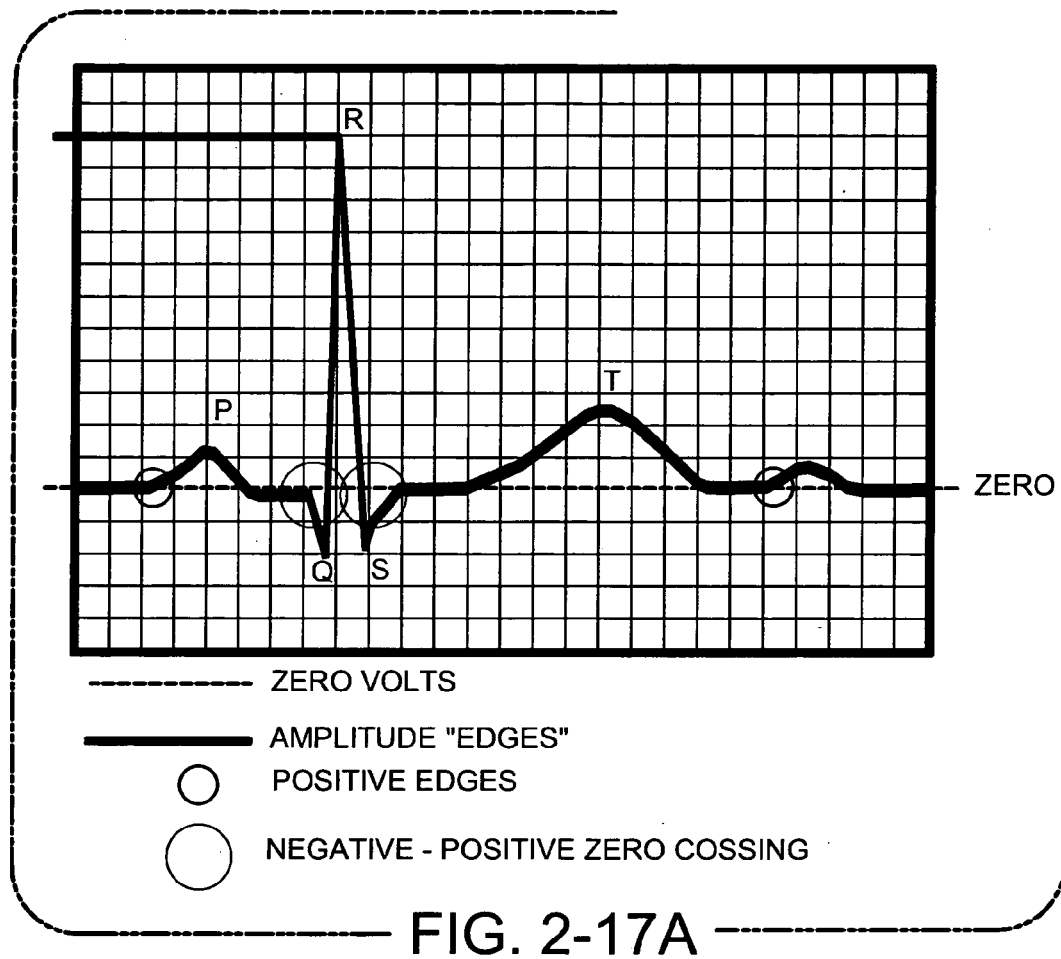
Figures 2, 3, 4, 5, 6, 7, 8, 9, 10, 11, 12, 13, 14, 15, 16, 17, 17B:
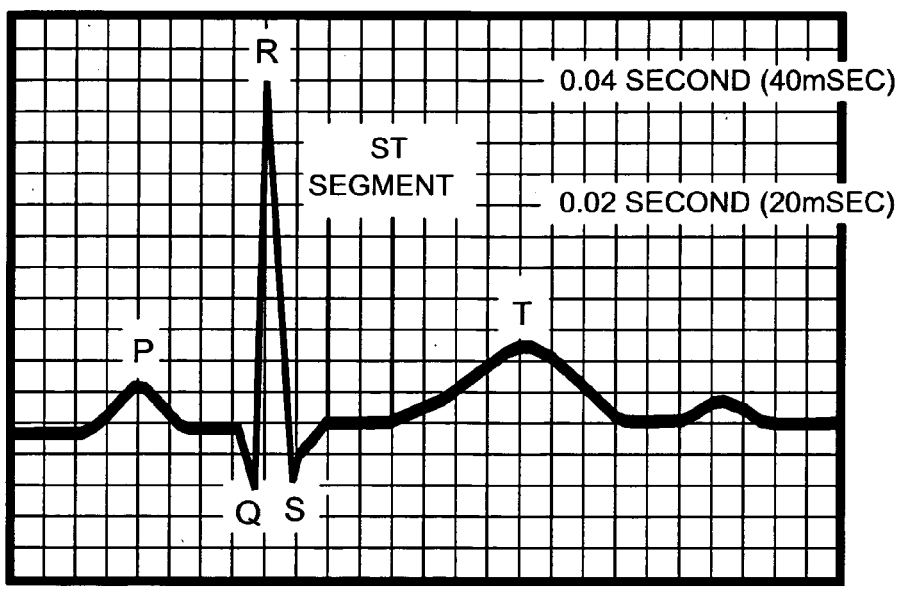
Figures 2, 3, 4, 5, 6, 7, 8, 9, 10, 11, 12, 13, 14, 15, 16, 17, 18, 19, 19A:
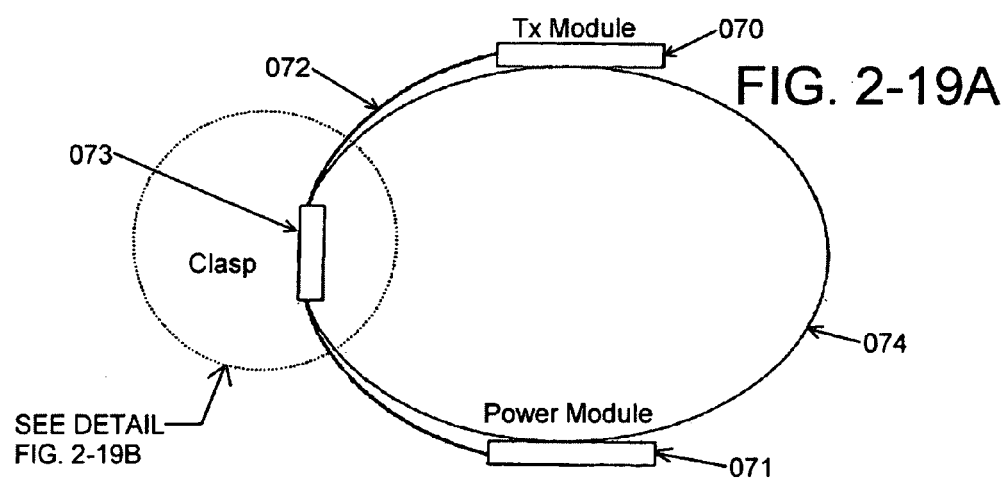
Figures 2, 3, 4, 5, 6, 7, 8, 9, 10, 11, 12, 13, 14, 15, 16, 17, 18, 19, 19B:
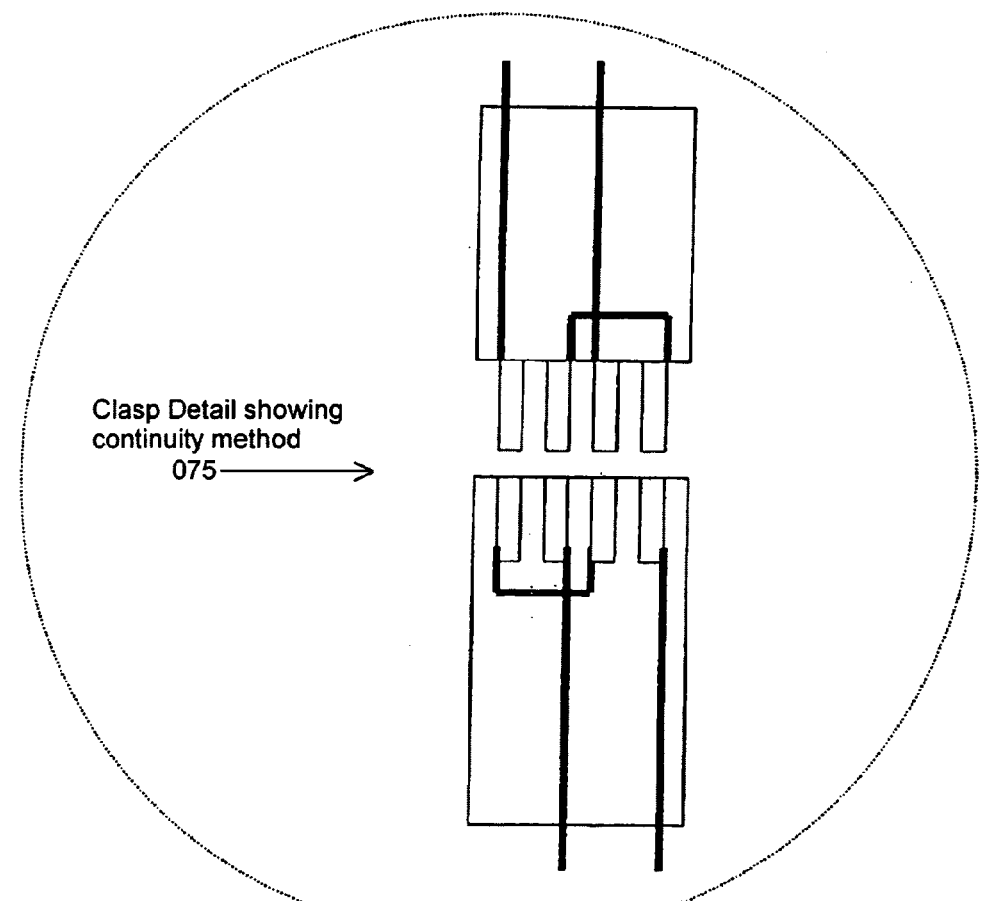
Figures 2, 3, 4, 5, 6, 7, 8, 9, 10, 11, 12, 13, 14, 15, 16, 17, 18, 19, 20, 20A:
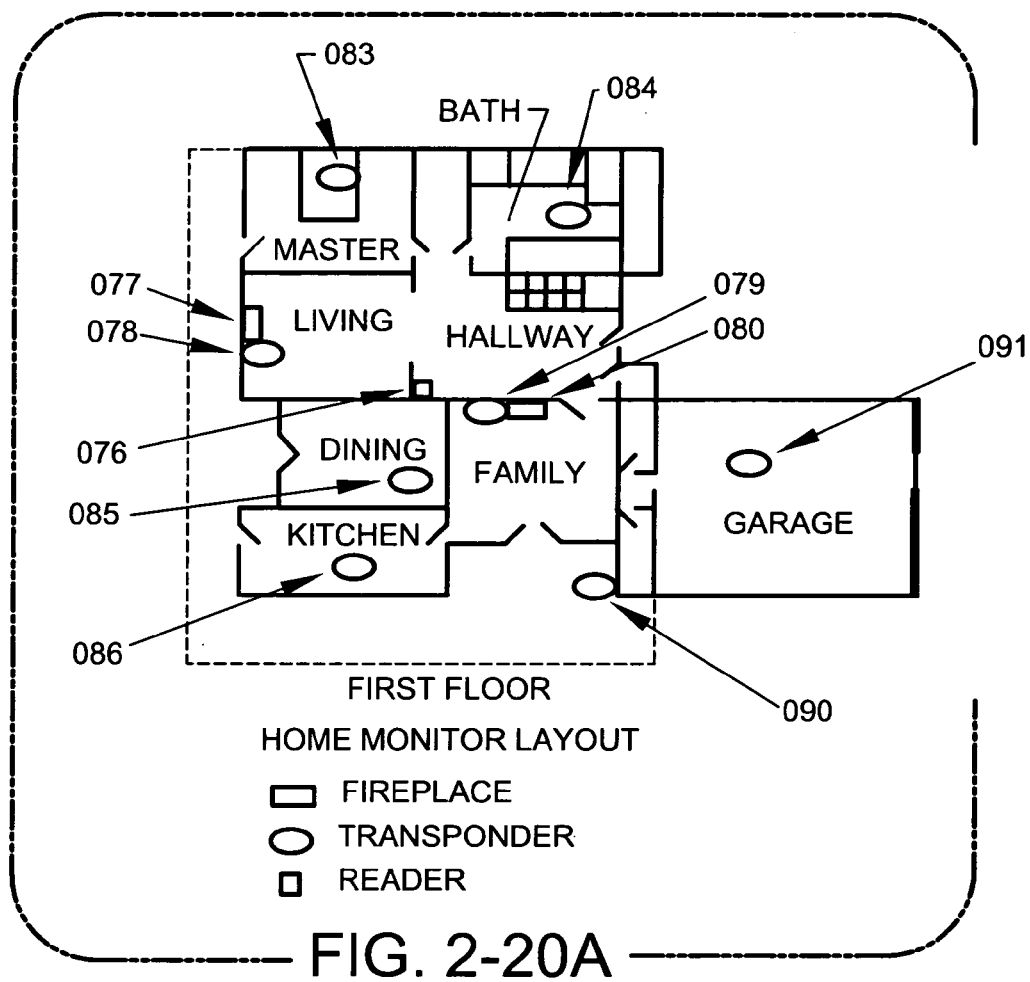
Figures 2, 3, 4, 5, 6, 7, 8, 9, 10, 11, 12, 13, 14, 15, 16, 17, 18, 19, 20, 20B:
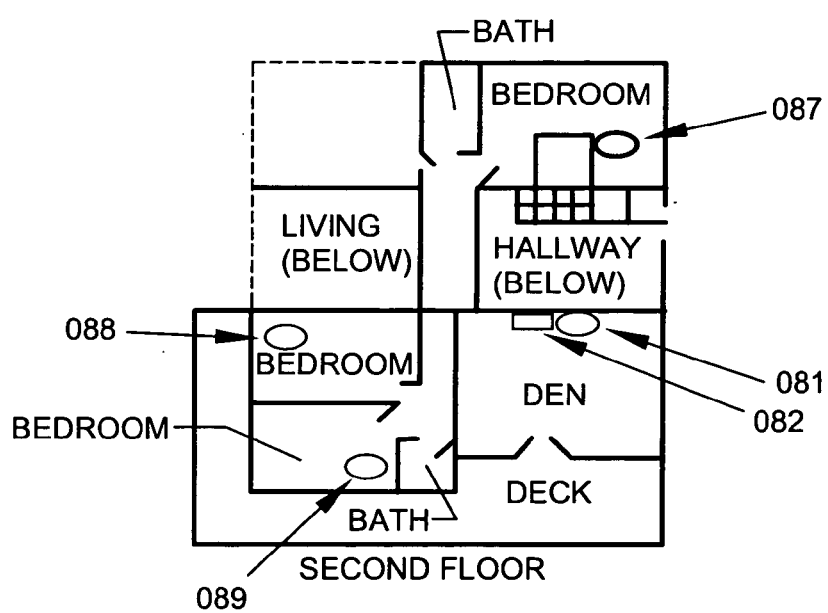
Figures 2, 3, 4, 5, 6, 7, 8, 9, 10, 11, 12, 13, 14, 15, 16, 17, 18, 19, 20, 21, 22:
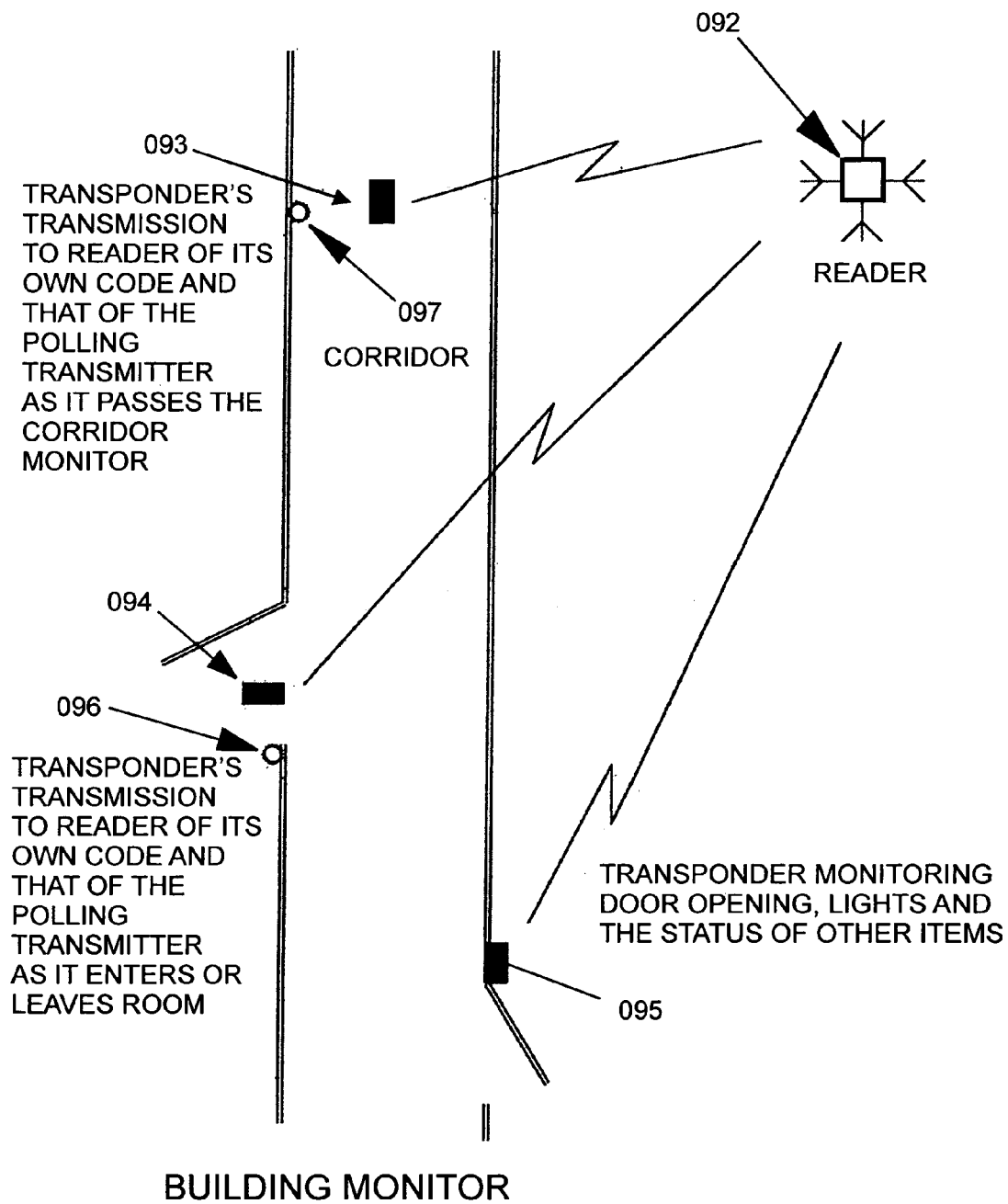
Figures 2, 3, 4, 5, 6, 7, 8, 9, 10, 11, 12, 13, 14, 15, 16, 17, 18, 19, 20, 21, 22, 23:
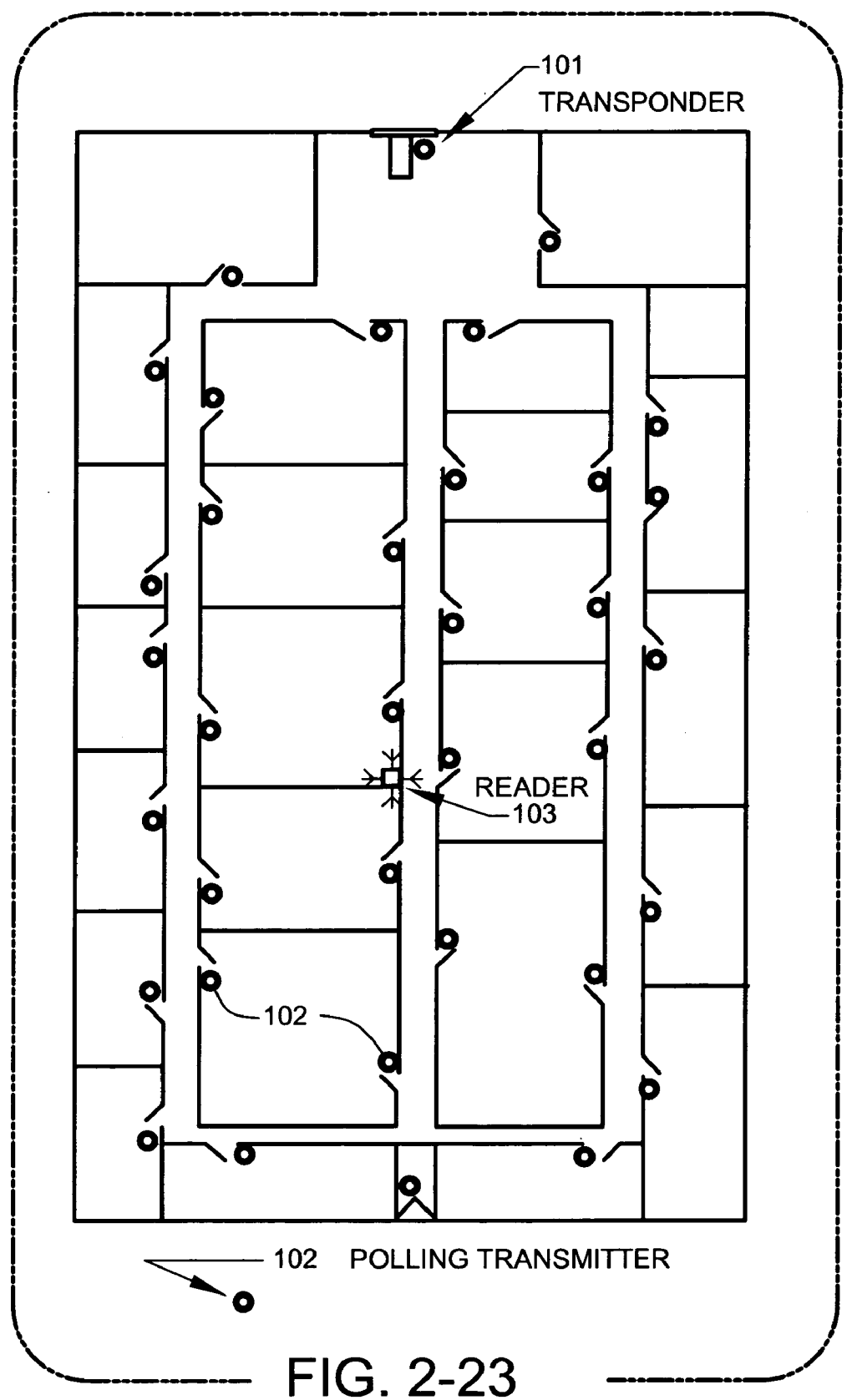
Figures 2, 3, 4, 5, 6, 7, 8, 9, 10, 11, 12, 13, 14, 15, 16, 17, 18, 19, 20, 21, 22, 23, 24:
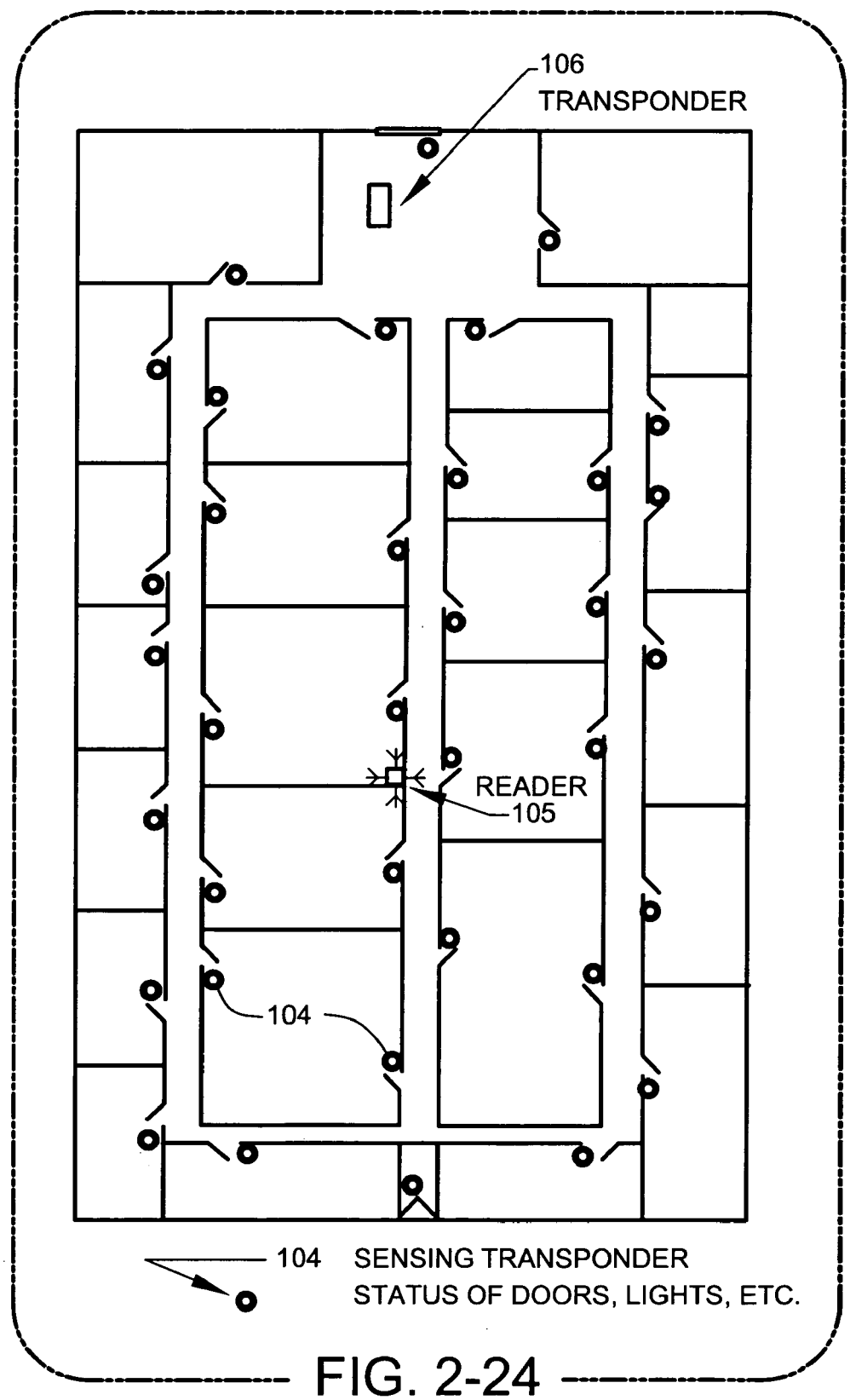
Figures 2, 3, 4, 5, 6, 7, 8, 9, 10, 11, 12, 13, 14, 15, 16, 17, 18, 19, 20, 21, 22, 23, 24, 25, 26, 27:
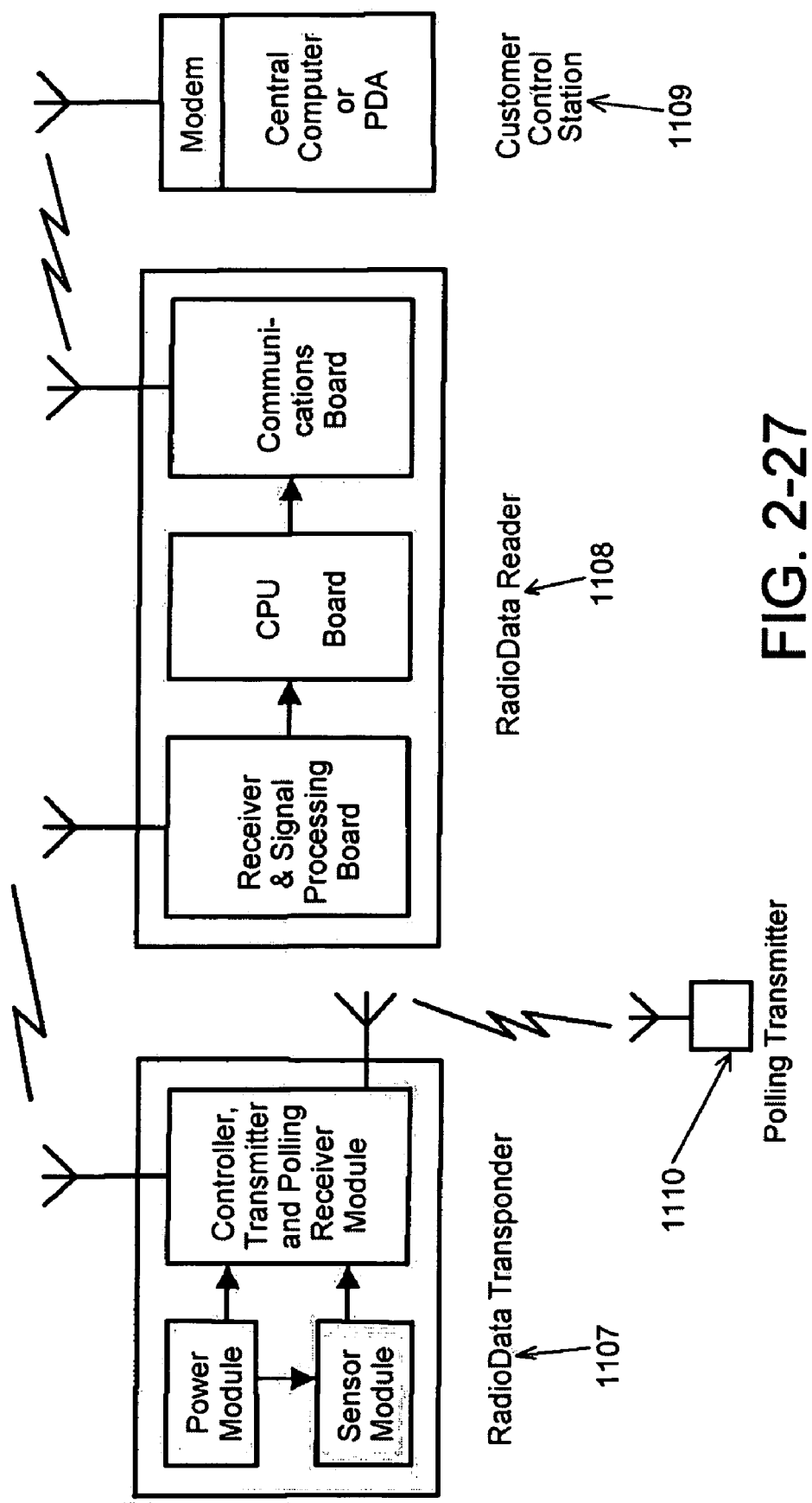
Figures 2, 3, 4, 5, 6, 7, 8, 9, 10, 11, 12, 13, 14, 15, 16, 17, 18, 19, 20, 21, 22, 23, 24, 25, 26, 27, 28:
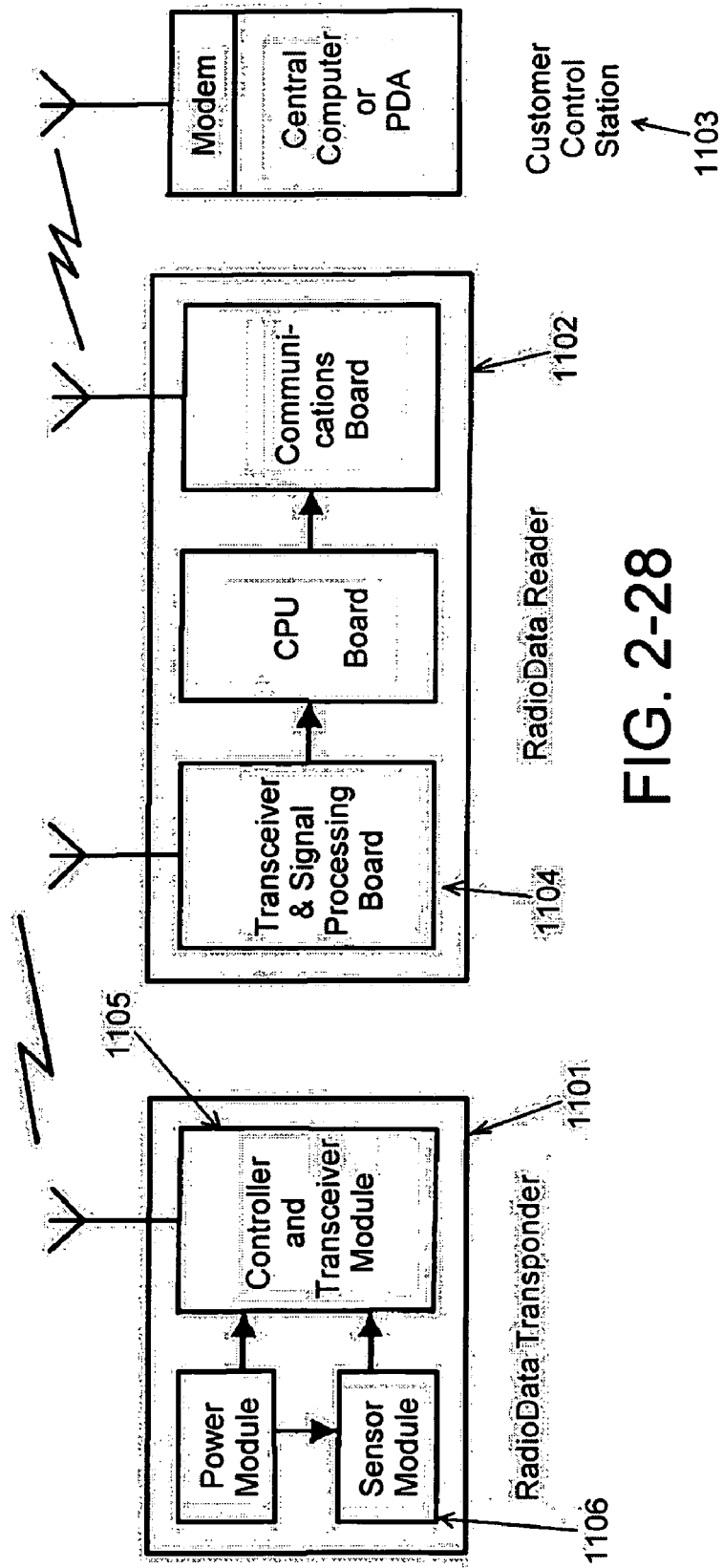
Figures 2, 3, 4, 5, 6, 7, 8, 9, 10, 11, 12, 13, 14, 15, 16, 17, 18, 19, 20, 21, 22, 23, 24, 25, 26, 27, 28, 29, 29C:
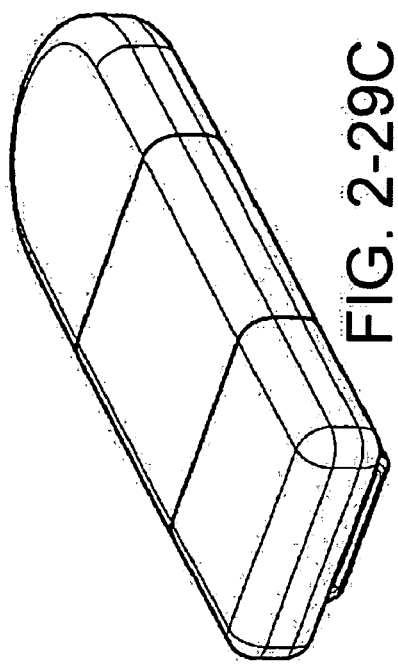
Figures 2, 3, 4, 5, 6, 7, 8, 9, 10, 11, 12, 13, 14, 15, 16, 17, 18, 19, 20, 21, 22, 23, 24, 25, 26, 27, 28, 29, 29D:
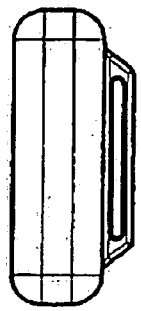
Figures 2, 3, 4, 5, 6, 7, 8, 9, 10, 11, 12, 13, 14, 15, 16, 17, 18, 19, 20, 21, 22, 23, 24, 25, 26, 27, 28, 29, 29A:
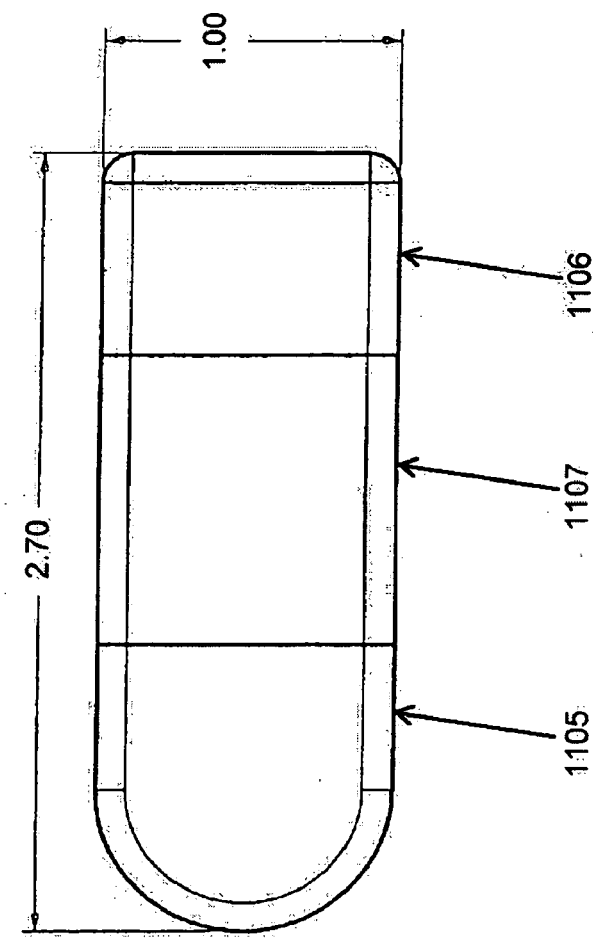
Figures 2, 3, 4, 5, 6, 7, 8, 9, 10, 11, 12, 13, 14, 15, 16, 17, 18, 19, 20, 21, 22, 23, 24, 25, 26, 27, 28, 29, 29B:
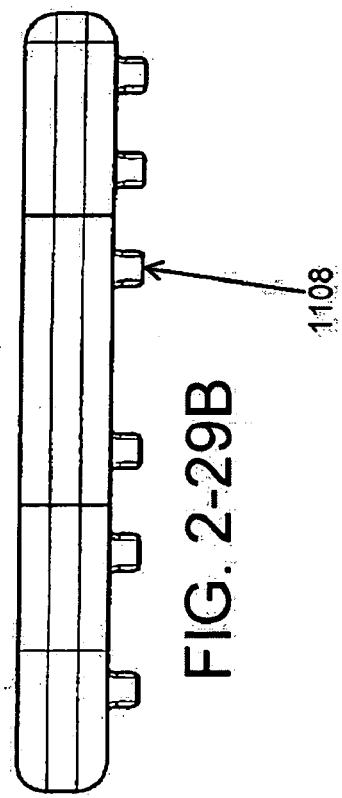
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30:
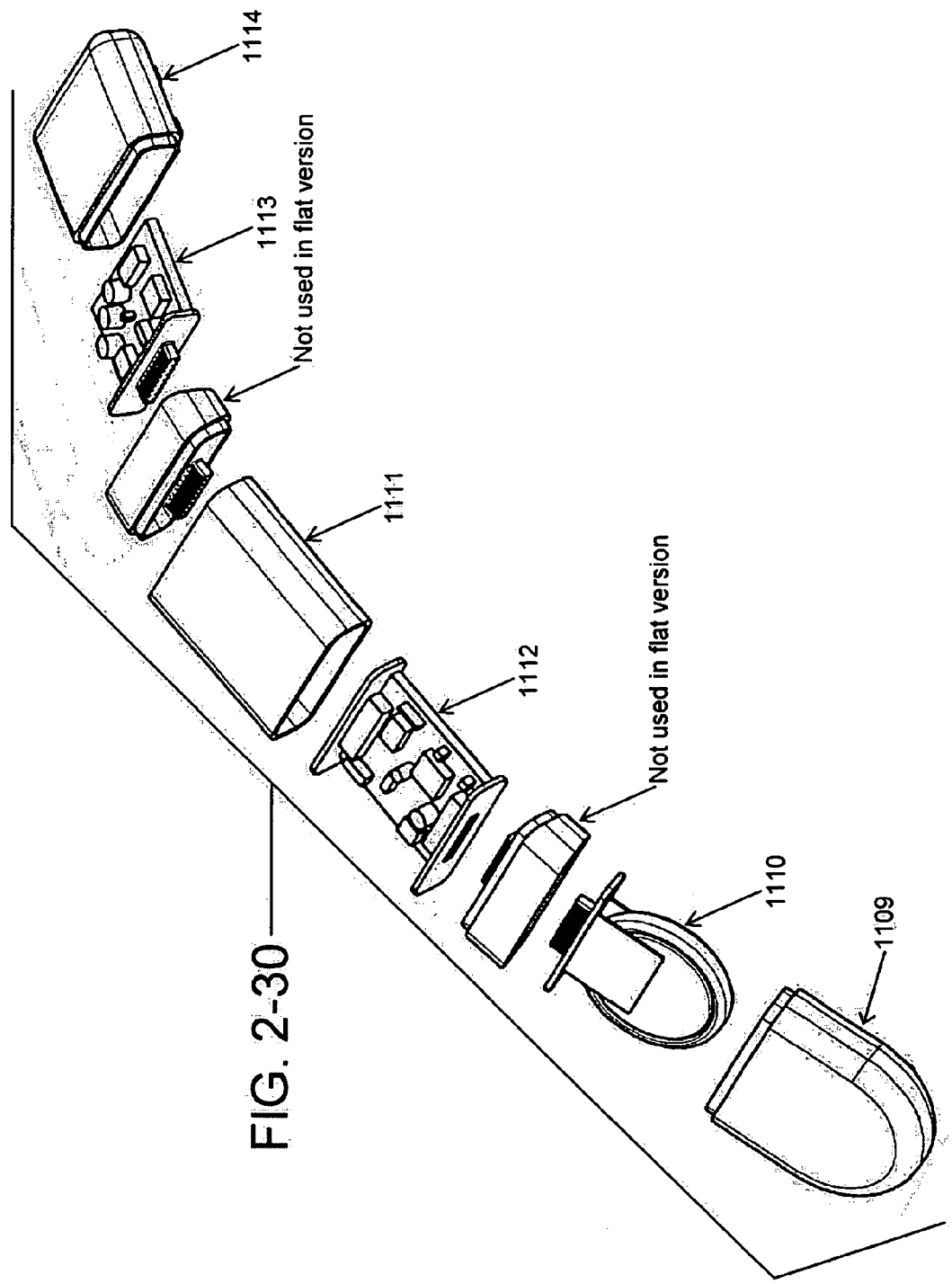
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
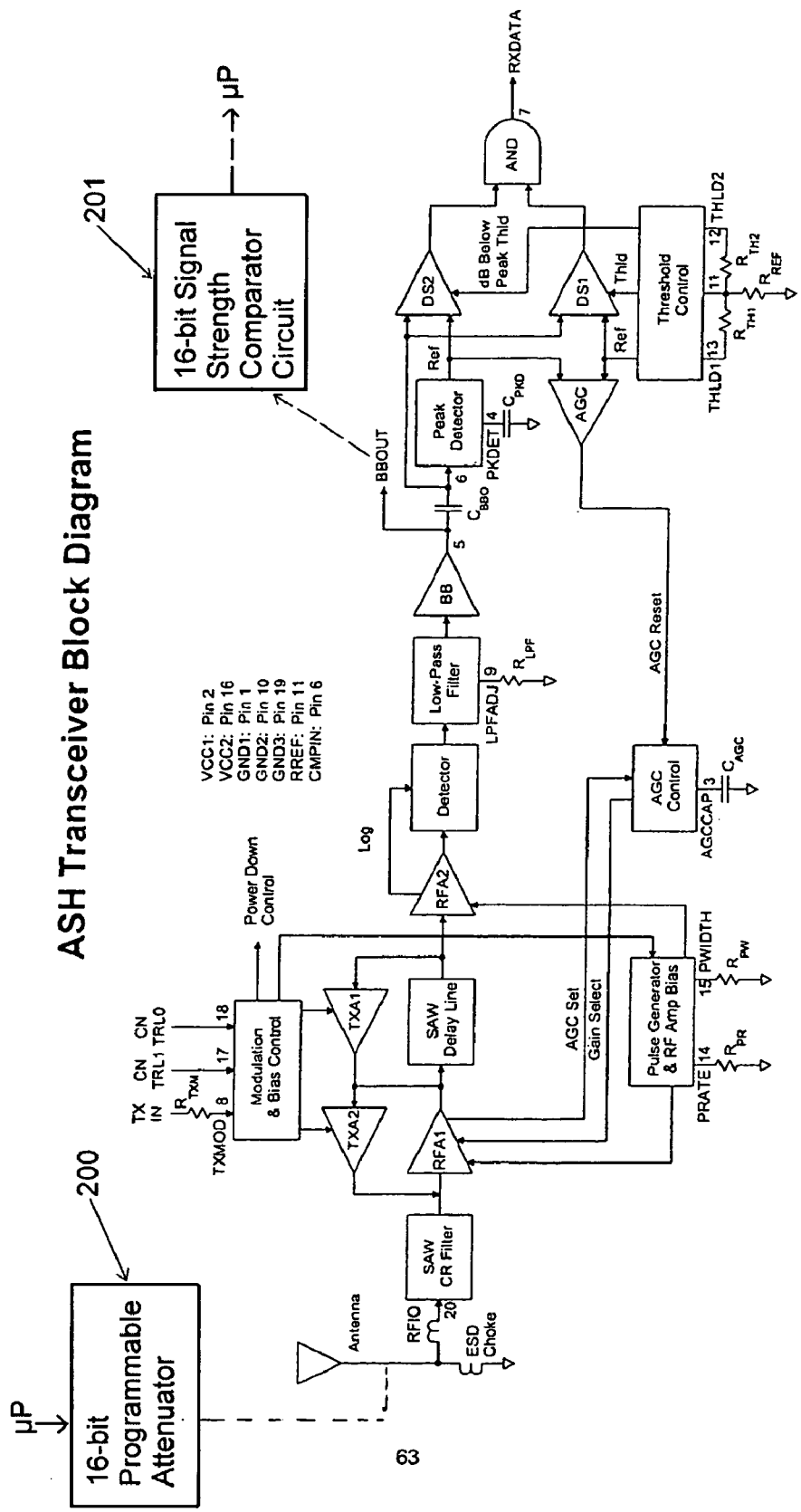
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 34A, 34B:
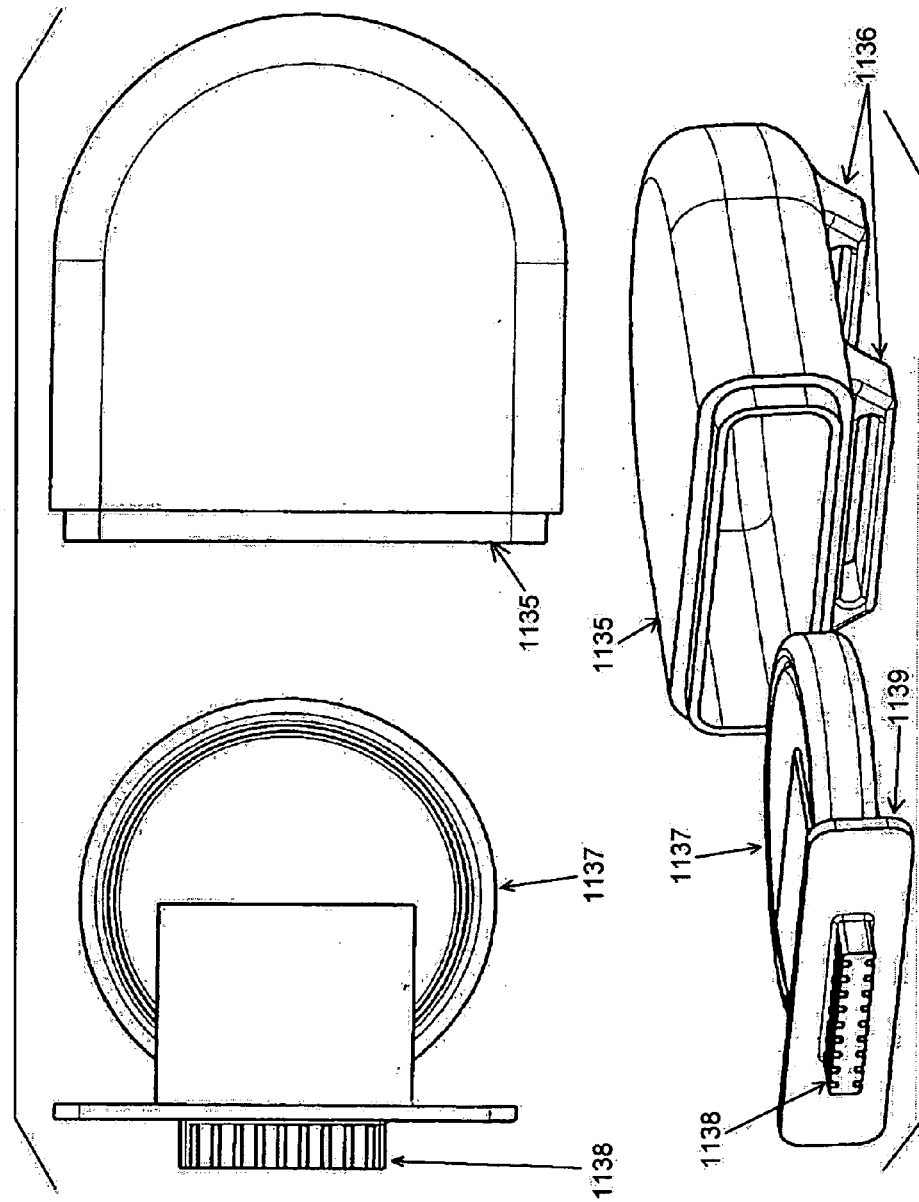
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37B:
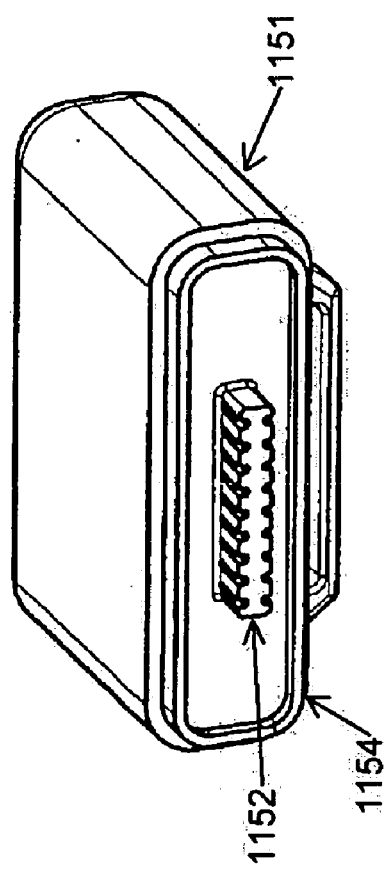
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37D:
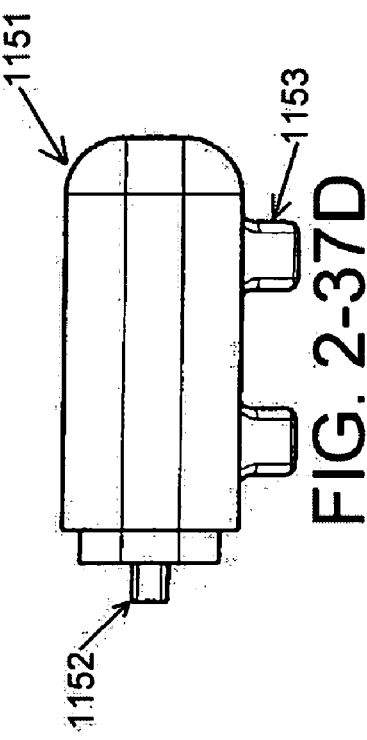
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37A:
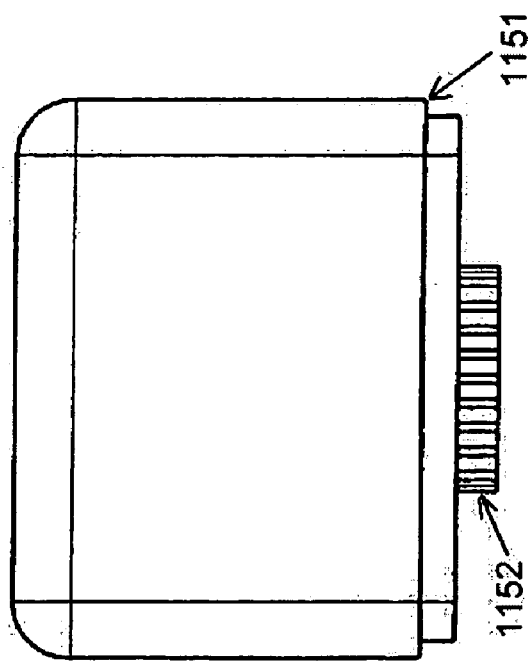
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37C:
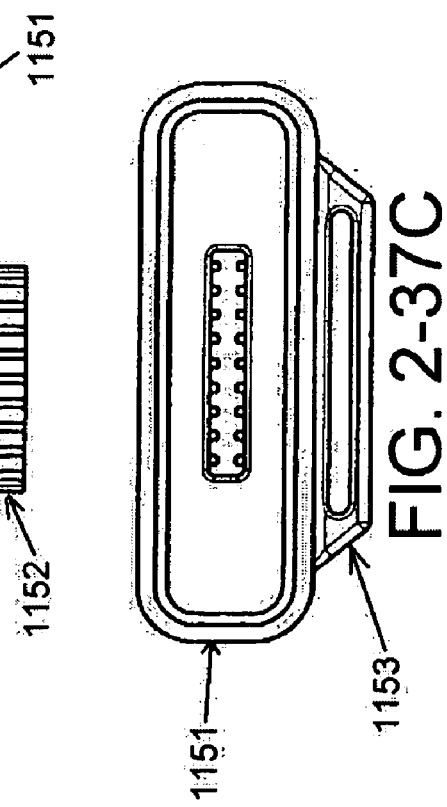
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 39B:
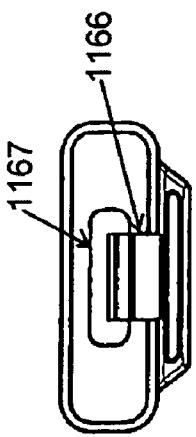
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 39D:
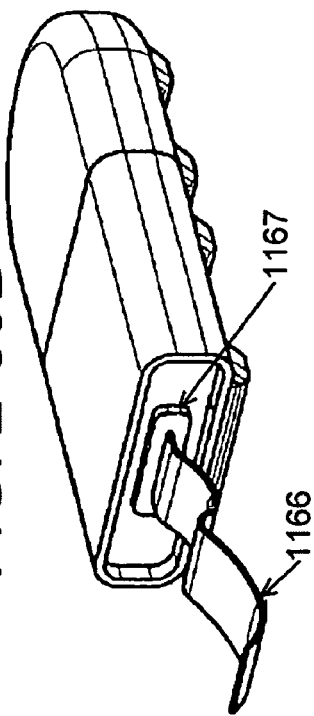
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 39A:
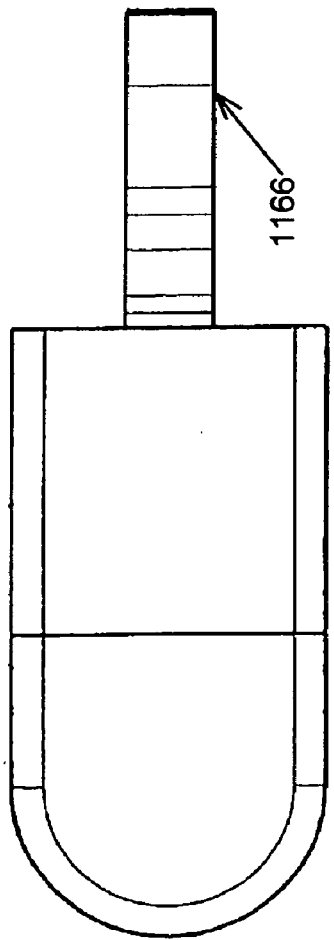
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 39C:
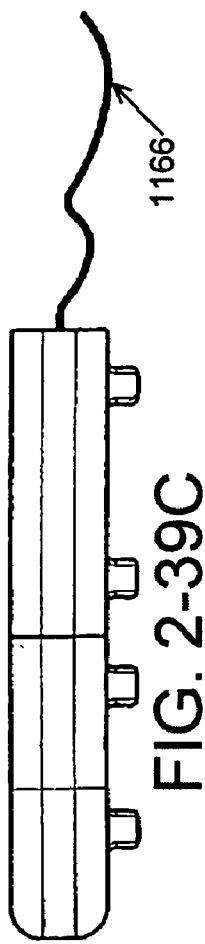
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41B:
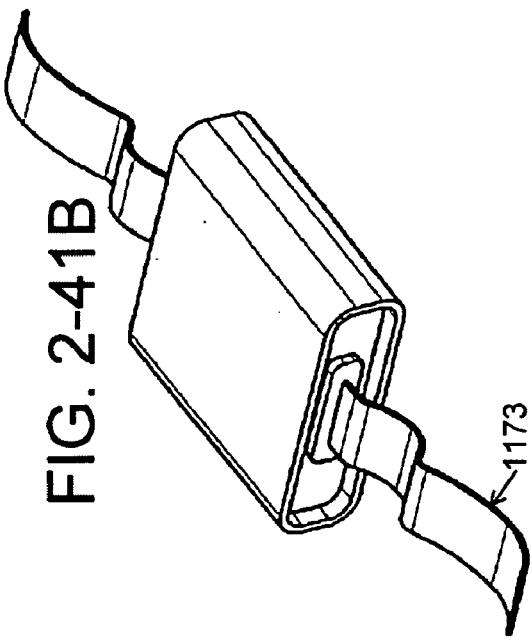
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41D:
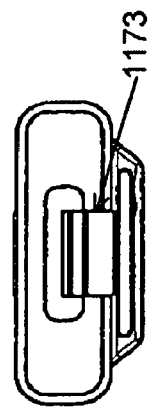
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41A:
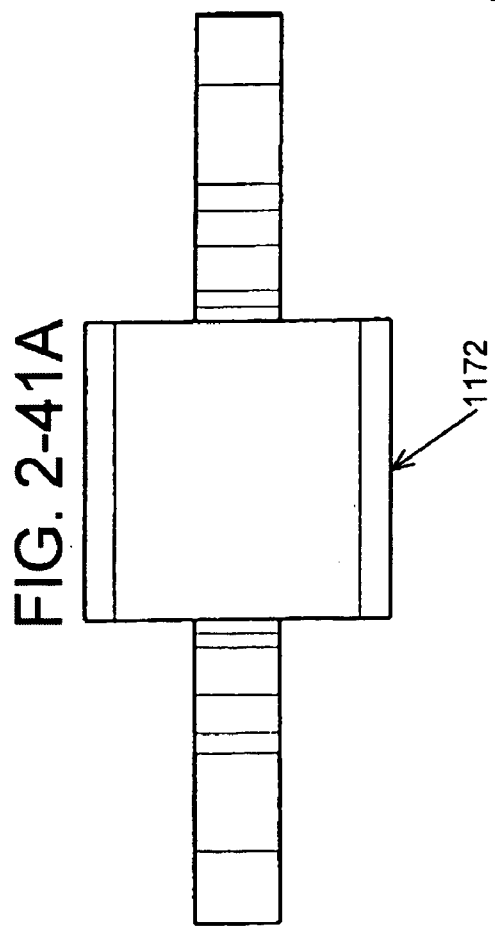
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41C:
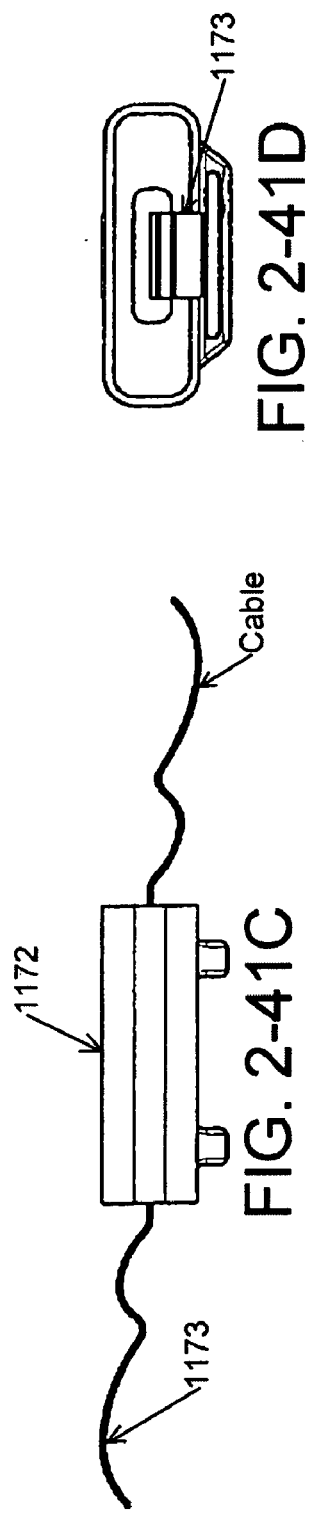
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
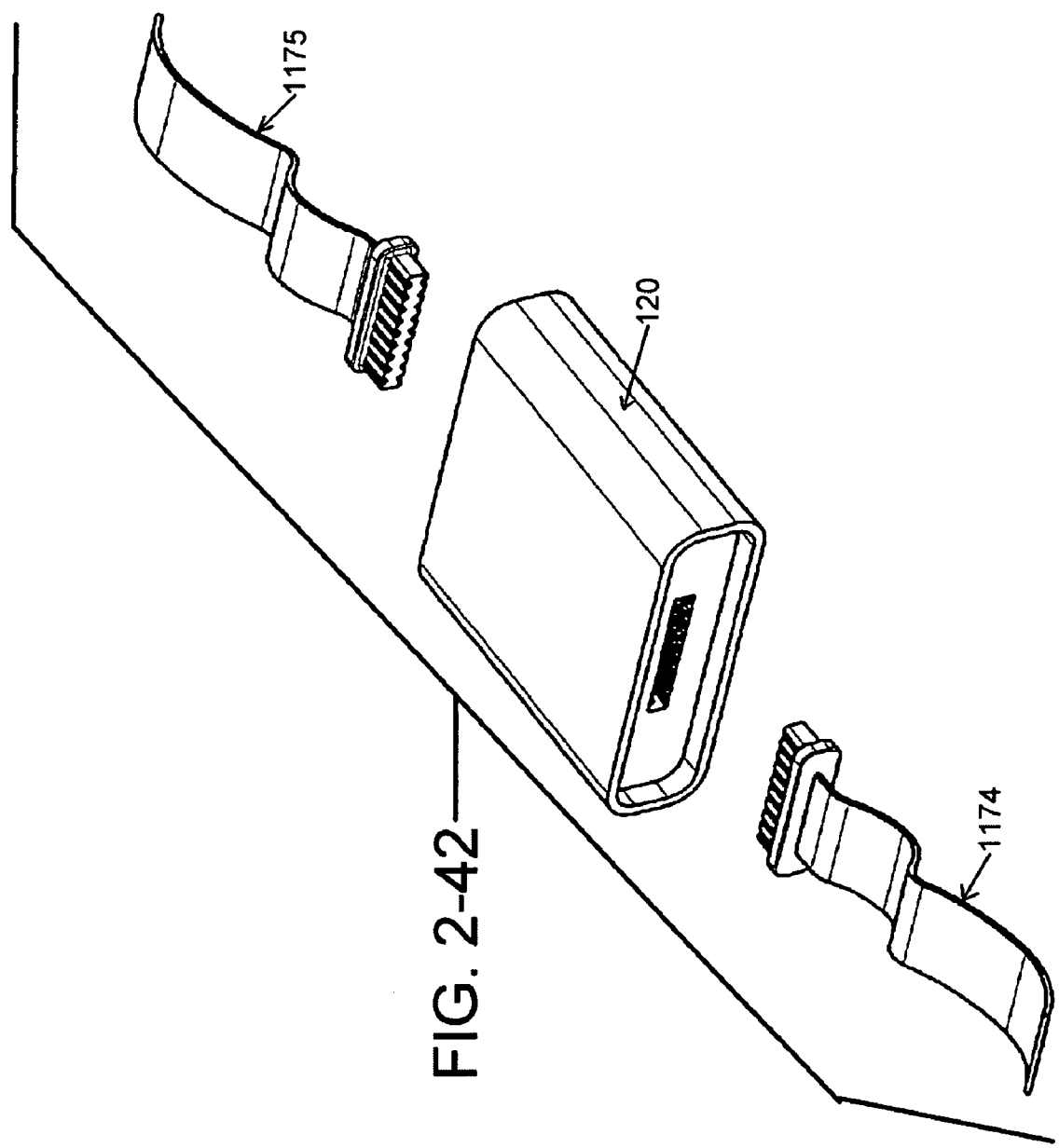
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 43A, 43B:
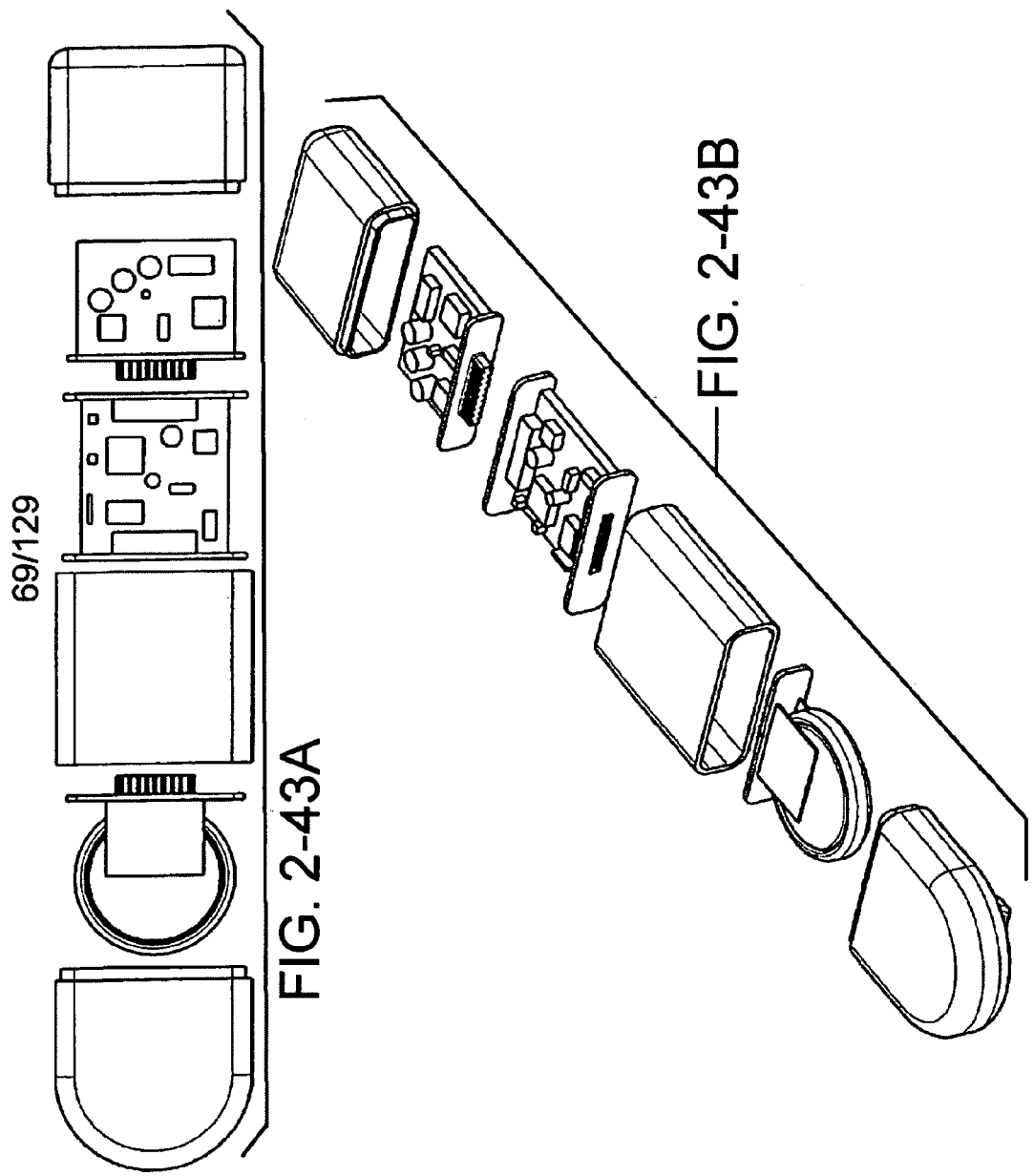
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
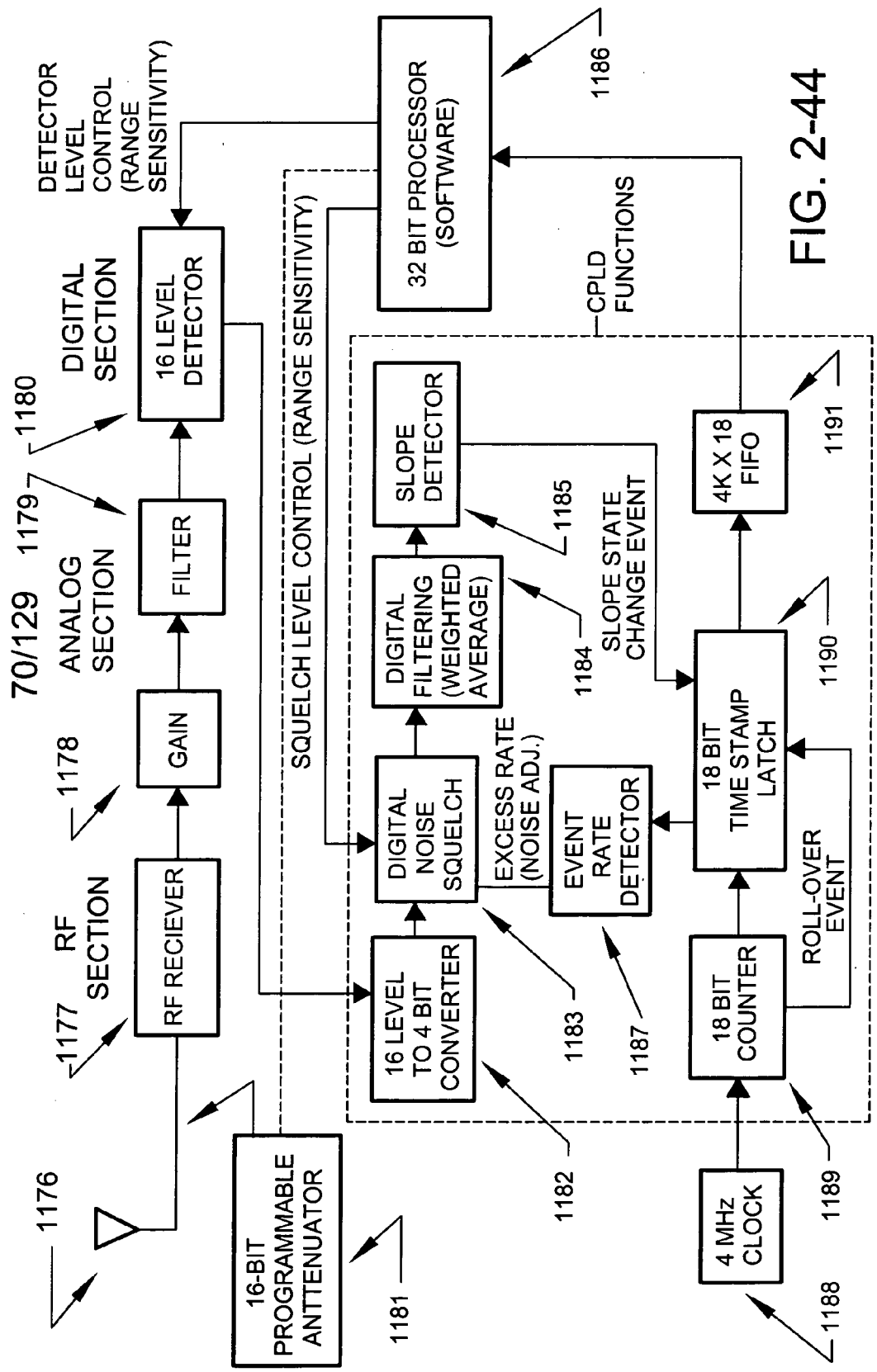
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
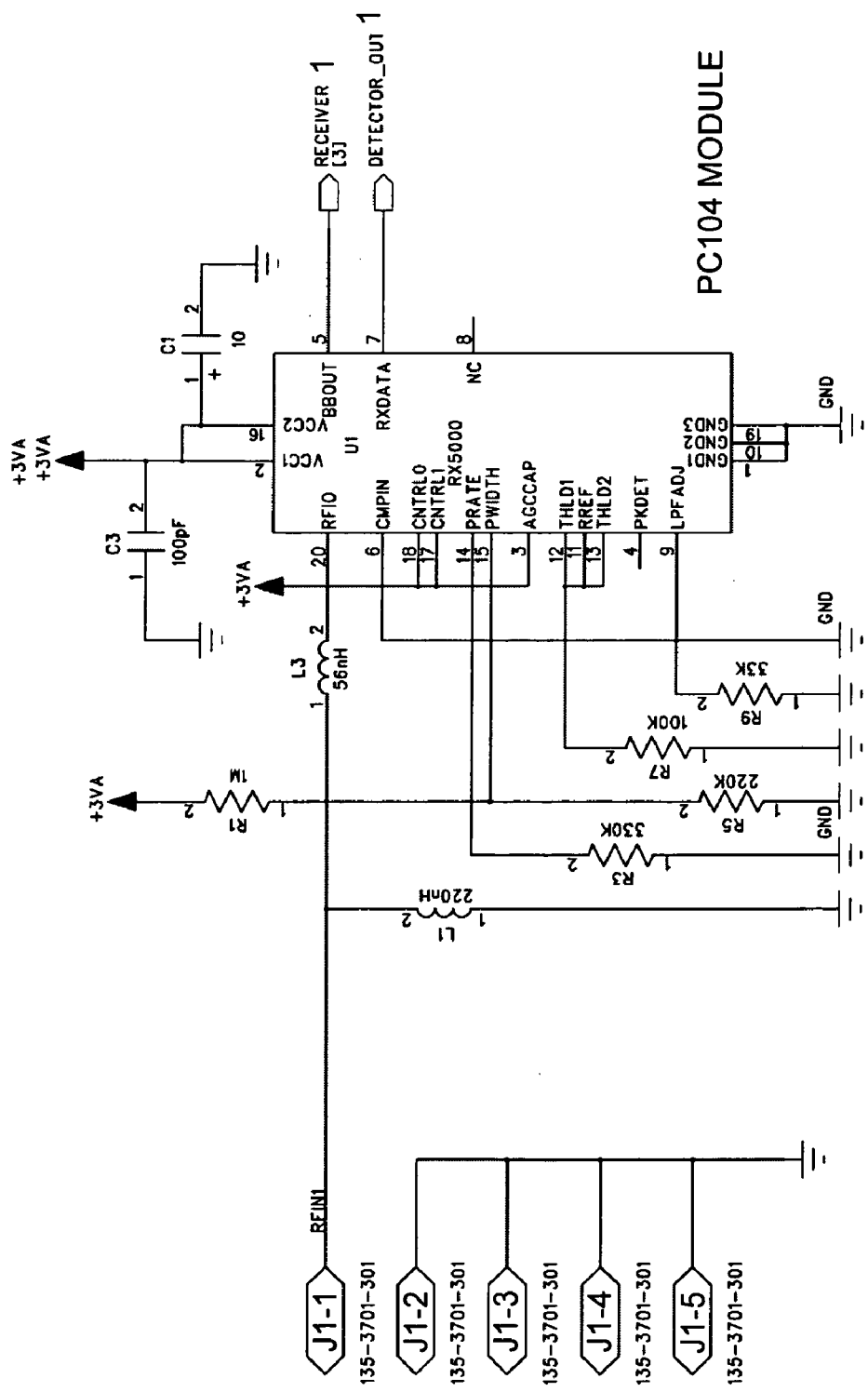
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
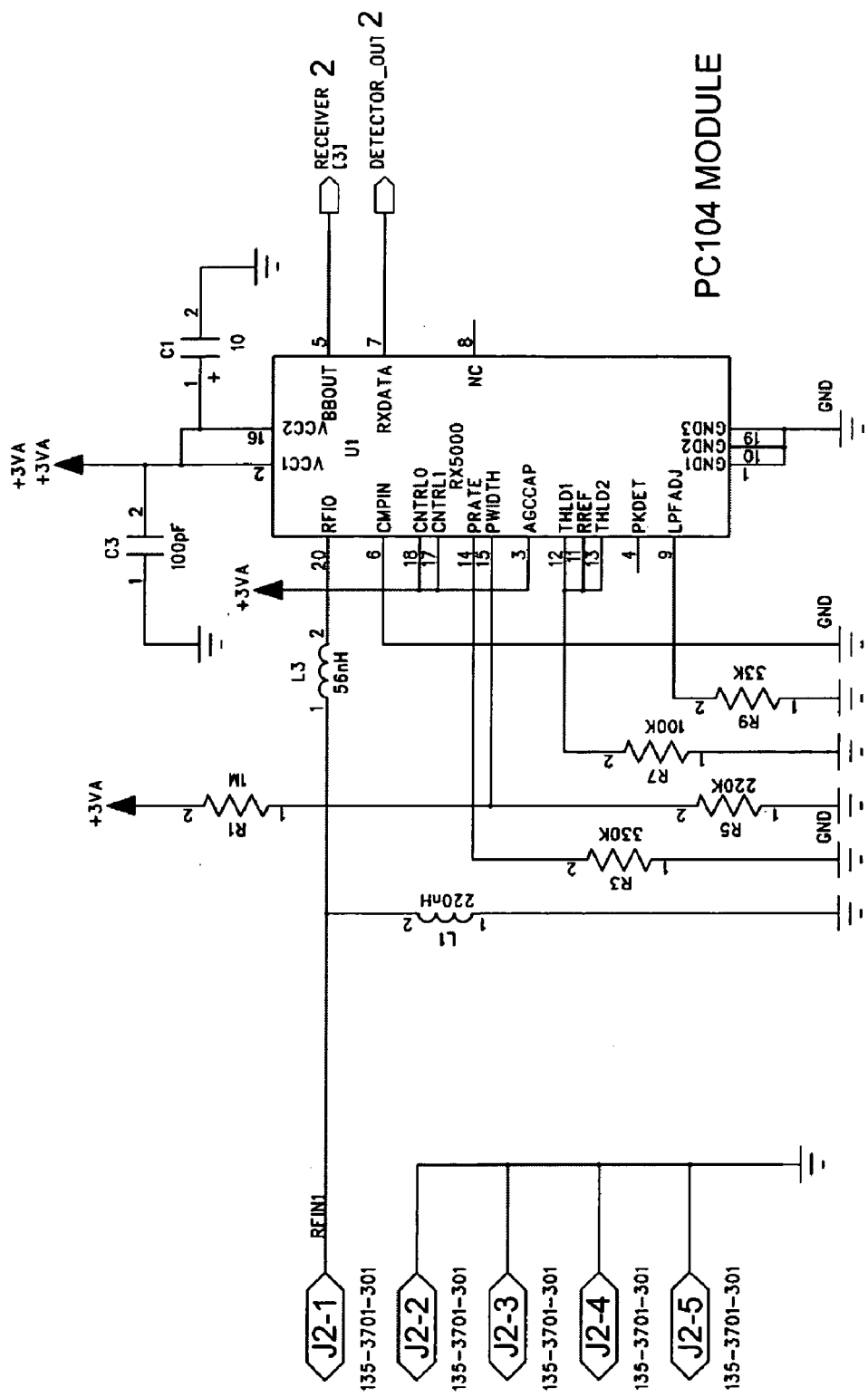
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
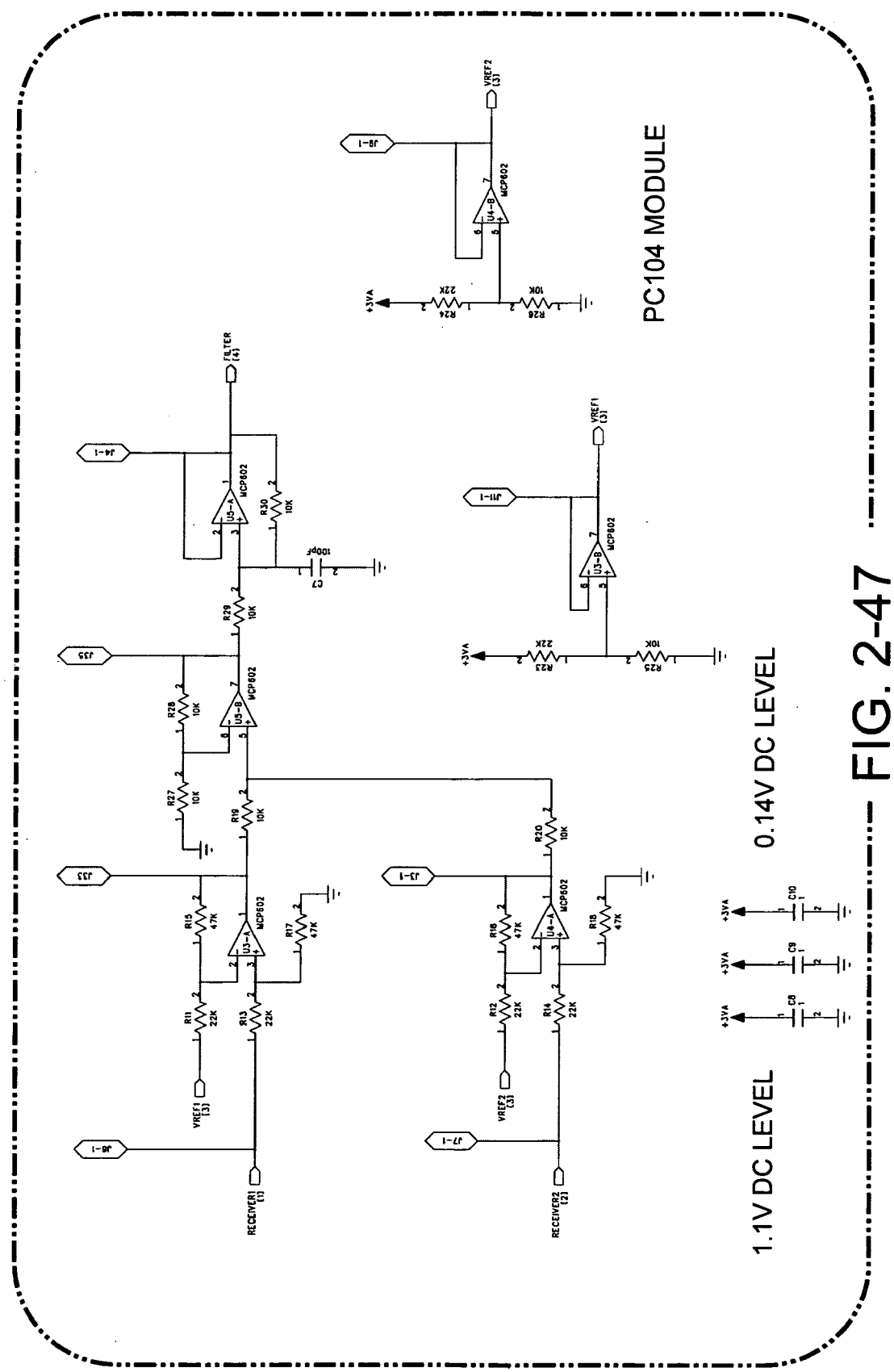
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
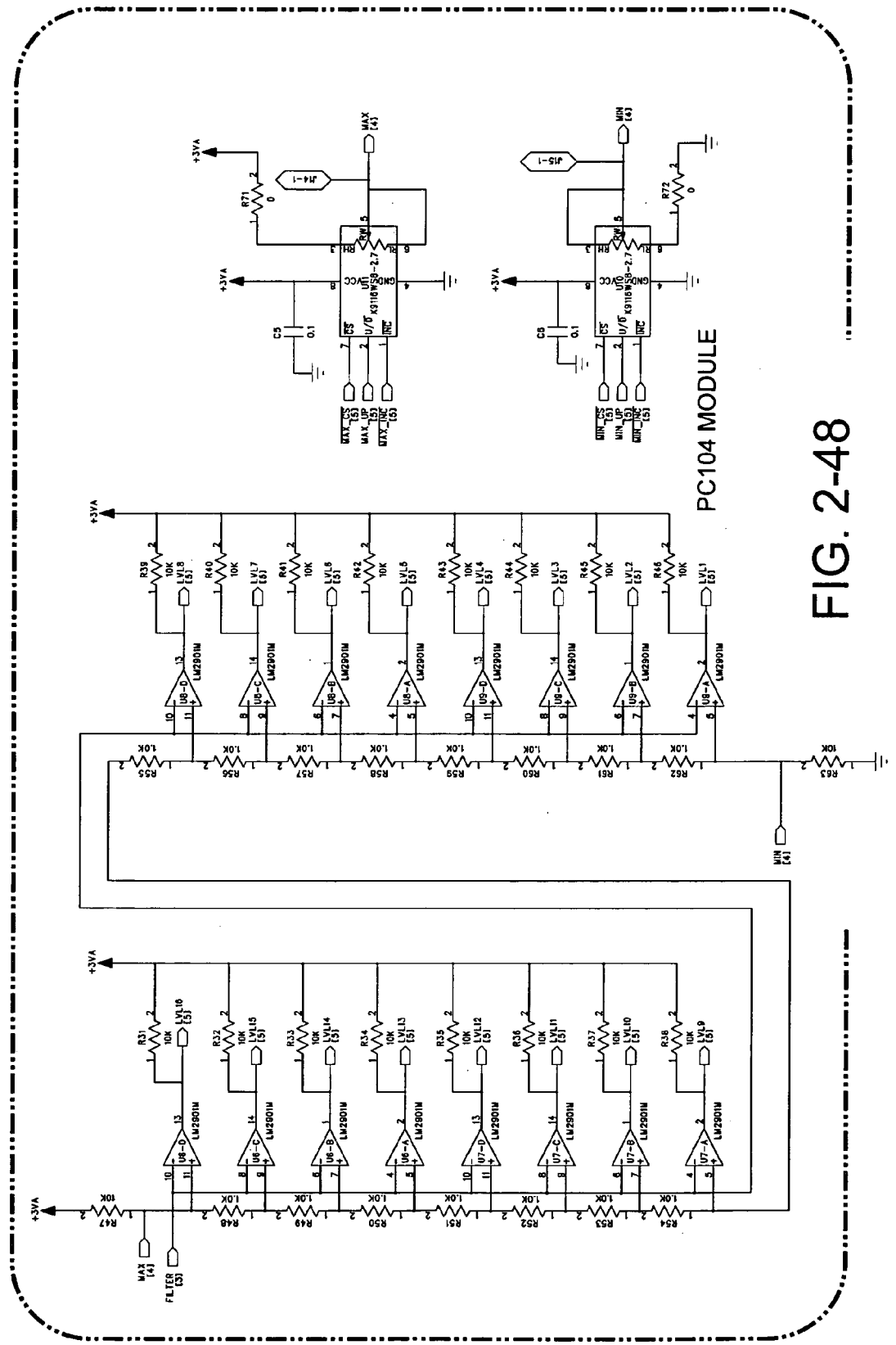
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
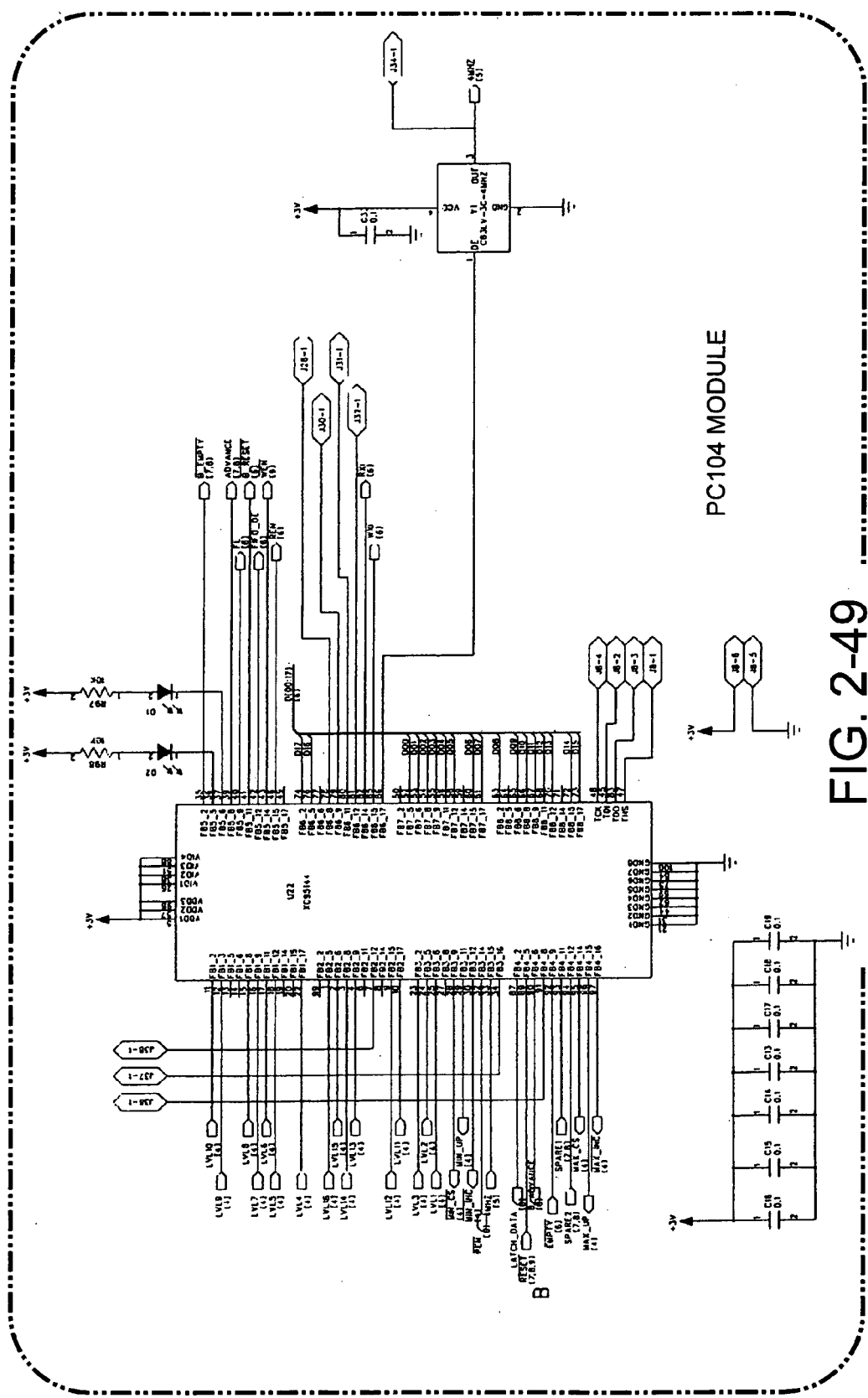
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
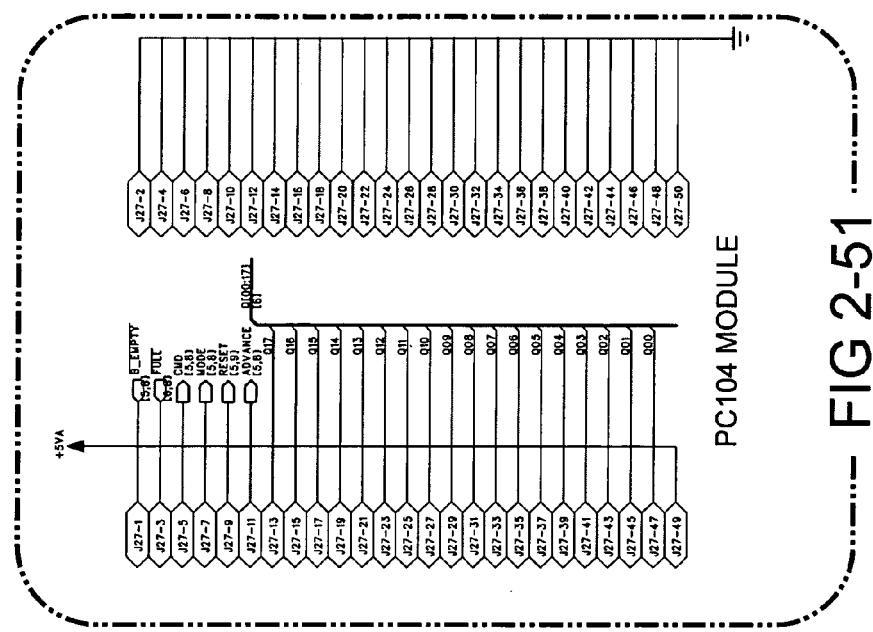
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
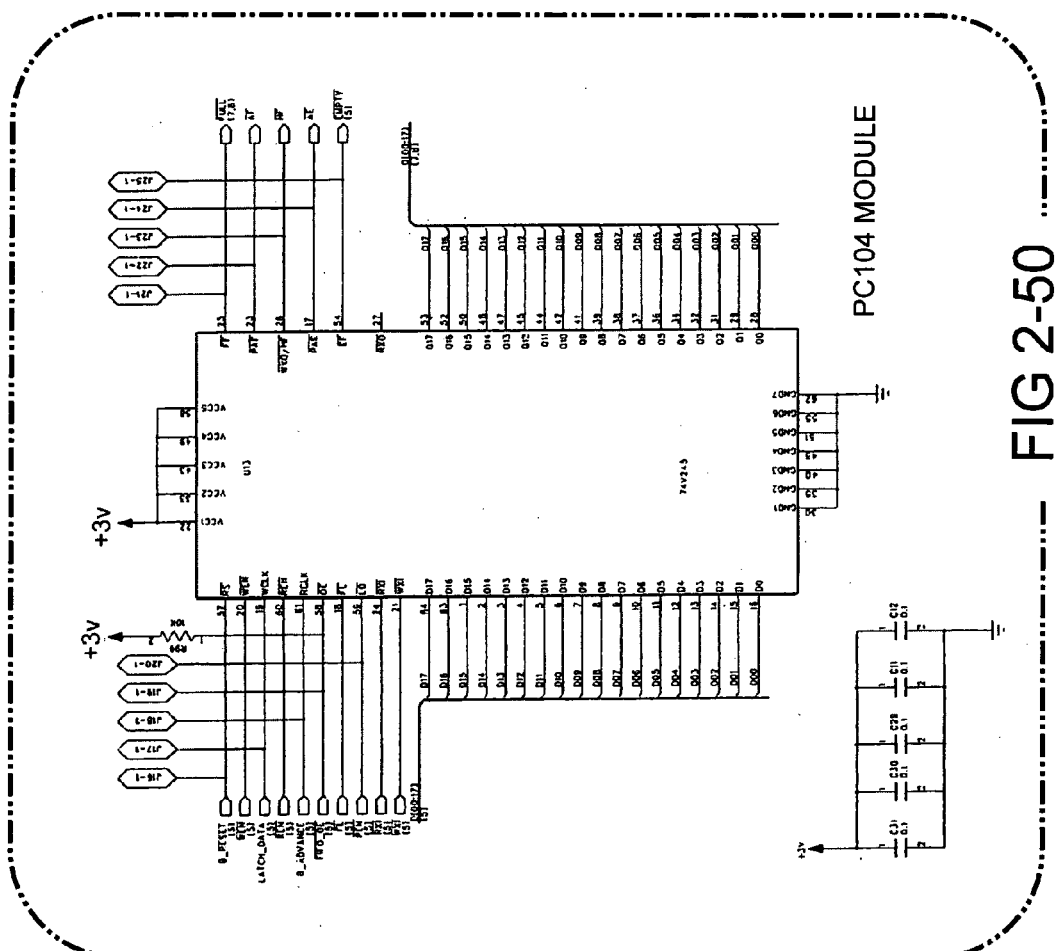
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
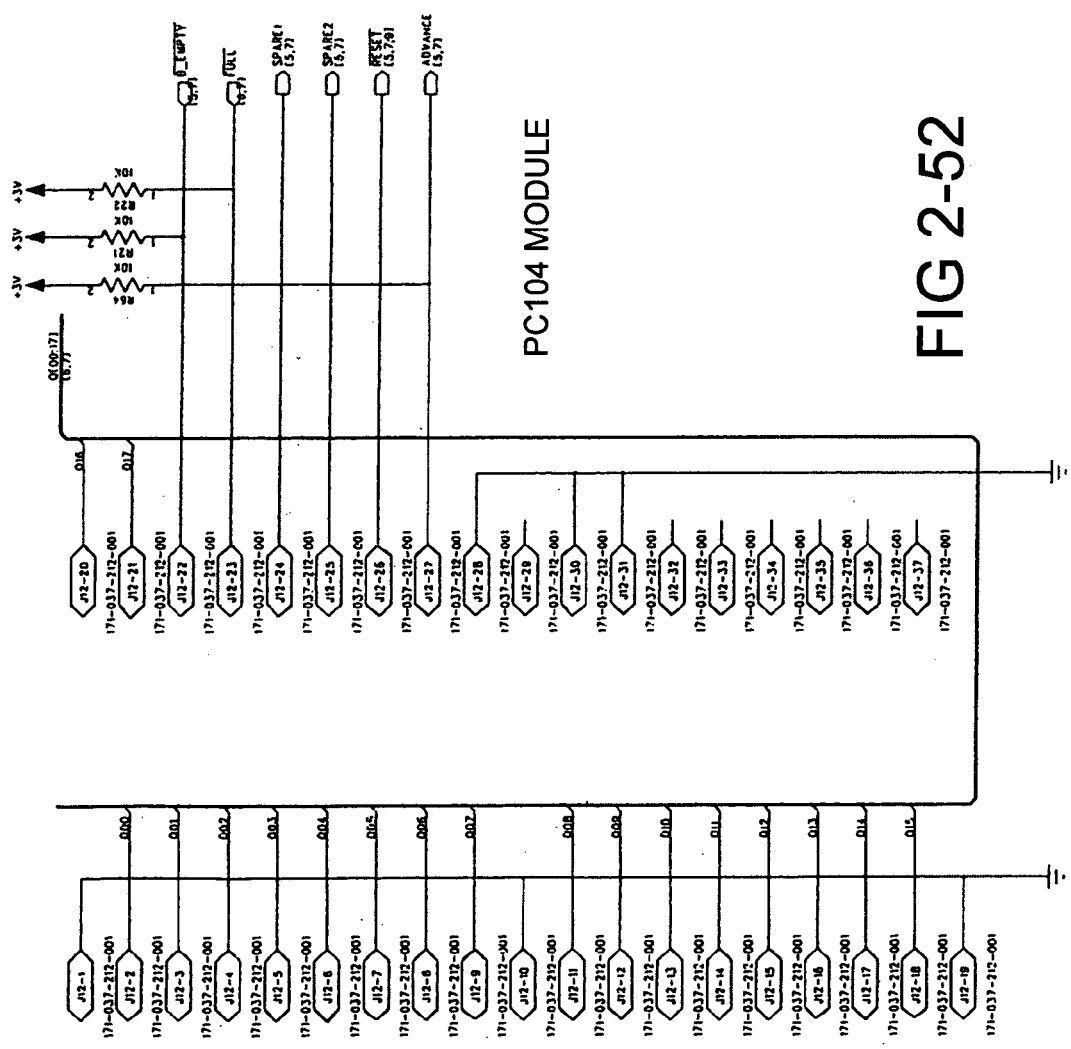
Figures 2, 53:
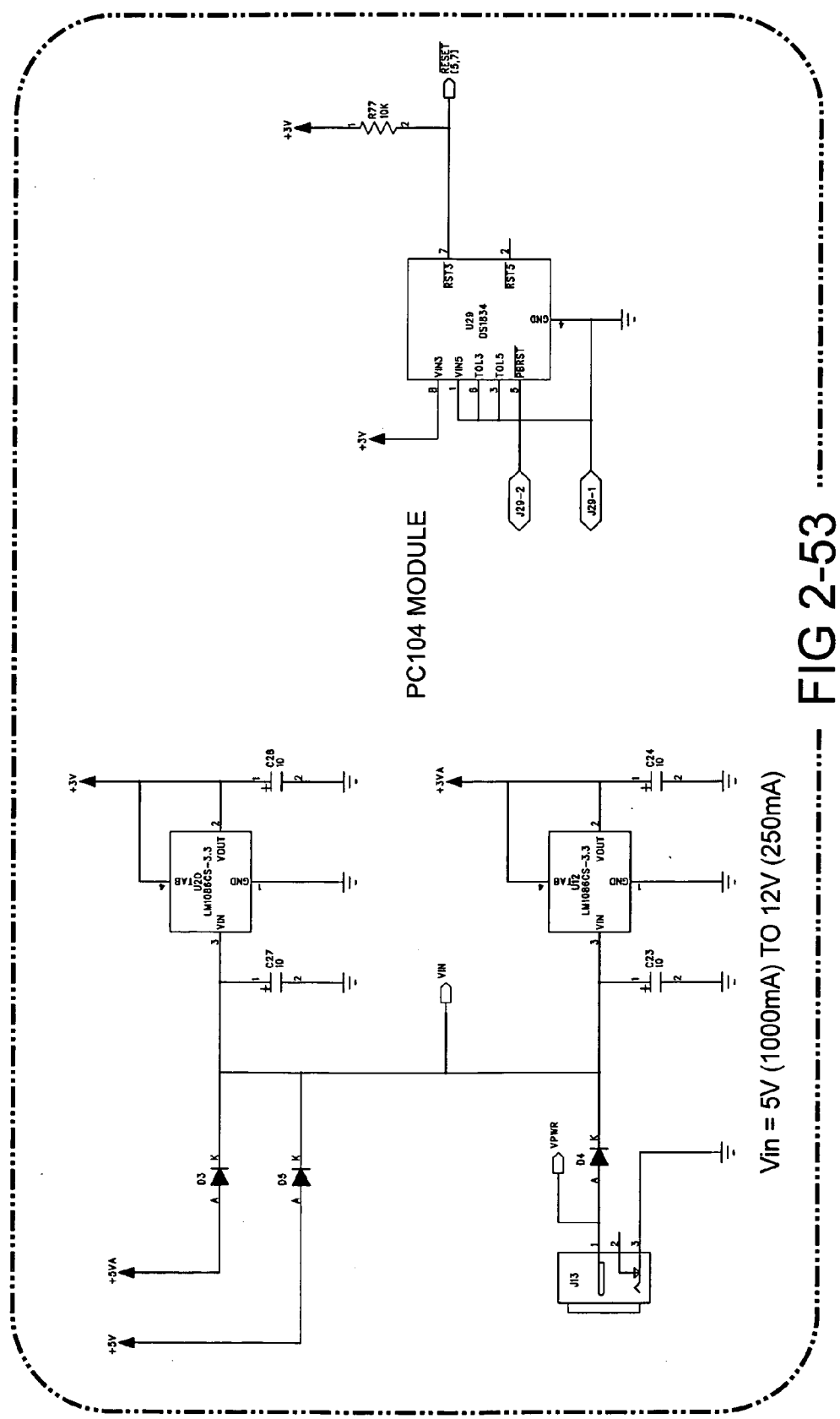
Figures 2, 55:
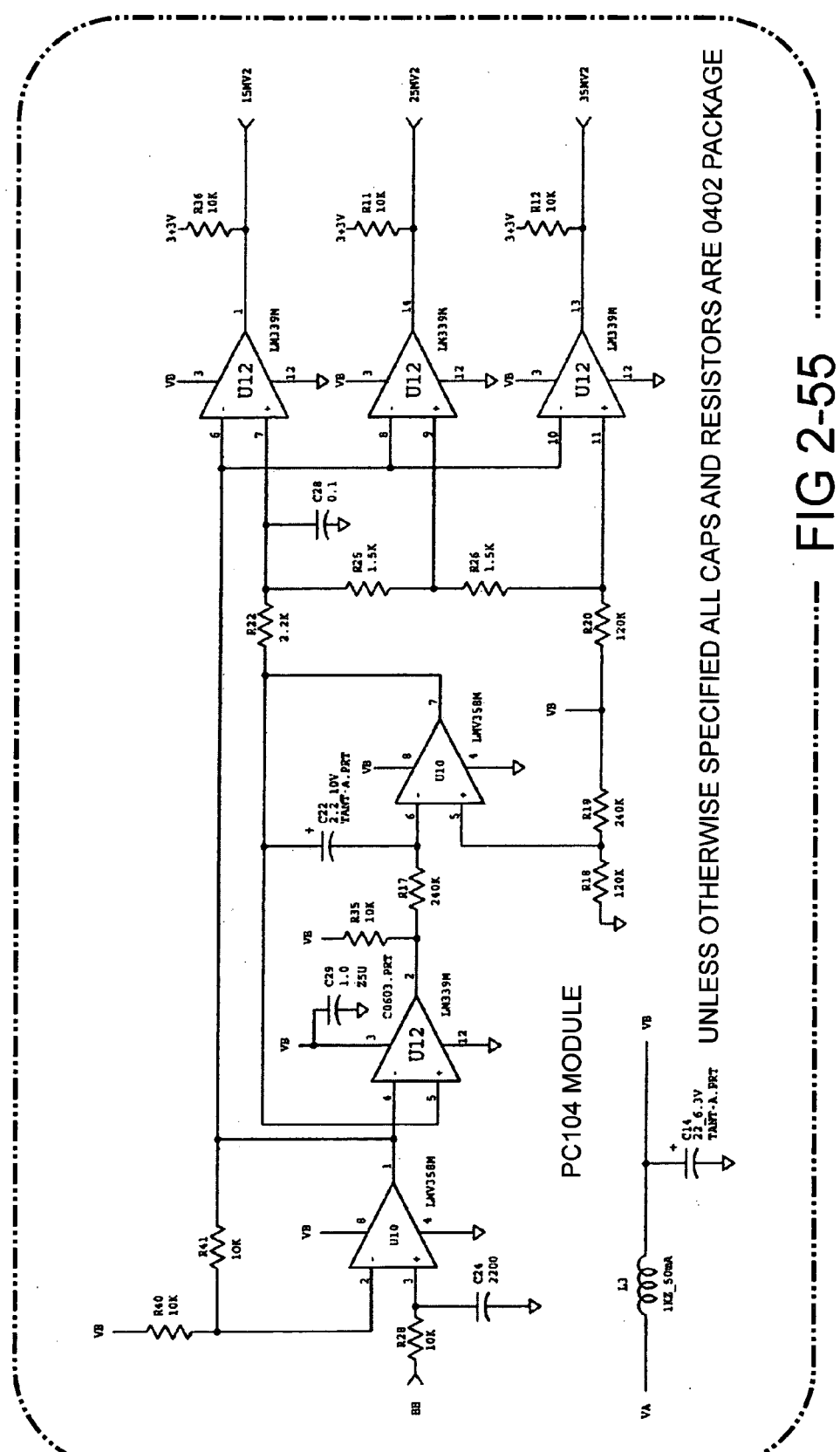
Figures 2, 56:
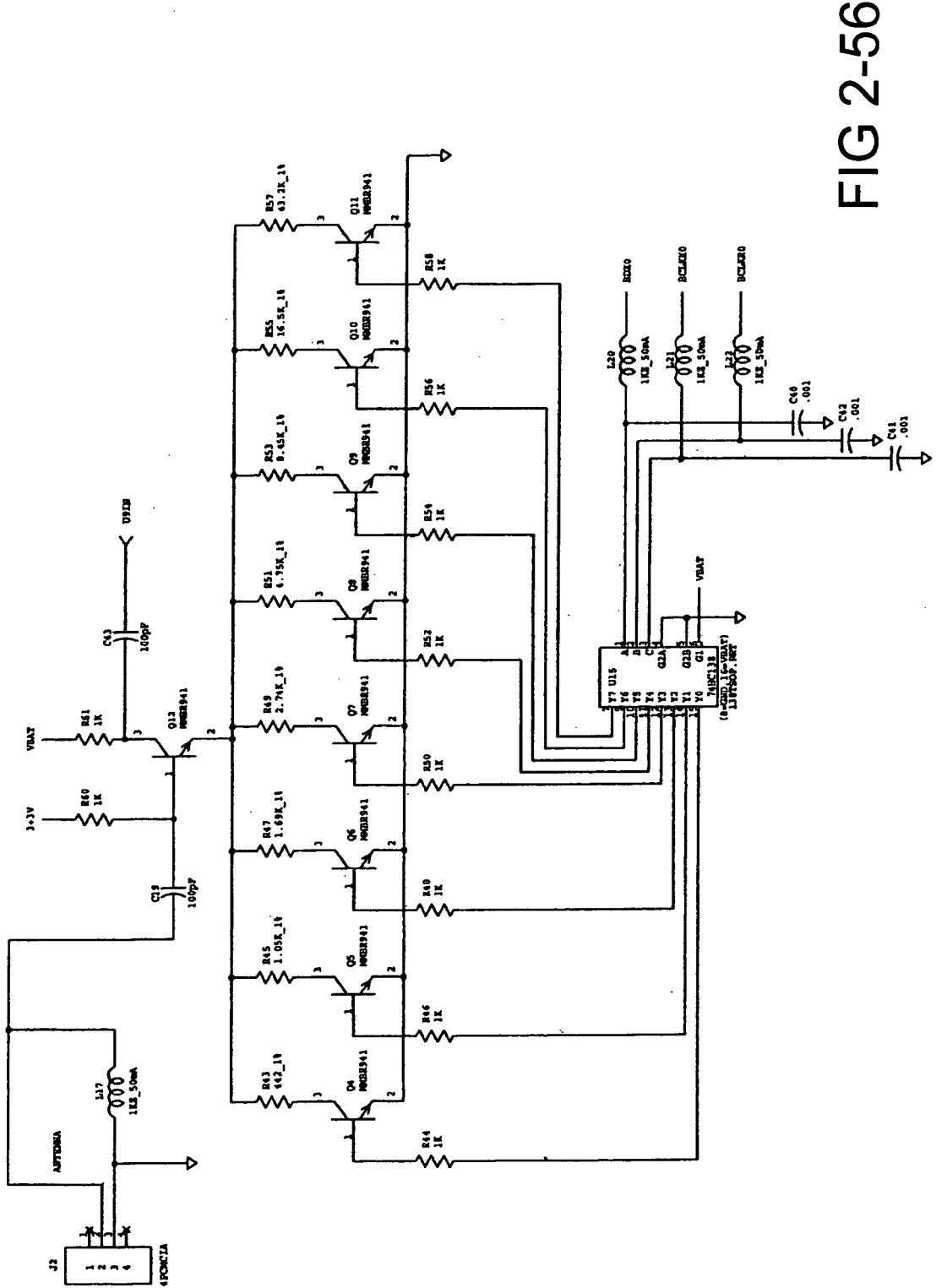
Figures 2, 57:
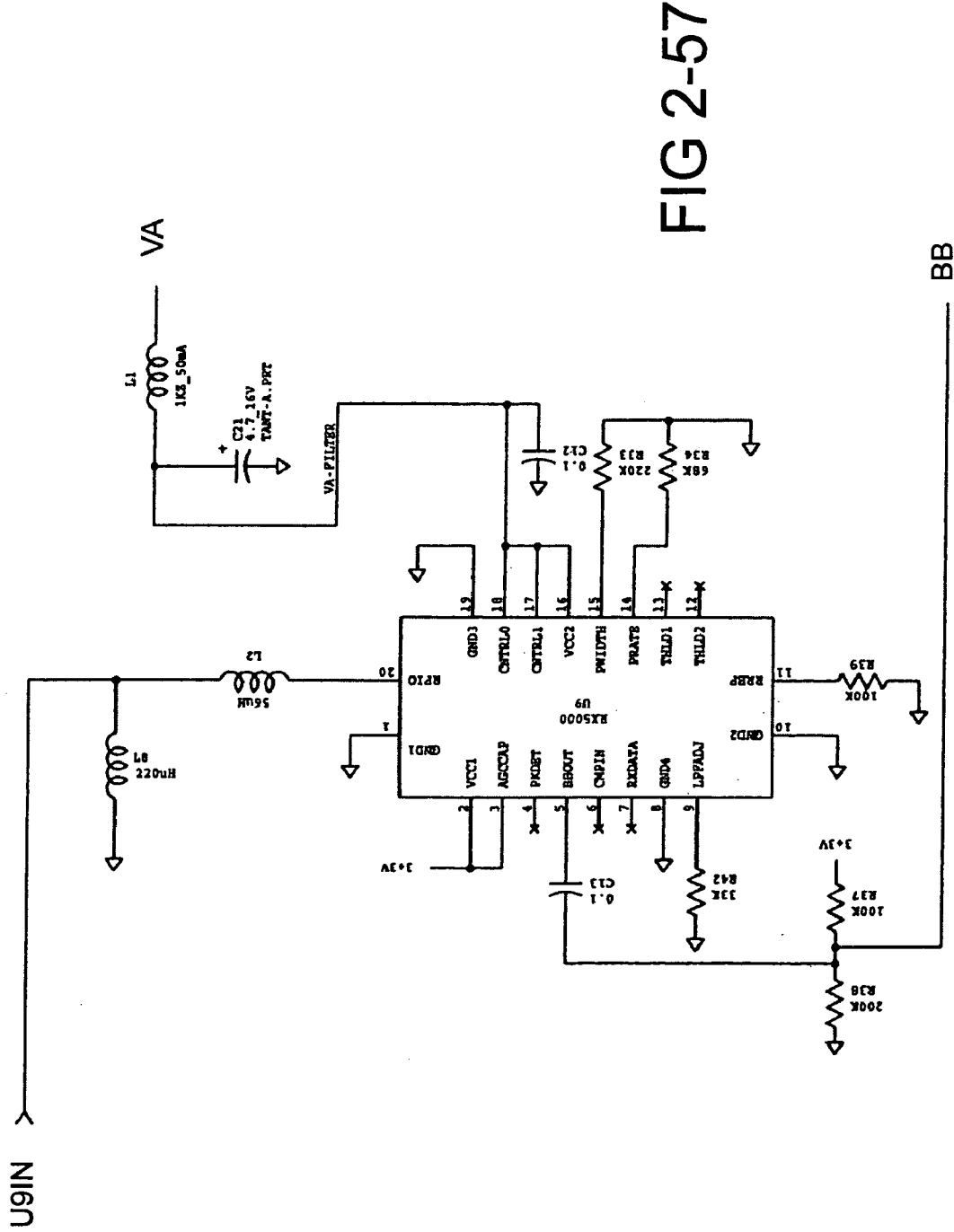
Figures 2, 58:
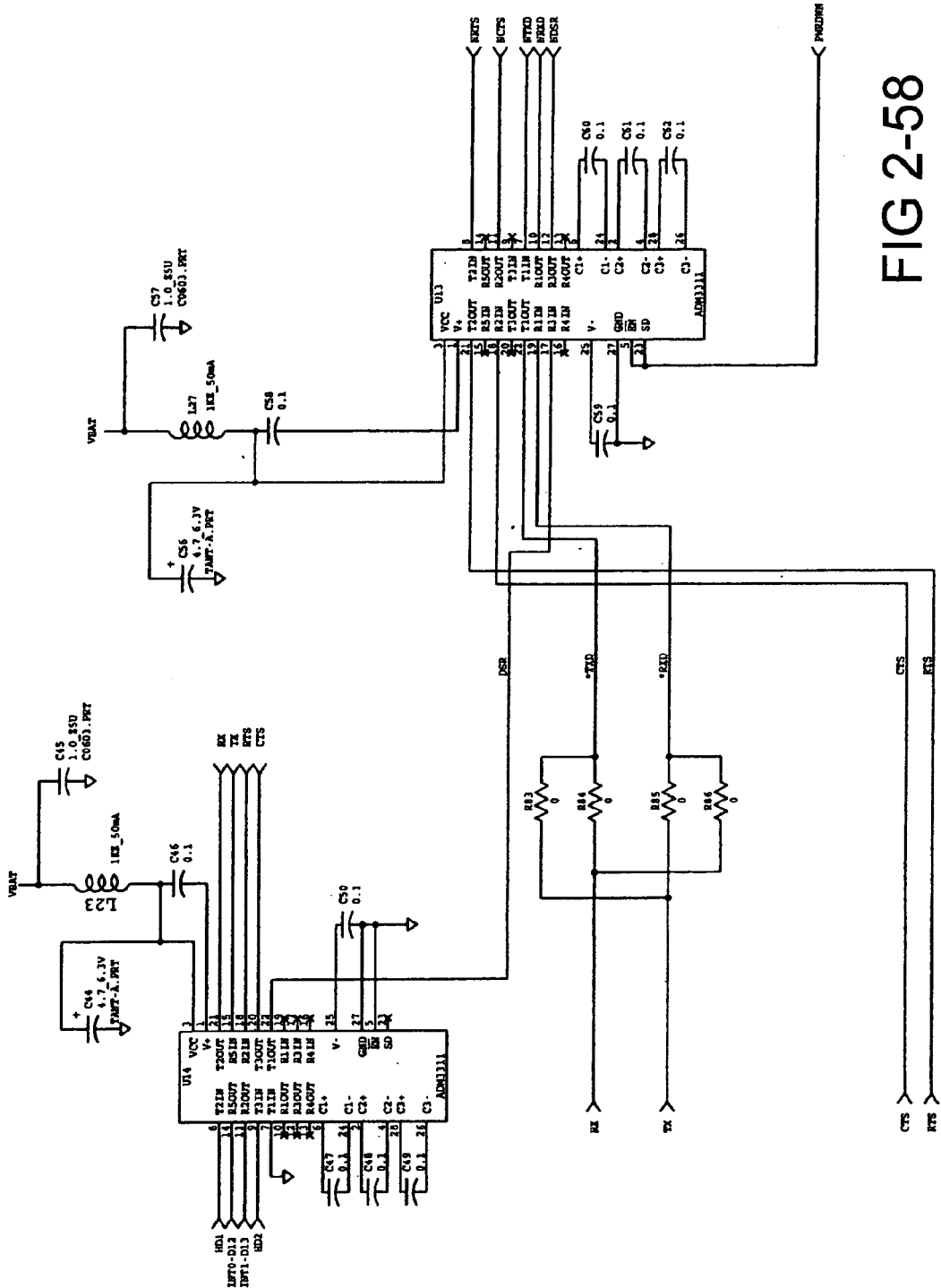
Figures 2, 59:
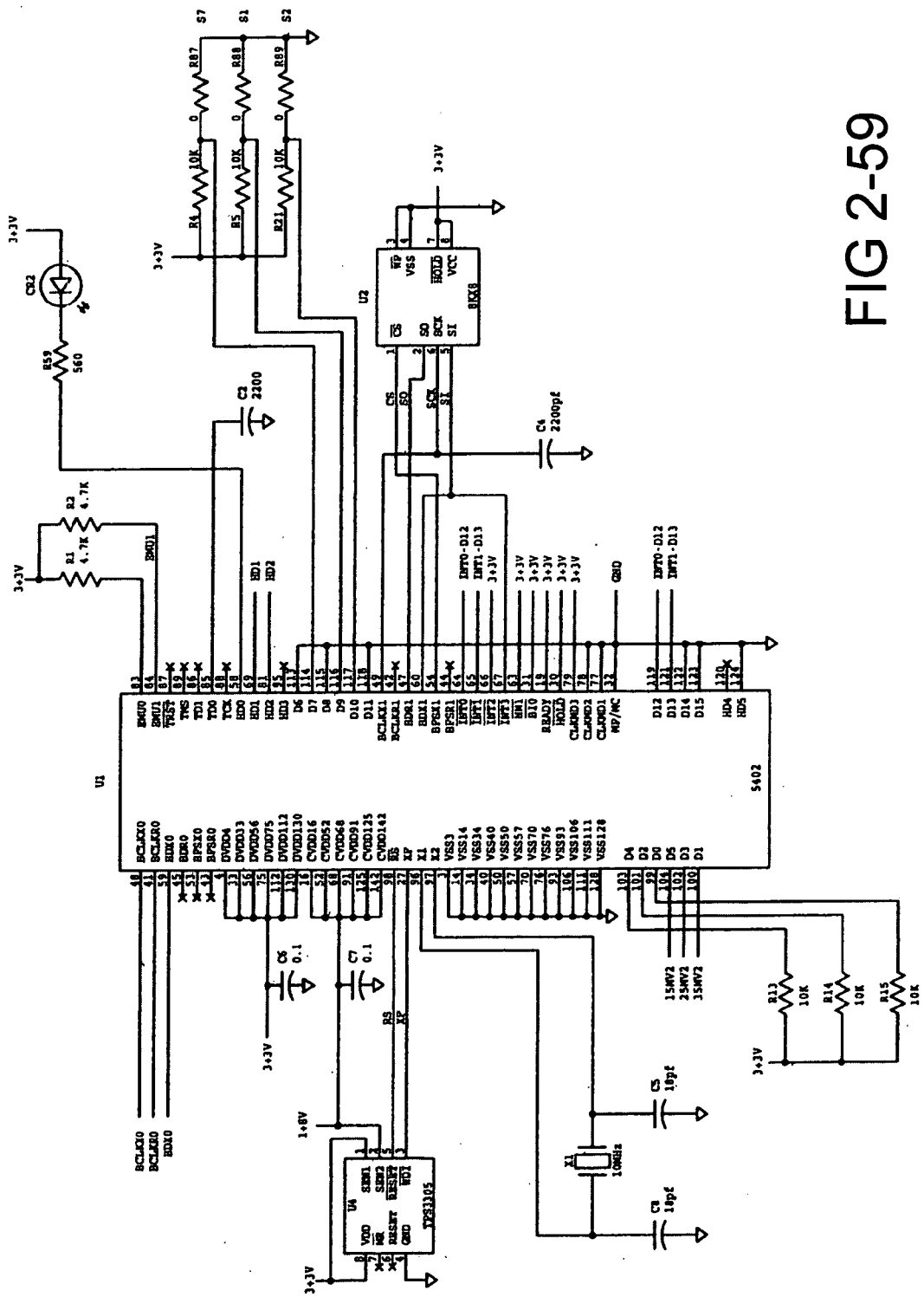
Figures 2, 60:
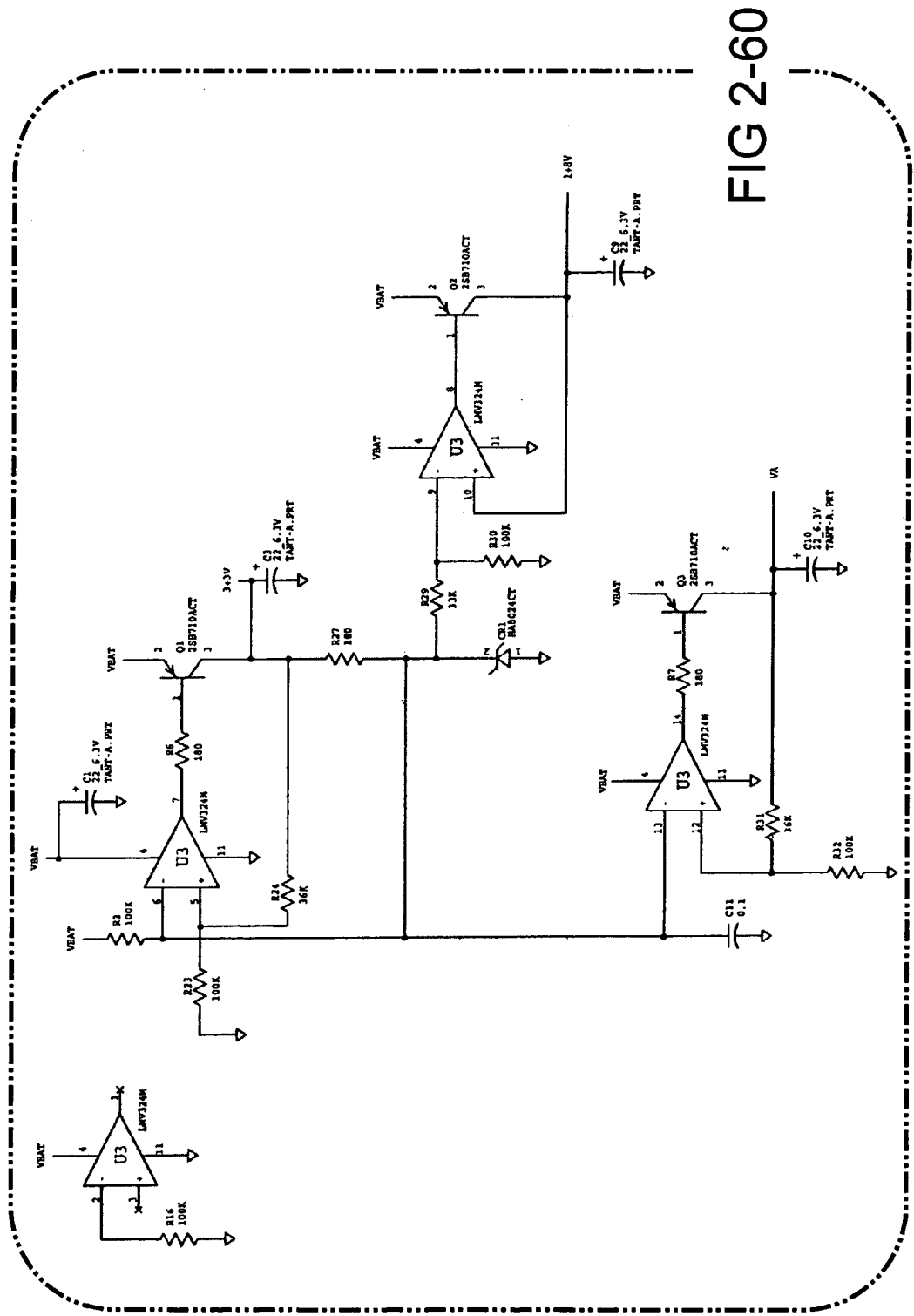
Figures 2, 61:
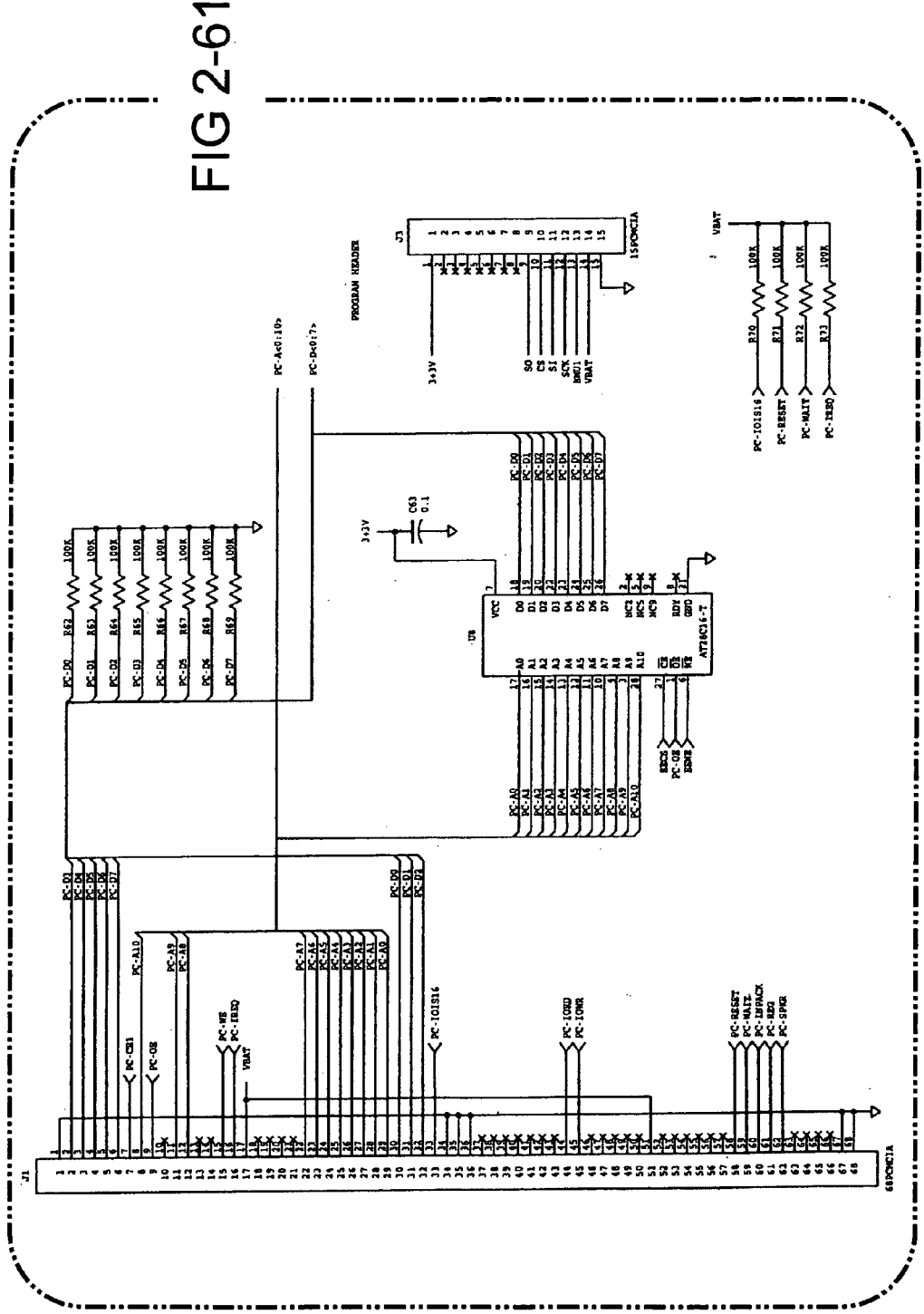
Figures 2, 62:
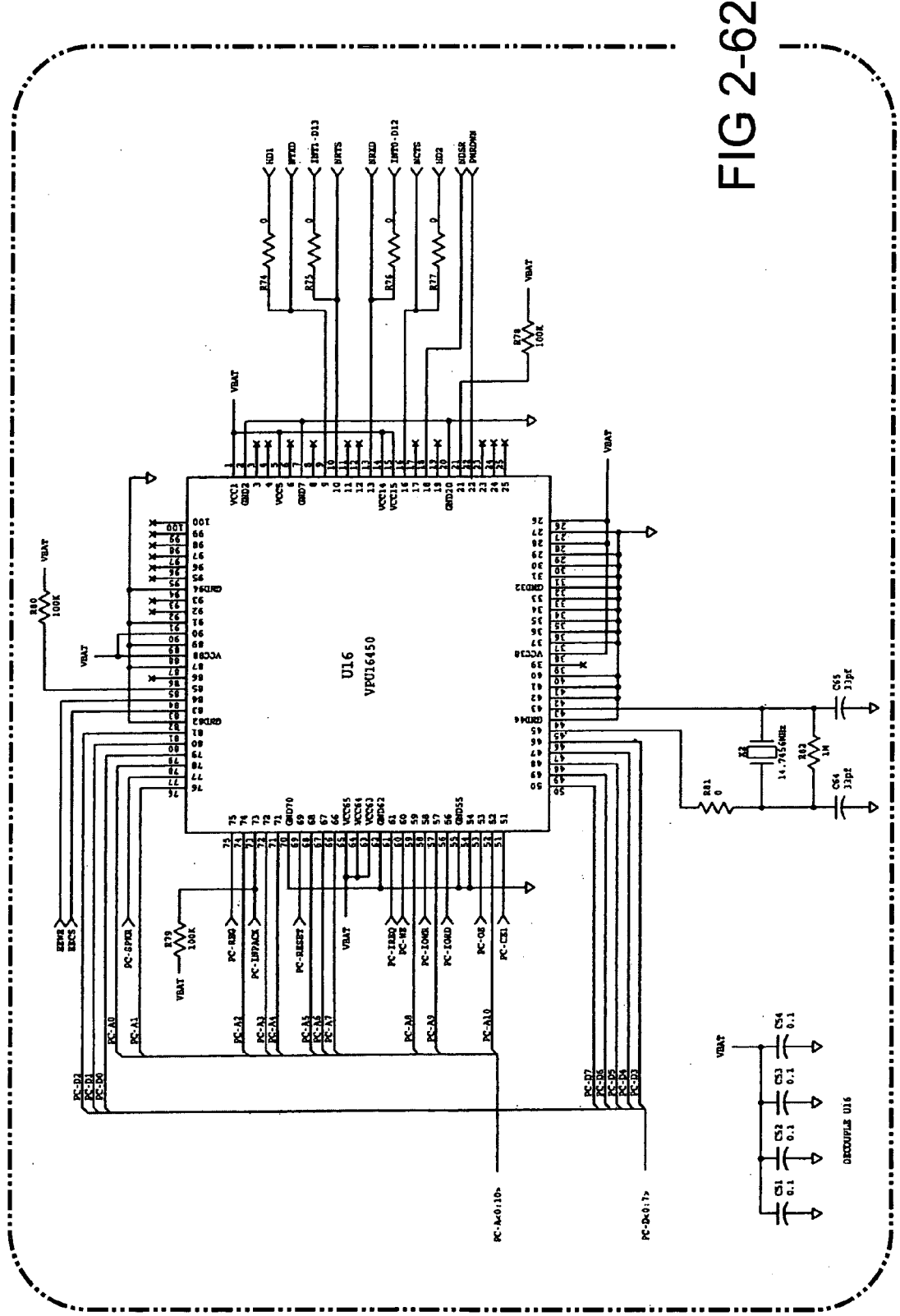
Figures 2, 63:
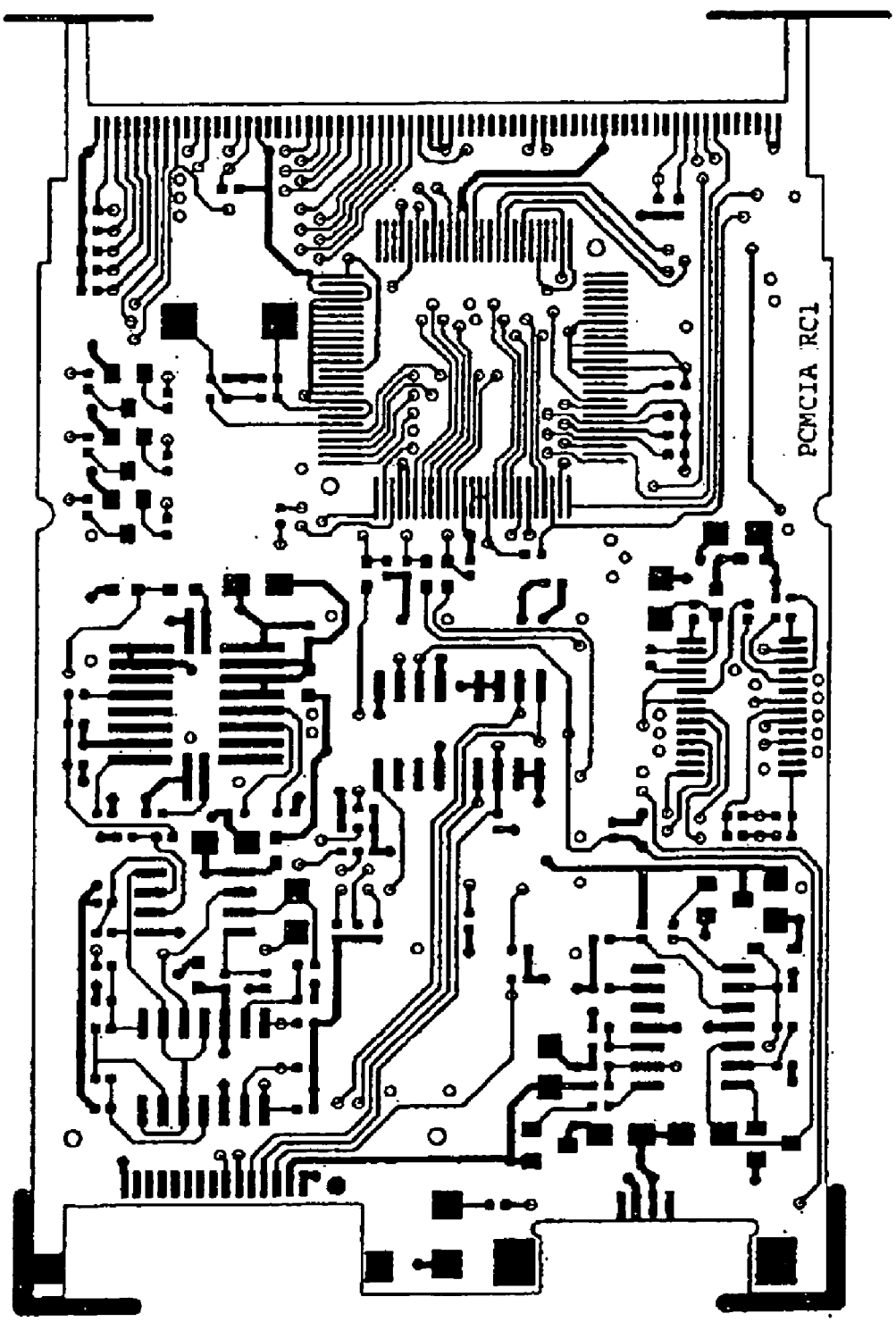
Figures 2, 64:
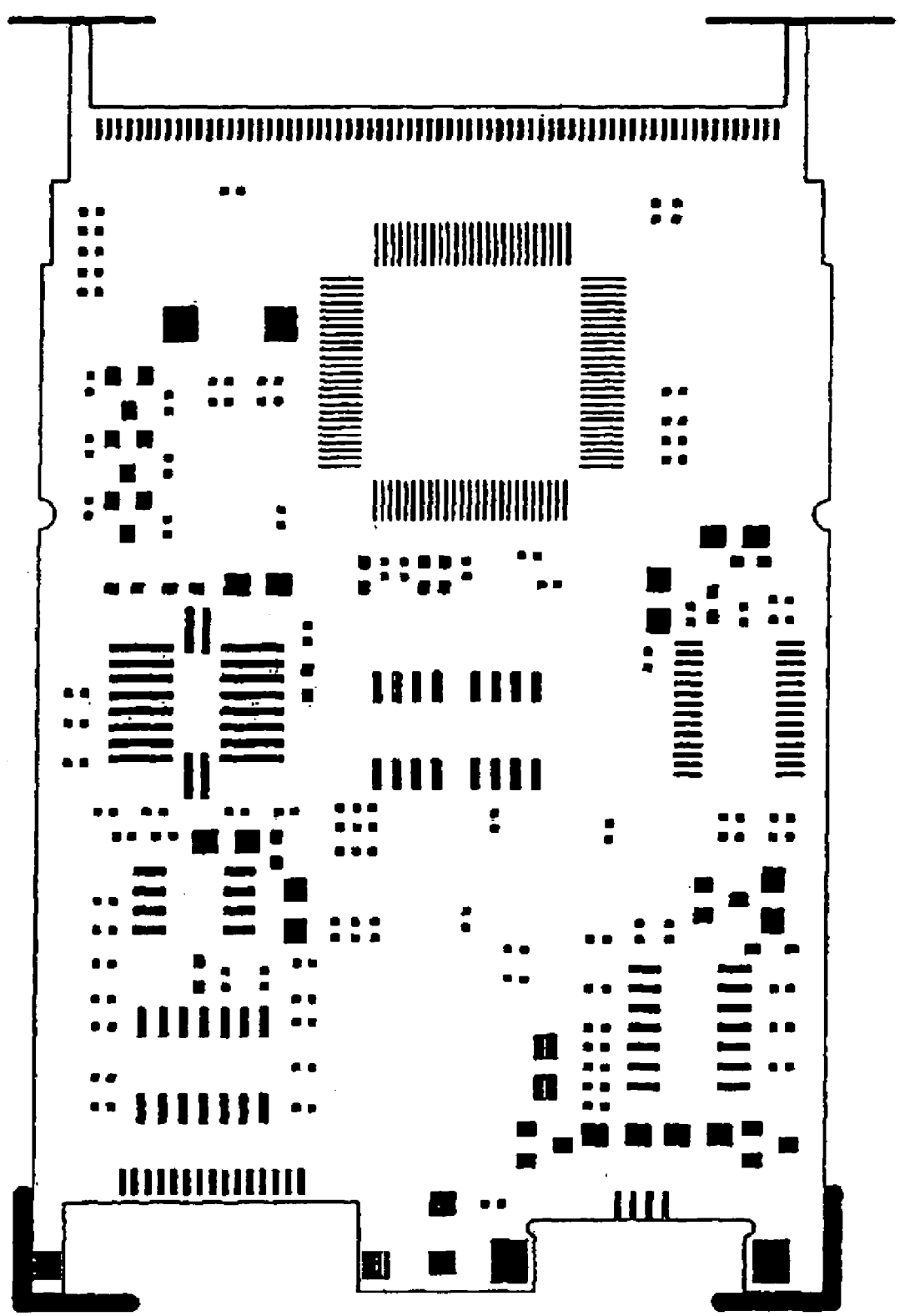
Figures 2, 65:
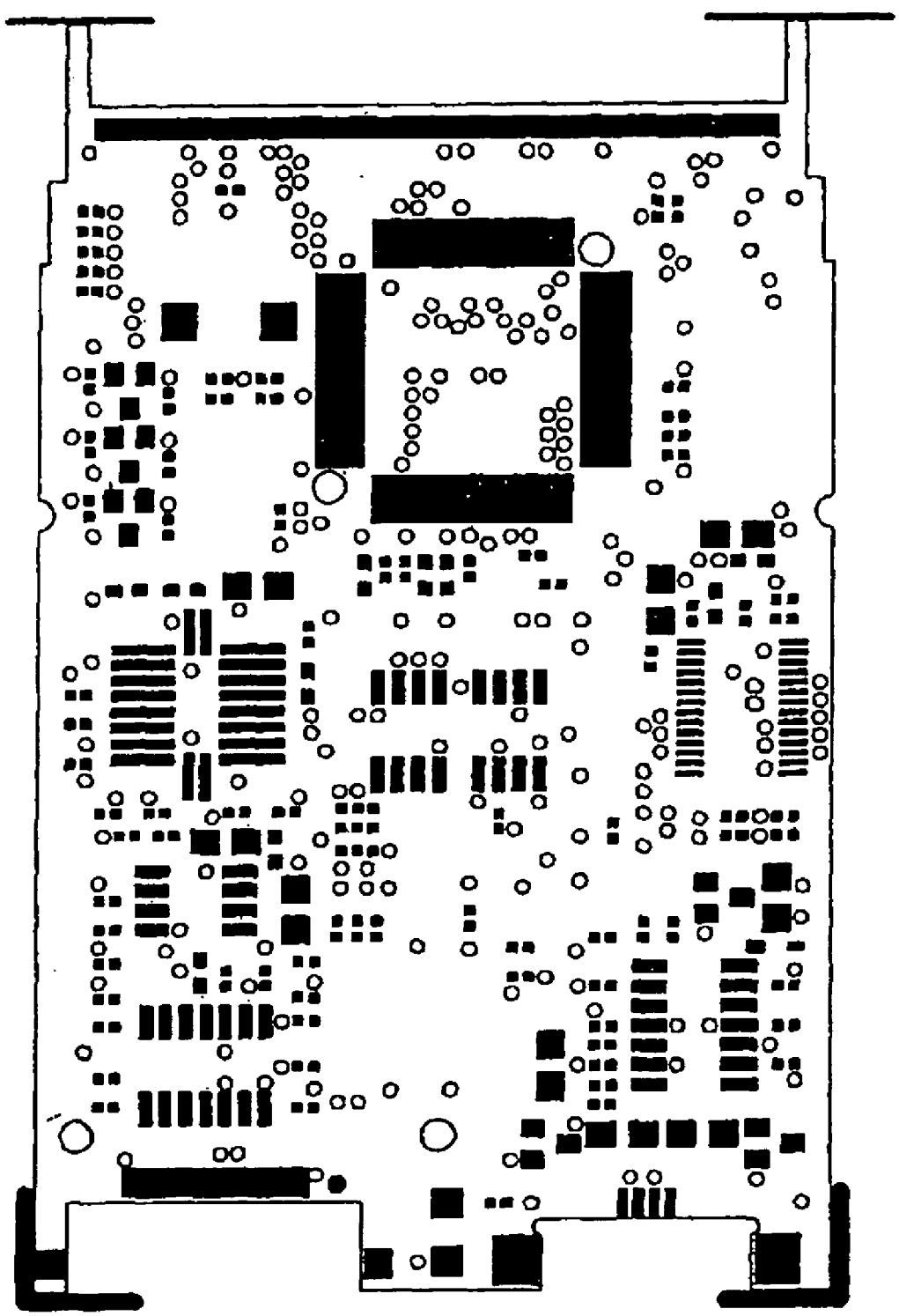
Figures 2, 66:
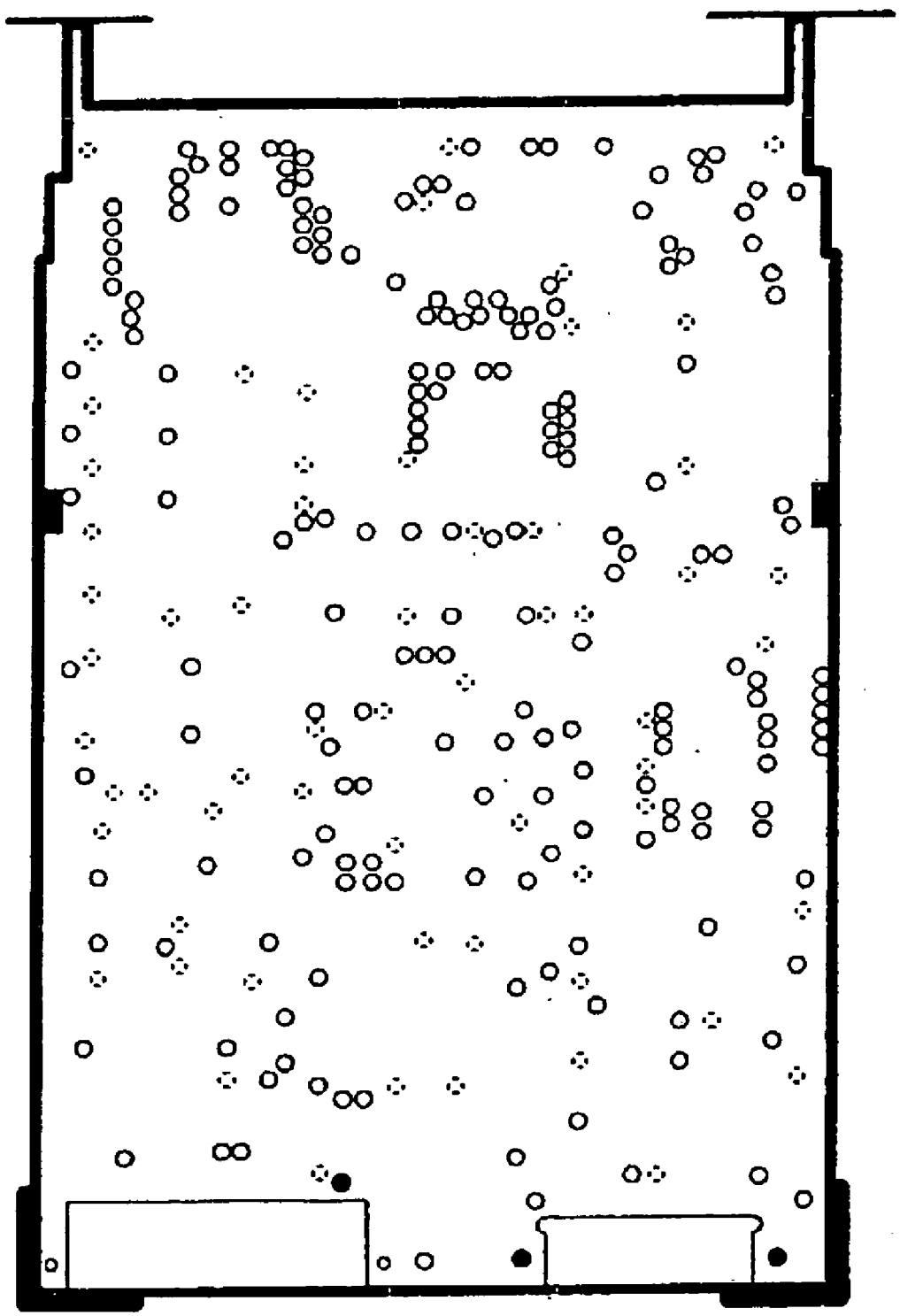
Figures 2, 67:
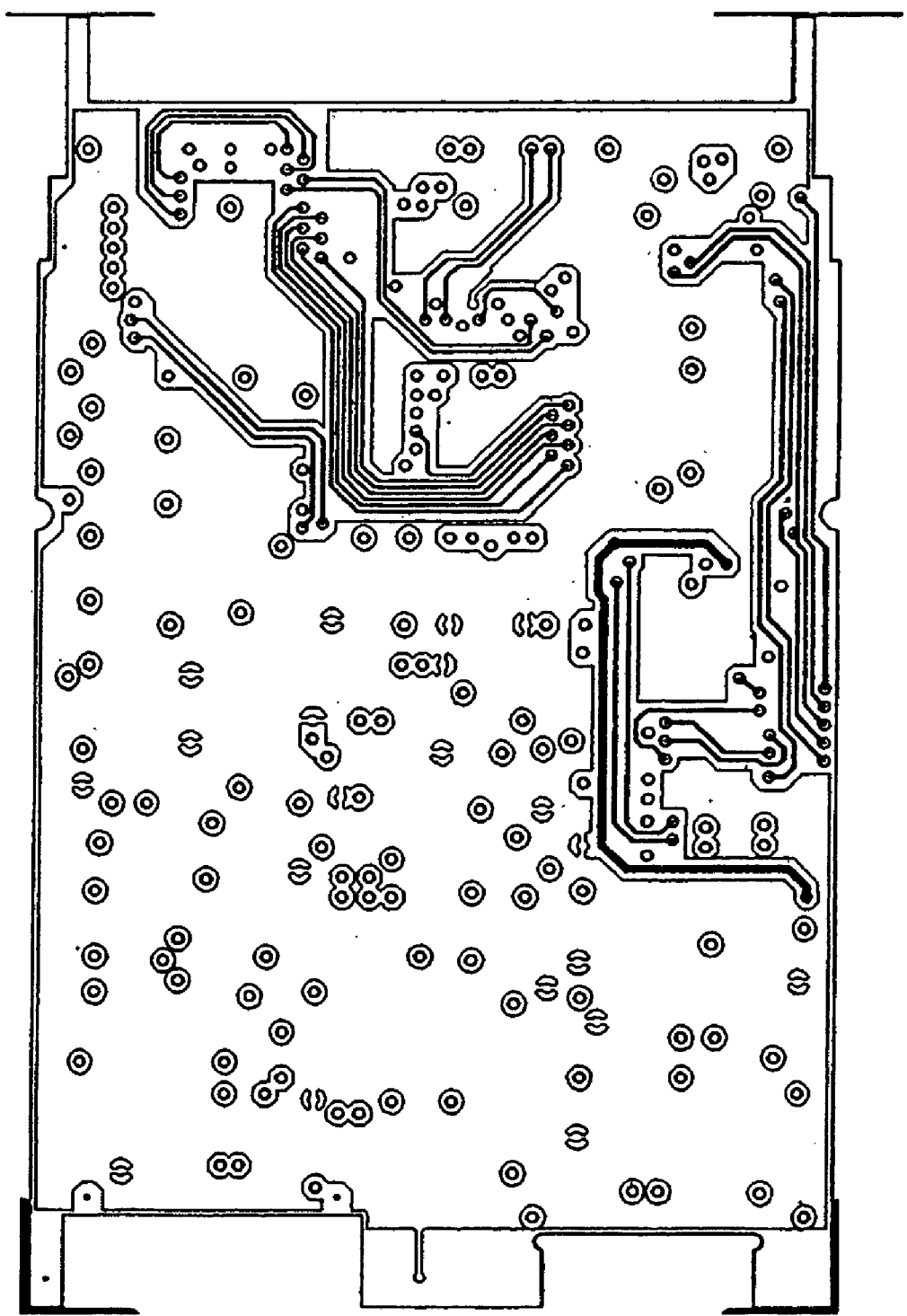
Figures 2, 68:
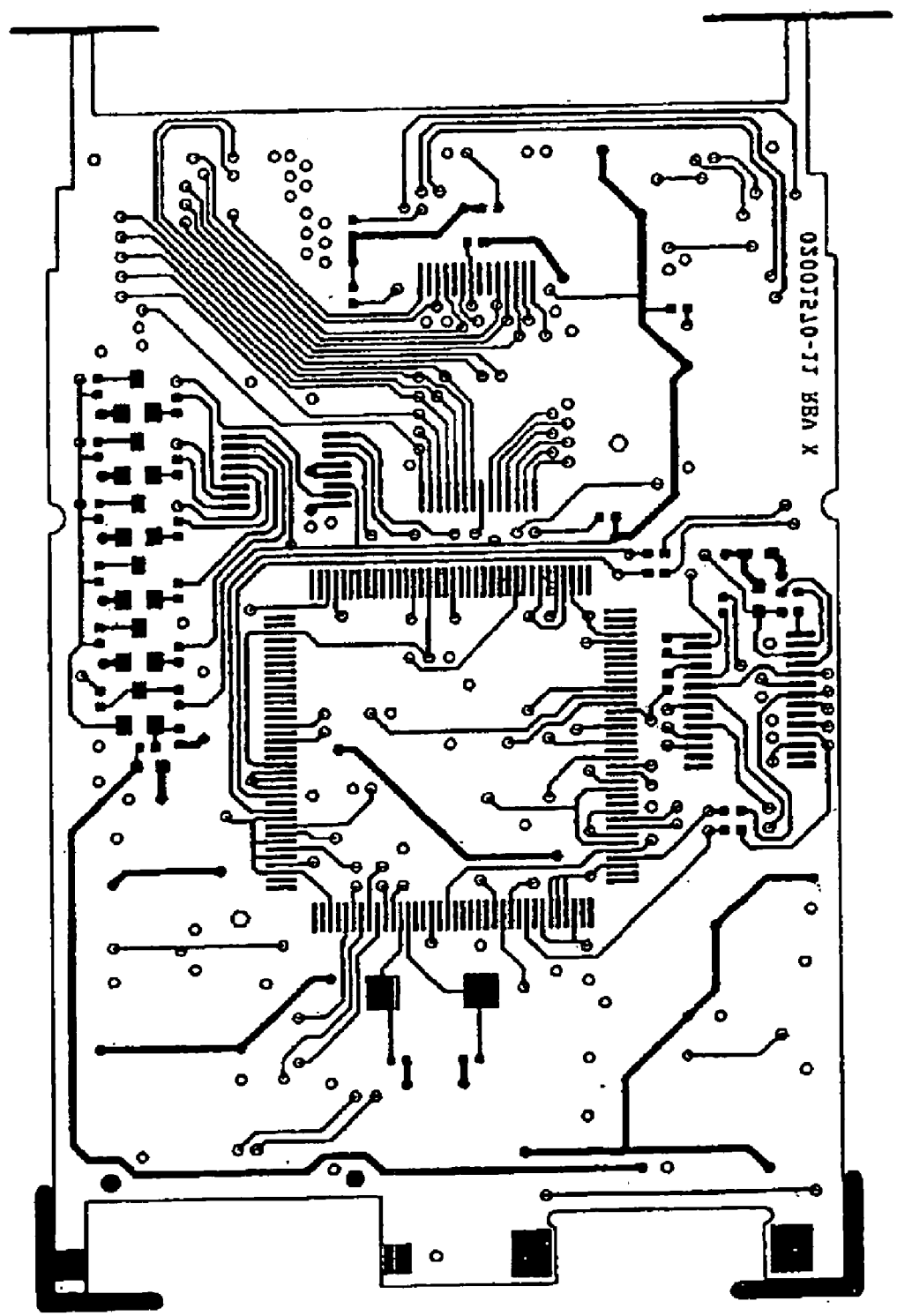
Figures 2, 69:
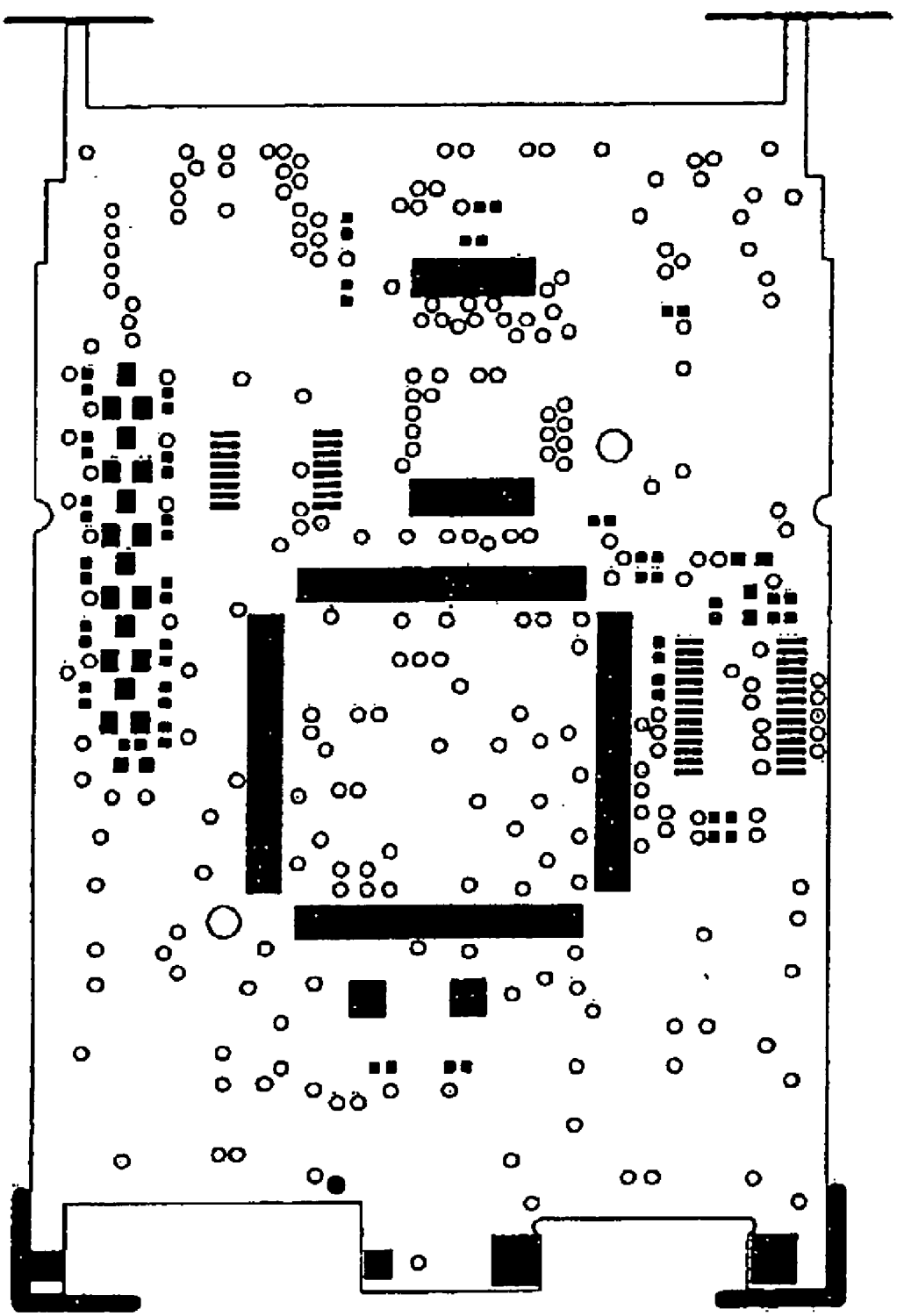
Figures 2, 70:
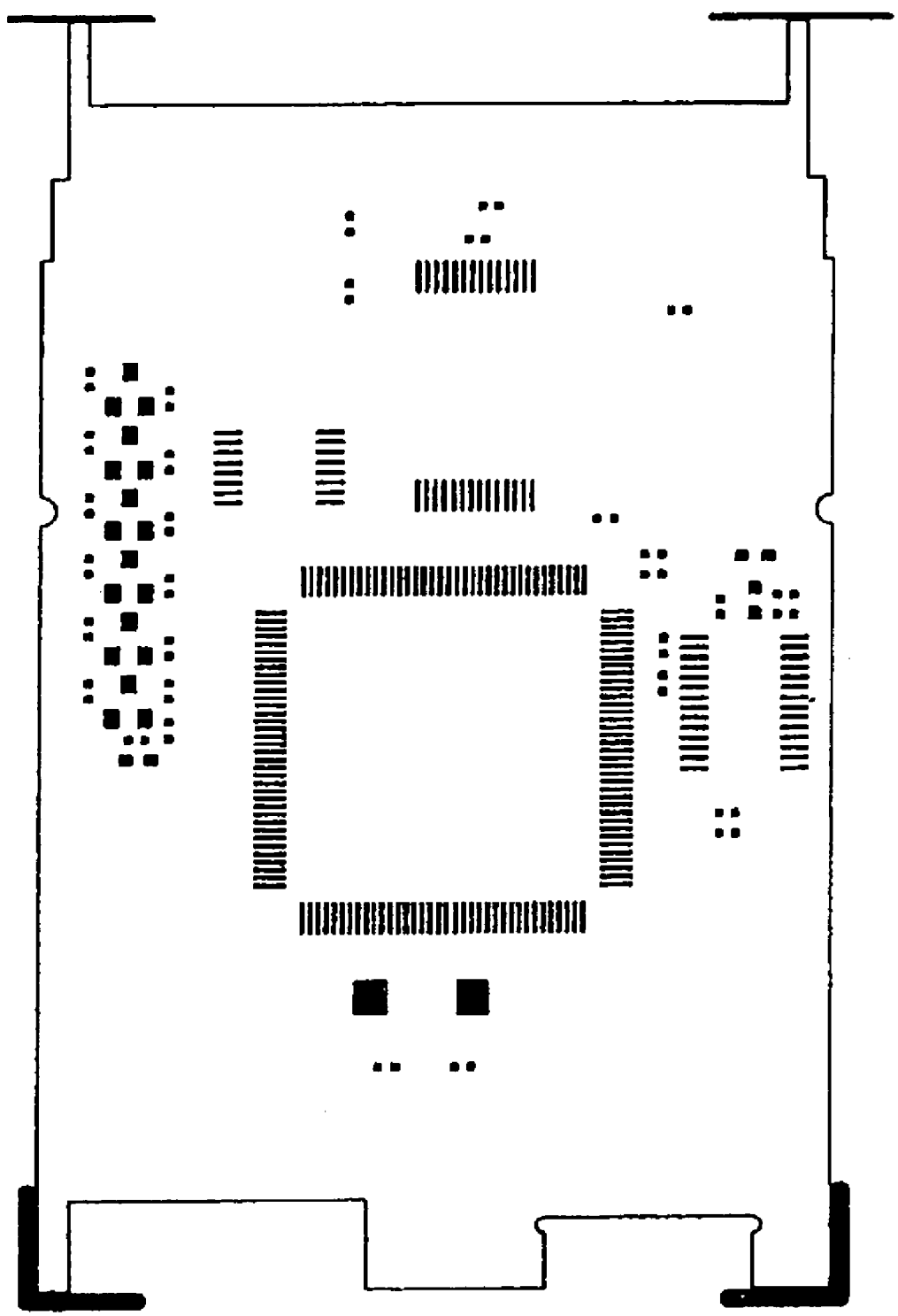
Figures 2, 71:
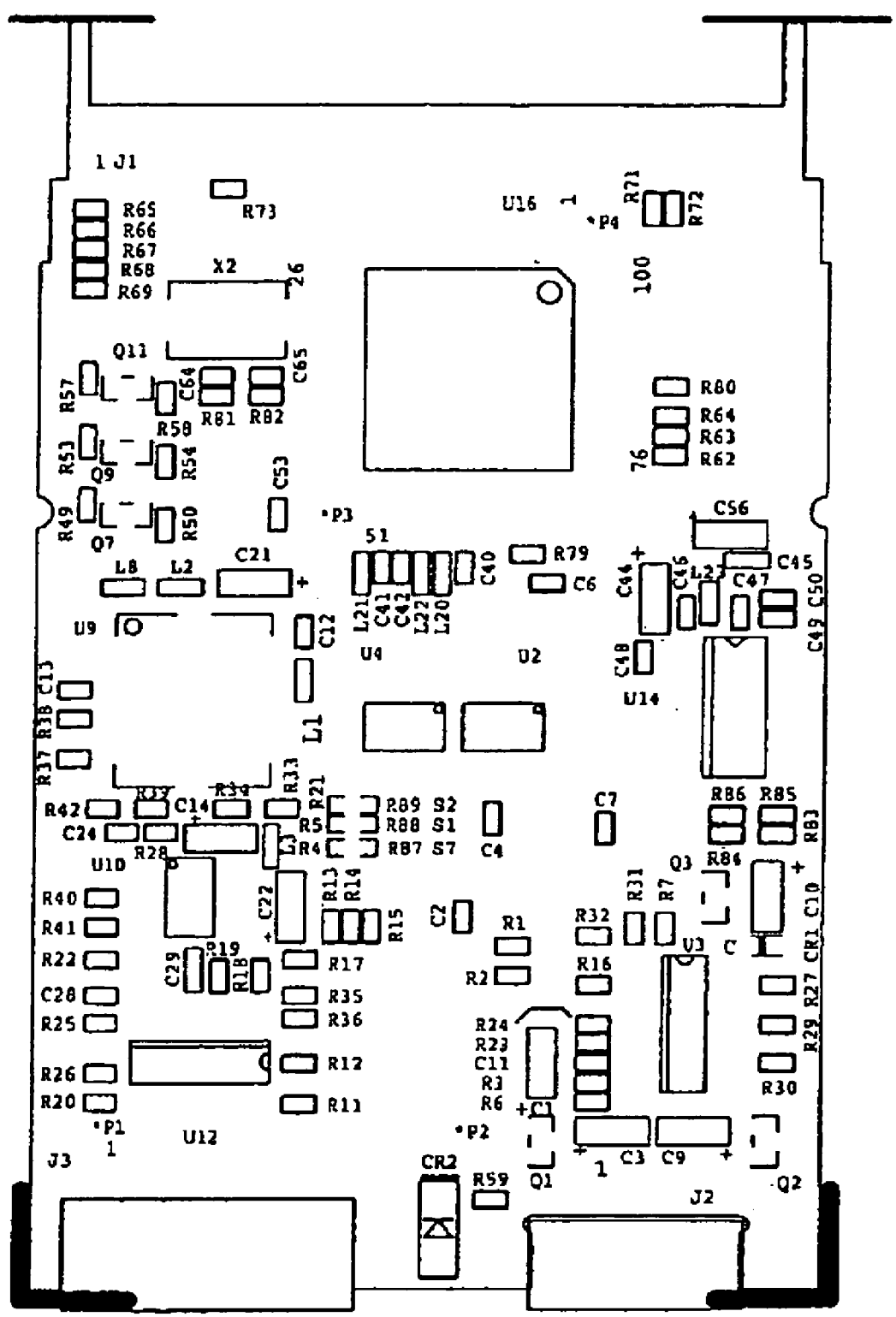
Figures 2, 72:
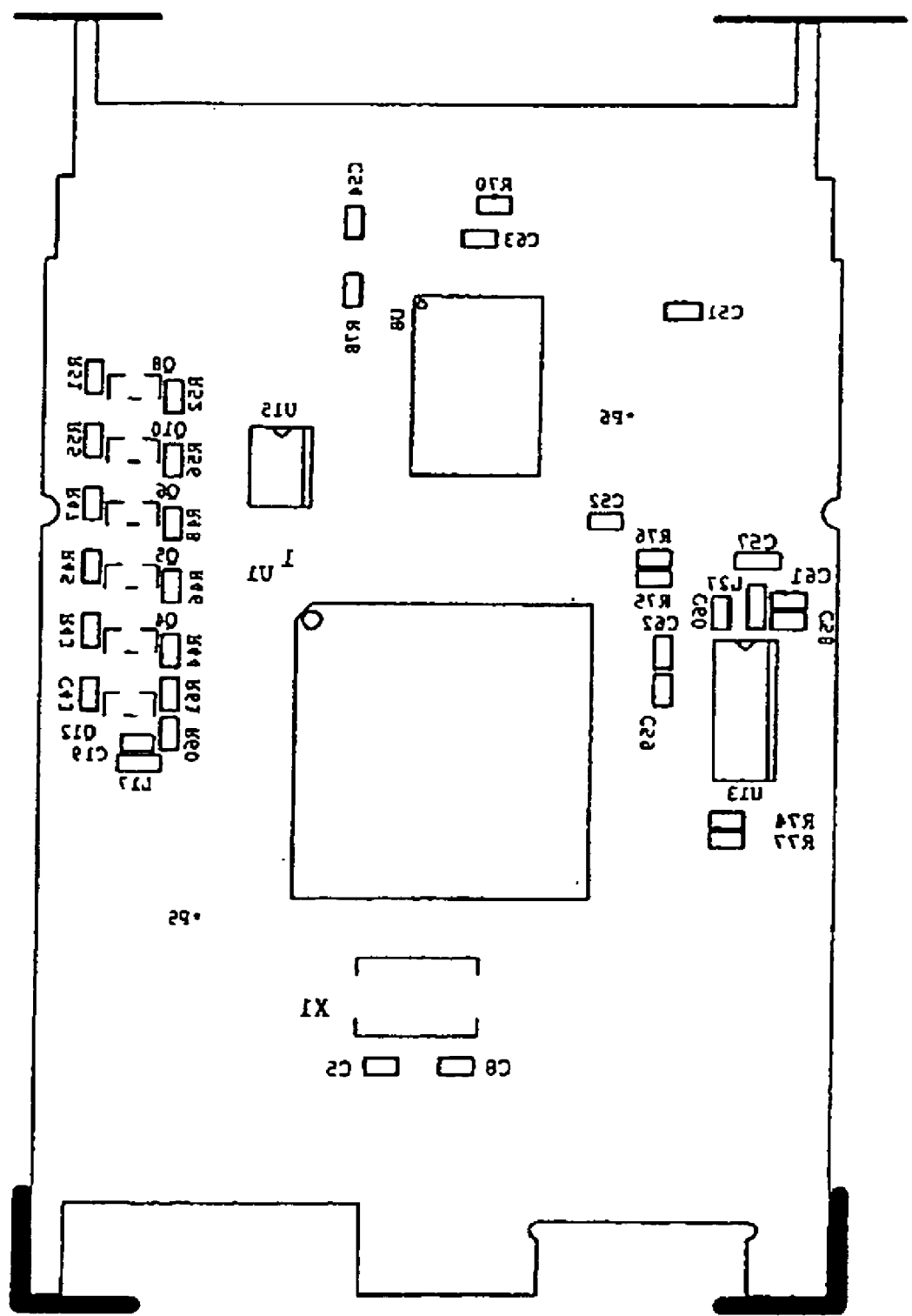
Figures 2, 73:
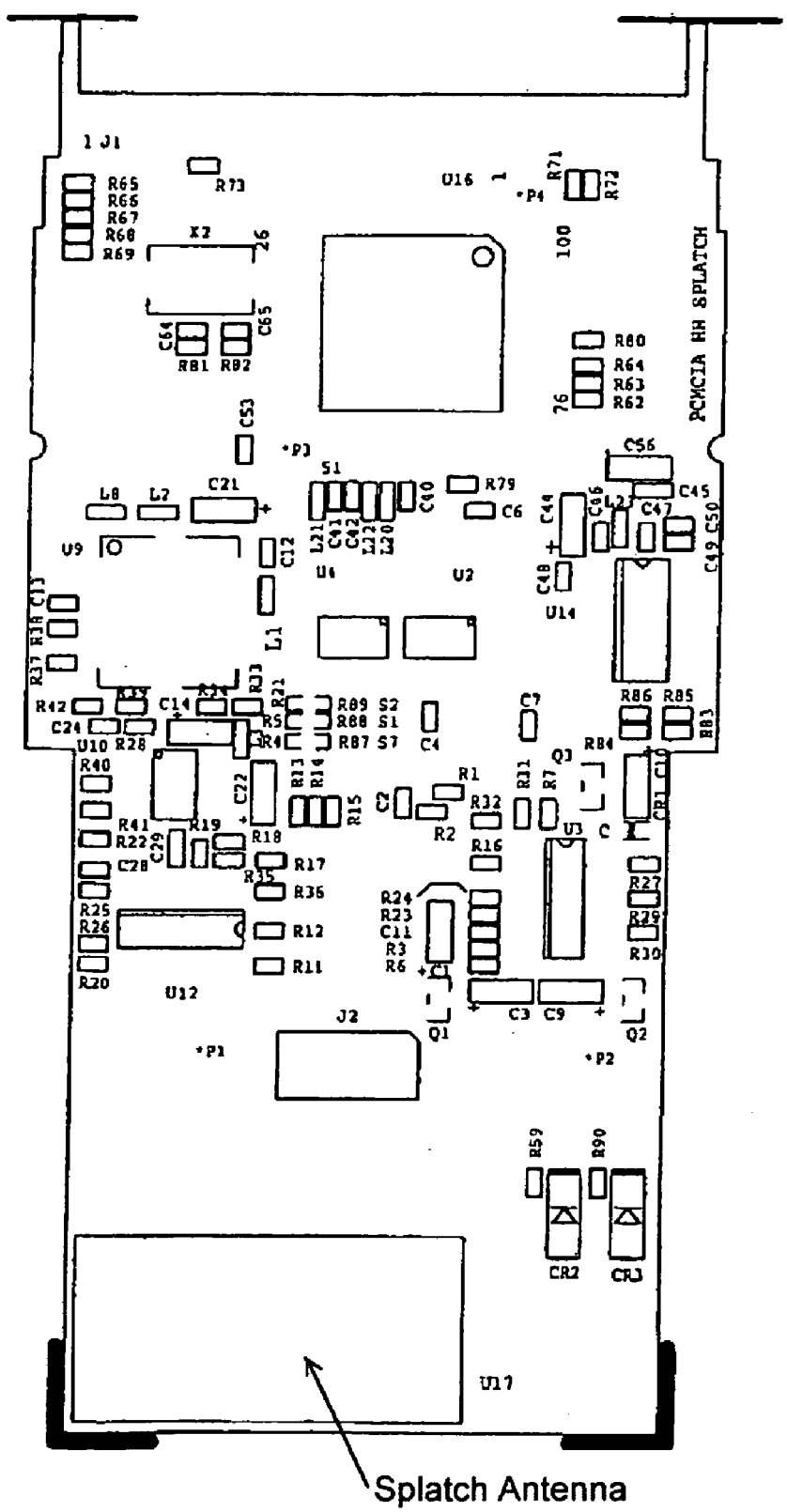

FIG. 2-45 to FIG. 2-54 show the PC-104 LITMIS Receiver Board detailed circuit schematic and FIG. 2-55 to FIG. 2-62 show the detailed LITMIS PCMCIA Receiver circuit schematic for the external antenna card with the range selection circuitry (FIG. 2-56). FIG. 2-63 to FIG. 2-72 show the PCMCIA Receiver board layout for the external antenna card, and FIG. 2-73 the layout with the internal Splatch component antenna. FIG. 2-74 shows the nature of the Splatch Planar Antenna this is used in the LITMIS PCMCIA Receiver. Another advantage of using a PCMCIA Receiver 130 is that, when used with a dual slot PCMCIA expansion Pak (such as iPAQ's), the second slot can be used with an 802.11 Modem for communication with the control center.

Figures 2, 75:
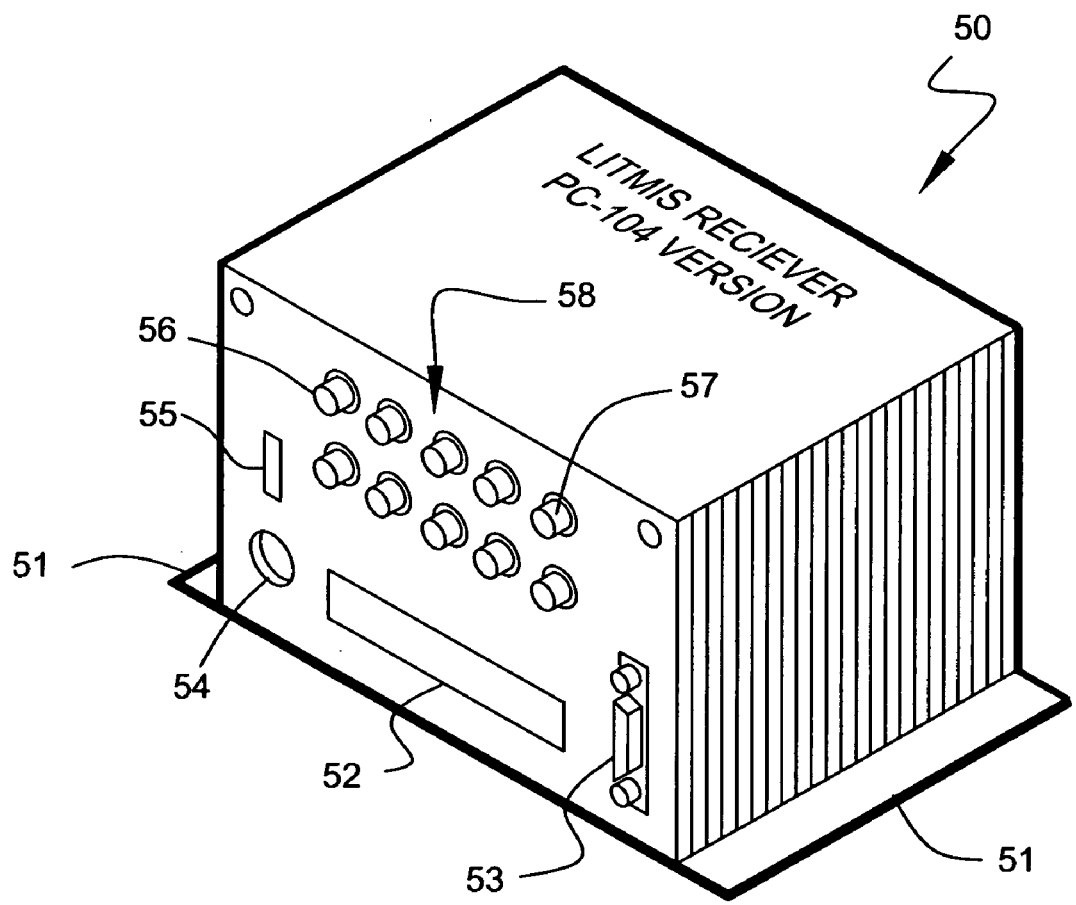

FIG. 2-75 shows a view of the assembled, fixed LITMIS PC-104 Receiver 50 with mounting flange 51. Also shown is the dual PCMCIA slot 52, serial connector 53, power connector 54 and LAN connector 55. Also shown are ten coaxial connectors, one for a WLAN antenna 56, one for a GPS antenna 57, and eight connectors 58 providing coax cable connections to the maximum number of four, dual (orthogonal) antennae.

Figures 2, 76:
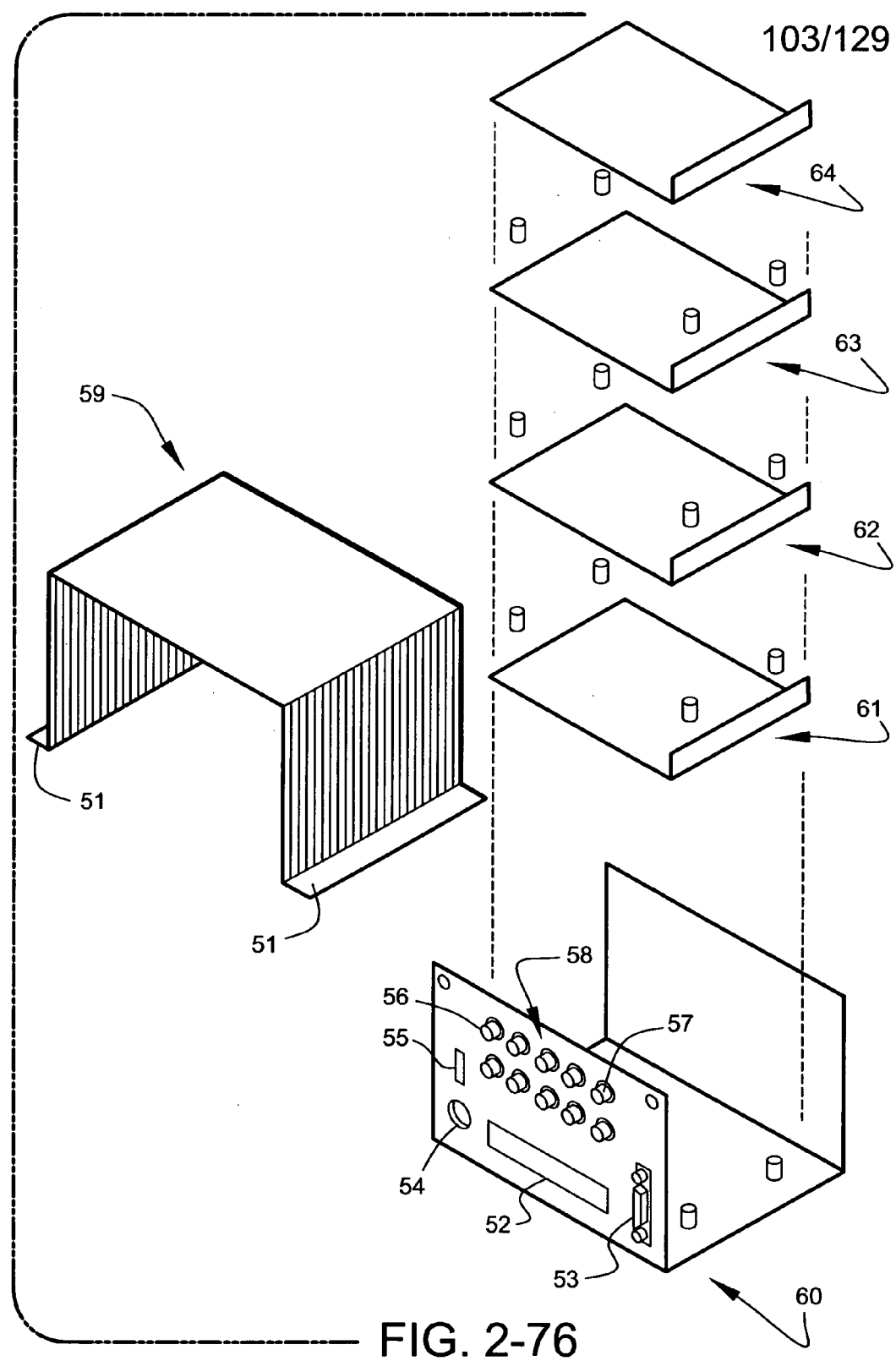

FIG. 2-76 shows an exploded view of the fixed LITMIS PC-104 Receiver showing the case 60, the cover 59 and mounting flanges 51, the dual PCMCIA slot 52, serial connector 53, power connector 54 and LAN connector 55 (also coax sockets 56, 57, and 58). The four PC-104 boards shown are PCMCIA two-slot Connectors 61 that can be used for GPS or 802.11 cards or even one of two LITMIS PCMCIA Receivers 130 (such as Aaeon PCM-3115B), CPU Connector 62 (such as Aaeon PCM-4335 or 3336), Ethernet Connector 63 (such as Aaeon PCM-3660) and the LITMIS Receiver 64. Other PC-104 options include a Vehicle Power Supply Connector for Wheel and Axle Monitoring Systems, fork lift, golf cart or similar applications, 48-channel DIO Connector such as Aaeon PCM-33724), Isolated RS232/

422/485 Connector (such as Aaeon PCM-3610), or a Cell Phone/Internet Communications Board (including boards such as Ubicom's PhantomServer). Preferably, the stack can be expanded to include combinations of the above options.

Figures 2, 77:
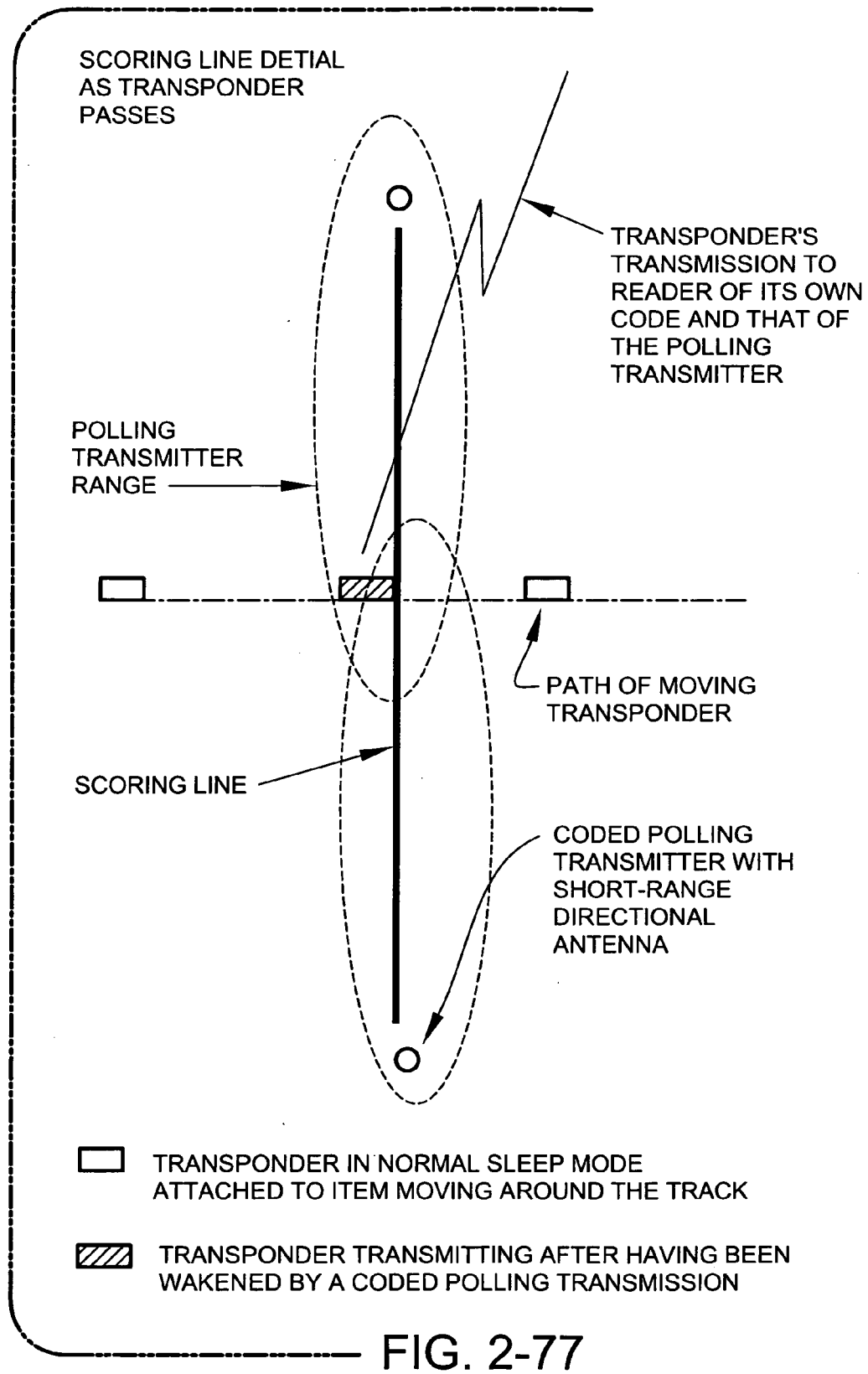

FIG. 2-77 shows a use of a pollable Second logic-processor (that doesn't transmit unless polled) and a repetitively transmitting First logic-processor, as a scoring method in a wide range of sporting events. A short-range First logic-processor with a directional antenna is located on either end of the scoring line with the transmissions directed across the track so as to cover the full width of the scoring line and assure that a Second logic-processor crossing the line will receive the polling signal. The instant the Second logic-processor receives the polling signal it transmits its code to the Receiver located nearby, thereby notifying the Receiver that the Second logic-processor has just crossed the scoring line and time stamping that reception.

Figures 2, 78:
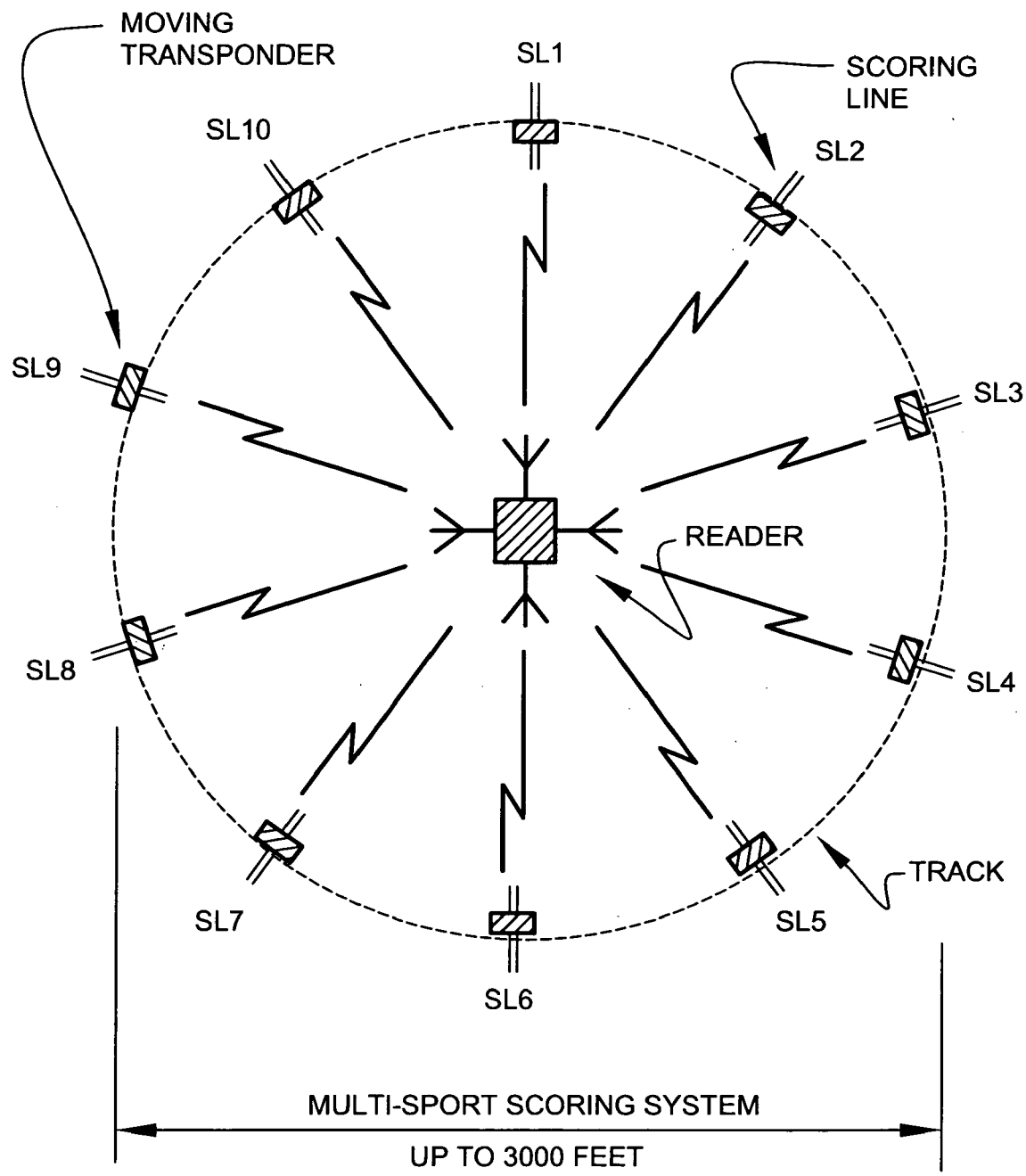

FIGS. 2-78 shows a use of a pollable Second logic-processor (that doesn't transmit unless polled) and a repetitively transmitting coded First logic-processor as a scoring device in sporting events where there are a number of scoring lines periodically spaced over a wide area. A short-range coded First logic-processor with a directional antenna is located on either end of the scoring line with the transmissions directed across the track so as to cover the full width of the scoring line and assure that a Second logic-processor 120 crossing the line will receive the polling signal. The instant the Second logic-processor receives the coded polling signal it transmits its code along with the First logic-processor's code to the Receiver located anywhere within a 1500 foot radius, thereby notifying the Receiver that the Second logic-processor has just crossed a specific scoring line, and time stamping that reception.

A further version of this scoring method involves replacing the coded First logic-processor with a coded Responder, a polling device that only transmits its code when it receives a prompt from a Second logic-processor in range. In this method the Second logic-processor, in addition to the functions described previously, also sends out a very narrow low power beacon pulse every tenth of a second to every second, depending on race speeds (walkers, runners, skiers, sleds, horses, vehicles), except when it is sending its polled data to the Receiver. The Responder acts as a pollable First logic-processor, in other words, a First logic-processor that only transmits a polling signal when it receives a beacon prompt.

Figures 2, 79A:
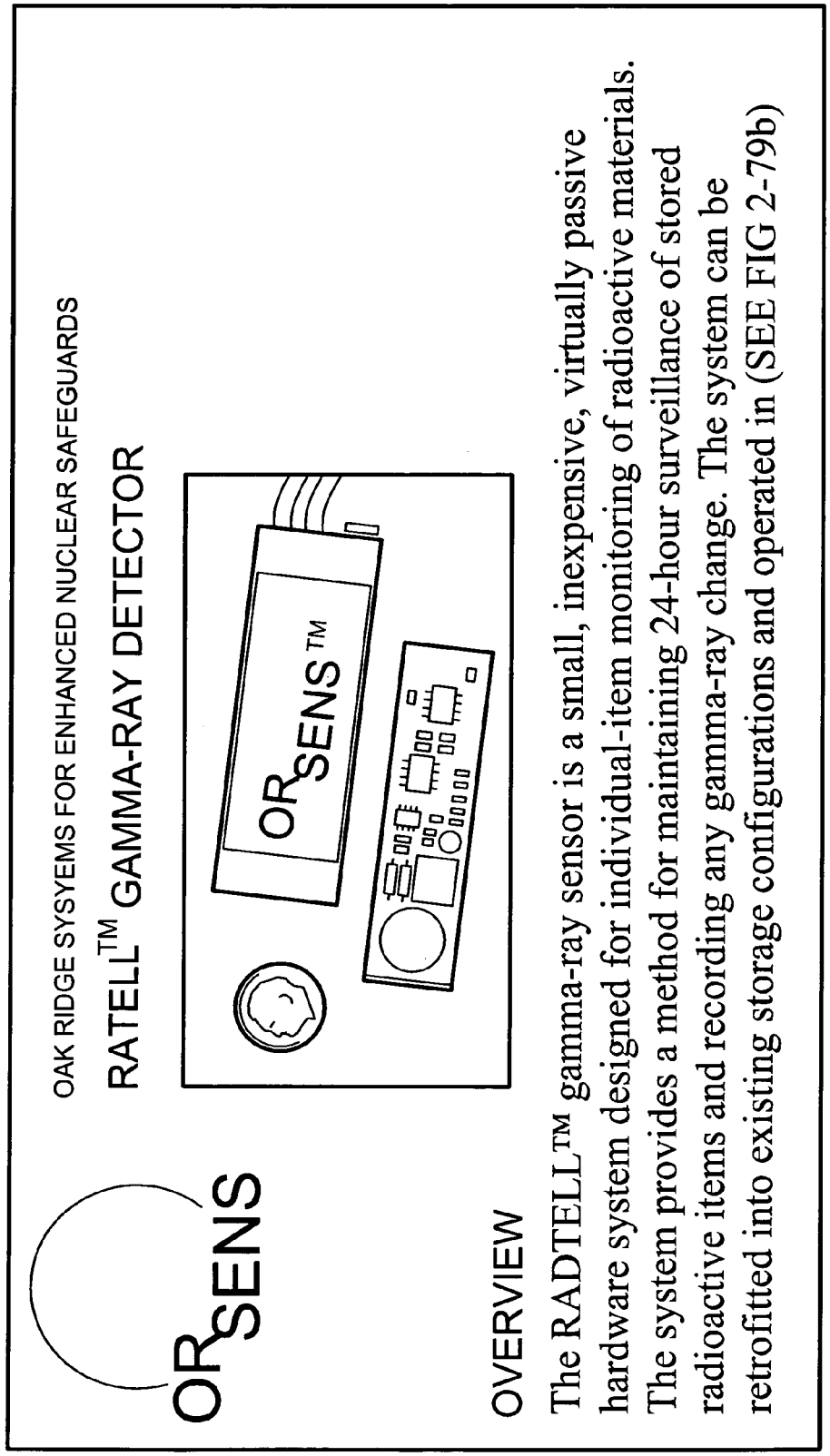

FIG. 2-79 shows a sensor application that provides the ability to provide remote surveillance of stored radioactive items and to detect radiation in monitored environments. The application has the ability to handle nonproliferation monitoring, spent fuel safeguards, and long term monitoring of stored radioactive wastes by using the features of LITMIS that sample, average, establish parameter normals, and then continuously compare readings every few seconds against absolute and rate of change limits. Data transmissions to the Receiver can be hourly or daily except when anomalies are detected, in which case transmissions can be repetitive or continuous depending on the seriousness of the condition.

Figures 2, 80:
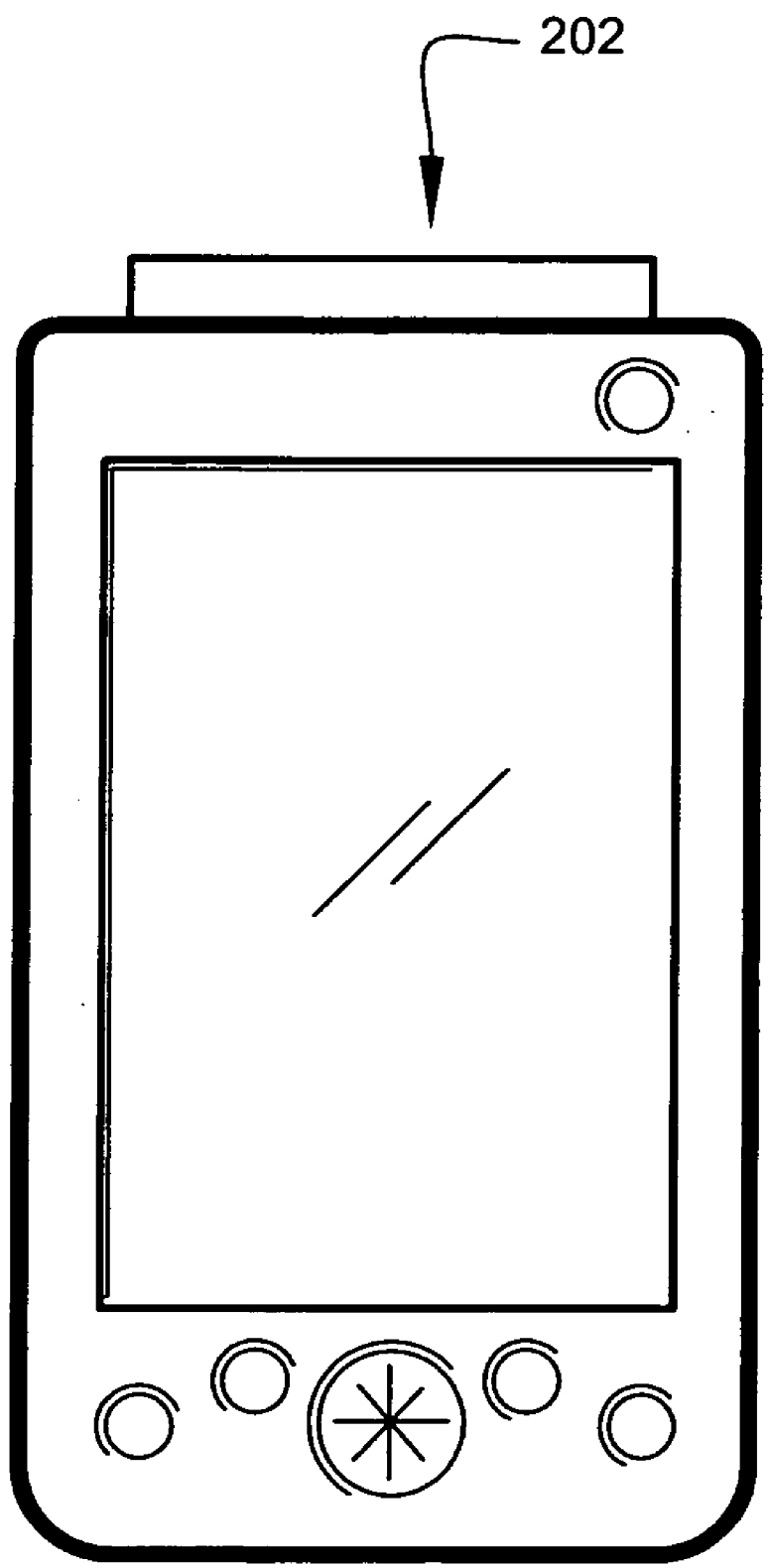

FIG. 2-80 shows a LITMIS PCMCIA Receiver card 202 plugged into an iPAQ PDA Expansion Pak. In this case the PCMCIA Receiver has an internal stub or Splatch antenna. Where a dual PCMCIA slot expansion Pak is used, an 802.11 modem card can also be inserted to provide radio communication to the central monitoring computer. In this configuration the LITMIS PCMCIA Receiver must be the Splatch version and the card must have a reverse connection into the slot compared to the 802.11 Modem. All Splatch versions of the PCMCIA Receiver are configured that way, thus avoiding communication problems because of the close proximity of the two PCMCIA cards. This orientation problem does not occur when PCMCIA Receivers have an external antenna. Another configuration option is to use both slots for LITMIS Receiver cards with external antennae that are designed to be extended into two perpendicular directions to provide a diversity feature if the application calls for it.

Figures 2, 81A:
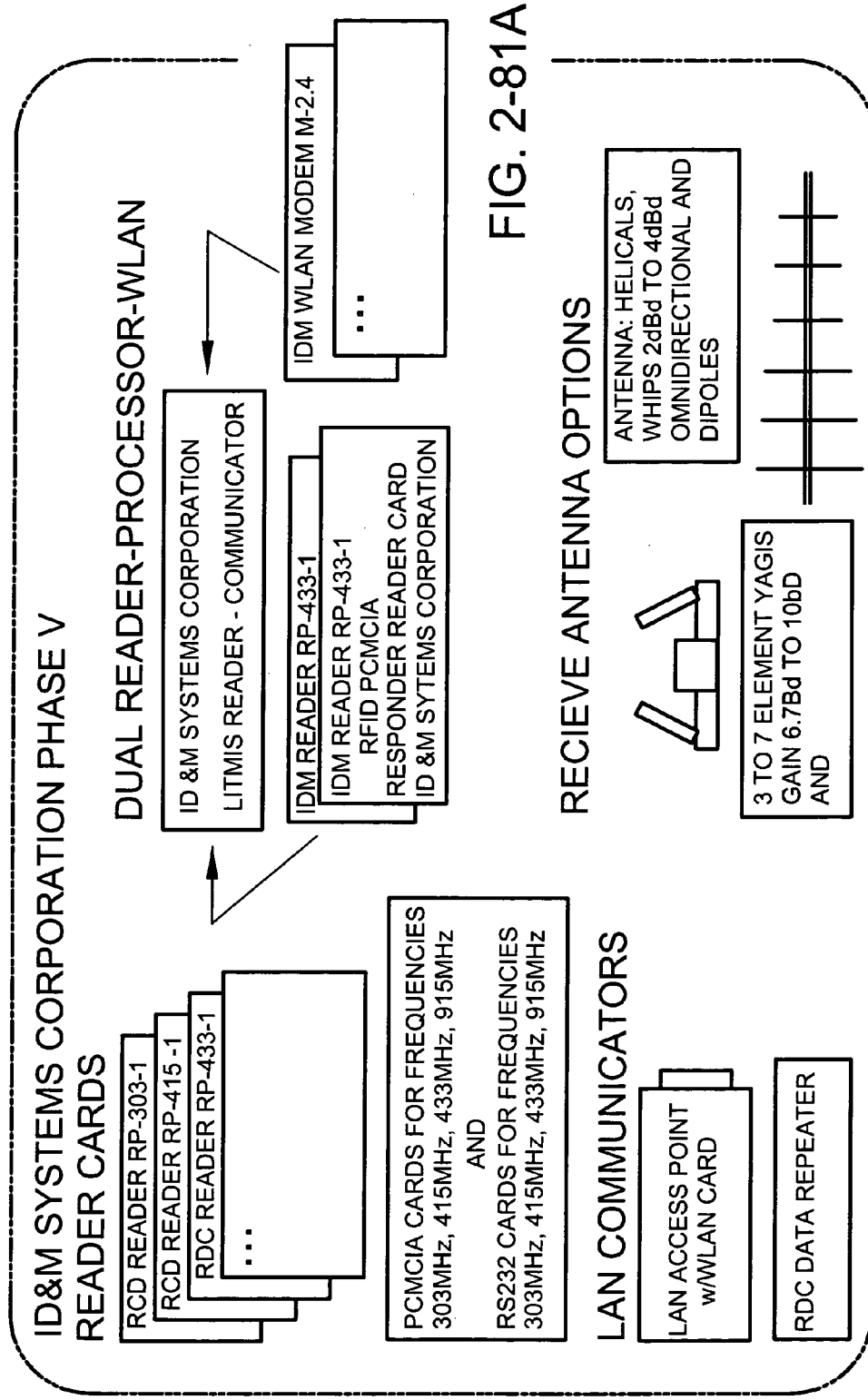
Figures 2, 81B:
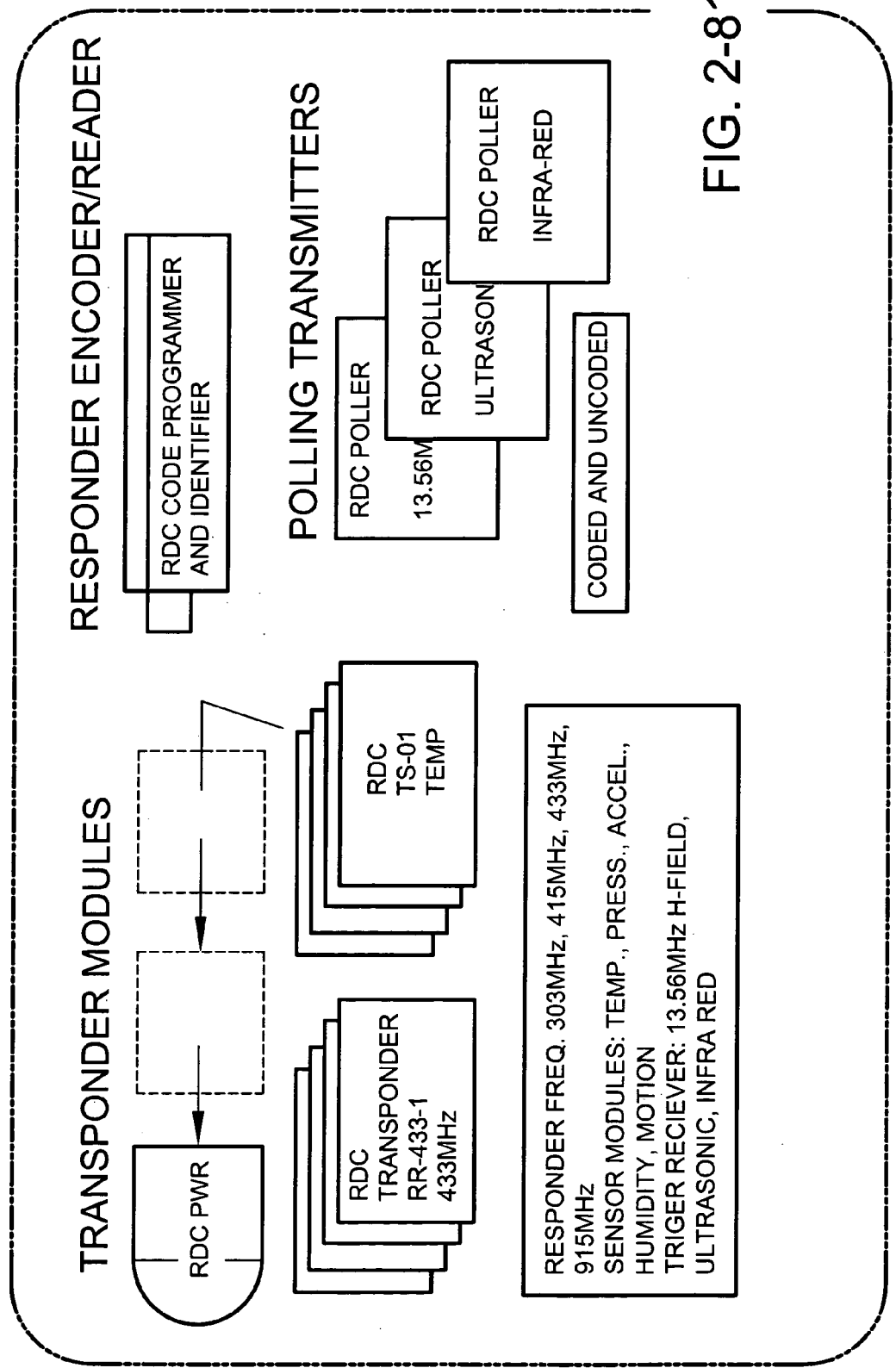
Figure 4:
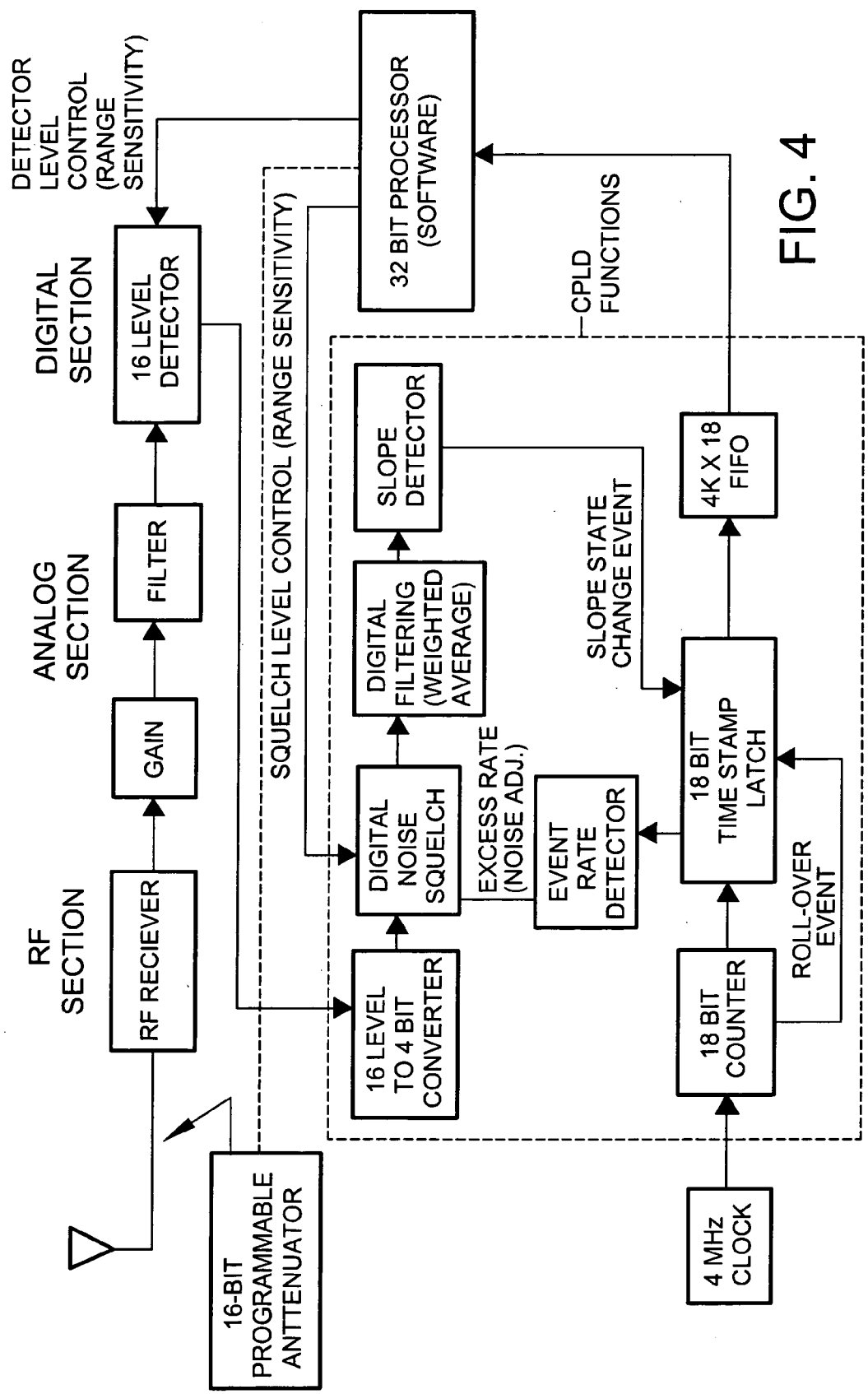
Figures 1, 6:
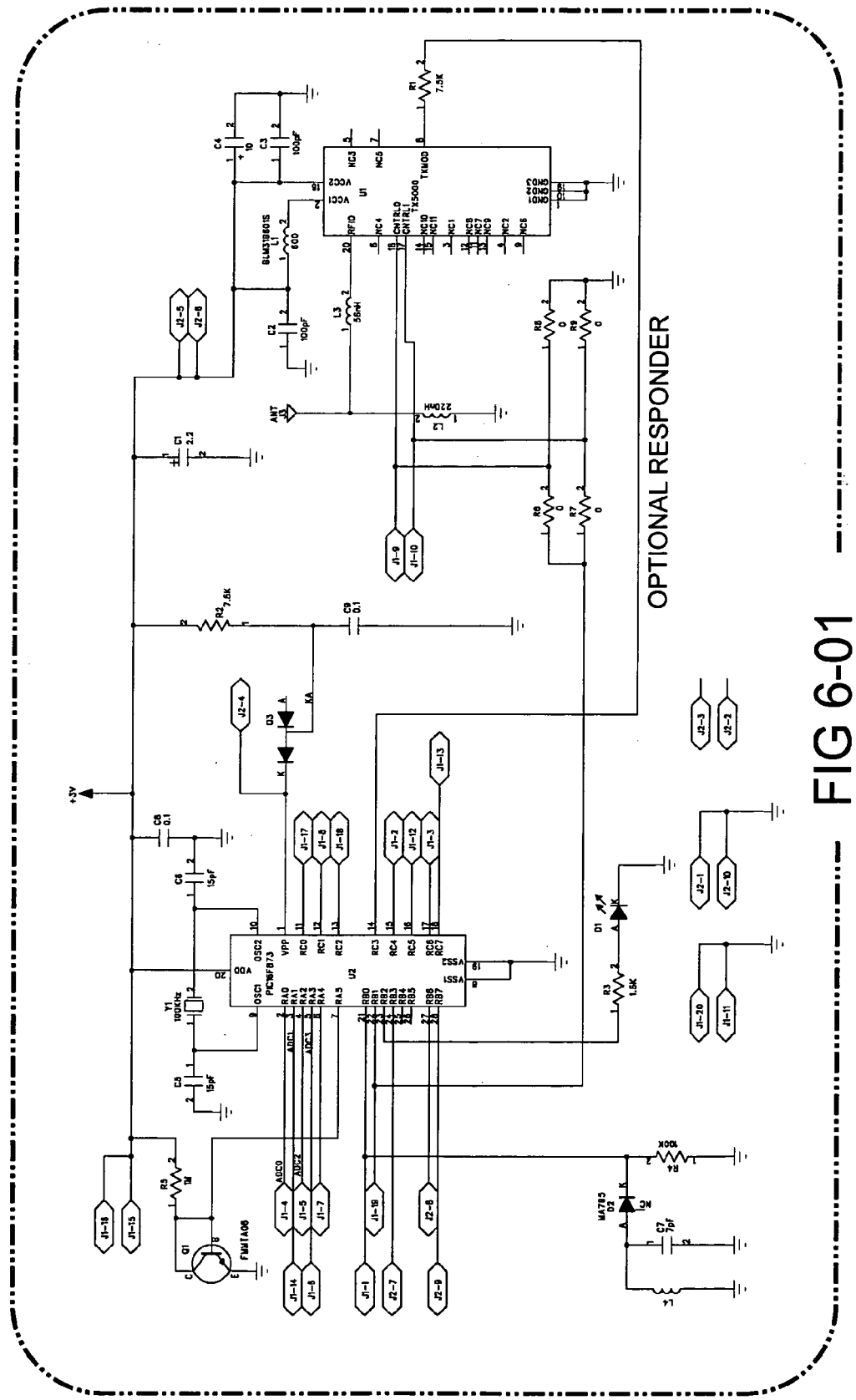
Figure 8:
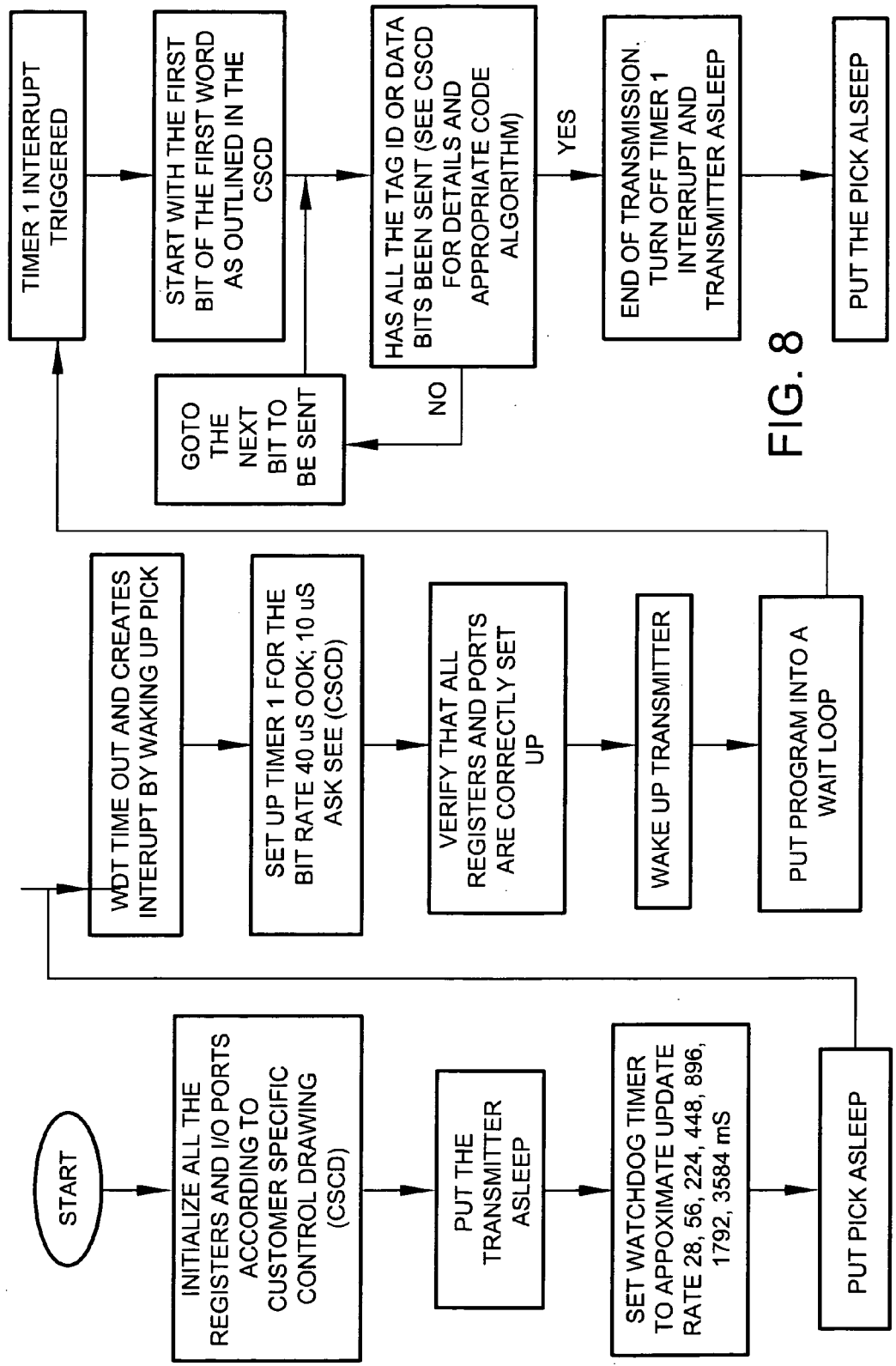
FIG. 8 is a firmware flowchart according to a preferred embodiment of the present invention.
Figure 9:
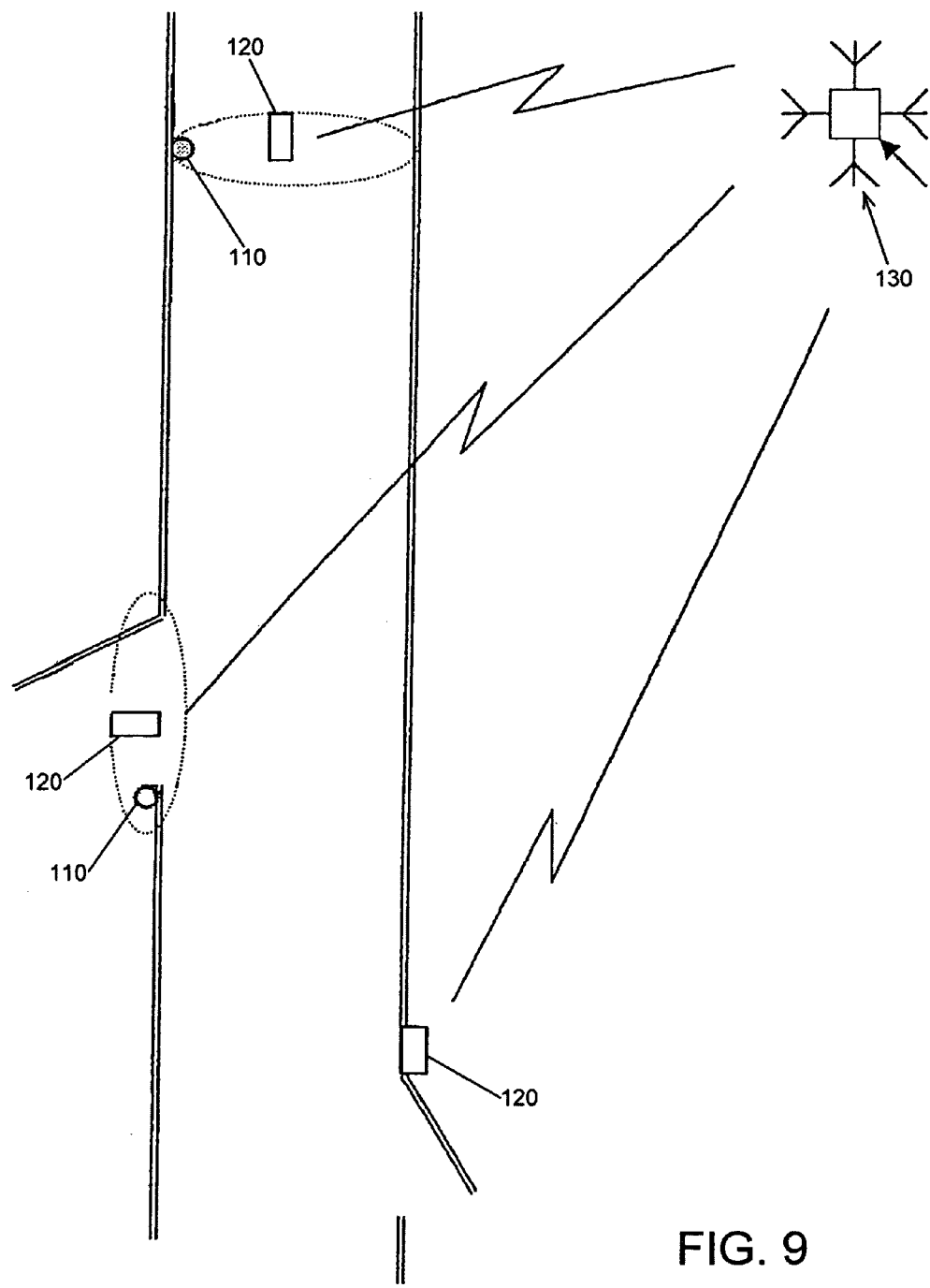
FIG. 9 is a perspective view of a network coupler according to a preferred embodiment of the present invention.
Figure 11:
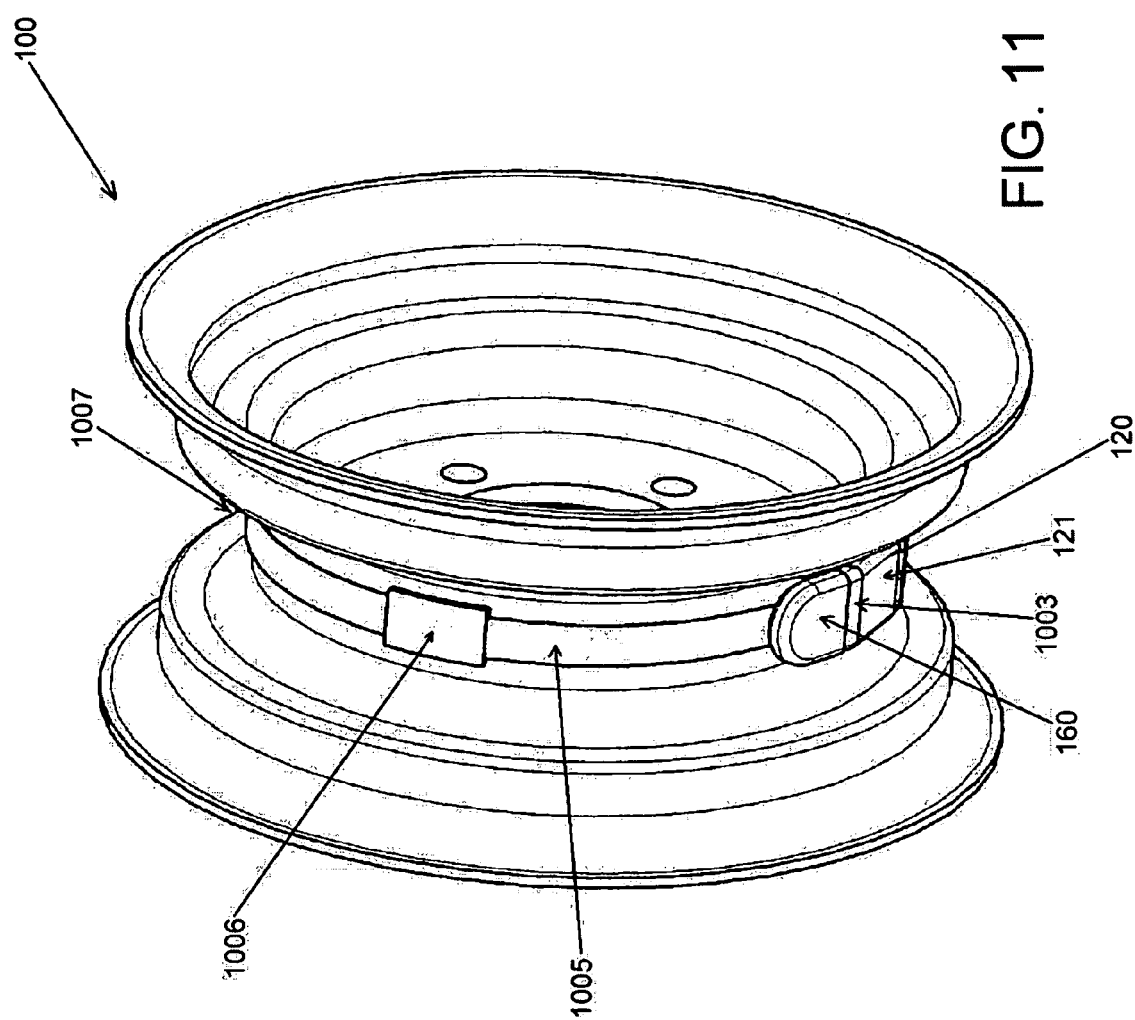
FIG. 11 is a perspective view of a Second logic-processor according to another preferred embodiment of the present invention.
Figure 14B:
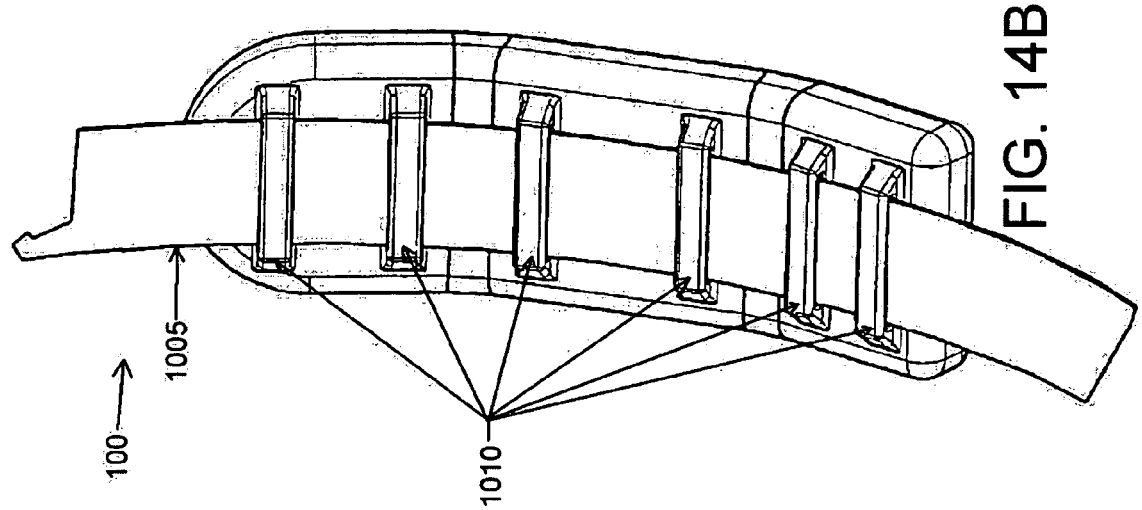
Figure 14A:
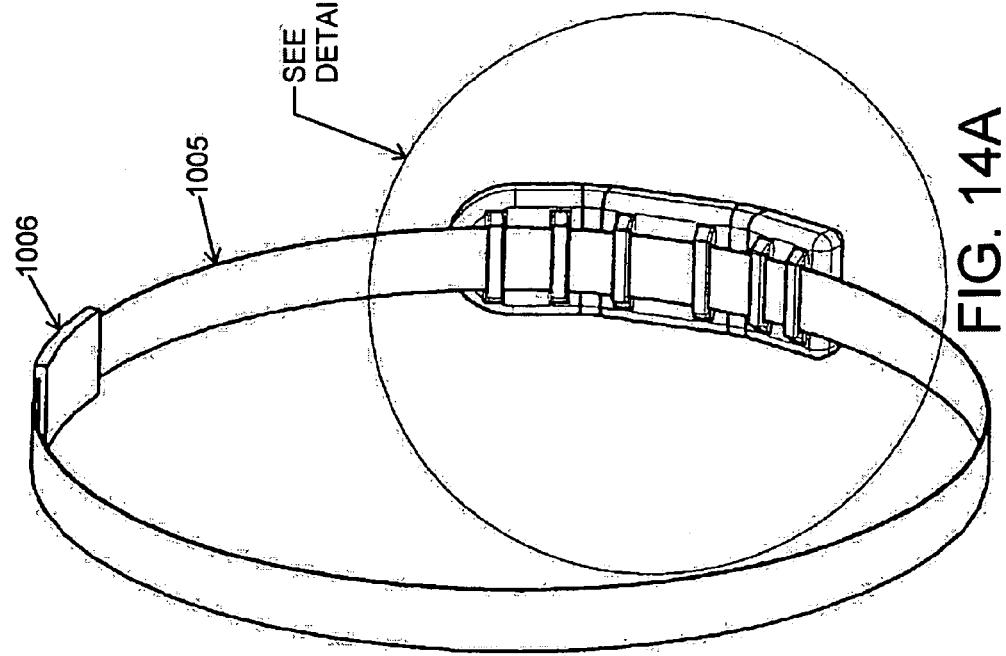

FIG. 2-81 shows the LITMIS system components concepts described in this document.

Under appropriate circumstances, an alternative encoding method can also be used with the LITMIS hardware where its use is intended for much larger numbers of Second logic-processor for a large number of potential customers.

The breadth of systems applications that can be covered by the modular, re-programmable, multi-sensor options of the Second logic-processor 120 and the ability to deliver the received information to remote locations, particularly involving cell phone and Internet connection is an innovative aspect of the invention. In many cases the Second logic-processor 120 itself, or the Receiver 130 or central computer, could allow monitoring of selected sensed parameter(s) for a period of time while it "learns" what the typical variation of that parameter is and establishes normal maximum and minimum values for it. After that period of time, the system would only notify the owner (or designated overseer) when a value goes outside that acceptable range.

As examples of security related applications beyond transport vehicles:

1. A multi-application installation is remote security and safety monitoring of containers, storage areas, warehouses, water supplies, utility plants, industrial and commercial facilities, and transportation centers.
2. Adaptable to any combination of sensors, transducers or detectors with analog or digital outputs.
3. Small, multi-application, field re-programmable wireless data monitoring of people and environments.
4. Continuous sampling to identify anomalous absolute and rate of change conditions.
5. Ability to notify programmed locations of emergencies and provide real-time data.
6. Provision for adding multiple sensors or sites for expanded monitoring or enhanced situation analysis.
7. Provides multiple level decisions from the Second logic-processor to the Control Center personnel.
8. Anomalous parametric data can be selectively presented as warnings, alerts or alarms.
9. All Internationally approved wireless bands, very low power, narrow pulse, periodic transmission.

As examples of monitored parameters:

1. Anomalous Radiation (indicating the presence of Radioactive Materials.
2. Explosives Emissions or detection of selected Chemical or Biological Agents.
3. Electricity Usage (abnormality indicating lost of power, a short or unusual usage).
4. Water Quality (identifying the presence of poisons or contaminants).
5. Natural Gas Usage (abnormality indicating a lost of service or a leak).
6. Fluid Level in Fuel Oil or Gas storage tanks (indicates a leak or refueling need).
7. Temperature (abnormality indicating a lost of heat or air conditioning, or a fire.
8. Humidity (abnormality indicating a medically required humidification system malfunction).

9. Allergens (medical risk from bacteria or other air born particulates or contaminants).
10. Light Level (abnormality indicating lights left on or a possible intrusion).
11. Noise Level (abnormality indicating dog barking, something breaking or phone ringing).
12. Circuit Breakers (indicating tripped breaker, perhaps an alarm failure).
13. Weight or Load (abnormality indicating overload or over stressed condition).
14. Identifying Movement (sensing of invaded premises or unauthorized presence).
15. Identifying Open Doors or Windows or other Security Breeches (monitoring locks/switches).
16. Locating or tracking Items, People, Vehicles and Objects.

The system has the ability to analyze simultaneous input from multiple sensors thus providing the means, as programmed by the user, to better understand the nature of anomalous data and the rate at which it is changing in real time and to be able to do this at a remote location. Similar sets of applications achievable with a single installation include commercial offices and workplaces, warehouses and factories, manufacturing plants and power stations, maintenance depots, theme parks, underground mines, military deployments, marshalling yards, airports, docks, shipping containers, vehicles, planes, ships and, in fact, in any situation, for example, where a combination of Location, Identification, Tracking, Monitoring, Interrogation and/or Sensing functions are required and particularly where real time notification of persons remote from the site is necessary.

A major feature of this innovation is the ability to accomplish all of the above functions with a single modularized, post-programmable design that can deliver the sensed or interrogated information from anywhere to anywhere instantly. The firmware 152 in Second logic-processor 120 can be re-programmed in the field and Receiver 130 software can be re-programmed through a wide choice of wired or wireless options. If it can be sensed, it can be remotely monitored without wired connections.

As examples of sensor applications in Residential Monitoring:
1. Monitoring Electricity Usage (abnormality indicating lost of power or a short)
2. Monitoring Natural Gas Usage (abnormality indicating a lost of service or a leak)
3. Monitoring Water Usage (abnormality indicating a lost of supply or a leak)
4. Monitoring Fluid Level in Fuel Oil or Gas storage tanks (indicates order needed)
5. Monitoring Temperature (abnormality indicating a lost of heat or air conditioning, or a fire or appliance/oven/hot plate left on)
6. Monitoring Humidity (abnormality indicating a medically required humidification system malfunction)
7. Monitoring Allergens (abnormality indicating a potential medical risk from excess pollen, dust, bacteria or other air born particulates or contaminants)
8. Monitoring Light Level (abnormality indicating lights left on or the sun is up)
9. Monitoring Noise Level (abnormality indicating dog barking, something breaking or phone ringing)
10. Monitoring Pool or Pond Water Level (abnormality indicating overflow or water needed)
11. Monitoring Pool Water Condition (abnormality indicating pH, Chlorine, hardness and contaminant problem)
12. Monitoring Pool or Pond Water Agitation (abnormality indicating something or someone fell or jumped into the pool, or there is a strong wind or an earthquake)
13. Monitoring Fish Pond Water Quality (abnormality indicating lack of Oxygen, presence of poisons or other contaminants)
14. Monitoring Soil Moisture Level (abnormality indicating failure of irrigation to expensive newly planted trees or broken line causing flooding)
15. Monitoring Lawn Moisture Level (abnormality indicating failure of irrigation or jammed sprinkler head)
16. Monitoring Rainfall/Snowfall and rate of precipitation (abnormality indicating a need for taking some action—perhaps turning off the sprinkler)
17. Monitoring Wind Speed/Gusts (abnormality indicating a need for taking some action—take down awnings and implement damage control)
18. Monitoring Density of Wooden Rafters and Studs (abnormality indicating possible infestation of Termites or Wood eating beetles)
19. Monitoring Freezer/Refrigerator Temperature (abnormality indicating failure and risk to food and perishables)
20. Monitoring Vehicle Tire Pressure from inside the house (abnormality indicating overnight air leak)
21. Monitoring Vehicle Fluid Levels from inside the house (abnormality indicating a need for coolant, fuel, oil or brake fluid before driving off)
22. Monitoring Solar Heating/Power Generation (abnormality indicating a system failure requiring attention)
23. Monitoring Elderly or Chronically Ill Patients (lack of movement or a fall indicating a need for checking on them, even monitoring blood sugar, pulse, etc.)
24. Monitoring Mail Box Opening (indicating delivery of mail, illegal removal of mail and mail box destruction)
25. Monitoring Circuit Breakers (indicating tripped breaker, perhaps an alarm failure)
26. Monitoring Weight or Load (abnormality indicating overload or over stressed condition)
27. Identifying Movement (sensing of invaded premises or unauthorized presence)
28. Identifying Open Doors or Windows (sensing a young child getting out, teens arriving home at night, a door or window left (or blown) open, garage door open)
29. Identifying Security Breeches (sensing a safe or security vault being opened, or a secure area being entered, or an valuable item being removed)
30. Locating Items, People or Pets (integrated into a single monitoring system)

Similar sets of applications achievable with a single installation include commercial offices and workplaces, warehouses and factories, manufacturing plants and power stations, maintenance depots, theme parks, underground mines, military deployments, marshalling yards, airports, docks, vehicles, planes, ships and, in fact, in any situation, for example, where a combination of Location, Identification, Tracking, Monitoring, Interrogation and Sensing functions are required and particularly where real time notification of persons remote from the site is required.

A major feature of this innovation is the ability to accomplish all of the above functions with a single modularized, post-programmable design that can deliver that information from anywhere to anywhere instantly. The firmware 152 in Second logic-processor 120 can be re-programmed in the field and software in the Receiver 130 can be re-programmed through a wide choice of wired or wireless options.

FIG. 3 is a perspective view of a Second logic-processor 120 according to a preferred embodiment of the present invention. Preferably, system 100 comprises Second logic-processors 120. Preferably, Second logic-processors 120 comprise second communicators 121, communicatively coupled with First logic-processors 110. Preferably, Second logic-processor 120 is capable of both stationary and in-motion operation. Preferably, a snap cap 1121 is used to seal the unused first connector 131.

In Stationary Operation, preferably, Second logic-processor 120 wakes up every five seconds (or as otherwise programmed or instructed by a First logic-processor 110) and checks for motion, polling reception and battery voltage change. If it has nothing significant to report, it returns to the sleep mode. Once an hour (or as otherwise programmed or instructed by a First logic-processor 110), the Second logic-processor 120 will re-transmit the last message sent (with a No-Change Bit indicating it as timed transmission not an event triggered transmission).

When a Second logic-processor 120 wakes up and it detects a rate of change of battery voltage or a limit failure (as defined by its programmed look-up table) not previously reported, it transmits the last message sent but with the new data (and with a Data Change Bit indicating an event triggered transmission).

If a Second logic-processor 120 detects a PDA polling message while stationary, it transmits its identity (TI) three times and returns to its sleep mode. The polling signal from a PDA has an identity code common to PDA's to distinguish it from location-polling First logic-processor 110. If a Second logic-processor 120 detects a location-polling message while stationary, it may be programmed to ignore it.

It should be noted that the person handling the PDA controls the polling message and the transmission is maintained long enough for the Second logic-processor 120 to wake up and receive it (over 5 seconds in this example). A location-polling First logic-processor 110 transmits a very short message every few seconds which is directed at moving Second logic-processor 120 that stay awake as long as it continue to move.

If a Second logic-processor 120, upon waking up, detects motion for the first time, it transmits its identity (TI) and other programmed information (and/or First logic-processor 110 instructed information), including a Start Motion Bit (SMB), and remains awake as long as the motion continues in order to be aware of a stopping of motion, unless the motion sensor/microprocessor interface enables a sleeping processor to be awakened by a the stopping of motion.

In In-Motion Operation, preferably, if a Second logic-processor 120, while in motion, detects a polling transmission, it checks the First logic-processor 110 Identity (PI) for authenticity and then checks against a Current Polling List to see if it is the first time it has received this poll since it started moving. If the PI is authenticated but it is not on the current Polling list, the Second logic-processor 120 appends First logic-processor 110 name to its data stream and transmits this information according to its programmed instructions or as modified by the First logic-processor 110 transmitted instructions with a First Time Polled (FTP) bit for that First logic-processor 110, and enters the First logic-processor 110 ID into the list of current First logic-processor 110.

As long as the Second logic-processor 120 continues to receive a specific First logic-processor 110 signal (in other words it is found on the Current Polling List), the Second logic-processor 120 will typically not repeat its previous transmission.

The Second logic-processor 120 will check every two seconds (or as otherwise programmed or instructed) to ascertain if a Current Polling List First logic-processor 110 transmission is still being received. When it first detects, for three consecutive sequences (or as otherwise programmed or instructed), that it has not received that First logic-processor 110 signal, it re-transmits the last message with a Last Time Polled (LTP1) bit for that First logic-processor 110, and removes that First logic-processor 110 ID from the current polling list.

If a second First logic-processor 110 transmission is received and authenticated while there is already another (active) First logic-processor 110 name on the Current Polling List, this name is also appended to the Second logic-processor 120 data stream and it transmits this information according to its programmed instructions or as modified by an earlier (still current) First logic-processor 110 transmitted instructions, or as superceded by the latest First logic-processor 110 instructions, with a First Time Polled bit for that First logic-processor 110 (FTP2), and enters the First logic-processor 110 ID into the list of Current First logic-processor 110.

If a third First logic-processor 110 authenticated transmission is received, then the Second logic-processor 120 will drop the first active First logic-processor 110 from the Current Polling List, replace it with the current second First logic-processor 110 ID and add the third First logic-processor 110 as though it was a second First logic-processor 110 (as indicated in the previous paragraph), except in product specifically designed to have a Current Polling List of more than two First logic-processor 110 ID's. If the Second logic-processor 120 continues to be in motion without any ID on the Current First logic-processor 110 list, its status returns to that described in the first paragraph of this In-Motion Operation section. If at any time during which First logic-processor 110 signals are being received, the Second logic-processor 120 motion stops, the last signal transmitted by the Second logic-processor 120 is repeated except with a Stopped Motion Bit and the Second logic-processor 120 status returns to that described in the first paragraph of this Stationary Operation section.

In other functions, Second logic-processor 120 has the ability to receive and analyze sensed information both digital and analog. In its simplest form it can receive a one bit state indicator such as off-on, open-closed, up-down, etc. In this application the Second logic-processor 120 can be used to monitor if the item to which the Second logic-processor 120 is attached is in use or not, either by sensing a power-on condition, using a thermal or mechanical sensor or by manual instruction, or a combination of these. This is indicated by an Equipment Status Bit (ESB) "0" for in use, "1" for available. Further status bits can be used to indicate a just completed calibration or an out-of-service condition. Other information can be provided to the Second logic-processor 120 to be relayed to the Receiver 130 either in the form of a state indication or as analog data. Examples of this are the amount of oxygen or other fluid remaining in a cylinder attached to a wheel chair or item of equipment, that the process of sterilization has been implemented between its being used for different patients, that tubes or needles have been replaced between being used for different patients or other consumable items have been replenished. The system can also be used to match equipment with a patient by having patient First logic-processor 110 (or Second logic-processor 120 with the First logic-processor 110 being on the equipment), when the equipment is in use (and stationary) adjacent to the patient the Second logic-processor 120 can relay this information to the Receiver 130 and then presented to the monitor, which software can be used to check treatment assignment and schedule to determine if a match has been achieved.

Fixed Second logic-processor 120 may be used to provide monitoring information for fixed equipment to provide information on operational status as well as service, calibration and other factors. They can also be used to monitor room environments and other areas for correct temperature, humidity, sound levels, light levels and warn for airborne contaminants such as biological and chemical agents, allergens and radioactive contamination.

Translogic-processors 190 are hermaphroditic logic-processors that can preferably serve as second logic-processors 120 or first logic-processors 110. Second logic-processor 120 utilize motion sensors to assist in locating hospital equipment and patients in multistory buildings by relating the start and stop of motion of specific items with the initial capture or ultimate loss of a local polling signal or a combination of local polling signals, thus providing the ability to track equipment and patients on elevators, in shielded or metal walled rooms and outside the building. A tri-axial accelerometer can be used to separate vertical motion in an elevator form horizontal motion along a corridor. This can be combined with the analysis of other sensed parameters such as whether a wheel chair holds a patient or is empty, or a piece of equipment is powered but not operating or powered and operating.

In a Translogic-processor 190, the Second logic-processor 120 and First logic-processor 110 are different configurations of the same system component. The Battery Connector is the same for both and the Second logic-processor hardware can be interchanged although the firmware 152 is different. The primary difference is the Second logic-processor 120 has a long-range transmitter while the First logic-processor 110 has a very short-range transmitter that can be achieved by a simple component value change biasing the transmitter stage differently and by reducing the length of the antenna. Additionally the Second logic-processor 120 has a polling Receiver 130 the First logic-processor 110 does not, but that can be achieved by simply not populating those circuit components when using the Second logic-processor as a First logic-processor 110.

The benefit of this concept is that it reduces tooling, manufacturing and parts inventory costs and provides the ability to quickly adjust to applications that have large differences in the ratio of Second logic-processor 120 to First logic-processor 110. Since the Second logic-processor 120 and First logic-processor 110 can be reprogrammed in the field, a Second logic-processor programmed at the factory as a Second logic-processor 120 can be reprogrammed into a First logic-processor 110 in the field. The reprogramming would also include disabling the polling Receiver 130 circuit. One other very unique aspect is that Second logic-processor 120 and First logic-processor 110 can be interchanged to provide greater functional versatility. For example, a Second logic-processor 120 could be located in a fixed location while a First logic-processor 110 could be located on movable piece of equipment or a person. In either case both the First logic-processor 110 and the Second logic-processor 120 could also have, or be connected to, sensors or state indicators. The difference is that the stationary system component relays the information back to the Receiver 130 instead of the movable component. When there are many doorways and other location sites but far fewer equipments or people to monitor, one benefit of system 100 is that it reduces the amount of radio frequency transmissions because the beacon component (the First logic-processor 110) is now only located on the equipment or people instead of every doorway or location site. Preferably, Second logic-processor 120 still only transmits when it has a status change to report. Another advantage of this configuration is that the relative positions of the Second logic-processor 120 and Receiver 130 can be adjusted during installation to provide the best and most reliable long range radio frequency communication. Because the moving component now only has to transmit a very short distance to a Second logic-processor 120 in an optimum location, that radio frequency communication will not be affected by the building structure or metal installations.

A further benefit of this system concept is that the interchange of Second logic-processor 120 and First logic-processor 110 can be selectively implemented around the facility depending on which provides the most optimum performance in a given area. An MRI room, for example, would need to have the long range Second logic-processor 120 located at a site known to be able communicate reliably with a Receiver 130, whereas in wards, lobbies, wide corridors, cafeterias and similar areas, the Second logic-processor 120 is more appropriately located on the movable items.

The beginning of the transmission of both Second logic-processor 120 and First logic-processor 110 contains a preamble that defines the format of the following transmission. This preamble also provides the identification of the transmission as coming from a Second logic-processor 120 and First logic-processor 110. Although Second logic-processor 120 and First logic-processor 110 can be the identical in terms of hardware, a First logic-processor 110 does not have a Receiver 130 or it is inhibited when a Second logic-processor 120 is used as a First logic-processor 110. A First logic-processor 110 will typically have a lower power transmitter or when a Second logic-processor 120 is used as a First logic-processor 110 it will normally have its transmitter powered down. Normally, a Receiver 130 is programmed only to accept a Second logic-processor 120's transmission and it has high gain antennae for that purpose, Second logic-processor 120 have the capability of receiving First logic-processor 110 signals and since they have very short range receive antenna this contributes to short range reception between First logic-processor 110 and Second logic-processor 120.

However, First logic-processor 110 can be located within range of a Receiver 130's high gain antenna and as indicated the typical application would require a First logic-processor 110 to contain a transmission bit showing it is a First logic-processor 110 and that its signal is to be ignored and the Receiver 130 is then also programmed to ignore signals received that include such a First logic-processor 110 transmission bit. However, there are circumstances where the First logic-processor 110's transmission is intended to be delivered to the Receiver 130 in which case the identification bit is modified to allow this, and then the Receiver 130 is programmed to ignore First logic-processor 110 transmissions except when this modification is present. This application is particularly valuable when a Receiver 130 is located close to an area or fixed object that needs to be monitored using a standard installed system in a dual-purpose mode.

Another unique variation of this system is an application involving transmissions between Second logic-processor 120. Normally a Second logic-processor 120 receiving a nearby signal from another Second logic-processor 120 will identify it as a Second logic-processor 120 transmission and ignore it. However, again for Second logic-processor 120 that intend their signals to be read by certain other Second logic-processor 120 the Second logic-processor 120 identification bit will be modified and the selected receiving Second logic-processor 120 will be programmed to receive these signals.

For fixed Second logic-processor 120 this feature can be used for relaying data around a hospital without requiring Receiver 130 participation such as within an MRI facility or other location where the long-range reception of a Receiver 130 is not possible. In this mode the Second logic-processor 120 are programmed to act as Repeaters.

In the case of moving Second logic-processor 120 it can be used to monitor the proximity of two Second logic-processor 120 or the lack of such proximity such as between a patient and a piece of equipment, between a mother and her recently delivered baby, a person and their assigned wheel chair, or a quarantined patient who shouldn't be near another person or in a restricted area.

The monitoring of many other parameters can be handled by the same system such as identifying the delivery and distribution of equipment and items around the hospital from drugs to transplantable organs, or matching blood and X-rays to the correct patient and for the inventorying of hospital capital assets such as computers, printers, shedders, scanners, televisions, phones all of which can be either located or tracked, if the have a Second logic-processor 120 and an alert can be displayed whenever these items are removed from their assigned location, or being removed from the building without authorization.

FIG. 4 is a receiver flowchart according to a preferred embodiment of the present invention. Preferably, system 100 further comprises Receiver 130. Preferably, Receiver 130 receives communicated information from first logic-processors 110. Preferably, Receiver 130 receives communicated information from second logic-processors 120. Preferably, Receiver 130 comprises wireless receptor 162. Preferably, wireless receptor 162 receives wireless communications. Preferably, wireless receptor 162 is structured to enhance sensitivity to signals intended for reception by wireless receptor 162.

Preferably, system 100 further comprises database 140. Preferably, database 140 manipulates the information communicated between Receiver 130, First logic-processor 110, and Second logic-processor 120. Preferably, the Receiver 130 can be embodied in a fixed format, preferably, using two receive channels for diversity or for a PDA application a single receive channel either integrated into the PDA using a serial interface or as a PCMCIA card. In the latter case the PCMCIA card may be implemented using a PCB thin film radiator on the card serving as the antenna, or a Splatch commercial networked antenna, or an external stub or whip antenna. All three versions have been build and tested. The external antenna version includes end connectors on the PCMCIA card, an MMCX connector for the antenna a 4-pin connector for programming and a 15 pin connector for testing or use in a serial output mode. The fixed Receiver 130 can be implemented in a PCI format for integration into a PC, a PC-104 format for use with an imbedded processor in a PC-104 styled Receiver 130, or a dual PCMCIA slot PC-104 board can be used and the external antenna PCMCIA card simply plugged into one slot. The second slot can either be used for a PCMCIA modem for transmitting information to a control center by radio frequency or to phone jack, or it can be used for a second PCMCIA Receiver 130 card to provide diversity. In the case of high gain antenna(s) requiring low loss cable connections, a bulkhead connector(s) would be provided on the Receiver 130 case for that connection and a micro-coax cable(s) would connect from the bulkhead connector(s) to the PCMCIA MMCX connector(s).

The Receiver 130 has a 16-bit attenuator ahead of the radio frequency Receiver 130 which with a wide choice of antennae from ¼ wave Helical antenna to high gain Yagi antenna can be used to limit the range of Receiver 130 both at the installation stage as well as by instructions delivered by the two-way wired or wireless Receiver 130 communications link.

The Receiver 130 is capable of receiving Second logic-processor 120 transmissions from a distance of up to 1500 feet depending on the nature of the receiving antenna. The Receiver 130 on receiving a Second logic-processor 120's transmission then extracts the Second logic-processor 120's unique code and the polling code, and time stamps the entry. This provides real time information on the identity and status of an item and the time it was at or passed a specific location. One Receiver 130 can cover an area having a radius of 1500 feet and can monitor a large number of items or people without risk of collision errors because the Second logic-processor 120 typically only transmit when they are moving and then only when they first receive a polling transmission and after loosing a polling transmission. The short range of the polling transmitter limits the number of Second logic-processor 120 responding to those within several feet of the timing location, and even then is limited to the first and last poll reception, although the system is capable of receiving transmissions from several hundred Second logic-processor 120 polled simultaneously.

FIG. 5 is a perspective view of a power source according to a preferred embodiment of the present invention. Preferably, first logic processors 110 and second logic-processors 120 each comprises power source 160. Preferably, power source 160 provides electrical power. Preferably, power source 160 comprises power life extender 161. Preferably, power life extender 161 extends the life of power source 160 by assisting intermittent operation.

FIG. 6-00 and FIG. 6-01 are perspective views of an electric circuit according to a preferred embodiment of the present invention. Preferably, First logic-processor 110 and second logic processor 120 each comprise electric circuit 151. Preferably, electric circuit 151 processes information. Preferably, electric circuit 151 processes information received from other logic-processors 110 and 120.

FIG. 7 is a perspective view of a wireless system according to a preferred embodiment of the present invention. Preferably, first communicators 111 and second communicators 121 each comprise wireless systems 155. Preferably, wireless systems 155 provide for wireless communication of information.

Preferably, first logic-processors 110 and second logic-processors 120 each comprise identifier 154. Preferably, identifier 154 uniquely identifies each of the first logic processors 110. Preferably, identifier 154 uniquely identifies each of the second logic processors 120. Preferably, first communicator 111 and second communicator 121 each operate at a frequency within the range consisting of radio frequency. Preferably, first communicator 111 and second communicator 121 each operate at a frequency within the range consisting of ultrasonic frequency. Preferably, first communicator 111 and second communicator 121 each operate at a frequency within the range consisting of UV frequency. Preferably, first communicator 111 and second communicator 121 each comprise non-continuous signaler 156. Preferably, non-continuous signaler 156 provides for non-continuous communication between first logic-processors 110, second logic processors 120, and receivers 130. Preferably, first communicator 111 and second communicator 121 each comprise optimized signaler 157. Preferably, optimized signaler 157 provides optimized power consumption when generating non-continuous communications.

FIG. 8 is a firmware flowchart according to a preferred embodiment of the present invention. Preferably, electric circuit 151 comprises firmware 152. Preferably, firmware 152 provides for hardware, which can be modified as if it were software. Firmware 152 is also referred to in the arts as "middleware". Preferably, firmware 152 can be modified by wireless system 155.

FIG. 9 is a perspective view of a network coupler according to a preferred embodiment of the present invention.

Preferably, Receiver 130 comprises network coupler 158. Preferably, network coupler 158 communicatively couples Receiver 130 to outside networks. Preferably, network coupler 158 comprises the internet, Personal Computers (PC's), Personal Digital Assistants (PDA's), Local Area Networks (LAN's), radios, cellular phones, and PCMCIA's. Upon reading the teachings of this specification, persons of ordinary skill in the art will now understand that, considering issues such as technology, cost, and efficiency, other network couplers such as radios, cellular phones, personal computers (PC's), etc., may suffice.

FIG. 10 is a sensor sampling table according to a preferred embodiment of the present invention. Preferably, system 100 further comprises sensor 150. Preferably, sensor 150 senses local information. Preferably, sensor 150 senses local information attachable to at least one subset first logic-processors 110. Preferably, sensor 150 senses local information attachable to at least one subset second logic-processors 120.

Preferably, system 100 receives the status or state change of an item from the state sensor 150 by way of a plurality of fixed status broadcasters. Preferably, system 100 receives the state change of the item from state sensor 150 by way of the plurality of mobile status broadcasters. Preferably, system 100 determines the requirement to broadcast the state change by the plurality of fixed status broadcasters. Preferably, system 100 determines the requirement to broadcast the state change by way of the plurality of mobile status broadcasters. Preferably, system 100 broadcasts the required state by the plurality of fixed status broadcasters. Preferably, system 100 broadcasts the required state change by way of the plurality of mobile status broadcasters. Preferably, system 100 receives the required state change from the plurality of fixed status broadcasters. Preferably, system 100 receives the required state change from the plurality of mobile status broadcasters. Preferably, system 100 stores the required state change in database 140. Preferably, system 100 reports the required state change to a proactive entity.

FIG. 11 is a perspective view of a second logic-processor according to another preferred embodiment of the present invention. Preferably, system 100 is used for remotely locating, identifying, tracking, monitoring, interrogating, and sensing such items as containers and container contents, vehicles, crates, packages and personal belongings; people in theme parks, cruise liners, multistory buildings, university campuses, golf courses and shopping malls; and the conditions of vehicle wheel and axle systems, clean room environments, water quality, aircraft systems and the contents of vending machines. Other remote access applications include video surveillance, radioactivity monitoring, sniffing for explosives and drugs, and other security and law enforcement activities. Preferably, second logic processor 120 is attached to wheels of cargo vessels. Preferably, Second logic-processor 120 comprises communicator 121, tapered separator 1003, and power source 160, as shown. Preferably, Second logic-processor 120 is attached with strap 1005 and grommet 1006. Preferably, Second logic-processor 120 is positioned in the drop center of the wheel 1007. Preferably, power source 160 comprises a battery. Preferably, First logic-processor 110 (not shown) polls for second logic-processors 120, and such information is received by Receiver 130 (not shown). Preferably, all logic processors 110 and 120, as well as Receiver 130, may be equipped with cleats that provide for the ability to withstand high shock and g-force stresses.

Furthermore with the ability to send emergency information immediately utilizing network couplers 158, any sensed or monitoring information can be delivered in real time to anywhere in the world, all with a single Receiver 130 or with an arrayed set of identical receivers 130. Preferably, Connectors 131 and 132 can have a variety of features from simply a sealed cap to protect the connector when used only for testing, programming and only beacon application, to a custom connector for interfacing with customer provided sensors, and a wide choice of active sensing and communicating connectors, that can range from GPS and fixed-frame video, to wheel and axle monitoring that includes pressure, temperature, acceleration and acoustic sensors, and to the inclusion of a variety of telemetry functions.

Preferably, the Signal Strength Indication (SSI) technology imbedded in Receiver 130 consists of a 16-bit comparator. The accurate location features of the system integrate this SSI feature with wireless receptor 162. Preferably, wireless receptor 162 comprises a PIN diode-switched eight-antenna array. Preferably, this eight-antenna array can be configured as four pairs of dual orthogonal antennae located equidistant from the Receiver 130 in a North, East, South and West type of deployment or if diversity is not required the Receiver 130 can handle a distributed array of eight antennae, providing an even more accurate location capability. In applications where the high gain antennae are used to provide significant range (such as omni angle or Yagi) a Low Noise Amplifier may be required at each antenna. For example, when using ¼ wave helical antennae, the Second logic-processor 120 read range is typically about 100 feet to about 125 feet. In this case, the antennae are located about 50 feet from the Receiver 130 in perpendicular directions. The SSI sensitivity is about ±1.5 feet near the Receiver 130 to about ±4 feet far from the Receiver 130, over an area of approximately 32,000 square feet, using a single Receiver 130. By using additional, appropriately located Receiver 130, the accuracy can be maintained at about ±1.5 feet over a much larger area. About 1000 receivers 130 would be required to cover a square mile instead of about 5000 conventional Receivers 130 with the same receptor 162.

Using ¼ wave whip antennae, Second logic-processor 120 read range is typically about 150 feet to about 175 feet. In this case the antennae are located about 75 feet from the Receiver 130 in perpendicular directions. The SSI sensitivity is about ±2.5 feet near the Receiver 130, to about ±6 feet far from the Receiver 130, over an area of approximately 65,000 square feet, using a single Receiver 130. By using additional, appropriately located receivers 130, the accuracy can be maintained at about ±2.5 feet over a much larger area. About 500 receivers 130 would be required to cover a square mile instead of about 2500 conventional receivers 130 with the same antenna. Using high-gain omni-antennae, Second logic-processor 120 read range is typically about 400 feet to about 450 feet. In this case, the antennae are located about 200 feet from the Receiver 130, preferably in perpendicular directions.

Receiver 130 has a number of wireless system 155 options that are achieved by using a multi-protocol processor and software platforms that address the 802.11, Bluetooth, HomePlug, Ethernet, SMS, GSM, CDSA and USB networking protocols, providing solutions that are designed for deployment in wireless access points, gateways and VoIP phones, and in commercial/industrial equipment. This provides the ability to standardize LITMIS systems around a single platform while preserving the flexibility to bring a wide variety of product variations into an integrated system via software changes only. This enables compliance with the latest specifications that can be executed instantaneously through software upgrade through the Internet. The integration of this technology in the Receiver 130 provides a single adaptable platform, enabling connectivity with numerous communications and device physical interfaces like 802.11, Ethernet, MII, I2C, SPI, GPSI, UART and USB. The heart of this feature is a 120MIPS deterministic processor, complemented with on-chip high-speed flash and SRAM memory. Preferably, two full-duplex serializers/deserializers enable software implementation of most common device I/O, including on-chip Ethernet MAC and PHY.

FIG. 12 is an alternative perspective view of a second logic processor according to a preferred embodiment of the present invention.

FIG. 13 is a side view of the sections of a second logic processor according to a preferred embodiment of the present invention. Preferably, system 100 comprises mounting cleats 1010, strap 1005, and grommet 1006.

FIG. 14 is a posterior view of the sections of a second logic-processor according to a preferred embodiment of the present invention. Preferably, cleats 1010 (two per connector) thread onto strap 1005, which attaches around the drop center of the wheel 1007, and is held tight with grommet 1006. Preferably, the underside of each cleat 1010 has a high friction surface to resist and assist in preventing the Second logic-processor 120 from slipping and moving from its installed location.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

What is claimed is:

1. A load safeguard system, co-operable with at least one database, for monitoring, within at least one determinable environment, at least one item requiring monitoring of at least one sensible condition, comprising, in combination:
    a) a set of first logic-processor means, for logical transacting with receivable information, respectively associated with a respective set of locations within at least one determinable environment; and
    b) a plurality of second logic-processor means, for logical transacting with receivable information, respectively associated with a plurality of such at least one items;
    c) wherein essentially each of said set of first logic-processor means comprises first communicator means for communicative coupling with essentially each of said plurality of second logic-processor means;
    d) wherein essentially each of said plurality of second logic-processor means comprises second communicator means for communicative coupling with essentially each of said set of first logic-processor means;
    e) wherein essentially each of said plurality of second logic-processor means comprises sensor means for sensing at least one environmental condition; and
    f) wherein essentially each of said set of first logic-processor means comprises third communicator means for communicative coupling with such at least one database.

2. The load safeguard system according to claim 1, wherein:
    a) such at least one item comprises at least one shippable package; and
    b) such at least one determinable environment comprises at least one shipping environment.

3. The load safeguard system according to claim 2, wherein:
    a) such at least one item comprises perishable produce; and
    b) such at least one determinable environment comprises at least one temperature-controllable shipping truck.

4. A system, co-operable with at least one database, for monitoring items within a local area, comprising, in combination:
    a) a set of first logic-processor means, for logical transacting with receivable information, respectively associated with a plurality of locations within the local area; and
    b) a plurality of second logic-processor means, for logical transacting with receivable information, respectively associated with a plurality of the items;
    c) wherein essentially each of said set of first logic-processor means comprises first communicator means for communicative coupling with essentially each of said plurality of second logic-processor means; and
    d) wherein essentially each of said plurality of second logic-processor means comprises second communicator means for communicative coupling with essentially each of said set of first logic-processor means.

5. A system, co-operable with at least one database, for monitoring items within a local area, comprising, in combination:
    a) a set of first logic-processors structured and arranged to provide logical transaction with receivable information, respectively associated with a plurality of locations within the local area; and
    b) a plurality of second logic-processors structured and arranged to provide logical transaction with receivable information, respectively associated with a plurality of the items;
    c) wherein essentially each of said set of first logic-processors comprises at least one first communicator structured and arranged to communicatively couple with essentially each of said plurality of second logic-processors; and
    d) wherein essentially each of said plurality of second logic-processors comprises at least one second communicator structured and arranged to communicatively couple with essentially each of said set of first logic-processors.

6. The system according to claim 5 further comprising at least one receiver structured and arranged to receive communicated information from at least one of the group consisting essentially of each of said set of first logic-processors and each of said plurality of second logic-processors.

7. The system according to claim 6 further comprising such at least one database structured and arranged to manipulate such receivable information.

8. The system according to claim 6 wherein said at least one receiver comprises at least one wireless receptor structured and arranged to receive such receivable information.

9. The system according to claim 6 wherein said at least one receiver comprises at least one network coupler structured and arranged to communicatively couple said at least one receiver with at least one of the group consisting of:
 a) Global System for Mobile Communications systems (GSM);
 b) Global Positioning Systems (GPS)
 c) Internet;
 d) personal computers;
 e) personal digital assistants;
 f) local area networks;
 g) radios;
 h) cellular phones;
 i) wireless networks; and
 j) personal computer memory card international associations (PCMCIA's) for wireless applications.

10. The system according to claim 5 wherein said at least one first communicator and said at least one second communicator each comprise at least one wireless system structured and arranged to wirelessly assist communicative coupling.

11. The system according to claim 10 wherein said at least one first communicator and said at least one second communicator comprise at least one frequency within the range consisting of about radio frequency.

12. The system according to claim 5 wherein essentially each of said set of first logic-processors and essentially each of said plurality of second logic-processors comprise at least one identifier structured and arranged to uniquely identify essentially each one of said plurality of first logic-processors and essentially each one of said plurality of second logic-processors.

13. The system according to claim 5 further comprising at least one sensor structured and arranged to sense local information, attachable to at least one subset of at least one of the group consisting essentially of each of said set of first logic-processors and each of said plurality of second logic-processors.

14. The system according to claim 5 wherein essentially each of said set of first logic-processors and essentially each of said plurality of second logic-processors comprise at least one power source structured and arranged to provide electrical power.

15. The system according to claim 5 wherein said at least one first communicator and said at least one second communicator comprise at least one non-continuous signaler structured and arranged to provide non-continuous communications.

16. The system according to claim 15 wherein said at least one non-continuous signaler comprises at least one optimized signaler structured and arranged to provide optimized power consumption when generating non-continuous communications.

17. The system according to claim 5 wherein essentially each of said set of first logic-processors and essentially each of said plurality of second logic-processors comprise at least one electric circuit structured and arranged to process data.

18. The system according to claim 17 wherein said at least one electric circuit comprises at least one firmware structured and arranged to provide modification of said set of first logic-processors and modification of said plurality of second logic-processors.

19. The system according to claim 18 wherein said at least one first communicator from at least one of said set of first logic-processors is communicatively coupleable with at least one of said plurality of second logic-processors so that said at least one firmware of said at least one of said plurality of second logic-processors may be modified by said at least one first communicator.

20. The system according to claim 18 wherein said at least one second communicator from at least one of said plurality of second logic-processors is communicatively coupleable with at least one of said plurality of first logic-processors so that said at least one firmware of said at least one of said plurality of first logic-processors may be modified by said at least one second communicator.

\* \* \* \* \*